(12) United States Patent
Otterlei

(10) Patent No.: US 11,246,907 B2
(45) Date of Patent: Feb. 15, 2022

(54) IMMUNOSUPPRESSIVE AGENTS AND THEIR USE IN THERAPY

(71) Applicant: Norwegian University of Science and Technology, Trondheim (NO)

(72) Inventor: Marit Otterlei, Trondheim (NO)

(73) Assignee: Norwegian University of Science and Technology, Trondheim (NO)

( * ) Notice: Subject to any disclaimer, the term of this patent is extended or adjusted under 35 U.S.C. 154(b) by 0 days.

(21) Appl. No.: 16/683,188

(22) Filed: Nov. 13, 2019

(65) Prior Publication Data

US 2020/0323953 A1    Oct. 15, 2020

Related U.S. Application Data

(62) Division of application No. 15/034,917, filed as application No. PCT/EP2014/073966 on Nov. 6, 2014, now Pat. No. 10,517,923.

(30) Foreign Application Priority Data

Nov. 6, 2013 (GB) .................................... 1319620

(51) Int. Cl.

| | |
|---|---|
| A61K 38/08 | (2019.01) |
| A61K 38/10 | (2006.01) |
| A61K 38/16 | (2006.01) |
| A61K 47/64 | (2017.01) |
| A61K 38/17 | (2006.01) |
| A61K 45/06 | (2006.01) |

(52) U.S. Cl.
CPC .......... *A61K 38/1709* (2013.01); *A61K 38/08* (2013.01); *A61K 38/10* (2013.01); *A61K 38/16* (2013.01); *A61K 45/06* (2013.01); *A61K 47/64* (2017.08); *A61K 47/645* (2017.08); *Y02A 50/30* (2018.01)

(58) Field of Classification Search
CPC ........ A61K 38/08; A61K 38/10; A61K 38/16; A61K 38/1709; A61K 38/1761; A61K 47/64; A61K 47/645; C07K 7/06; C07K 7/08; C07K 14/47; C07K 14/4747; C07K 2319/03; C07K 2319/09; C07K 2319/10
See application file for complete search history.

(56) References Cited

U.S. PATENT DOCUMENTS

| | | | |
|---|---|---|---|
| 5,198,541 A | 3/1993 | Elsbach et al. | |
| 5,439,807 A | 8/1995 | Grinna | |
| 5,447,913 A | 9/1995 | Ammons et al. | |
| 5,643,578 A | 7/1997 | Robinson et al. | |
| 7,579,318 B2 | 8/2009 | Divita et al. | |
| 7,695,716 B2 * | 4/2010 | Drachman | A61P 17/06 424/133.1 |
| 10,450,348 B2 * | 10/2019 | Otterlei | A01N 25/08 |
| 10,517,923 B2 * | 12/2019 | Otterlei | A61K 47/64 |
| 2002/0119918 A1 | 8/2002 | Carroll | |
| 2002/0150954 A1 * | 10/2002 | Durden | A61P 37/06 435/7.23 |
| 2003/0171265 A1 | 9/2003 | Ammons et al. | |
| 2003/0176337 A1 | 9/2003 | Hancock | |
| 2006/0270612 A1 * | 11/2006 | Blatt | A61P 9/10 514/23 |
| 2007/0219139 A1 | 9/2007 | Sung-Ho et al. | |
| 2007/0280950 A1 * | 12/2007 | Okabe | A61P 43/00 424/158.1 |

(Continued)

FOREIGN PATENT DOCUMENTS

| | | |
|---|---|---|
| WO | 93/23540 A2 | 11/1993 |
| WO | 94/18323 A1 | 8/1994 |

(Continued)

OTHER PUBLICATIONS

Patterson et al. Protein kinase inhibitors in the treatment of inflammatory and autoimmune diseases. Clinical and Experimental Immunology. 2013, vol. 176, pp. 1-10. (Year: 2013).*
International Search Report, International Application PCT/EP2014/073966, dated Mar. 12, 2015.
De Chiara, et al., Targeting cytosolic proliferating cell nuclear antigen . . . , Frontiers in Immunology, vol. 3, 2012.
Cassatella M.A., et al., "Cytokine expression and release by neutrophils", Annals of the New York Academy of Sciences, vol. 832, Dec. 15, 1997.
Bacquin A, Pouvelle C, Siaud N, Perderiset M, Salomé-Desnoulez S, Tellier-Lebegue C, Lopez B, Charbonnier JB, Kannouche PL. The helicase FBH1 is tightly regulated by PCNA via CRL4(Cdt2)-mediated proteolysis in human cells. Nucleic Acids Res. Jul. 2013;41(13):6501-13.

(Continued)

*Primary Examiner* — Jeffrey E. Russel
(74) *Attorney, Agent, or Firm* — Mintz Levin Cohn Ferris Glovsky and Popeo, P.C.; Peter F. Corless

(57) ABSTRACT

The present invention provides an agent, or composition containing an agent, for use in treating or preventing hypercytokinemia in a subject resulting from cytokine release from non-proliferating immune cells in blood, wherein the agent comprises:
(i) an oligopeptidic compound comprising a PCNA interacting motif and a domain that facilitates the cellular uptake of said compound, wherein the PCNA interacting motif is $X_1X_2X_3X_4X_5$ (SEQ ID NO: 1) and wherein:
$X_1$ is a basic amino acid;
$X_2$ is an aromatic amino acid;
$X_3$ is an uncharged amino acid other than an aromatic amino acid, Glycine (G) and Proline (P);
$X_4$ is any amino acid other than Proline (P), an acidic amino acid or an aromatic amino acid; and
$X_5$ is a basic amino acid or Proline (P); or
(ii) a nucleic acid molecule comprising a sequence encoding the oligopeptidic compound of (i).
In certain aspects the agent and compositions of the invention may be used as single agents. In other aspects of the invention agents and compositions of the invention may be used in conjunction with one or more additional active agents, such as kinase inhibitors.

25 Claims, 8 Drawing Sheets

Figure 1:
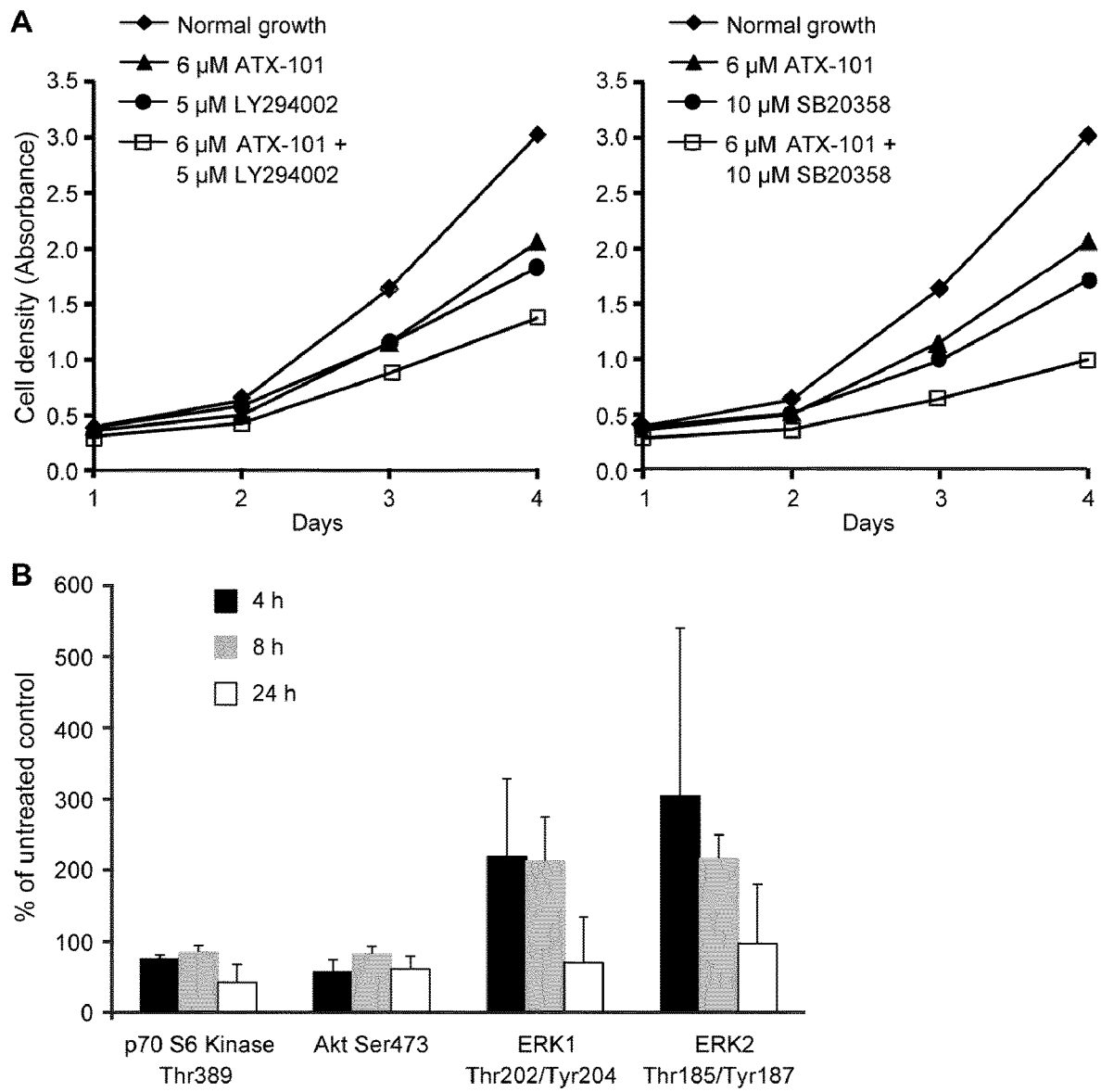

Specification includes a Sequence Listing.

(56) References Cited

U.S. PATENT DOCUMENTS

| | | | | |
|---|---|---|---|---|
| 2010/0047239 | A1* | 2/2010 | Wu | A61P 13/12 424/133.1 |
| 2011/0293641 | A1 | 12/2011 | Bowie | |
| 2012/0289511 | A1* | 11/2012 | Alam | A61K 31/5025 514/248 |
| 2013/0052258 | A1* | 2/2013 | Kalle | A61K 38/4833 424/445 |
| 2013/0059773 | A1 | 3/2013 | Witko-Sarsat | |
| 2013/0196433 | A1 | 8/2013 | Raines | |
| 2013/0251702 | A1* | 9/2013 | Chung | G01N 33/74 424/130.1 |
| 2016/0289272 | A1* | 10/2016 | Otterlei | A61K 38/16 |

FOREIGN PATENT DOCUMENTS

| | | | | |
|---|---|---|---|---|
| WO | 94/20128 | A1 | 9/1994 | |
| WO | 94/20532 | A1 | 9/1994 | |
| WO | 95/10297 | A1 | 4/1995 | |
| WO | 95/19179 | A1 | 7/1995 | |
| WO | 95/19180 | A1 | 7/1995 | |
| WO | 95/19784 | A1 | 7/1995 | |
| WO | 95/24209 | A1 | 9/1995 | |
| WO | 96/01647 | A1 | 1/1996 | |
| WO | 96/08509 | A1 | 3/1996 | |
| WO | 96/21436 | A1 | 7/1996 | |
| WO | 96/30037 | A1 | 10/1996 | |
| WO | 97/04008 | A1 | 2/1997 | |
| WO | 97/17989 | A1 | 5/1997 | |
| WO | 97/35009 | A1 | 9/1997 | |
| WO | 97/42966 | A1 | 11/1997 | |
| WO | 97/42967 | A1 | 11/1997 | |
| WO | 97/44056 | A1 | 11/1997 | |
| WO | 98/06415 | A2 | 2/1998 | |
| WO | 98/19694 | A1 | 5/1998 | |
| WO | 98/58961 | A1 | 12/1998 | |
| WO | 99/66044 | A1 | 12/1999 | |
| WO | 00/00655 | A1 | 1/2000 | |
| WO | 00/18798 | A1 | 4/2000 | |
| WO | 00/43028 | A2 | 7/2000 | |
| WO | 00/59531 | A2 | 10/2000 | |
| WO | 01/00671 | A1 | 1/2001 | |
| WO | 01/03724 | A1 | 1/2001 | |
| WO | 01/04346 | A1 | 1/2001 | |
| WO | 01/04347 | A1 | 1/2001 | |
| WO | 01/04348 | A1 | 1/2001 | |
| WO | 0230975 | A2 | 4/2002 | |
| WO | 02/055099 | A2 | 7/2002 | |
| WO | 02/079408 | A2 | 10/2002 | |
| WO | 2009/104001 | A2 | 8/2009 | |
| WO | 11/043740 | A1 | 4/2011 | |
| WO | WO-2011043740 | A1* | 4/2011 | C07K 14/705 |
| WO | 2011/104309 | A1 | 9/2011 | |
| WO | 12/177892 | A2 | 12/2012 | |
| WO | WO-2013006978 | A1* | 1/2013 | A61K 47/645 |

OTHER PUBLICATIONS

Bahnsen JS, Franzyk H, Sandberg-Schaal A, Nielsen HM. Antimicrobial and cell-penetrating properties of penetratin analogs: effect of sequence and secondary structure. Biochim Biophys Acta. Feb. 2013;1828(2):223-32.

Clark IA, Budd AC, Alleva LM, Cowden WB. Human malarial disease: a consequence of inflammatory cytokine release. Malar J. Oct. 10, 2006;5:85. Review.

Dalrymple BP, Kongsuwan K, Wijffels G, Dixon NE, Jennings PA. A universal protein-protein interaction motif in the eubacterial DNA replication and repair systems. Proc Natl Acad Sci U S A. Sep. 25, 2001;98(20):11627-32.

Elizur A, Cannon CL, Ferkol TW. Airway inflammation in cystic fibrosis. Chest. Feb. 2008;133(2):489-95. doi: 10.1378/chest.07-1631. Review.

Feldmann M. Many cytokines are very useful therapeutic targets in disease. J Clin Invest. Nov. 2008;118(11):3533-6. doi: 10.1172/JCI37346. Review.

Gazzano-Santoro H, Parent JB, Grinna L, Horwitz A, Parsons T, Theofan G, Elsbach P, Weiss J, Conlon PJ. High-affinity binding of the bactericidal/permeability-increasing protein and a recombinant amino-terminal fragment to the lipid A region of lipopolysaccharide. Infect Immun. Nov. 1992;60(11):4754-61.

Gilljam KM, Feyzi E, Aas PA, Sousa MM, Müller R, Vågbø CB, Catterall TC, Liabakk NB, Slupphaug G, Drabløs F, Krokan HE, Otterlei M. Identification of a novel, widespread, and functionally important PCNA-binding motif. J Cell Biol. Sep. 7, 2009;186(5):645-54.

Müller R, Misund K, Holien T, Bachke S, Gilljam KM, Våtsveen TK, Rø TB, Bellacchio E, Sundan A, Otterlei M. Targeting proliferating cell nuclear antigen and its protein interactions induces apoptosis in multiple myeloma cells. PLoS One. Jul. 31, 2013;8(7):e70430.

Ooi CE, Weiss J, Doerfler ME, Elsbach P. Endotoxin-neutralizing properties of the 25 kD N-terminal fragment and a newly isolated 30 kD C-terminal fragment of the 55-60 kD bactericidal/permeability-increasing protein of human neutrophils. J Exp Med. Sep. 1, 1991;174(3):649-55.

Whicher JT, Evans SW. Cytokines in disease. Clin Chem. Jul. 1990;36(7):1269-81. Review.

Witko-Sarsat V, Mocek J, Bouayad D, Tamassia N, Ribeil JA, Candalh C, Davezac N, Reuter N, Mouthon L, Hermine O, Pederzoli-Ribeil M, Cassatella MA. Proliferating cell nuclear antigen acts as a cytoplasmic platform controlling human neutrophil survival. J Exp Med. Nov. 22, 2010;207(12):2631-45.

Search Report for priority application GB1319620.0, dated Jul. 29, 2014.

Avbelj et al., "The Role of Intermediary Domain of MyD88 in Cell Activation and Therapeutic Inhibition of TLRs." The Journal of Immunology, 187:2394-2404, 2011.

* cited by examiner

Figure 2
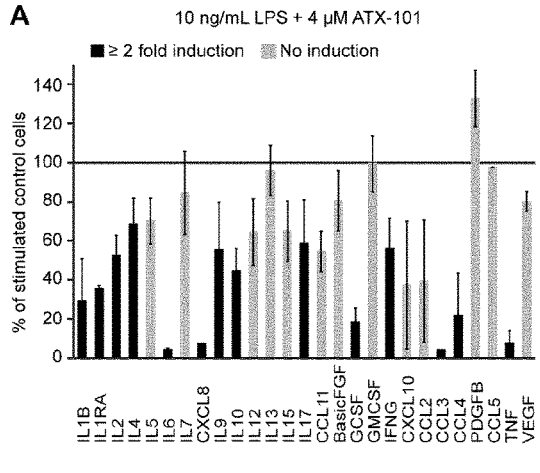
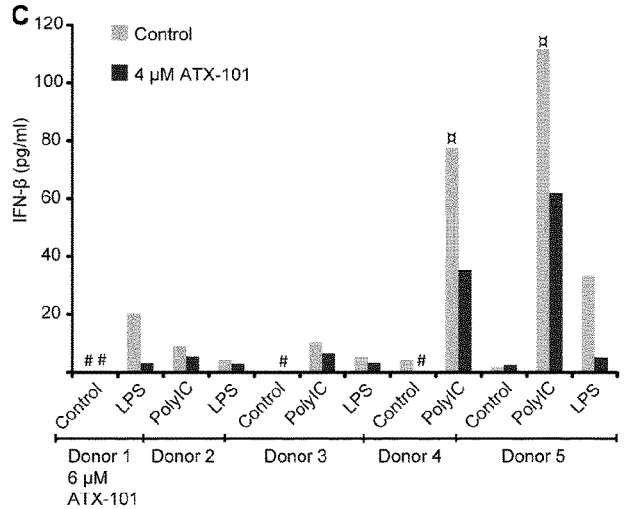
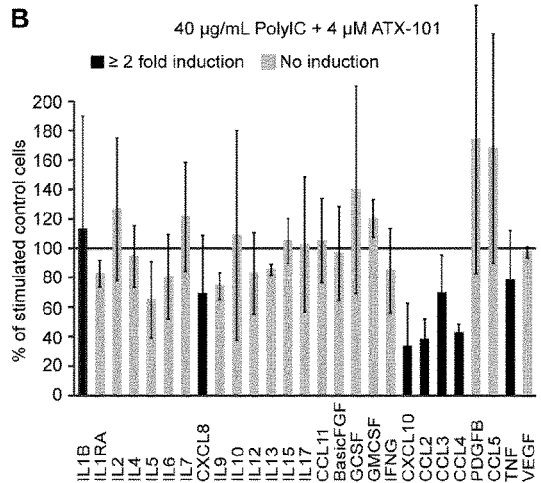
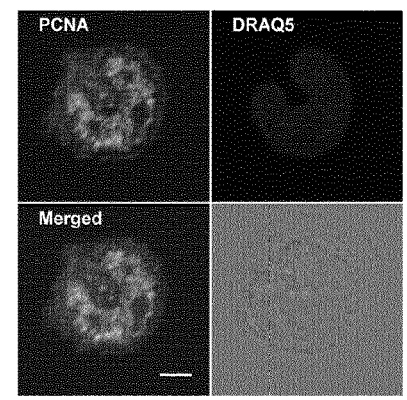

Figure 4
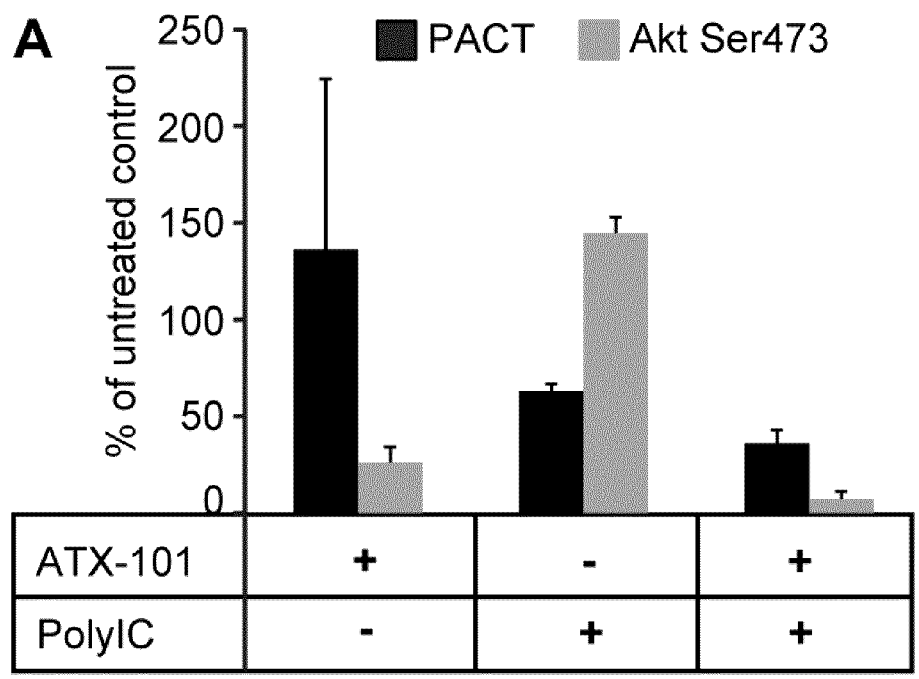
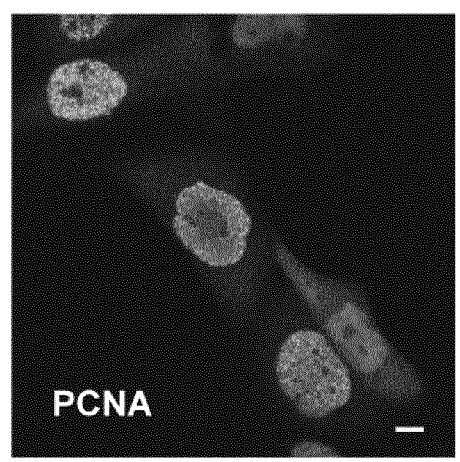

Figure 5
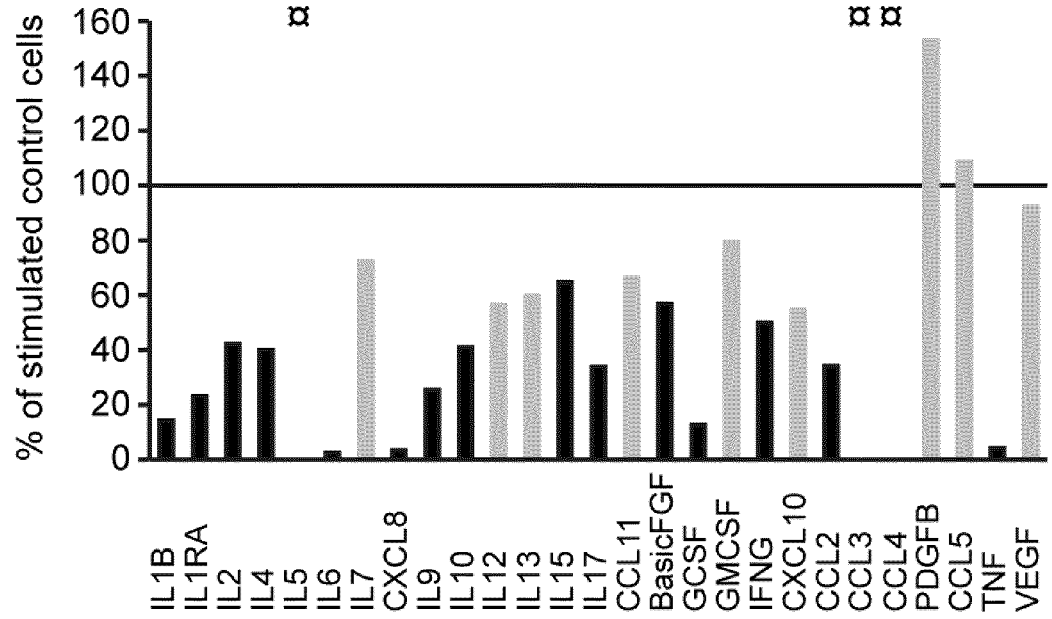
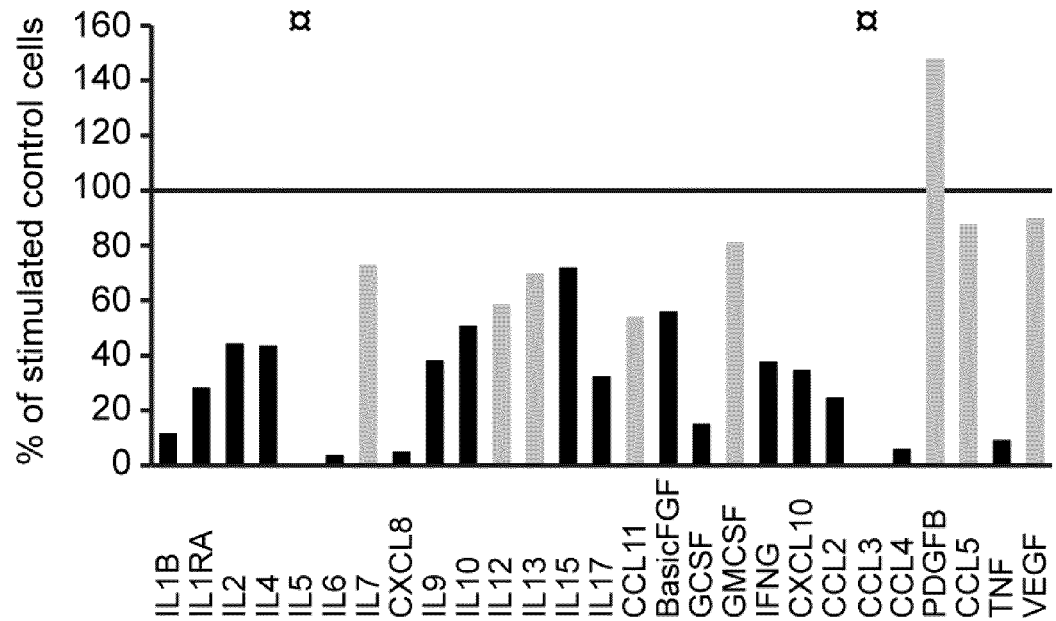

Figure 7
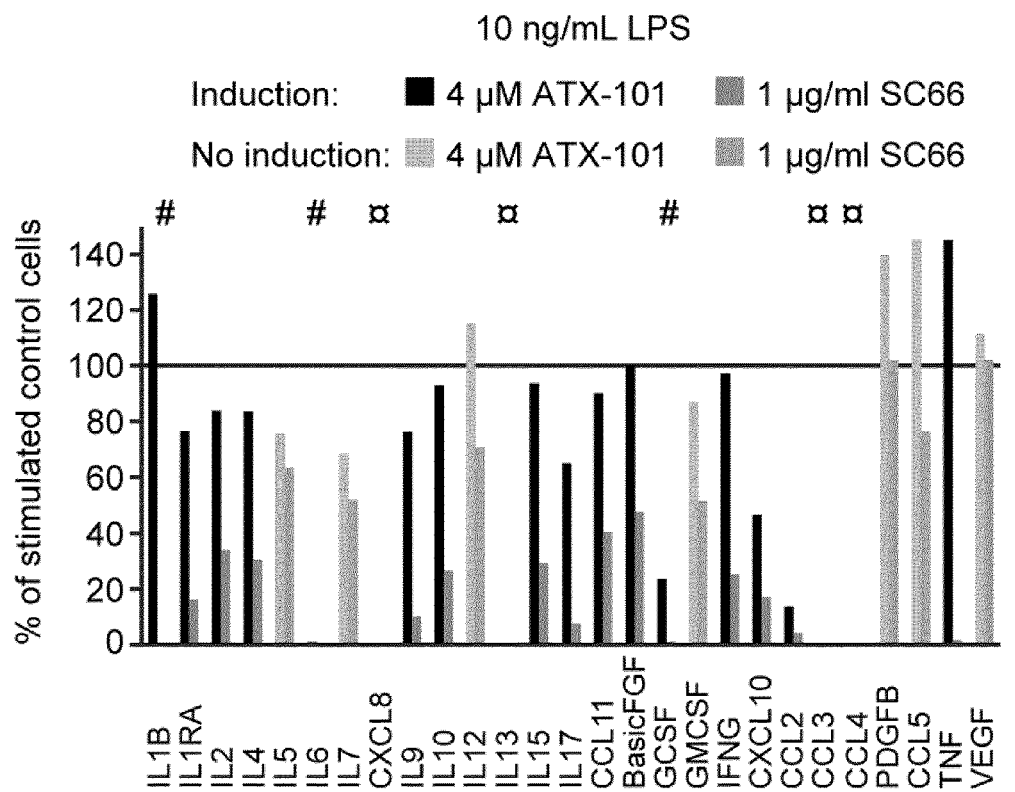
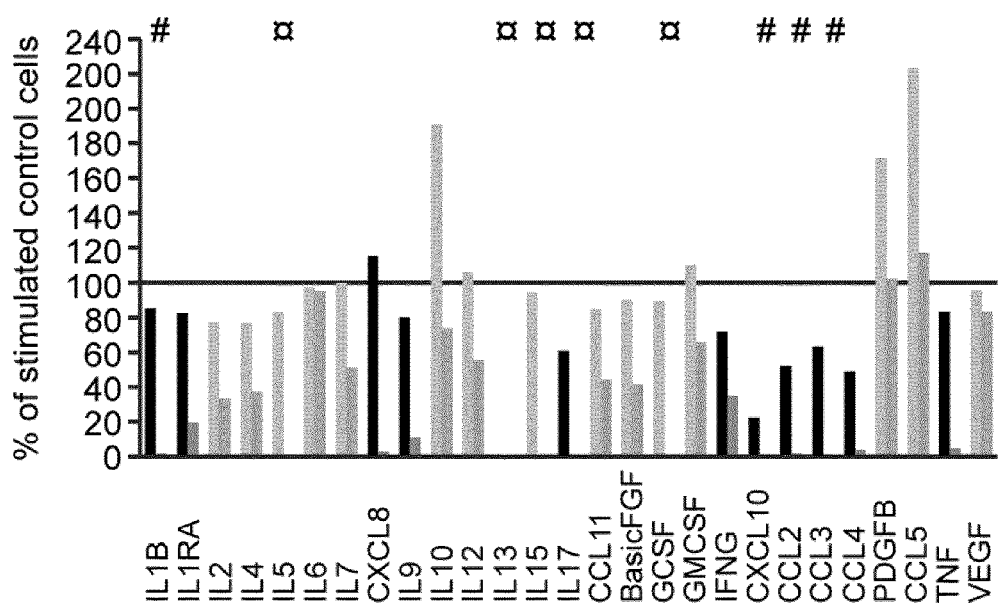

IMMUNOSUPPRESSIVE AGENTS AND THEIR USE IN THERAPY

CROSS-REFERENCE TO RELATED APPLICATIONS

This application is a divisional of U.S. application Ser. No. 15/034,917, filed May 6, 2016, which is a National Phase application filed under 35 USC 371 of PCT International Application No. PCT/EP2014/073966 with an International Filing Date of Nov. 6, 2014, which claims under 35 USC 119(a) the benefit of United Kingdom Application No. 1319620.9, filed Nov. 6, 2013. The entire contents of U.S. application Ser. No. 15/034,917 and PCT International Application No. PCT/EP2014/073966 are incorporated herein.

SEQUENCE LISTING

The instant application contains a Sequence Listing which has been submitted electronically in ASCII format and is hereby incorporated by reference in its entirety. Said ASCII copy, created on Jul. 12, 2017, is named 50955-501NO1US_SL.txt and is 276,771 bytes in size.

The present invention relates to novel agents, particularly peptides or mimetics thereof and their encoding nucleic acids, pharmaceutical compositions comprising at least one of said agents, and their use in the suppression of cellular immune system responses and/or the treatment of infectious diseases. The agents find particular use in the treatment of disorders or conditions associated with cytokine release from non-proliferating immune cells, e.g. unwanted, undesirable or excessive cytokine release. The agents may be useful alone or in combination with other therapeutically active compounds, such as immunosuppressive compounds, anti-inflammatory compounds, anti-microbial compounds etc. Such compounds may be, for instance, antagonists or inhibitors of signal transduction pathways, particularly toll-like receptor signalling pathways, such as toll-receptor antagonists and/or protein kinase inhibitors. Also provided are therapeutic methods which comprise the use of said agents for the aforementioned uses. The agents may also be used in the manufacture or preparation of medicaments for the aforementioned therapies.

APIM peptides are a group of peptides that interact with PCNA (proliferating cell nuclear antigen) via a novel PCNA interacting motif (Gilljam et al., 2009. Identification of a novel, widespread, and functionally important PCNA-binding motif, J. Cell Biol. 186(5), pp. 645-654). The motif has been termed APIM (AlkB homologue 2 (hABH2) PCNA-interacting motif) since it was first identified as mediating the interaction between hABH2 and PCNA, but as will be clear from the disclosure below, APIM motifs have now been identified in a wide range of proteins.

The, PCNA binding motif found in APIM peptides typically is defined using the consensus sequence, [R/K]-[F/W/Y]-[L/I/V/A]-[L/I/V/A]-[K/R](SEQ ID NO:19).

PCNA is a member of the sliding clamp family of proteins, which is known to be involved in both DNA replication and DNA repair. The main function of PCNA is to provide replicative polymerases with the high processivity needed for duplication of the genome. In live S-phase cells, PCNA tagged with green fluorescent protein (GFP) forms distinct foci representing sites of replication. It can therefore be used as an S-phase marker.

Numerous proteins involved in cellular processes such as DNA repair, chromatin assembly, epigenetic and chromatin remodelling, sister-chromatid cohesion, cell cycle control and survival are localised in so-called replication factories which contain more than a dozen replication forks. Many of these proteins interact with PCNA and have been shown to co-localise with PCNA in replication foci. PCNA-interacting proteins have particularly been thought to be involved in DNA repair and replication and cell proliferation.

Thus, various proteins interact with PCNA and it is thought that many of these interactions are mediated via a conserved PCNA interacting peptide sequence called the PIP-box (QxxL/I/MxxF/DF/Y [SEQ ID NO: 1205]), wherein x can be any amino acid. However, peptides that contain a PIP-box typically are extremely cytotoxic and therefore unsuitable for use in therapy.

However, APIM peptides have been shown to be useful in therapy. Specifically APIM peptides have been shown to be effective in sensitizing cells to cytotoxic and cytostatic agents, particularly DNA-damaging agents (WO 2009/104001) and indeed as an apoptosis-inducing cytotoxic agent in its own right (Müller et al., 2013. Targeting Proliferating Cell Nuclear Antigen and Its Protein Interactions Induces Apoptosis in Multiple Myeloma Cells, PLOS One, 8(7), e70430, pp. 1-12). Thus, APIM peptides have been shown to be useful in combination with cytotoxic and/or cytostatic agents in the treatment of a disorder or condition where it is desirable to inhibit the growth of cells, or in a treatment which involves cytostatic therapy, i.e. to prevent or inhibit the unwanted proliferation of cells.

In work leading up to the present invention, it was determined that PCNA is present in the cytosol in some cell types, particularly terminally differentiated cells, where it is thought it interacts with a variety of cytosolic polypeptides in the regulation of apoptosis, e.g. via caspases. Accordingly, PCNA was not expected to be present in the cytosol of non-proliferating cells, particularly cells that are not terminally differentiated.

However, the inventors have surprisingly found that APIM peptides have an effect on non-proliferating cells. Additionally, APIM peptides have been shown by the inventors to interfere with protein interactions between proteins involved in various signal transduction pathways, particularly toll-like receptor signal transduction pathways. As shown in more detail in the Examples, the inventors determined that APIM peptides can reduce the release of pro-inflammatory cytokines from non-proliferating immune cells, e.g. non-terminally differentiated immune cells, such as monocytes, without inducing apoptosis.

Toll-like receptors (TLRs) form one of the major classes of transmembrane pattern-recognition receptors (PRRs). In this respect, cells of the innate immune system recognize pathogen associated molecular patterns (PAMPs) through PRRs. In humans, ten different TLRs have been identified that recognize a variety of PAMPs.

TLR1, 2, 4, 5, and 6 are localized at the cell surface and detect mainly bacterial cell wall components, such as lipopolysaccharide (LPS) from gram-negative bacteria. LPS is recognized by TLR4. TLR3, 7, 8, and 9 localize to intracellular membrane-bound compartments, including endolysosomes, where they recognize viral and bacterial nucleic acids. TLR3 recognizes double-stranded RNA (dsRNA) from viruses and the synthetic dsRNA analog polyinosinic-polycytidylic acid (polyIC).

Once activated, PRRs induce intracellular signal transduction pathways that result in the expression and secretion of cytokines and chemokines, which function to coordinate the immune response in-host defense against microbial pathogens.

Upon ligand binding, TLRs recruit the main adaptor proteins MyD88 and/or TRIF and activate signal transduction pathways that trigger the expression and secretion of cytokines needed to induce an immune response. The MyD88-dependent pathway is used by all TLRs except TLR3. Activation of the MyD88 pathway induces the production of inflammatory cytokines via the transcription factor NF-κB and mitogen-activated protein kinases (MAPKs). TLR3 and TLR4 both recruit the adaptor TRIF and induce type I interferons (IFNs) via the transcription factor IRF3. In addition, TRIF activates NF-κB and MAPKs.

TLR signalling also activates the phosphatidylinositide 3-kinase (PI3K)/Akt pathway. It has been suggested that PI3K/Akt activity is required for full activation of IRF3 in the TRIF-dependent pathway during TLR3 and 4 signalling. In addition to TLR3, cytosolic receptors including RIG-1, MDA5 and PKR also recognize dsRNA and mediate antiviral responses via signaling pathways similar to TLRs.

Thus, various signalling pathways are involved in coordinating the responses of the innate cellular immune defense system, which is central to surviving microbial and parasitic challenges. This system is also relevant for managing deviant cells after viral infections and in autoimmune diseases. The system uses cytokines and chemokines to communicate and coordinate immune responses and these signals are immensely important in controlling local and systemic responses. However, cytokines and chemokines have been linked to a variety of diseases and disorders, typically as a result of abnormal levels of these molecules, which can trigger undesirable responses in vivo. For instance, the over-secretion of cytokines, such as in a so-called "cytokine storm", can have severe adverse effects on health.

Cytokines and chemokines are peptide, protein or glycoprotein signalling molecules that are used extensively in cellular communication. The terms cytokine and chemokine are used interchangeably herein and encompass large and diverse families of molecules that are produced widely throughout the body. Whilst virtually all nucleated cells are capable of producing cytokines and chemokines, immune cells are a particularly important source of cytokines and chemokines. Immune cells may be identified and characterised, at least to some extent, by the mixture of cytokines and chemokines that they secrete, as this forms a crucial part of their role in the immune system.

Monocytes are a type of immune cell (leukocyte or white blood cell) that are produced by the bone marrow from hematopoietic stem cell precursors called monoblasts. Monocytes are non-proliferating cells that are not terminally differentiated. Accordingly, monocytes are primarily found in blood and the spleen, and typically constitute between about 3-8% of the leukocytes in the blood. These cells tend to circulate in the bloodstream for about one to three days before moving into tissues throughout the body, where they terminally differentiate into different types of macrophages, depending on the anatomical location.

Monocytes characteristically display the cell surface receptor CD14 and may also express and display the cell surface receptor CD16. These cells are particularly associated with the release of pro-inflammatory cytokines and chemokines such as TNFα, IL1RA, IL-1β, IL-2, IL-4, IL-5, IL-6, IL-7, IL-8 (CXCL8), IL-9, IL-10, IL-12, IL-13, IL-15, IL-17, CCL11, BasicFGF, G-CSF, GM-CSF, INFγ, CXCL10, CCL2, CCL3, CCL4, PDGF-β, CCL5 and VEGF, particularly following stimulation by components of microbial cells (such as LPS) and/or viruses (such as double stranded nucleic acids). Monocytes are often found at very high levels in subjects with severe infections, e.g. in cases of sepsis and septicaemia, where it is thought that overproduction of cytokines and chemokines contributes to symptoms and complications associated with these conditions, e.g. multiple organ dysfunction syndrome (i.e. multiple organ failure).

Indeed uncontrolled or excessive cytokine and/or chemokine release (e.g. hypercytokinemia) from immune cells in blood, such as monocytes, is associated with a variety of disorders. For instance, it is thought that the excess release of pro-inflammatory cytokines and/or chemokines is the primary driving force of disease and death caused by *Plasmodium falciparum* infections, i.e. malaria. Other infectious diseases, including bacterial, fungal and some viral infections (e.g. influenza, such as swine influenza, avian influenza), may result in excessive pro-inflammatory cytokine and/or chemokine release in blood. Such infections may be local or systemic. In addition, allogenic tissue transplants can result in graft versus host disease, in which immune cells produce excess levels of cytokines and chemokines, such as TNFα.

Therapies for disorders caused by, or associated with, excessive release of cytokines and chemokines have typically focused on the inhibition of particular cytokines and chemokines or small groups of related cytokines and chemokines. For instance, therapies may utilize specific binding proteins, such as antibodies or soluble receptors, to neutralise the released and undesirable cytokines and chemokines. Alternatively, binding proteins or small molecule antagonists may be used to block cytokine and chemokine receptors to prevent downstream signalling. However, a combination of such therapies may be required to deal with an excess of several cytokines and chemokines, and combining multiple therapeutic agents can be expensive and may have undesirable and unpredictable side effects. Whilst the use of corticosteroids has been suggested for use in subjects suffering from hypercytokinemia, there is limited evidence that such treatments are effective. Furthermore, therapies to date have centred on the treatment of particular tissues, such as the lungs, e.g. the treatment of COPD (chronic obstructive pulmonary disease) by, for instance, inhibiting G-CSF (Granulocyte colony-stimulating factor).

Accordingly, there remains a need for effective therapies suitable for the treatment of diseases, disorders or conditions caused by, or associated with, excessive release of cytokines and chemokines (e.g. infectious diseases), which also have minimal side effects.

As mentioned above, the inventors have surprisingly found that APIM peptides can reduce the release of pro-inflammatory cytokines and chemokines from non-proliferating immune cells, e.g. non-terminally differentiated immune cells, such as monocytes, without inducing apoptosis. Thus, the inventors have determined that APIM peptides may function via a general mechanism on non-proliferating immune cells to inhibit (e.g. reduce, diminish, lessen etc) the release of cytokines and/or chemokines from said cells, e.g. when the cells have been stimulated with any one of a variety of components, e.g. components from infectious entities (microbial, viral and parasitic), such as LPS or double stranded nucleic acid.

These surprising findings have led the inventors to propose new therapeutic uses for APIM peptides, i.e. peptides comprising a PCNA binding motif, namely for use in treating a condition or disorder associated with cytokine release from non-proliferating immune cells in blood, particularly conditions or disorders associated with excessive, undesirable or uncontrolled pro-inflammatory cytokine release from non-proliferating immune cells in blood, e.g. an infectious disease or infection or a disease or condition exacerbated or caused by an infection.

Alternatively viewed, the inventors propose the use of APIM peptides for treating or preventing excessive, undesirable or uncontrolled pro-inflammatory cytokine release from non-proliferating immune cells in blood in a subject, e.g. a subject with an infectious disease or infection or a disease or condition exacerbated or caused by an infection.

Thus, at its broadest, the invention can be seen to provide a method of treating or preventing a disorder or condition associated with cytokine release from non-proliferating immune cells in blood, particularly a disorder or condition which results in or from, or is associated with, hypercytokinemia, said method comprising administering (particularly administering an effective amount of) an agent comprising or encoding a peptide comprising an APIM motif or a composition (e.g. a pharmaceutical composition) containing an agent comprising or encoding a peptide comprising an APIM motif to a subject in need thereof.

Thus, the invention provides an agent comprising or encoding a peptide comprising an APIM motif or a composition (e.g. a pharmaceutical composition) containing an agent comprising or encoding a peptide comprising an APIM motif, for use in treating or preventing a disorder or condition associated with cytokine release from non-proliferating immune cells in blood, particularly a disorder or condition resulting in or from, or associated with, hypercytokinemia.

In another aspect, there is provided the use of an agent comprising or encoding a peptide comprising an APIM motif in the manufacture of a medicament for the treatment or prevention of a disorder or condition associated with cytokine release from non-proliferating immune cells in blood, particularly a disorder or condition resulting in or from, or associated with, hypercytokinemia.

More particularly, the invention provides a method of treating or preventing a disorder or condition associated with cytokine release from non-proliferating immune cells in blood, particularly a disorder or condition which results in or from, or is associated with, hypercytokinemia, said method comprising administering (particularly administering an effective amount of) an agent or a composition (e.g. a pharmaceutical composition) containing an agent to a subject in need thereof, wherein said agent comprises:

(i) an oligopeptidic compound comprising a PCNA interacting motif and a domain that facilitates the cellular uptake of said compound, wherein the PCNA interacting motif is $X_1X_2X_3X_4X_5$ (SEQ ID NO: 1) and wherein:
  $X_1$ is a basic amino acid;
  $X_2$ is an aromatic amino acid;
  $X_3$ is an uncharged amino acid other than an aromatic amino acid, Glycine (G) and Proline (P);
  $X_4$ is any amino acid other than Proline (P), an acidic amino acid or an aromatic amino acid; and
  $X_5$ is a basic amino acid or Proline (P); or
(ii) a nucleic acid molecule comprising a sequence encoding the oligopeptidic compound of (i).

In another aspect, there is provided an agent or a composition (e.g. a pharmaceutical composition) containing an agent for use in treating or preventing a disorder or condition associated with cytokine release from non-proliferating immune cells in blood, particularly a disorder or condition resulting in or from, or associated with, hypercytokinemia, wherein said agent comprises:

(i) an oligopeptidic compound comprising a PCNA interacting motif and a domain that facilitates the cellular uptake of said compound, wherein the PCNA interacting motif is $X_1X_2X_3X_4X_5$ (SEQ ID NO: 1) and wherein:
  $X_1$ is a basic amino acid;
  $X_2$ is an aromatic amino acid;
  $X_3$ is an uncharged amino acid other than an aromatic amino acid, Glycine (G) and Proline (P);
  $X_4$ is any amino acid other than Proline (P), an acidic amino acid or an aromatic amino acid; and
  $X_5$ is a basic amino acid or Proline (P); or
(ii) a nucleic acid molecule comprising a sequence encoding the oligopeptidic compound of (i).

In a further aspect, there is provided the use of an agent in the manufacture of a medicament for the treatment or prevention of a disorder or condition associated with cytokine release from non-proliferating immune cells in blood, particularly a disorder or condition resulting in or from, or associated with, hypercytokinemia, wherein said agent comprises:

(i) an oligopeptidic compound comprising a PCNA interacting motif and a domain that facilitates the cellular uptake of said compound, wherein the PCNA interacting motif is $X_1X_2X_3X_4X_5$ (SEQ ID NO: 1) and wherein:
  $X_1$ is a basic amino acid;
  $X_2$ is an aromatic amino acid;
  $X_3$ is an uncharged amino acid other than an aromatic amino acid, Glycine (G) and Proline (P);
  $X_4$ is any amino acid other than Proline (P), an acidic amino acid or an aromatic amino acid; and
  $X_5$ is a basic amino acid or Proline (P); or
(ii) a nucleic acid molecule comprising a sequence encoding the oligopeptidic compound of (i).

In particular embodiments the invention provides a method of treating or preventing hypercytokinemia resulting from cytokine release from non-proliferating immune cells in blood, said method comprising administering an agent, or a composition containing an agent, to a subject in need thereof, wherein said agent comprises:

(i) an oligopeptidic compound comprising a PCNA interacting motif and a domain that facilitates the cellular uptake of said compound, wherein the PCNA interacting motif is $X_1X_2X_3X_4X_5$ (SEQ ID NO: 1) and wherein:
  $X_1$ is a basic amino acid;
  $X_2$ is an aromatic amino acid;
  $X_3$ is an uncharged amino acid other than an aromatic amino acid, Glycine (G) and Proline (P);
  $X_4$ is any amino acid other than Proline (P), an acidic amino acid or an aromatic amino acid; and
  $X_5$ is a basic amino acid or Proline (P); or
(ii) a nucleic acid molecule comprising a sequence encoding the oligopeptidic compound of (i).

In a further embodiment, the invention provides an agent, or composition containing an agent, for use in treating or preventing hypercytokinemia in a subject resulting from cytokine release from non-proliferating immune cells in blood, wherein said agent comprises:

(i) an oligopeptidic compound comprising a PCNA interacting motif and a domain that facilitates the cellular uptake of said compound, wherein the PCNA interacting motif is $X_1X_2X_3X_4X_5$ (SEQ ID NO: 1) and wherein:
  $X_1$ is a basic amino acid;
  $X_2$ is an aromatic amino acid;
  $X_3$ is an uncharged amino acid other than an aromatic amino acid, Glycine (G) and Proline (P);
  $X_4$ is any amino acid other than Proline (P), an acidic amino acid or an aromatic amino acid; and
  $X_5$ is a basic amino acid or Proline (P); or (ii) a nucleic acid molecule comprising a sequence encoding the oligopeptidic compound of (i).

In still further embodiments, the invention provides the use of an agent in the manufacture of a medicament for the treatment or prevention of hypercytokinemia in a subject resulting from cytokine release from non-proliferating immune cells in blood, wherein said agent comprises:

(i) an oligopeptidic compound comprising a PCNA interacting motif and a domain that facilitates the cellular uptake of said compound, wherein the PCNA interacting motif is $X_1X_2X_3X_4X_5$ (SEQ ID NO: 1) and wherein:

$X_1$ is a basic amino acid;
$X_2$ is an aromatic amino acid;
$X_3$ is an uncharged amino acid other than an aromatic amino acid, Glycine (G) and Proline (P);
$X_4$ is any amino acid other than Proline (P), an acidic amino acid or an aromatic amino acid; and
$X_5$ is a basic amino acid or Proline (P); or (ii) a nucleic acid molecule comprising a sequence encoding the oligopeptidic compound of (i).

In some embodiments, the agent as defined herein may be used in combination with one or more additional active agents, e.g. other therapeutically active agents, such as immunosuppressive compounds, anti-inflammatory compounds, anti-microbial compounds, steroids (e.g. corticosteroid), kinase inhibitors (such as p38 MAPK inhibitors, class I PI3K inhibitors) etc., in order to enhance the effect of the agent. However, in some embodiments, the agent as defined herein may be used alone, i.e. as the only active agent in a composition and/or medicament.

Accordingly, in yet another aspect, there is provided a method of treating or preventing a disorder or condition associated with cytokine release from non-proliferating immune cells in blood, particularly a disorder or condition which results in or from, or is associated with, hypercytokinemia, said method comprising administering (particularly administering an effective amount of) an agent or a composition (e.g. a pharmaceutical composition) containing an agent and separately, simultaneously or sequentially administering of one or more additional active agents, e.g. a therapeutically active agent, to a subject in need thereof, wherein said agent comprises:

(i) an oligopeptidic compound comprising a PCNA interacting motif and a domain that facilitates the cellular uptake of said compound, wherein the PCNA interacting motif is $X_1X_2X_3X_4X_5$ (SEQ ID NO: 1) and wherein:

$X_1$ is a basic amino acid;
$X_2$ is an aromatic amino acid;
$X_3$ is an uncharged amino acid other than an aromatic amino acid, Glycine (G) and Proline (P);
$X_4$ is any amino acid other than Proline (P), an acidic amino acid or an aromatic amino acid; and
$X_5$ is a basic amino acid or Proline (P); or (ii) a nucleic acid molecule comprising a sequence encoding the oligopeptidic compound of (i).

In a particular embodiment, the invention provides a method of treating or preventing hypercytokinemia resulting from cytokine release from non-proliferating immune cells in blood, said method comprising administering (particularly administering an effective amount of) an agent as defined herein or a composition (e.g. a pharmaceutical composition) containing an agent as defined herein and separately, simultaneously or sequentially administering of one or more additional active agents, e.g. a therapeutically active agent, to a subject in need thereof.

Alternatively viewed, there is provided an agent or composition (e.g. a pharmaceutical composition) as defined herein for use in combination with one or more additional active agents, e.g. a therapeutically active agent, in the treatment or prevention of a disorder or condition associated with cytokine release from non-proliferating immune cells in blood, particularly a disorder or condition which results in or from, or is associated with, hypercytokinemia.

For instance, there is provided an agent or composition (e.g. a pharmaceutical composition) as defined herein for use in combination with one or more additional active agents, e.g. a therapeutically active agent, in the treatment or prevention of hypercytokinemia in a subject resulting from cytokine release from non-proliferating immune cells in blood.

Thus, also provided is the use of an agent as defined herein in the manufacture of a medicament for use in combination with one or more additional active agents, e.g. a therapeutically active agent, in the treatment or prevention of a disorder or condition associated with cytokine release from non-proliferating immune cells in blood, particularly a disorder or condition which results in or from, or is associated with, hypercytokinemia.

For instance, in some embodiments the invention provides the use of an agent as defined herein in the manufacture of a medicament for use in combination with one or more additional active agents, e.g. a therapeutically active agent, in the treatment or prevention of hypercytokinemia in a subject resulting from cytokine release from non-proliferating immune cells in blood.

Thus, in one embodiment the medicament may further comprise one or more additional active agents, such as a therapeutically active agent that is useful in treating or preventing the disease or condition (or the symptoms of, or associated with the disease or condition, e.g. hypercytokinemia), associated with cytokine release from non-proliferating immune cells in blood. The therapeutically active agent may be, but is not limited to, an immunosuppressive compound, an anti-inflammatory compound, anti-microbial compound, a steroid (e.g. a corticosteroid) or a kinase inhibitor (such as a p38 MAPK inhibitor or a class I PI3K inhibitor).

The medicament may be in the form of a single composition (e.g. a pharmaceutical composition) comprising both the agent as defined herein and the one or more additional active agents, e.g. therapeutically active agent, or it may be in the form of a kit or product containing them for separate (e.g. simultaneous or sequential) administration.

There is thus also provided the use of an agent as defined herein in the manufacture of a medicament for the treatment or prevention of a disorder or condition associated with cytokine release from non-proliferating immune cells in blood, particularly a disorder or condition which results in or from, or is associated with, hypercytokinemia, wherein the medicament is administered separately, simultaneously or sequentially with one or more additional active agents, e.g. a therapeutically active agent.

Thus, in some embodiments, there is provided the use of an agent as defined herein in the manufacture of a medicament for the treatment or prevention hypercytokinemia in a subject resulting from cytokine release from non-proliferating immune cells in blood, wherein the medicament is administered separately, simultaneously or sequentially with one or more additional active agents, e.g. a therapeutically active agent.

In another aspect, the invention provides a product or kit containing an agent as defined herein together with one or more additional active agents, e.g. a therapeutically active agent, as a combined preparation for separate, simultaneous or sequential use in the treatment or prevention of a disorder or condition associated with cytokine release from non-proliferating immune cells in blood, particularly a disorder or condition which results in or from, or is associated with, hypercytokinemia.

For instance, the invention provides a product or kit containing an agent as defined herein together with one or more additional active agents, e.g. a therapeutically active agent, as a combined preparation for separate, simultaneous or sequential use in the treatment or prevention of hypercytokinemia in a subject resulting from cytokine release from non-proliferating immune cells in blood.

Thus, an oligopeptidic compound (e.g. a peptide) capable of interacting with PCNA may contain or comprise a peptide motif (or sequence) that may be defined generally as:

$X_1X_2X_3X_4X_5$ (SEQ ID NO: 1), wherein:
$X_1$ is a basic amino acid;
$X_2$ is an aromatic amino acid;
$X_3$ is an uncharged amino acid other than an aromatic amino acid, Glycine (G) and Proline (P);
$X_4$ is any amino acid other than Proline (P), an acidic amino acid or an aromatic amino acid; and
$X_5$ is a basic amino acid or Proline (P).

In order that the oligopeptidic compound, which is capable of interacting with PCNA, or its encoding nucleic acid, may function in the methods and uses of the invention, the compound must be capable of entering the cell, i.e. crossing the cell membrane into the cytosol (cytoplasm), and optionally into one or more other cellular locations, e.g. the nucleus. This may be achieved using any convenient mechanism, e.g. associating directly or indirectly the oligopeptidic compound or its encoding nucleic acid molecule with one or more molecules capable of facilitating the uptake of said molecule into a cell, such as with a liposome or import peptide. A particularly advantageous mechanism may be to generate an oligopeptidic compound that comprises a domain that assists the transit of the compound across the cell membrane, i.e. to generate a fusion peptide or chimeric peptide (a peptide formed from two or more domains that are not normally found together in nature). For instance, a peptide comprising a cell membrane permeable motif, e.g. a cell penetrating peptide (an uptake or import peptide, or a peptide transduction domain). The fusion peptide (an oligopeptidic compound) may optionally comprise further sequences to facilitate the targeting of the peptide (i.e. to direct the peptide) to a particular sub-cellular location, e.g. a target peptide, signal peptide or transit peptide.

As the oligopeptidic compound comprises a PCNA interacting motif and a domain that facilitates its uptake, it will be evident that the compound comprises at least 5 residues and the final size of the compound will be dependent on the size and number of the domains that make up said compound, i.e. the PCNA interacting motif and uptake (import) peptide may be viewed as domains of the oligopeptidic compound. Thus, a domain may be viewed as a distinct portion (i.e. a sequence within the full-length peptidic sequence) of the oligopeptidic compound that can be assigned or ascribed a particular function or property.

In some embodiments, the oligopeptidic compound for use in the methods and uses of the invention comprises at least 2 domains, i.e. the PCNA interacting motif domain and the domain that facilitates the cellular uptake of said compound, e.g. uptake (import) peptide sequence domain. However, the oligopeptidic compound may comprise additional domains that may facilitate its function and/or stability, e.g. the capacity of the peptide to interact with its target, i.e. PCNA or an equivalent protein. Thus, the oligopeptidic compound may comprise at least 2, 3, 4 or 5 domains, e.g. 6, 7, 8, 9, 10, 12, 15 or more domains. For example, in some embodiments the oligopeptidic compound may comprise one or more linker domains, i.e. a domain that interspaces between two other domains, i.e. occupies the space in between and connects two domains of the oligopeptidic compound. In further embodiments, the oligopeptidic compound may comprise a domain that directs the oligopeptidic compound to a cellular or subcellular location, e.g. a signal peptide (also known as a target or transit peptide), such as a nuclear localization signal (NLS) sequence. In still further embodiments, the one or more linker domains may have an additional function, i.e. a linker domain may also function as a signal peptide, e.g. a NLS. Alternatively put, a signal peptide domain may function as a linker domain in some embodiments.

In an exemplary embodiment, the oligopeptidic compound may comprise a PCNA interacting motif domain, a domain that facilitates its cellular uptake (e.g. an uptake (import) peptide sequence domain) and a linker domain. In a further exemplary embodiment, the oligopeptidic compound may also comprise a nuclear localisation signal sequence domain. In still another embodiment the nuclear localization signal sequence domain may function as a linker domain.

Thus, it will be seen that in such embodiments the agent of the invention may take the form of a construct containing (i.e. comprising) an oligopeptidic compound which comprises a PCNA interacting motif as defined herein, together with a domain that facilitates its cellular uptake (e.g. an uptake peptide sequence) and optionally additional domains. In this aspect the invention may accordingly be seen to provide a construct comprising an oligopeptidic compound which is capable of interacting with PCNA.

As noted above the PCNA motif of the invention has been determined to mediate the interaction of an oligopeptidic compound (e.g. peptide) or protein containing such a motif with PCNA. Thus, the compound may be characterised insofar as it must be capable of interacting with PCNA, i.e. the oligopeptidic compounds for use in the methods and uses of the invention must be competent and/or proficient PCNA interacting molecules. The PCNA protein used to determine the capacity and/or affinity of the oligopeptidic compound: PCNA interaction may be from any suitable source, e.g. a PCNA from any animal, particularly a mammal such as a human, rodent (e.g. mouse, rat), canine or any other non-human animal. In preferred embodiments, the oligopeptidic compound:PCNA interaction is determined, characterised or assessed using human PCNA protein.

The interaction may be direct or indirect, and may involve direct binding of the motif to the PCNA protein, or the motif may bind indirectly, for example binding may be mediated by another molecule. This reference to "PCNA-interacting" or "PCNA-binding" can thus include any form of interaction, and both direct and indirect binding.

Any reference herein to a "motif" should be understood to mean $X_1X_2X_3X_4X_5$ as defined herein.

$X_1$ is preferably selected from lysine (K), arginine (R), histidine (H), ornithine (Orn), methyllysine (MeK), diaminobutyric acid (Dbu), citrulline (Cit), acetyllysine (AcK), and any suitable basic amino acid selected from the non-conventional amino acids in Table 2. Whilst the standard or conventional basic amino acids are preferred, e.g. K, R and H, particularly K and R, these may be substituted by any functionally equivalent non-conventional basic amino acid.

$X_2$ is preferably selected from phenylalanine (F), tryptophan (W), tyrosine (Y), tert.-butylglycine, cyclohexylalanine, tert.-butylphenylalanine, biphenylalanine and tri tert.-butyltryptophan (in certain embodiments this list may exclude F). Whilst the standard or conventional aromatic amino acids are preferred, e.g. F, W and Y, these may be substituted by any functionally equivalent non-conventional aromatic amino acid, e.g. from Table 2. In some embodiments, $X_2$ may be selected from W and Y, F and Y, or F and W or in specific embodiments $X_2$ may be F, or W or Y, or functionally equivalent non-conventional aromatic amino acids.

The binding of the motif to PCNA may in certain embodiments be improved when $X_2$ is W or Y. Thus, in one embodiment, $X_2$ is not F. However, as indicated above, in other embodiments it may be F.

$X_3$ is preferably a hydrophobic or polar amino acid, particularly an aliphatic amino acid or polar amino acid. Thus, in some embodiments, $X_3$ may be selected from leucine (L), isoleucine (I), valine (V), alanine (A) methionine (M), norleucine (Nor), serine (S), threonine (T), glutamine (Q), aspargine (N) or cysteine (C) or any suitable hydrophobic or polar amino acid selected from the non-conventional amino acids in Table 2. More particularly, $X_3$ may be selected from L, I, V, A, M, Nor, S or T and any suitable hydrophobic (preferably aliphatic) or polar (preferably a polar amino acid that does not contain an amine group ($NH_2$) in the R-group) amino acid selected from the non-conventional amino acids in Table 2. Preferably, $X_3$ is not N or Q or a non-conventional functional equivalent thereof and/or in certain embodiments $X_3$ is not M, S and/or T or a non-conventional functional equivalent thereof. $X_3$ may not be glycine (G) or proline (P) and this limitation is also intended to exclude non-conventional functional equivalents thereof.

Thus, in some embodiments, $X_3$ may be selected from L, I, A, V, M, S and T, and preferably from L, I, A, V, S and T and optionally non-conventional functional equivalents thereof.

In some embodiments, $X_3$ may be a hydrophobic, and more preferably an aliphatic amino acid. Thus, in some embodiments, $X_3$ may be selected from L, I, A, V, M, and preferably from L, I, V and A and optionally non-conventional functional equivalents thereof.

$X_4$ is preferably a hydrophobic, polar, basic or thiol-containing amino acid. Thus, in some embodiments $X_4$ an aliphatic amino acid or a polar amino acid. In some preferred embodiments, the polar amino acid does not contain an amine group ($NH_2$) in the R-group. Thus, $X_4$ preferably may be selected from L, I, V, A, M, Nor, S, T, Q, N, H, K, R, G or C and any suitable hydrophobic (preferably aliphatic) or polar (preferably a polar amino acid that does not contain an amine group ($NH_2$) in the R-group), basic or thiol-containing amino acid selected from the non-conventional amino acids in Table 2. Thus, in some embodiments, the basic amino acid may be selected from the amino acids as defined in $X_1$. In certain embodiments $X_4$ is not C or a non-conventional functional equivalent thereof and/or N or Q or a non-conventional functional equivalent thereof. In certain embodiments $X_4$ is not H and preferably $X_4$ is not R, K or H or a non-conventional functional equivalent thereof. In still further embodiments $X_4$ is not S or T or a non-conventional functional equivalent thereof. $X_4$ may not be P, an aromatic amino acid (as defined in $X_2$) or acidic amino acid, e.g. aspartic acid (D) or glutamic acid (E), and this limitation is also intended to exclude non-conventional functional equivalents thereof.

Thus, in some embodiments, $X_4$ may be selected from L, V, I, A, M, S, T and G, and preferably from L, V, A, I, S and T and optionally non-conventional functional equivalents thereof.

In other embodiments, $X_4$ may be a hydrophobic amino acid, and more preferably an aliphatic amino acid or G. Thus, in some embodiments, $X_4$ may be selected from L, I, A, V, M, and G and preferably from L, V, I and A and optionally non-conventional functional equivalents thereof.

$X_5$ is preferably selected from K, R, H, Orn, MeK, Dbu, Cit, AcK, P and any functionally equivalent amino acid selected from the non-conventional amino acids in Table 2. Whilst the standard or conventional amino acids are preferred, e.g. K, R, H and P, particularly K, R and H, e.g. K and R, these may be substituted by any functionally equivalent non-conventional basic amino acid.

Thus, in some embodiments $X_5$ is a basic amino acid, preferably selected from K, R and H and optionally non-conventional functional equivalents thereof. Thus, in some embodiments $X_3$ and/or $X_4$ is a polar amino acid. Accordingly, in certain embodiments only one of $X_3$ and $X_4$ is a polar amino acid. In some embodiments $X_4$ and/or $X_5$ is a basic amino acid. Accordingly, in certain embodiments $X_5$ is a basic amino acid.

A functionally equivalent amino acid may be defined as an amino acid that may be used as a substitute in a peptide or protein for a conventional amino acid without affecting significantly the function of the peptide or protein (or an amino acid that would not be expected to affect or alter significantly the function of the peptide or protein), e.g. an amino acid that has similar structural and/or chemical properties to the conventional amino acid. Thus, a functionally equivalent amino acid may be viewed as having the base structure of a standard amino acid, with a non-standard or non-conventional R-group that is structurally and/or chemically similar to the standard R-group. Preferably, the R-group is structurally similar to the standard R-group of the amino acid being substituted.

A conventional or standard amino acid is an amino acid that is used in vivo to produce a polypeptide or protein molecule, i.e. a proteinogenic amino acid. In other words, an amino acid with a standard or conventional R-group or an amino acid which possesses a side chain that is coded for by the standard genetic code, i.e. "coded amino acids".

Thus, the invention may provide an oligopeptidic compound comprising the motif [R/K/H]-[W/F/Y]-[L/I/V/A/M/S/T/N/Q/C]-[L/I/V/A/M/G/S/T/N/Q/R/H/K/C]-[K/R/H/P] (SEQ ID NO: 2), wherein said oligopeptidic compound is capable of interacting with PCNA.

In another embodiment the motif may be defined as:

```
                                              (SEQ ID NO: 3)
[R/K/H]-[W/F/Y]-[L/I/V/A/M/S/T/N/Q]-

[L/I/V/A/M/G/S/T/N/Q/R/H/K]-[K/R/H/P].
```

In another embodiment the motif may be defined as:

```
                                              (SEQ ID NO: 4)
[R/K/H]-[W/F/Y]-[L/I/V/A/M/S/T]-

[L/I/V/A/M/G/S/T/N/Q/R/H/K]-[K/R/H/P].
```

In another embodiment the motif may be defined as:

(SEQ ID NO: 5)
[R/K/H]-[W/F/Y]-[L/I/V/A/M/S/T]-
[L/I/V/A/M/G/S/T/N/Q/R/H/K]-[K/R/H].

In another embodiment the motif may be defined as:

(SEQ ID NO: 6)
[R/K/H]-[W/F/Y]-[L/I/V/A/M/S/T]-
[L/I/V/A/M/G/S/T/R/K]-[K/R/H].

In another embodiment the motif may be defined as:

(SEQ ID NO: 7)
[R/K/H]-[W/F/Y]-[L/I/V/A/M/S/T]-
[L/I/V/A/M/G/S/T]-[K/R/H].

In another embodiment the motif may be defined as:

(SEQ ID NO: 8)
[R/K]-[W/F/Y]-[L/I/V/A/M/S/T]-[L/I/V/A/M/G/S/T]-
[K/R].

In another embodiment the motif may be defined as:

(SEQ ID NO:9)
[R/K]-[W/F]-[L/I/V/A/M/S/T]-[L/I/V/A/M/G/S/T]-
[K/R].

In another embodiment the motif may be defined as:

(SEQ ID NO: 10)
[R/K]-[W/F]-[L/I/V/A/M/T]-[L/I/V/A/M/G/S/T]-[K/R].

In another embodiment the motif may be defined as:

(SEQ ID NO: 11)
[R/K]-[W/F]-[L/I/V/A/M/T]-[L/I/V/A/M/S/T]-[K/R].

In another embodiment the motif may be defined as:

(SEQ ID NO: 12)
[R/K]-[W/F]-[L/I/V/A/M/S/T]-[L/I/V/A/M/G]-[K/R].

In another embodiment the motif may be defined as:

(SEQ ID NO: 13)
[R/K]-[W/F]-[L/I/A/V/M/T]-[L/I/V/A/M/S/T]-[K/R].

In another embodiment the motif may be defined as:

(SEQ ID NO: 14)
[R/K]-[W/F]-[L/I/V/A/M/S/T]-[L/V/A/I/S/T]-[K/R].

In another embodiment the motif may be defined as:

(SEQ ID NO: 15)
[R/K]-[W/F]-[L/V/I/A/T]-[L/V/A/I/S/T]-[K/R].

In another embodiment the motif may be defined as:

(SEQ ID NO: 16)
[R]-[W/F/Y]-[L/V/I/A]-[L/V/A/S/T/M]-[K/R].

In another embodiment the motif may be defined as:

(SEQ ID NO: 17)
[R]-[W/F/Y]-[L/V/I/A/T]-[L/V/A/S/T/M]-[K].

In another embodiment the motif may be defined as:

(SEQ ID NO: 18)
[R/K]-[F/Y]-[L/V/I/A]-[L/V/A/I/M]-[K/R].

In another embodiment the motif may be defined as:

(SEQ ID NO: 19)
[R/K]-[F/W/Y]-[L/I/V/A]-[L/I/V/A]-[K/R].

In yet another embodiment the motif may be defined as:

(SEQ ID NO: 20)
[R/K]-[W/Y]-[L/V/I/A/S/T]-[L/V/A/S/T/M]-[K/R].

In yet another embodiment the motif may be defined as:

(SEQ ID NO: 21)
[K]-[F/Y/W]-[L/V/I/A/T]-[L/V/A/I/S/T/M]-[K].

In some embodiments $X_1$ and $X_2$ are RW, RF, KF, KW, RY or KY. In some embodiments $X_3$ and $X_4$ are LL, LA, LV, AL, VL, VI, LI, IL, VV, VA, IV, II, AV, IA, AI, AM, LM, LS, LT, IS, MV, TV, AA, IM, LN, LQ, VM, TL, SL, IT, VT, LG, MA, ML, NL, QL, QI, TI, SI, AS, VS, SV, CA, IG, LR, VR, TK or IR. In some embodiments $X_3$ and $X_4$ are LL, LA, LV, AL, VL, VI, LI, IL, VV, VA, IV, II, AV, IA, AI, AM, LM, LS, LT, IS, MV, TV, AA, IM, LN, LQ or VM. In some embodiments $X_3$ and $X_4$ are LV, IV, SV, LS, AV, LG, LA, IR, LR, VR, AR, IK, LK, VK or AK. In particularly preferred embodiments $X_3$ and $X_4$ are LL, LA, LV, AL, VL, VI, LI, IL, W, VA, IV, II, AV, IA, AI, AM, LM, LS or LT, preferably LL, LA, LV, AL, VL, VI, LI, IL, VV, VA, IV, II, AV, IA or AI. Thus, in certain embodiments $X_3$ and $X_4$ are not AG, AC, CC, NN, QQ, NQ, QN, TS, SS, ST or TT.

In some embodiments $X_2$ and $X_3$ are not FS or FT.

In some embodiments $X_5$ is K.

Thus, in a preferred embodiment, the oligopeptidic compound has or comprises the sequence RWLVK (SEQ ID NO: 28). In other preferred embodiments, the oligopeptidic compound has or comprises a sequence selected from any one or more of: RWLLK (SEQ ID NO: 22); RFLLK (SEQ ID NO: 23); RYLLK (SEQ ID NO: 24); RWLLR (SEQ ID NO: 25); RFLLR (SEQ ID NO: 26); RYLLR (SEQ ID NO: 27); RWLVK (SEQ ID NO: 28); RFLVK (SEQ ID NO: 29); RYLVK (SEQ ID NO: 30); RWLVR (SEQ ID NO: 31); RFLVR (SEQ ID NO: 32); RYLVR (SEQ ID NO: 33); RWIVK (SEQ ID NO: 34); RFIVK (SEQ ID NO: 35); RYIVK (SEQ ID NO: 36); RWIVR (SEQ ID NO: 37); RFIVR (SEQ ID NO: 38); RYIVR (SEQ ID NO: 39); RWLSK (SEQ ID NO: 40); RFLSK (SEQ ID NO: 41); RYLSK (SEQ ID NO: 42); RWLSR (SEQ ID NO: 43); RFLSR (SEQ ID NO: 44); RYLSR (SEQ ID NO: 45); RWISK (SEQ ID NO: 46); RFISK (SEQ ID NO: 47); RYISK (SEQ ID NO: 48); RWISR (SEQ ID NO: 49);

RFISR (SEQ ID NO: 50); RYISR (SEQ ID NO: 51); RWSVK (SEQ ID NO: 52); RFSVK (SEQ ID NO: 53); RYSVK (SEQ ID NO: 54); RWSVR (SEQ ID NO: 55); RFSVR (SEQ ID NO: 56); RYSVR (SEQ ID NO: 57); RWAVK (SEQ ID NO: 58); RFAVK (SEQ ID NO: 59); RYAVK (SEQ ID NO: 60); RWAVR (SEQ ID NO: 61); RFAVR (SEQ ID NO: 62); RYAVR (SEQ ID NO: 63); RWLGR (SEQ ID NO: 64); RFLGR (SEQ ID NO: 65); RYLGR (SEQ ID NO: 66); RWLGK (SEQ ID NO: 67); RFLGK (SEQ ID NO: 68); RYLGK (SEQ ID NO: 69); RWLAR (SEQ ID NO: 70); RFLAR (SEQ ID NO: 71); RYLAR (SEQ ID NO: 72); RWLAK (SEQ ID NO: 73); RFLAK (SEQ ID NO: 74); RYLAK (SEQ ID NO: 75); RWLTK (SEQ ID NO: 76); RFLTK (SEQ ID NO: 77); RYLTK (SEQ ID NO: 78); RWLTR (SEQ ID NO: 79); RFLTR (SEQ ID NO: 80); RYLTR (SEQ ID NO: 81); RWITK (SEQ ID NO: 82); RFITK (SEQ ID NO: 83); RYITK (SEQ ID NO: 84); RWITR (SEQ ID NO: 85); RFITR (SEQ ID NO: 86); RYITR (SEQ ID NO: 87); RWTVK (SEQ ID NO: 88); RFTVK (SEQ ID NO: 89); RYTVK (SEQ ID NO: 90); RWTVR (SEQ ID NO: 91); RFTVR (SEQ ID NO: 92); RYTVR (SEQ ID NO: 93); RWIRK (SEQ ID NO: 94); RFIRK (SEQ ID NO: 95); RYIRK (SEQ ID NO: 96); RWIRR (SEQ ID NO: 97); RFIRR (SEQ ID NO: 98); RYIRR (SEQ ID NO: 99); RWLRK (SEQ ID NO: 100); RFLRK (SEQ ID NO: 101); RYLRK (SEQ ID NO: 102); RWLRR (SEQ ID NO: 103); RFLRR (SEQ ID NO: 104); RYLRR (SEQ ID NO: 105); KWLLK (SEQ ID NO: 106); KFLLK (SEQ ID NO: 107); KYLLK (SEQ ID NO: 108); KWLLR (SEQ ID NO: 109); KFLLR (SEQ ID NO: 110); KYLLR (SEQ ID NO: 111); KWLVK (SEQ ID NO: 112); KFLVK (SEQ ID NO: 113); KYLVK (SEQ ID NO: 114); KWLVR (SEQ ID NO: 115); KFLVR (SEQ ID NO: 116); KYLVR (SEQ ID NO: 117); KWIVK (SEQ ID NO: 118); KFIVK (SEQ ID NO: 119); KYIVK (SEQ ID NO: 120); KWIVR (SEQ ID NO: 121); KFIVR (SEQ ID NO: 122); KYIVR (SEQ ID NO: 123); KWLSK (SEQ ID NO: 124); KFLSK (SEQ ID NO: 125); KYLSK (SEQ ID NO: 126); KWLSR (SEQ ID NO: 127); KFLSR (SEQ ID NO: 128); KYLSR (SEQ ID NO: 129); KWISK (SEQ ID NO: 130); KFISK (SEQ ID NO: 131); KYISK (SEQ ID NO: 132); KWISR (SEQ ID NO: 133); KFISR (SEQ ID NO: 134); KYISR (SEQ ID NO: 135); KWSVK (SEQ ID NO: 136); KFSVK (SEQ ID NO: 137); KYSVK (SEQ ID NO: 138); KWSVR (SEQ ID NO: 139); KFSVR (SEQ ID NO: 140); KYSVR (SEQ ID NO: 141); KWAVK (SEQ ID NO: 142); KFAVK (SEQ ID NO: 143); KYAVK (SEQ ID NO: 144); KWAVR (SEQ ID NO: 145); KFAVR (SEQ ID NO: 146); KYAVR (SEQ ID NO: 147); KWLGR (SEQ ID NO: 148); KFLGR (SEQ ID NO: 149); KYLGR (SEQ ID NO: 150); KWLGK (SEQ ID NO: 151); KFLGK (SEQ ID NO: 152); KYLGK (SEQ ID NO: 153); KWLAR (SEQ ID NO: 154); KFLAR (SEQ ID NO: 155); KYLAR (SEQ ID NO: 156); KWLAK (SEQ ID NO: 157); KFLAK (SEQ ID NO: 158); KYLAK (SEQ ID NO: 159); KWLTK (SEQ ID NO: 160); KFLTK (SEQ ID NO: 161); KYLTK (SEQ ID NO: 162); KWLTR (SEQ ID NO: 163); KFLTR (SEQ ID NO: 164); KYLTR (SEQ ID NO: 165); KWITK (SEQ ID NO: 166); KFITK (SEQ ID NO: 167); KYITK (SEQ ID NO: 168); KWITR (SEQ ID NO: 169); KFITR (SEQ ID NO: 170); KYITR (SEQ ID NO: 171); KWTVK (SEQ ID NO: 172); KFTVK (SEQ ID NO: 173); KYTVK (SEQ ID NO: 174); KWTVR (SEQ ID NO: 175); KFTVR (SEQ ID NO: 176); KYTVR (SEQ ID NO: 177); KWLRK (SEQ ID NO: 178); KFLRK (SEQ ID NO: 179); KYLRK (SEQ ID NO: 180); KWLRR (SEQ ID NO: 181); KFLRR (SEQ ID NO: 182); KYLRR (SEQ ID NO: 183); KWIRK (SEQ ID NO: 184); KFIRK (SEQ ID NO: 185); KYIRK (SEQ ID NO: 186); KWIRR (SEQ ID NO: 187); KFIRR (SEQ ID NO: 188); KYIRR (SEQ ID NO: 189); RWVVK (SEQ ID NO: 190); RFWK (SEQ ID NO: 191); RYVVK (SEQ ID NO: 192); RWVVR (SEQ ID NO: 193); RFWR (SEQ ID NO: 194); RYWR (SEQ ID NO: 195); KWVVK (SEQ ID NO: 196); KFWK (SEQ ID NO: 197); KYVVK (SEQ ID NO: 198); KWVVR (SEQ ID NO: 199); KFWR (SEQ ID NO: 200); KYVVR (SEQ ID NO: 201); RWALK (SEQ ID NO: 202); RFALK (SEQ ID NO: 203); RYALK (SEQ ID NO: 204); RWALR (SEQ ID NO: 205); RFALR (SEQ ID NO: 206); RYALR (SEQ ID NO: 207); KWALK (SEQ ID NO: 208); KFALK (SEQ ID NO: 209); KYALK (SEQ ID NO: 210); KWALR (SEQ ID NO: 211); KFALR (SEQ ID NO: 212); KYALR (SEQ ID NO: 213); RWVLK (SEQ ID NO: 214); RFVLK (SEQ ID NO: 215); RYVLK (SEQ ID NO: 216); RWVLR (SEQ ID NO: 217); RFVLR (SEQ ID NO: 218); RYVLR (SEQ ID NO: 219); KWVLK (SEQ ID NO: 220); KFVLK (SEQ ID NO: 221); KYVLK (SEQ ID NO: 222); KWVLR (SEQ ID NO: 223); KFVLR (SEQ ID NO: 224); KYVLR (SEQ ID NO: 225); RWILK (SEQ ID NO: 226); RFILK (SEQ ID NO: 227); RYILK (SEQ ID NO: 228); RWILR (SEQ ID NO: 229); RFILR (SEQ ID NO: 230); RYILR (SEQ ID NO: 231); KWILK (SEQ ID NO: 232); KFILK (SEQ ID NO: 233); KYILK (SEQ ID NO: 234); KWILR (SEQ ID NO: 235); KFILR (SEQ ID NO: 236); KYILR (SEQ ID NO: 237); RWVIK (SEQ ID NO: 238); RFVIK (SEQ ID NO: 239); RYVIK (SEQ ID NO: 240); RWVIR (SEQ ID NO: 241); RFVIR (SEQ ID NO: 242); RYVIR (SEQ ID NO: 243); KWVIK (SEQ ID NO: 244); KFVIK (SEQ ID NO: 245); KYVIK (SEQ ID NO: 246); KWVIR (SEQ ID NO: 247); KFVIR (SEQ ID NO: 248); KYVIR (SEQ ID NO: 249); RWIIK (SEQ ID NO: 250); RFIIK (SEQ ID NO: 251); RYIIK (SEQ ID NO: 252); RWIIR (SEQ ID NO: 253); RFIIR (SEQ ID NO: 254); RYIIR (SEQ ID NO: 255); KWIIK (SEQ ID NO: 256); KFIIK (SEQ ID NO: 257); KYIIK (SEQ ID NO: 258); KWIIR (SEQ ID NO: 259); KFIIR (SEQ ID NO: 260); KYIIR (SEQ ID NO: 261); RWLIK (SEQ ID NO: 262); RFLIK (SEQ ID NO: 263); RYLIK (SEQ ID NO: 264); RWLIR (SEQ ID NO: 265); RFLIR (SEQ ID NO: 266); RYLIR (SEQ ID NO: 267); KWLIK (SEQ ID NO: 268); KFLIK (SEQ ID NO: 269); KYLIK (SEQ ID NO: 270); KWLIR (SEQ ID NO: 271); KFLIR (SEQ ID NO: 272); KYLIR (SEQ ID NO: 273); RWIAK (SEQ ID NO: 274); RFIAK (SEQ ID NO: 275); RYIAK (SEQ ID NO: 276); RWIAR (SEQ ID NO: 277); RFIAR (SEQ ID NO: 278); RYIAR (SEQ ID NO: 279); KWIAK (SEQ ID NO: 280); KFIAK (SEQ ID NO: 281); KYIAK (SEQ ID NO: 282); KWIAR (SEQ ID NO: 283); KFIAR (SEQ ID NO: 284); KYIAR (SEQ ID NO: 285); RWVAK (SEQ ID NO: 286); RFVAK (SEQ ID NO: 287); RYVAK (SEQ ID NO: 288); RWVAR (SEQ ID NO: 289); RFVAR (SEQ ID NO: 290); RYVAR (SEQ ID NO: 291); KWVAK (SEQ ID NO: 292); KFVAK (SEQ ID NO: 293); KYVAK (SEQ ID NO: 294); KWVAR (SEQ ID NO: 295); KFVAR (SEQ ID NO: 296); KYVAR (SEQ ID NO: 297); and RWLVP (SEQ ID NO: 1209).

These specific sequences are listed by way of example and they are not intended to be limiting on the scope of the present invention. In some preferred embodiments the oligopeptidic compound has or comprises the sequence RWLVK (SEQ ID NO: 28) or KFIVK (SEQ ID NO: 119) or RWLVP (SEQ ID NO: 1209).

Whilst the PCNA interacting motifs listed above are preferred motifs of the invention, in some embodiments any one or more of these motifs may be excluded, e.g. any 1, 2, 3, 4, 5, 6, 7, 8, 9, 10, 12, 15, 20 or more motifs may be excluded, such as any 25, 30, 40, 50 or more motifs or any integer in this range. Thus, in some embodiments the oligopeptidic compound does not have or comprise a sequence selected from any one or more of SEQ ID NOs: 22-297 and 1209.

Particular PCNA interacting motifs that may be excluded or disclaimed include any one or more of the following: KYMVR (SEQ ID NO: 298), KFLAK (SEQ ID NO: 158), KWLIK (SEQ ID NO: 268), KFLIK (SEQ ID NO: 269), KWLIOrn (SEQ ID NO: 299), KWLIDbu (SEQ ID NO: 300), and KWQLR (SEQ ID NO: 301).

The oligopeptidic compound is preferably an isolated compound, e.g. an isolated peptide and most preferably the oligopeptidic compound is a synthetic compound, e.g. a synthetic peptide. The nucleic acid molecule encoding the oligopeptidic compound is preferably an isolated nucleic acid molecule and most preferably the nucleic acid molecule is a synthetic nucleic acid molecule. In other words, the oligopeptidic compound and its encoding nucleic acid molecule are non-native, i.e. non-naturally occurring, molecules.

The domain that facilitates the uptake of the oligopeptidic compound may be an uptake (import) peptide sequence, which may be a sequence which acts to transport the oligopeptidic compound into a cell, or across a cell membrane (i.e. into the interior of a cell). It may thus be a so-called "cell penetrating" sequence (or more particularly "cell penetrating peptide") also known in the art as a protein transduction domain (PTD) or protein transduction sequence.

Accordingly, as noted above the invention may provide an agent or construct comprising (i) an oligopeptidic compound comprising an APIM motif (i.e. a PCNA-interacting motif) as defined herein, and (ii) a cell penetrating sequence (more particularly a cell penetrating peptide).

Cell penetrating peptide (CPP) technology has developed greatly over recent years and a wide variety of cell penetrating peptides are known and described in the art and indeed a range of such peptides are commercially available. Cell penetrating peptides may vary greatly in size, sequence and charge, and indeed in their mechanism of function (which is presently not known for some peptides and not fully elucidated for others), but share the common ability to translocate across the plasma membrane and deliver an attached or associated moiety (the so-called "cargo") into the cytoplasm of a cell. CPPs are thus peptide-based delivery vectors.

Whilst CPPs are not characterized by a single structural or functional motif, tools to identify CPPs are available and the skilled person can readily determine whether a peptide sequence may function to facilitate the uptake of the peptide of which it forms a domain, i.e. whether a domain may function as an uptake (import) peptide, e.g. a CPP. For example, Hansen et al (Predicting cell-penetrating peptides, Advanced Drug Delivery Reviews, 2008, 60, pp. 572-579), provides a review of methods for CPP prediction based on the use of principal component analysis ("z-predictors") and corresponding algorithms based on original work by Hällbrink et al (Prediction of Cell-Penetrating Peptides, International Journal of Peptide Research and Therapeutics, 2005, 11(4), pp. 249-259). In brief, the methodology works by computing z-scores of a candidate peptide as based on a numerical value and an associate range. If the z-scores fall within the range of known CPP z-scores, the examined peptides are classified as CPPs. The method was shown to have high accuracy (about 95% prediction of known CPPs).

Additional methods for the prediction of CPPs have been developed subsequently (see e.g. Sanders et al., Prediction of Cell Penetrating Peptides by Support Vector Machines, PLOS Computational Biology, 2011, 7(7), pp. 1-12, herein incorporated by reference) and a CPP database is available (Gautam et al., CPPSite: a curated database of cell penetrating peptides, Database, 2012, Article ID bas015 and crd-d.osdd.net/raghava/cppsite/index.php, both herein incorporated by reference). Accordingly, any suitable CPP may find utility in the invention and, as discussed below, a variety of CPPs have already been identified and tested and could form the basis for determining and identifying new CPPs.

CPPs may be derived from naturally-occurring proteins which are able to translocate across cell membranes such as the *Drosophila* homeobox protein Antennapedia (a transcriptional factor), viral proteins such as the HIV-1 transcriptional factor TAT and the capsid protein VP22 from HSV-1, and/or they may be synthetically-derived, e.g. from chimeric proteins or synthetic polypeptides such as polyarginine. As noted above, there is not a single mechanism responsible for the transduction effect and hence the design of CPPs may be based on different structures and sequences. Cell penetrating peptides are also reviewed in Jarver et al. 2006 (Biochimica et Biophysica Acta 1758, pages 260-263) and Table 1 below lists various representative peptides. U.S. Pat. No. 6,645,501 (herein incorporated by reference) further describes various cell penetrating peptides which might be used.

TABLE 1

| CPP | SEQUENCE | REFERENCE |
|---|---|---|
| Antp Class | | |
| Penetratin | RQIKIWFQNRRMKWKK (SEQ ID NO: 302) | Bolton (2000) Eur. J. Neuro. 12:287 |
| Penatratin derivatives | RRMKWKK (SEQ ID NO: 303) NRRMKWKK (SEQ ID NO: 304) QNRRMKWKK (SEQ ID NO: 305) FQNRRMKWKK (SEQ ID NO: 306) RREKWKK (SEQ ID NO: 307) RRQKWKK (SEQ ID NO: 308) KRMKWKK (SEQ ID NO: 309) RKMKWKK (SEQ ID NO: 310) RROKWKK (SEQ ID NO: 311) RRMKQKK (SEQ ID NO: 312) RRMKWFK (SEQ ID NO: 313) RORKWKK (SEQ ID NO: 314) | U.S. Pat. No. 6,472,507 EP4855781 WO 97/12912 |

TABLE 1-continued

| CPP | SEQUENCE | REFERENCE |
|---|---|---|
| | RRMWKKK (SEQ ID NO: 315)<br>RRMKKWK (SEQ ID NO: 316)<br>(using standard single amino acid notation, ornithine (O), diamino-butyric acid (B), norleucine (N)) | |
| D-Penetratin | rqikiwfqnrrmkwkk (SEQ ID NO: 317) | Rouselle, C. et al. (2000) Mol. Pharm 57:679 |
| Protegrin Class | | |
| Pegelin (SynB) | RGGRLSYSRRRFSTSTGR (SEQ ID NO: 318) | Rouselle, C. et al. (2000) Mol. Pharm 57:679 |
| HIV-TAT Class | | |
| HIV-TAT | GRKKRRQRRRPPQ (SEQ ID NO: 319) | Vives E.J Biol, Chem 1997, 272:16010 Snyder (2004) PLOS 2: 186 |
| 47-57 OF HIV-TAT | YGRKKRRQRRR (SEQ ID NO: 320) | Potocky et al. (2003) JBC |
| VP22 | DAATATRGRSAASRPTERPRAPARSASRPRRVD (SEQ ID NO: 321) | Elliott g. Cell 1997, 88:223-233 |
| Amphipathic peptides | | |
| MAP | KLALKLALKALKAALKLA (SEQ ID NO: 322) | Morris MC., Nat Biotechnol. 2001, 19:1173-1176 |
| Transportan | GWTLNSAGYLLGKINLKALAALAKKIL (SEQ ID NO: 323) | Pooga M, FASEB J 1998, 12:67-77 |
| Transportan-10 | AGYLLGKINLKALAALAKKIL (SEQ ID NO: 324) | Soomets U, Biochim Biophys Acta 2000, 1467:165-176 |
| KALA | WEAKLAKALAKALAKHLAKALAKALKACEA (SEQ ID NO: 325) | Oehlke J., Biochim Biophys Acta 1998, 1414:127-139 |
| Pep-1 | KETWWETWWTEWSQPKKKRKV (SEQ ID NO: 326) | Wyman Biochemistry 1997, 36:3008-3017 |
| Pep-2 | KETWFETWFTEWSQPKKKRKV (SEQ ID NO: 327) | |
| MPG | GALFLGFLGAAGSTMGAWSQPKSKRKV (SEQ ID NO: 328) | Wagstaff KM Curr Med Chem 2006, 13:1371-1387 |

TABLE 1-continued

| CPP | SEQUENCE | REFERENCE |
|---|---|---|
| Vectocell peptides | VKRGLKLRHVRPRVTRMDV (SEQ ID NO: 329)<br>SRRARRSPRHLGSG* (SEQ ID NO: 330)<br>LRRERQSRLRRERQSR* (SEQ ID NO: 331)<br>GAYDLRRRERQSRLRRRERQSR<br>(SEQ ID NO: 332)<br>*indicates addition of cys for conjugation to cargo | Coupade (2005) Biochem. J. 407 |
| Wr-T transporter | KETWWETWWTEVWVTEWSQ-GPG-rrrrrrrr (SEQ ID NO: 333)<br>r = D-enantiomer arginine | Kondo (2004) Mol. Can. Thera 1623 |
| Other peptides | | |
| R7 | RRRRRRR (SEQ ID NO: 334) | Rothbard et al., Nat. Med 6 (2000) 1253-1257 |

Antennapedia-derived CPPs (Antp class) represent a class of particular interest, based around the 16 amino acid Penetratin sequence as shown in Table 1, which corresponds to the third loop of antennapedia protein and was shown to be responsible for translocation of the protein. Penetratin has been extensively developed as a delivery vehicle, including particularly for pharmaceutical use, and a wide range of Penetratin derivatives and modified sequences have been proposed and described. Reference may be made in particular to WO 91/1891, WO 00/1417, WO 00/29427, WO 2004/069279 and U.S. Pat. No. 6,080,724 (herein incorporated by reference). Thus, the 16 amino acid sequence of Penetratin may be modified and/or truncated, or the peptide may be chemically-modified or retro-, inverso- or retro-inverso analogues may be made whilst retaining cell-penetrating activity.

Another group of cell penetrating peptides which may advantageously be used are based on the HIV-TAT sequence and HIV-TAT and fragments thereof represent a preferred class of CPPs for use according to the present invention. Various TAT-based CPPs are described in U.S. Pat. No. 5,656,122 (herein incorporated by reference). An exemplary HIV-TAT peptide as used in the Examples below is RKKRRQRRR (SEQ ID NO: 335) but it will readily be appreciated that longer or shorter TAT fragments may be used.

As mentioned above no particular structural features or sequence motifs are common to all CPPs. However, various classes of CPPs may be identified by particular features, such as for example peptides which are amphipathic and net positively charged. Other groups of CPPs may have a structure exhibiting high α-helical content. Another group may be peptides characterised by a high content of basic amino acids. CPPs may thus be or may comprise oligomers of basic amino acids such as arginine e.g. 5 to 20, 6 to 15 or 6 to 12 R residues e.g. $R_7$ (SEQ ID NO: 334), $R_8$ (SEQ ID NO: 336) or $R_{11}$ (SEQ ID NO: 337) or $QSR_8$ (SEQ ID NO: 338).

Proline-rich amphipathic peptides are another class of CPP and such peptides characterised by the presence of pyrrolidine rings from prolines are described in Pujals et al. 2008 Advanced Drug Delivery Reviews 60, pages 473-484 (herein incorporated by reference).

Other successfully developed CPPs include pVEC (Elmquist et al. 2003 Biol. Chem 384, pages 387-393; Holm et al. 2005 Febs Lett. 579, pages 5217-5222, all herein incorporated by reference) and calcitonin-derived peptides (Krauss et al. 2004 Bioorg. Med. Chem. Lett., 14, pages 51-54 herein incorporated by reference).

Commercially available CPPs include Chariot, based on the Pep-1 peptide (Active Motif, France), the Syn-B vectors based on the protegrin peptide PG-1 (Syntem, France), and Express-si Delivery based on the MPG peptide from Genospectra, USA.

Other CPPs include the R41, R8, M918 and YTA-4 peptides (SEQ ID NOs: 1210-1213, respectively) disclosed in Eriksson et al. 2013, Antimicrobial Agents and Chemotherapy, vol. 57(8), pp. 3704-3712 (incorporated herein by reference).

In some embodiments the CPPs may be cyclic peptides, such as those disclosed in Oh et al., 2014, Mol. Pharmaceutics, vol. 11, pp. 3528-3536 (incorporated herein by reference). In particular, the CPPs may be amphiphilic cyclic CPPs, particularly containing tryptophan and arginine residues. In some embodiments the CPPs may be cyclic polyarginine peptides and may be modified by the addition of a fatty acyl moiety, e.g. octanoyl, dodecanoyl, hexadecanoyl, N-acetyl-L-tryptophanyl-12-aminododecanoyl etc. Suitable cyclic CPPs for use in the invention are presented in SEQ ID NOs: 1214-1220.

In addition to publically available and reported CPPs, novel or derivative CPP peptides may be designed and synthesized based on known or reported criteria (e.g. known CPP sequences or features such as basic amino acid content, α-helical content etc. as discussed above). Additionally, randomly-designed or other peptides may be screened for CPP activity, for example by coupling or attaching such a peptide containing a reporter molecule, e.g. a detectable label or tag such as a fluorescent tag to the desired cargo (e.g. an oligopeptidic compound as described herein) and testing to see if the construct is translocated across the cell membrane, for example by adding these peptides to live cells followed by examination of cellular import e.g. using confocal microscopy.

Indeed, whilst it is generally the case that a CPP will penetrate or enter virtually any cell type, it may in some cases be observed that successful or efficient delivery may be dependent, or may vary depending, on the precise nature of the cargo (e.g. cargo peptide sequence) and/or the CPP used. It would be well within the routine skill of the person skilled in the art to determine optimum peptide sequences and combinations etc, and to test and/or modify cargo and/or CPP sequence or structure etc.

Thus, by way of summary, the skilled person will be aware of suitable peptide sequences that may facilitate the uptake of the oligopeptidic compound, but by way of example the sequences may include Penetratin™, a 16-amino acid peptide corresponding to the third helix of the homeodomain of Antennapedia protein, R rich tags such as R6-Penetratin (in which arginine-residues were added to the N-terminus of Penetratin) and derivatives of the HIV Tat protein such as GRKKRRQRRRPPQQ (SEQ ID NO: 339).

Thus, in some embodiments the domain that facilitates the cellular uptake of the oligopeptidic compound is a CPP and may be selected from any one of:
(i) an antennapedia class peptide;
(ii) a protegrin class peptide;
(iii) a HIV-TAT class peptide;
(iv) an amphipathic class peptide selected from an amphipathic and net positively charged peptide, a proline-rich amphipathic peptide, a peptide based on the Pep-1 peptide and a peptide based on the MPG peptide;
(v) a peptide exhibiting high α-helical content;
(vi) a peptide comprising oligomers of basic amino acids;
(vii) pVEC;
(viii) a calcitonin-derived peptide; and
(ix) an amphiphilic cyclic CPP.

In some embodiments the domain that facilitates the cellular uptake of the oligopeptidic compound is a CPP and may be selected from a sequence selected from any one of SEQ ID NOs: 302-1162 or a fragment and/or derivative thereof. The details and properties of the CPPs identified in SEQ ID NOs: 340-1162 can be found at crdd.osdd.net/raghava/cppsite/index.php, CPPSite: A database of cell penetrating peptides (herein incorporated by reference).

In some embodiments the domain that facilitates the cellular uptake of the oligopeptidic compound is SEQ ID NO: 337.

In some embodiments, the oligopeptidic compound also comprises one or more domains that provide a signal (target or transit) sequence. In some embodiments, the signal sequence may target the oligopeptidic compound to a specific cell type. Additionally or alternatively, in some embodiments the oligopeptidic compound may comprise a signal peptide that localises the compound to a specific intracellular compartment, e.g. the nucleus. In some embodiments, the oligopeptidic compound is targeted to the cytosol, which may be achieved without an additional signal peptide, i.e. the uptake (import) peptide, e.g. CPP, may be sufficient to direct or localise the oligopeptidic compound to the cytosol of a cell.

The signal sequence or signal sequence domain may thus be viewed as any sequence which acts to localise, or alternatively put, to direct, translocate or transport, the oligopeptidic compound to any desired location e.g. to any desired cell type or subcellular location, e.g. nucleus.

As mentioned above, the oligopeptidic compound (or constructs) for use in the use and methods of the invention may comprise one or more signal sequences (i.e. one or more domains that function as signal sequences), e.g. a signal peptide which directs the compound (or construct) into a particular sub-cellular compartment, such as the nucleus. Nuclear localisation signals (NLSs) are again well known in the art and widely described in the literature. For instance, a searchable database of known and predicted NLSs is available, see e.g. Cokol et al (Finding nuclear localization signals, EMBO Reports, 2000, 1(5), pp. 411-415, herein incorporated by reference). The PSORT II database, psort.hgc.jp/(herein incorporated by reference) can be used for the prediction of nuclear localization of proteins based on NLSs. Accordingly, any known or functional NLS may find utility in the invention.

An NLS may vary in length and/or sequence and a wide range of specific NLS sequences have been described. In general, however, it has been found that peptides comprising positively charged amino acids (notably lysine (K), arginine (R) and/or histidine (H)) may function as an NLS. An exemplary NLS may thus be a peptide of e.g. 4-20, more particularly 4-15, 4-12, 4-10 or 4-8 amino acids, wherein at least 4 amino acids (and more particularly at least 60, 70, 75, 80, 85, or 90% of the amino acid residues in the NLS peptide) are positively charged amino acids, preferably selected from K, R or H. Such an exemplary NLS may for example have or comprise the sequence RKRH (SEQ ID NO: 1163).

Nuclear localisation signals, including both actual experimentally-determined and predicted or proposed NLS sequences, and strategies for identifying NLSs are also described in Lange et al., J. Biol. Chem. 2007, 282(8), 5101-5105; Makkerh et al., Current Biology 1996, 6(8), 1025-1027; Leslie et al., Methods 2006, 39, 291-308; and Lusk et al. Nature Reviews MCB 2007, 8, 414-420 (all herein incorporated by reference).

A classical NLS consists of either one (monopartite) or two (bipartite) stretches of basic amino acids. A monopartite NLS may be exemplified by the SV40 large T antigen NLS ($^{126}$PKKKRKV$^{132}$ [SEQ ID NO: 1164]) and a bipartite NLS by the nucleoplasmin NLS ($^{166}$KRPAATKK-AGQAKKKK$^{17o}$ [SEQ ID NO: 1165]). The monopartite NLS consensus sequence K-[K/R]-X-[K/R] (SEQ ID NO: 1166) has been proposed and accordingly an NLS according to the present invention may in one embodiment comprise or consist of such a consensus sequence (where X is any amino acid).

A representative bipartite NLS according to the invention may have the sequence KR-[X]$_{5-20}$-KKKK (SEQ ID NO: 1167), e.g. KR-X$_{10}$-KKKK (SEQ ID NO: 1168) (where X is any amino acid).

An alternative exemplary bipartite NLS may take the form RKRH-[X]$_{2-10}$-KK (SEQ ID NO: 1169) e.g. RKRH—X$_2$-KK (SEQ ID NO: 1170), for example RKRH—II-KK (SEQ ID NO: 1171).

The oncoprotein c-myc NLS differs from classical NLSs in that only 3 of 9 amino acid residues are basic (PAAKRVKLD [SEQ ID NO: 1172]), indicating that an NLS need not necessarily conform to the consensus or classical sequences given above. Makkerh et al (supra) describe NLS sequences in which a cluster of basic amino acids (e.g. KKKK [SEQ ID NO: 1173]) is flanked by neutral and acidic residues, for example PAAKKKKLD (SEQ ID NO: 1174).

Other possible NLS sequences which may be given by way of example include: PKKKRKVL (SEQ ID NO: 1175), KKKRK (SEQ ID NO: 1176), KKKRVK (SEQ ID NO: 1177), KKKRKVL (SEQ ID NO: 1178) and RKKRKVL (SEQ ID NO: 1179). Any NLS which is a derivative of a known NLS e.g. the SV40, nucleoplasmin, UNG2 or c-myc NLS may be used.

A putative, proposed or predicted NLS sequence can be tested for NLS activity using principles and assays known and described in the art. For example, a candidate NLS sequence may be attached to the desired cargo (in this case an oligopeptidic compound as defined herein) and the construct may be provided with a detectable reporter molecule (e.g. a tag or label which may be visualised, for example a fluorescent label) and contacted with a test cell. Distribution of the construct in the cell may then be determined.

Thus, by way of summary, the skilled person will be aware of suitable signal sequences, but by way of example the following are mentioned herein Examples of nuclear localisation sequences include the SV40 protein derivative KKKRK (SEQ ID NO: 1176).

Thus, in some embodiments the oligopeptidic compound comprises a signal sequence (i.e. a domain comprising a signal peptide) that localizes or directs the oligopeptidic compound to a sub-cellular location, such as a NLS and may be selected from any one of:
  (i) a peptide of 4-20 amino acids, wherein at least 4 amino acids are positively charged amino acids, preferably selected from K, R or H; and/or
  (ii) a sequence selected from any one of SEQ ID NOs: 1163-1179 or a fragment and/or derivative thereof.

In some embodiments the nuclear localisation signal sequence comprises a sequence selected from any one of SEQ ID NOs: 1163-1179 or a fragment and/or derivative thereof, preferably wherein said fragment and/or derivative comprises at least 4 positively charged amino acids, preferably selected from any of K, R or H.

In some embodiments an oligopeptidic compound or construct according to the present invention may comprise at least three domains, including (i) an APIM motif domain as defined herein, (ii) a linker domain, which may in some embodiments comprise a nuclear localisation signal sequence, and (iii) a peptide sequence domain that facilitates the cellular uptake of said compound or construct (i.e. an uptake/import peptide sequence domain, e.g. cell penetrating signal sequence domain).

The separate elements or components (domains) of a construct according to the present invention may be contained or presented in any order, but preferably in the orders indicated above (e.g. APIM oligopeptidic compound-CPP or APIM oligopeptidic compound-linker-CPP).

In some embodiments, the APIM motif is located at or towards the N-terminus of the peptide. For instance, the APIM motif may be described as being N-terminal to the peptide sequence domain that facilitates the cellular uptake of said compound (e.g. the CPP) and optionally N-terminal to the linker sequence, if present.

In a preferred embodiment, the oligopeptidic compound comprises a PCNA interacting motif as set forth in SEQ ID NO: 28, a nuclear localisation signal sequence as set forth in SEQ ID NO: 1176 and a cell penetrating signal sequence as set forth in SEQ ID NO: 337.

Furthermore, in some embodiments an oligopeptidic compound or construct according to the invention may contain more than one PCNA-interacting motif. Thus, alternatively put, an agent for use in the uses and methods of the present invention may contain or encode an oligopeptidic compound comprising more than one PCNA-interacting motif. A construct or oligopeptidic compound may for example contain 1-10, e.g. 1-6, or 1-4 or 1-3 or one or two motifs. Within a construct also containing a signal sequence, such motifs may be spaced or located according to choice, e.g. they may be grouped together, or they may be separated by signal sequence elements e.g. motif-motif-CPP, motif-linker-motif-CPP; or motif-linker-motif-motif-CPP; or motif-motif-linker-CPP etc.

As referred to herein a "fragment" may comprise at least 30, 40, 50, 60, 70, 80, 85, 90, 95, 96, 97, 98 or 99% of the amino acids of the sequence from which it is derived. Said fragment may be obtained from a central or N-terminal or C-terminal portions of the sequence. Whilst the size of the fragment will depend on the size of the original sequence, in some embodiments the fragments may be 1, 2, 3, 4, 5, 6, 7, 8, 9, 10, 11, 12, 13, 14, 15 or more amino acid residues shorter than the sequence from which it is derived, e.g. 1-10, 2-9, 3-8, 4-7 amino acid residues shorter than the sequence from which it is derived.

As referred to herein a "derivative" of a sequence is at least 55, 60, 65, 70, 75, 80, 85, 90, 95, 96, 97, 98 or 99% identical to the sequence to which it is compared.

Sequence identity may be determined by, e.g. using the SWISS-PROT protein sequence databank using FASTA pep-cmp with a variable pamfactor, and gap creation penalty set at 12.0 and gap extension penalty set at 4.0, and a window of 2 amino acids. Preferably said comparison is made over the full length of the sequence, but may be made over a smaller window of comparison, e.g. less than 200, 100, 50, 20 or 10 contiguous amino acids.

Preferably such sequence identity related polypeptides, i.e. derivatives, are functionally equivalent to the peptides which are set forth in the recited SEQ ID NOs. Similarly, the peptides with sequences as set forth in the SEQ ID NOs. may be modified without affecting the sequence of the polypeptide as described below. Furthermore, "fragments" as described herein may be functional equivalents. Preferably these fragments satisfy the identity (relative to a comparable region) conditions mentioned herein.

As referred to herein, to achieve "functional equivalence" the peptide may show some reduced efficacy in performing the function relative to the parent molecule (i.e. the molecule from which it was derived, e.g. by amino acid substitution), but preferably is as efficient or is more efficient. Thus, functional equivalence may relate to a peptide which is effective in localizing or directing the oligopeptidic compound to the cell type or cellular location, e.g. to facilitate to the uptake of the peptide as described above. This may be tested by comparison of the effects of the derivative peptide relative to the peptide from which it is derived in a qualitative or quantitative manner, e.g. by performing the in vitro analyses described above. Where quantitative results are possible, the derivative is at least 30, 50, 70 or 90% as effective as the parent peptide.

Functionally-equivalent peptides which are related to or derived from the parent peptide, may be obtained by modifying the parent amino acid sequence by single or multiple amino acid substitution, addition and/or deletion (providing they satisfy the above-mentioned sequence identity requirements), but without destroying the molecule's function. Preferably the parent sequence has less than 20 substitutions, additions or deletions, e.g. less than 10, 5, 4, 3, 2, or 1 such modifications. Such peptides may be encoded by "functionally-equivalent nucleic acid molecules" which may be generated by appropriate substitution, addition and/or deletion of one or more bases.

The domains (which may be viewed as components, elements or separate parts) of an oligopeptidic compound or construct as described herein may be attached or linked to one another in any desired or convenient way according to techniques well known in the art. Thus, the domains may be linked or conjugated chemically, e.g. using known chemical coupling technologies or the compound or constructs may be formed as a single whole using genetic engineering techniques e.g. techniques for forming fusion proteins, or they may simply be synthesized as a whole, e.g. using peptide synthesis techniques.

The domains may be linked directly to each other or they may be linked indirectly by means of one or more linker (or spacer) sequences. Thus, a linker sequence may interspace or separate two or more individual domains (i.e. parts, e.g. or separate motif elements) in an oligopeptidic construct or compound. The precise nature of the linker sequence is not critical and it may be of variable length and/or sequence, for example it may have 0-40, more particularly 0-20, 0-15, 0-12, 0-10, 0-8, or 0-6, 0-4 or 0-3 residues e.g. 1, 2 or 3 or more residues. By way of representative example the linker sequence, if present, may have 1-15, 1-12, 1-10, 1-8, 1-6 or 1-4 residues etc. The nature of the residues is not critical and they may for example be any amino acid, e.g. a neutral amino acid, or an aliphatic amino acid, or alternatively they may be hydrophobic, or polar or charged or structure-forming e.g. proline. A range of different linker sequences have been shown to be of use, including short (e.g. 1-6) sequences of neutral and/or aliphatic amino acids.

Exemplary linker sequences thus include any single amino acid residue, e.g. A, I, L, V, G, R, Q, T, or W, or a di-, tri- tetra- penta- or hexa-peptide composed of such residues.

As representative linkers may be mentioned I, II, IL, R, W, WW, WWW, RIL, RIW, GAQ, GAW, VAT, IILVI (SEQ ID NO: 1180), IILVIII (SEQ ID NO: 1181) etc.

The linkers between different domains (components, elements or parts) may be the same or different.

As mentioned above, in some embodiments the linker may comprise or consist of an NLS. Alternatively viewed, in some embodiments an NLS, when present, may function both as a signal peptide and a linker. Thus, the oligopeptidic compound may comprise a signal peptide (e.g. an NLS) and a linker.

Representative compounds (or more particularly constructs) for use in the methods and uses of the invention include:

```
                                         (SEQ ID NO: 1182)
MDRWLVKRILVATK, (SEQ ID NO: 1183)
MDRWLVKRILKKKRKVATKG, (SEQ ID NO: 1184)
MDRWLVKGAQPKKKRKVLRQIKIWFQNRRMKWKK, (SEQ ID NO: 1185)
MDRWLVKGAWKKKRVKIIRKKRRQRRRK, (SEQ ID NO: 1186)
MDRWLVKGAWKKKRKIIRKKRRQRRRG, (SEQ ID NO: 1187)
MDRWLVKGAWKKKRKIIRKKRRQRRRK, (SEQ ID NO: 1188)
MDRWLVKRIWKKKRKIIRKKRRQRRRK, (SEQ ID NO: 1189)
MDRWLVKWWWKKKRKIIRKKRRQRRRK, (SEQ ID NO: 1190)
MDRWLVKWWRKRHIIKKRKKRRQRRRK, (SEQ ID NO: 1191)
MDRWLVKRIWKKKRKIIRRRRRRRRRRRK, (SEQ ID NO: 1192)
MDRWLVKRIWKKKRKIIRQIKIWFQNRRMKWKK, (SEQ ID NO: 1193)
MDRFLVKGAWRKRHIIKKRKKRRQRRRK, (SEQ ID NO: 1194)
MDRWLVKWKKKRKIRRRRRRRRRRRK,
```

-continued
```
                                         (SEQ ID NO: 1195)
MDRWLVKWKKKRKIRKKRRQRRRK, (SEQ ID NO: 1196)
MDRWLVKWRKRHIRKKRRQRRRK, (SEQ ID NO: 1197)
Ac-MDRWLVKGAWRKRHIRKKRRQRRRK, (SEQ ID NO: 1198)
Ac-MDRWLVKWKKKRKIRRRRRRRRRR, (SEQ ID NO: 1199)
Ac-MDRFLVKWKKKRKIRRRRRRRRRR, (SEQ ID NO: 1200)
Ac-MDRWLVKKKKRKRRRRRRRRRRK, (SEQ ID NO: 1201)
Ac-MDRWLVKKKKRKRRRRRRRRRR, (SEQ ID NO: 1202)
MDRWLVKRIWKKKRKIIRWLVKWWWRKKRRQRRRK, (SEQ ID NO: 1203)
MDRWSVKWKKKRKIRRRRRRRRRR (SEQ ID NO: 1204)
MDRWAVKWKKKRKIRRRRRRRRRR
or (SEQ ID NO: 1208)
MDRWLVPWKKKRKIRRRRRRRRRR.
```

In a particularly preferred embodiment, the oligopeptidic compound comprises a sequence as set forth in SEQ ID NO: 1198, 1203, 1204 or 1208. The oligopeptidic compounds shown above comprise N-terminal amino acids that do not form part of the domains that are essential for the compounds to have activity in the methods and uses of the invention, i.e. an "MD" sequence. Some of the peptides also comprise N-terminal modification, e.g. acetyl groups. These additional amino acids and modifications may facilitate the production of the oligopeptidic compounds, e.g. in vitro or in vivo, and/or help to protect the compounds from degradation in vivo. It will be evident that the oligopeptidic compounds do not require these additional amino acids or modifications for their activity. Accordingly, further representative sequences according to the invention include any of SEQ ID NOs: 1182 to 1204 or 1208, omitting the N-terminal "MD" and/or "Ac" groups. In other embodiments, a C-terminal K or G residue may additionally or alternatively be omitted. Furthermore, the presence of additional amino acids or modifications at either terminus would not be expected to disrupt or inhibit the function of the oligopeptidic compounds described herein. Thus, in some embodiments, the oligopeptidic compound may comprise an N-terminal sequence, e.g. a sequence at the N-terminus that does not comprise a domain defined above, e.g. a so-called N-terminal flanking sequence. In some embodiments, the oligopeptidic compound may comprise a C-terminal sequence, e.g. a sequence at the C-terminus that does not comprise a domain defined above, e.g. a so-called C-terminal flanking sequence. In some embodiments, the oligopeptidic compound may comprise an N-terminal and C-terminal flanking sequence.

A flanking sequence may comprise from about 1-150 amino acids, such as 1-120, 1-100, 1-90, 1-80, 1-70, 1-60, 1-50, 1-40, 1-35, 1-30 etc. Thus, a flanking sequence may comprise 1, 2, 3, 4, 5, 6, 7, 8, 9, 10, 11, 12, 13, 14, 15, 16, 17, 18, 19, 20, 21, 22, 23, 24 or 25 amino acids, e.g. 1-40, 2-39, 3-38, 4-37, 5-36, 6-35, 7-34, 8-33, 9-32, 10-31, 11-30, 12-29, 13-28, 14-27, 15-26 amino acids or any combination thereof.

Oligopeptidic compounds having sequences as set out in SEQ ID NOs. 1182-1204 and 1208 comprise separate domains (i.e. components) making up the constructs (i.e. motif-containing sequence, linker/NLS, CPP, etc.) Thus, it will be seen that SEQ ID NOs. 1182-1204 and 1208 represent constructs comprising at least one motif-containing sequence, a linker/NLS and a CPP, in some cases linked by linker sequences which may vary in sequence, as specified. NLS sequences based on the SV40 or UNG2 NLS sequences are used, and CPP sequences based on Penetratin, HIV-TAT or an R-rich peptide.

The standard amino acid one letter code is used herein, so K stands for lysine (Lys), I stands for isoleucine (Ile) and so on.

As mentioned above, the oligopeptidic compound, and more particularly, the APIM motif, may comprise non-conventional or non-standard amino acids. Other domains in the oligopeptidic compound may also incorporate non-standard amino acids. In some embodiments, the oligopeptidic compound may comprise one or more, e.g. at least 1, 2, 3, 4 or 5 non-conventional amino acids, i.e. amino acids which possess a side chain that is not coded for by the standard genetic code, termed herein "non-coded amino acids" (see e.g. Table 2). These may be selected from amino acids which are formed through metabolic processes such as ornithine or taurine, and/or artificially modified amino acids such as 9H-fluoren-9-ylmethoxycarbonyl (Fmoc), (tert)-(B)utyl (o)xy (c)arbonyl (Boc), 2,2,5,7,8-pentamethylchroman-6-sulphonyl (Pmc) protected amino acids, or amino acids having the benzyloxy-carbonyl (Z) group. Preferably, where such non-coded amino acids are present, they are not located within the motif, but in some embodiments one or more non-coded amino acids are present within the motif. In some embodiments, non-coded amino acids are present in more than one domain of the oligopeptidic compound.

In vitro and/or in vivo stability of the oligopeptidic compound may be improved or enhanced through the use of stabilising or protecting means known in the art, for example the addition of protecting or stabilising groups, incorporation of amino acid derivatives or analogues or chemical modification of amino acids. Such protecting or stabilising groups may for example be added at the N and/or C-terminus. An example of such a group is an acetyl group and other protecting groups or groups which might stabilise a peptide are known in the art. The oligopeptidic compounds of the invention will typically comprise only amino acids having the L-configuration, but one or more amino acids having the D configuration may be present. In some embodiments the oligopeptidic compound contains at least 1, 2, 3, 4 or 5 D-amino acids and they are preferably found in the motif, but in another embodiment, D-amino acids are present only outside of the motif. In a still further embodiments, D-amino acids may be found in more than one domain of the oligopeptidic compound. The oligopeptidic compound may be linear or cyclic.

Thus, included particularly are retro-inverso oligopeptidic compounds of the oligopeptidic compounds of the invention (and more particularly retro-inverso peptides). Retro-inverso oligopeptidic compounds comprise D-amino acids in reverse (opposite) order to the parental or reference compound sequence. A retro-inverso analogue thus has reversed termini and reversed order of e.g. peptide bonds, while approximately maintaining the topology of the side chains as in the parental or reference sequence.

The oligopeptidic compound may include partial retro-inverso sequences, i.e. a domain or part of a domain may comprise a retro-inverso sequence.

By "oligopeptidic compound" is meant a compound which is composed of amino acids or equivalent subunits, which are linked together by peptide or equivalent bonds. Thus, the term "oligopeptidic compound" includes peptides and peptidomimetics.

By "equivalent subunit" is meant a subunit which is structurally and functionally similar to an amino acid. The backbone moiety of the subunit may differ from a standard amino acid, e.g. it may incorporate one or more nitrogen atoms instead of one or more carbon atoms. In preferred embodiments, the subunit comprises a standard amino acid backbone, i.e. the backbone of a standard or coded amino acid. In other words, preferably the subunit is an amino acid. However, the amino acid subunit may comprise a non-standard (non-coded) R-group.

By "peptidomimetic" is meant a compound which is functionally equivalent or similar to a peptide and which can adopt a three-dimensional structure similar to its peptide counterparts, but which is not solely composed of amino acids linked by peptide bonds. A preferred class of peptidomimetics are peptoids, i.e. N-substituted glycines. Peptoids are closely related to their natural peptide counterparts, but they differ chemically in that their side chains are appended to nitrogen atoms along the molecule's backbone, rather than to the α-carbons as they are in amino acids.

Peptidomimetics, particularly non-peptidic molecules may be generated through various processes, including conformational-based drug design, screening, focused library design and classical medicinal chemistry. Not only may oligomers of unnatural amino acids or other organic building blocks be used, but also carbohydrates, heterocyclic or macrocyclic compounds or any organic molecule that comprises structural elements and conformation that provides a molecular electrostatic surface that mimics the same properties of the 3-dimensional conformation of the peptide may be used by methods known in the art.

Thus the peptidomimetics may bear little or no resemblance to a peptide backbone. Peptidomimetics may comprise an entirely synthetic non-peptide form (e.g. based on a carbohydrate backbone with appropriate substituents) or may retain one or more elements of the peptide on which it is based, e.g. by derivatizing one or more amino acids or replacing one or more amino acids with alternative non-peptide components. Peptide-like templates include pseudo-peptides and cyclic peptides. Structural elements considered redundant for the function of the peptide may be minimized to retain a scaffold function only or removed where appropriate.

In preferred embodiments, peptidomimetics retain one or more peptide elements, i.e. more than one amino acid, although such amino acids may be replaced with a non-standard or structural analogue thereof. Amino acids retained in the sequences may also be derivatised or modified (e.g. labelled, glycosylated or methylated) as long as the functional properties of the oligopeptidic compound are retained. The peptidomimetics are referred to as being "derivable from" a certain polypeptide sequence. By this it is meant that the peptidomimetic is designed with reference to the peptide sequence defined above, such that it retains the structural features of the peptide which are essential for its function. This may be the particular side chains of the peptide, or hydrogen bonding potential of the structure. Such features may be provided by non-peptide components or one or more of the amino acid residues or the bonds linking said amino acid residues of the polypeptide may be modified so as to improve certain functions of the peptide such as stability or protease resistance, while retaining the structural features of the peptide which are essential for its function.

Examples of non-standard or structural analogue amino acids which may be used are D amino acids, amide isosteres (such as N-methyl amide, retro-inverse amide, thioamide, thioester, phosphonate, ketomethylene, hydroxymethylene, fluorovinyl, (E)-vinyl, methyleneamino, methylenethio or alkane), L-N methylamino acids, D-α methylamino acids, D-N-methylamino acids. Examples of non-conventional, i.e. non-coded, amino acids are listed in Table 2.

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
| | | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
| | | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |

TABLE 2-continued

| Non-conventional amino acid | Code | Non-conventional amino acid | Code |
|---|---|---|---|
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | L-O-methyl serine | Omser |
| | | L-O-methyl homoserine | Omhse |

In preferred embodiments, the oligopeptidic compound is a peptide. In particularly preferred embodiments, the oligopeptidic compound is a peptide consisting of L-amino acids. In yet a further preferred embodiment, the oligopeptidic compound is a peptide consisting of standard or coded L-amino acids.

As mentioned above, the oligopeptidic compound may comprise non-standard amino acids. Thus, in some embodiments the oligopeptidic compound may incorporate di-amino acids and/or β-amino acids. However, in preferred embodiments, at least the APIM motif domain, consists of α-amino acids. Most preferably, the oligopeptidic compound, i.e. all domains and optionally all flanking sequences, consists of α-amino acids.

As mentioned above, the oligopeptidic compound defined herein comprises more than 5 subunits, but the length of the construct will depend on the size of the uptake peptide sequence and on the number and size of other domains, e.g. linker domains, flanking sequences etc, if present. Thus, the prefix "oligo" is used to designate a relatively small number of subunits such as amino acids, i.e. less than 200, preferably less than 150, 100, 90, 80, 70, 60 or 50 subunits. The oligopeptidic compound of the invention may thus comprise more than 5 but no more than 200 subunits. Preferably, it comprises at least 12, 13, 14, 15, 16, 17, 18, 19, 20, 21, 22, 23, 24 or 25 subunits. Alternatively defined it comprises no more than 50, 45, 40, 35, 34, 33, 32, 31 or 30 subunits. Representative subunit ranges thus include 12-50, 12-45, 12-40, 12-35, 12-30, 12-25, 12-22, 12-20, 12-18 etc, 12-30 and 12-40 being preferred.

The nature of the subunits of the oligopeptidic compound outside of the APIM motif domain and the uptake peptide sequence is not critical, so the subunits outside of the motif may for example be those found in a native protein comprising the motif, such as hABH2, or they may be alanine residues or any other suitable residues.

Peptidomimetics typically have a longer half life within a patient's body, so they may be preferred in embodiments where a longer lasting effect is desired. This can help reduce the frequency at which the composition has to be re-administered. However, for bio-safety reasons a shorter half life may be preferred in other embodiments; in those embodiments peptides are preferred.

The oligopeptidic compound may form part of a larger unit, e.g. it may be fused to a polypeptide to form a recombinant fusion protein or attached to a scaffold to form a peptide aptamer. Thus, fusion proteins or aptamers incorporating the oligopeptidic compound may also find utility in the uses and methods of the invention, i.e. in some embodiments the agent may be a fusion protein or aptamer comprising the oligopeptidic compound defined above.

Yet further aspects include pharmaceutical compositions comprising the agent defined herein, e.g. comprising the oligopeptidic compound, fusion protein or aptamer, together with at least one pharmacologically acceptable carrier or excipient, wherein said composition is for use in the uses and methods of the invention defined below.

In a further aspect, a nucleic acid molecule encoding a peptide having or comprising (e.g. of) SEQ ID NO: 1, as defined above, is provided for use in the methods and uses of the invention. Alternatively viewed, the agent for use in the uses and methods of the invention may be a nucleic acid molecule encoding a peptide having or comprising (e.g. of) SEQ ID NO: 1, as defined above. In this respect, the nucleic acid molecule may not need to encode all of the domains of the oligopeptidic compound described above, e.g. the domain that facilitates the cellular uptake of the peptide. For instance, the nucleic acid molecule may be delivered into the cell by another mechanism, e.g. via a liposome. However, in a preferred embodiment, the invention provides a nucleic acid molecule encoding an oligopeptidic compound or construct (e.g. a peptide) as defined above, comprising a PCNA interacting motif (APIM motif) domain and a peptide sequence (domain) that facilitates the uptake of said peptide. Also provided is the complement of such a nucleic acid molecule for use in the uses and methods of the invention. Thus, in some embodiments the nucleic acid molecule may also encode one or more linker and/or signal sequences, as defined above.

The nucleic acid molecule of the invention comprises at least 15 nucleotides, preferably at least 36 nucleotides, and preferably no more than 800 nucleotides, more preferably no more than 700, 650, 600, 550, 500, 450, 400, 350, 300, 250, 200, 150, 100, 75 or 50 nucleotides. The nucleic acid molecule is preferably an isolated or synthetic molecule.

A further aspect relates to a vector comprising a nucleic acid molecule as defined herein for use in the uses and methods defined below. Preferably, the vector comprises a promoter sequence operably linked to the sequence encoding a peptide as defined above. The vector may also contain further elements typically found in a vector such as an origin of replication, a selectable marker such as antibiotic resistance, and/or a multiple cloning site. The vector may further be an expression vector, and may comprise further elements, e.g. transcriptional and/or translational control or regulatory elements for expression of the nucleic acid molecules. Such control elements, e.g. promoters, ribosome binding sites, enhancers, terminators etc. are well known and widely described in the art.

The vector may for example be a plasmid or a viral genome (or part thereof), preferably the viral gemone is from a virus selected from a retrovirus, an adenovirus and an adenovirus-associated virus. Thus, in some embodiments, the vector may be administered in the form of a virus comprising a vector containing a nucleic acid molecule encoding an oligopeptidic compound described above. Alternatively viewed, in some embodiments the vector may be a virus.

As mentioned above, there is provided a composition (e.g. a pharmaceutical composition) comprising an agent as defined herein for use in the methods and uses of the invention. Accordingly, said composition (e.g. a pharmaceutical composition) may comprise an oligopeptidic compound (including a fusion protein or aptamer) and/or nucleic acid molecule as defined herein and/or a vector as defined herein, together with at least one pharmacologically (or pharmaceutically) acceptable carrier or excipient.

The excipient may include any excipients known in the art, for example any carrier or diluent or any other ingredient or agent such as buffer, antioxidant, chelator, binder, coating, disintegrant, filler, flavour, colour, glidant, lubricant, preservative, sorbent and/or sweetener etc.

The excipient may be selected from, for example, lactic acid, dextrose, sodium metabisulfate, benzyl alcohol, polyethylene glycol, propylene glycol, microcrystalline cellulose, lactose, starch, chitosan, pregelatinized starch, calcium carbonate, calcium sulfate, dextrates, dextrin, dextrose, dibasic calcium phosphate dihydrate, tribasic calcium phosphate, magnesium carbonate, magnesium oxide, maltodextrin, mannitol, powdered cellulose, sodium chloride, sorbitol and/or talc.

The pharmaceutical composition may be provided in any form known in the art, for example as a tablet, capsule, coated tablet, liquid, suspension, tab, sachet, implant, inhalant, powder, pellet, emulsion, lyophilisate, effervescent, spray, salve, emulsion, balm, plaster or any mixtures thereof. It may be provided e.g. as a gastric fluid-resistant preparation and/or in sustained action form. It may be a form suitable for oral, parenteral, topical, rectal, genital, subcutaneous, transurethral, transdermal, intranasal, intraperitoneal, intramuscular and/or intravenous administration and/or for administration by inhalation.

In a representative embodiment, the pharmaceutical composition may be in a form suitable for liposomal administration, so preferably liposomes containing the pharmaceutical composition are provided. When liposomes are used, it may not be necessary to include a further excipient, so also provided are liposomes containing an agent, e.g. oligopeptidic compound, as defined herein, for use in the methods and uses of the invention.

As mentioned above, the agents defined herein, i.e. oligopeptidic compounds and nucleic acid molecules, and pharmaceutical compositions comprising said agents exhibit therapeutic properties in the treatment of various conditions or disorders, particularly disorders associated with cytokine release from non-proliferating immune cells in blood and infectious diseases or disorders or conditions exacerbated or caused by an infection.

As referred to herein a "disorder", "disease" or "condition" refers to an underlying pathological disturbance in a symptomatic or asymptomatic organism (subject) relative to a normal organism (subject), which may result, for example, from infection and/or an acquired or congenital genetic imperfection.

As set forth in the Examples, the inventors have determined that oligopeptidic compounds comprising a PCNA interacting motif can reduce cytokine release in blood, particularly from non-proliferating immune cells in the blood, e.g. monocytes. Cytokines may be released into blood on stimulation with a variety of substances and artificial/synthetic substances. For instance, LPS and poly I:C can be used to simulate or represent bacterial and viral infections, respectively. Excessive levels of pro-inflammatory cytokines are associated with a variety of diseases, e.g. infectious diseases, and it is expected that the agents defined herein may be effective in the treatment or prevention of said disorders. For example, the symptoms and complications associated with sepsis are thought to arise from the overproduction of pro-inflammatory cytokines in blood. The introduction or administration of the agents of the invention, e.g. intravenously, would therefore be expected to treat or prevent sepsis by reducing or inhibiting the release of said cytokines in blood. Thus, the agents described herein may be expected to find utility in the treatment or prevention of any disease or disorder associated with uncontrolled, undesirable or excessive cytokine release (e.g. hypercytokinemia) from immune cells in blood, e.g. particularly uncontrolled, undesirable or excessive release of one or more pro-inflammatory cytokines.

The inventors have demonstrated that some of the proteins involved in the toll-like receptor signal transduction pathways, which as discussed above are involved in the regulation of immune responses, comprise a PCNA interacting motif. Accordingly, it is thought that the oligopeptidic compounds disclosed herein are able to interfere with the interaction of said proteins with PCNA, e.g. in non-proliferating cells in blood, thereby inhibiting the release of pro-inflammatory cytokines into blood. Accordingly, the oligopeptidic compounds disclosed herein find particular utility in the treatment or prevention of a condition or disorder associated with cytokine release from non-proliferating immune cells in blood, particularly conditions or disorders associated with excessive, undesirable or uncontrolled pro-inflammatory cytokine release from non-proliferating immune cells in blood, e.g. an infectious disease or infection or a disease or condition exacerbated or caused by an infection.

In other words, the oligopeptidic compounds disclosed herein find particular utility in the treatment or prevention of excessive, undesirable or uncontrolled pro-inflammatory cytokine from non-proliferating immune cells in blood in a subject, e.g. a subject with an infectious disease or infection or a disease or condition exacerbated or caused by an infection.

Whilst not wishing to be bound by theory, it is thought that the effect of APIM peptides on cytokine release may be dependent on the strength of the interaction between the APIM peptide and its polypeptide target(s). Thus, as different APIM peptides may interact with target polypeptides with different affinities, it is thought that the dose of any one APIM peptide may determined independently. However, the dose for any APIM peptide may be determined as a matter of routine. In general, a suitable dose may be defined as a dose that does not induce apoptosis, i.e. an apoptosis non-inducing dose, which may be deduced by analysing the minimum concentration of oligopeptidic compound required to induce apopotosis in a cell, e.g. using a standard in vitro assay.

Since the therapeutic applications and utilities of the present invention may generally involve inhibiting the release of cytokines from non-proliferating immune cells in blood, any non-proliferating immune cells in blood may be targeted in the therapies and utilities disclosed and encompassed herein. Such non-proliferating immune cells may include healthy or diseased cells, and particularly cells that are involved in cytokine release. For example, such cells may include in particular monocytes, e.g. cells that display the cell surface receptor CD14 and/or the cell surface receptor CD16.

The cells to be targeted in the therapies and utilities disclosed and encompassed herein are particularly associated with the release of pro-inflammatory cytokines and chemokines. Thus, in some embodiments, in addition, or as an alternative, to the cell surface receptors displayed, the non-proliferating immune cells, e.g. monocytes, may be characterised or defined by their capacity to release (e.g. secrete) any one or more of the cytokines or chemokines selected from TNFα, IL1RA, IL-1β, IL-2, IL-4, IL-5, IL-6, IL-7, IL-8 (CXCL8), IL-9, IL-10, IL-12, IL-13, IL-15, IL-17, CCL11, BasicFGF, G-CSF, GM-CSF, INFγ, CXCL10, CCL2, CCL3, CCL4, PDGF-β, CCLS and VEGF.

Thus, in some embodiments, the non-proliferating immune cells are monocytes, particularly monocytes that display the cell surface receptor CD14 and/or the cell surface receptor CD16. In some embodiments the non-proliferating immune cells are monocytes that are capable of releasing (e.g. monocytes that secrete or release) any one or more of the cytokines or chemokines selected from TNFα, IL1RA, IL-1β, IL-2, IL-4, IL-5, IL-6, IL-7, IL-8 (CXCL8), IL-9, IL-10, IL-12, IL-13, IL-15, IL-17, CCL11, BasicFGF, G-CSF, GM-CSF, INFγ, CXCL10, CCL2, CCL3, CCL4, PDGF-β, CCLS and VEGF.

The term "treatment" as used herein refers broadly to any effect or step (or intervention) beneficial in the management of a clinical condition or disorder and thus includes both therapeutic and prophylactic treatments. Treatment may include reducing, alleviating, ameliorating, slowing the development of, or eliminating the condition or one or more symptoms thereof, which is being treated, relative to the condition or symptom prior to the treatment, or in any way improving the clinical status of the subject. A treatment may include any clinical step or intervention which contributes to, or is a part of, a treatment programme or regimen. A prophylactic treatment may include delaying, limiting, reducing or preventing the condition or the onset of the condition, or one or more symptoms thereof, for example relative to the condition or symptom prior to the prophylactic treatment. Prophylaxis thus explicitly includes both absolute prevention of occurrence or development of the condition, or symptom thereof, and any delay in the onset or development of the condition or symptom, or reduction or limitation on the development or progression of the condition or symptom.

Treatment according to some aspects of the invention thus includes reducing or lowering the levels or amounts of one or more cytokines released into the blood from non-proliferating immune cells, e.g. in response to an infection, such as a microbial, viral or parasitic infection. Treatment also includes the prevention or inhibition of the release into the blood of one or more cytokines from non-proliferating immune cells, e.g. the prevention or inhibition of the release of cytokines above a level or amount considered to be within a normal range. Thus, in some aspects of the invention, treatment may be viewed as maintaining the level or amount of one or more cytokines in blood within a normal range. A normal range may depend on the subject being treated. Thus, for instance, a normal range may be the amount or level of said one or more cytokines in a healthy subject. Alternatively, a normal range may be the average or typical level or amount of said one or more cytokines in subjects suffering from a particular disease or condition as defined herein, e.g. an infection. Hence, the treatment may involve reducing or lowering an excessive, unwanted or above normal level or amount of one or more cytokines that have been released into blood from non-proliferating immune cells. Treatment may also encompass the prevention or inhibition of the release of unwanted, excessive or above normal amounts or levels of one of more cytokines from non-proliferating immune cells in blood. The term "treatment" does not necessarily imply cure or complete abolition or elimination of unwanted, excessive or above normal cytokine release from non-proliferating immune cells in blood.

The term "disorder or condition associated with cytokine release from non-proliferating immune cells in blood" is used broadly herein to include any disorder or condition which involves increased, undesired, unwanted or excessive amounts or levels of cytokines in blood as a result of the release of cytokines from non-proliferating immune cells. Thus included are not only conditions in which the levels of one or more cytokines is increased in blood, for example relative to normal or healthy cytokine levels, or cytokine levels in the absence of the condition in question (e.g. compared or relative to a healthy or control subject, or compared or relative to cytokine levels taken from healthy or unaffected tissue in the same subject), but also conditions in which level of cytokines is not increased (or not greatly or significantly increased) over normal, but in which the cytokine level that occurs is unwanted or undesired, whether generally or in a particular context. This may include for example an unwanted or undesired release of cytokines which may occur in a "normal" response, e.g. an immune response or an inflammatory response etc. (in other words a "normal" response which may occur in a particular (e.g. normal) context, but which may nonetheless be unwanted). Such an unwanted cytokine release response may for example be the release of cytokines resulting in an unwanted inflammatory response, or an unwanted immune response such as an autoimmune response, an allergic reaction, rejection of a transplanted organ or tissue etc.

In some embodiments the disorder or condition associated with cytokine release from non-proliferating immune cells in blood may be characterised as hypercytokinemia, which may be viewed as an unwanted or excessive release, or increase in the level or amount, of one or more cytokines in blood. In some embodiments, hypercytokinemia may be a global cytokine release, comprising the unwanted (e.g. uncontrolled, excessive or above normal) release or increase of multiple cytokines, e.g. an increase in the level of at least 2 cytokines defined herein, such as an increase of at least 3, 4, 5, 6, 7, 8, 9, 10 or more cytokines as defined herein. A release or increase in multiple cytokines may be termed a "cytokine storm". Accordingly, the disorder or condition to be treated may be a condition that results in, e.g. can lead to, hypercytokinemia, such as a cytokine storm, e.g. sepsis or malaria. In other embodiments, hypercytokinemia may be associated with the release of specific cytokines in blood, e.g. an increase in a particular cytokine. For instance, the excessive or increased release of interferon-β(INF-β) in response to a viral infection, e.g. an acute or persistent (chronic) virus infection, can ultimately lead to a number of inflammatory or autoimmune diseases, such as systemic lupus erythematosus, anaemia and other autoimmune diseases.

Thus, in some embodiments, the agent disclosed herein may be used as a preventative, prophylactic or protective agent against an unwanted or excessive (above normal) cytokine release (i.e. hypercytokinemia) or to maintain cytokine levels or amounts within a normal range, e.g. may be useful in treatment via the prevention of disorder or condition (or the exacerbation of a disorder or condition) associated with cytokine release from non-proliferating immune cells in blood. In some embodiments, the agent described herein may be used as a direct therapeutic agent, e.g. to treat a disorder or condition associated with hypercytokinemia, i.e. to facilitate the reduction in the levels or amounts of said unwanted or excessive (above normal) one or more cytokines in a subject in which a disorder or condition has already progressed to hypercytokinemia. Thus, in some embodiments the disorder or condition associated with cytokine release from non-proliferating immune cells in blood may be viewed as a disorder or condition that results in (may lead to) hypercytokinemia or a disorder or condition that is associated with hypercytokinemia. Alternatively viewed, the disorder or condition associated with cytokine release from non-proliferating immune cells in blood may be viewed as hypercytokinemia resulting from an associated disorder or condition, e.g. hypercytokinemia resulting from an infection.

An unwanted or excessive release (e.g. uncontrolled or above normal) or increase in the level or amount of one or more cytokines in blood may be defined as an increase in one or more cytokines by at least 10% relative to normal levels. As mentioned above, normal levels may be defined, e.g. relative to the levels in the blood of a healthy subject or the levels in another tissue of the subject to be treated. In some embodiments the normal levels may be defined relative to the average or typical levels in a subject with the disorder or condition to be treated or prevented, e.g. the average or typical levels in a subject at an early stage of the disorder or condition, i.e. a condition where progression of the condition will result in an undesirable release of one or more cytokines. In some embodiments, the unwanted or excessive release or increase may be an increase by at least 15, 20, 25, 30, 35, 40, 45 or 50%, e.g. at least 60, 70, 80, 90 or 100%. In still further embodiments, it may be an increase of at least 2, 3, 4, 5, 6, 7, 8, 9 or 10 fold of normal levels, such as at least 15, 20, 30, 40, 50 or 100 fold normal levels. It will be evident that the range of the increase will, to some extent, be dependent on the nature of the one or more cytokines in question. Hence, the above values may be applied to a single cytokine or the increase may be measured as an average of the total increase, i.e. where more than one cytokine is increased.

A reduction of unwanted or excessive (e.g. uncontrolled or above normal) levels or amounts of one or more cytokines in blood may be defined as a decrease in one or more cytokines by at least 10%, e.g. relative to the levels prior to treatment. In some embodiments, the unwanted or excessive levels or amounts may be decreased by at least 15, 20, 25, 30, 35, 40, 45 or 50%, e.g. at least 60, 70, 80, 90 or 100%. In still further embodiments, it may be a decrease of at least 2, 3, 4, 5, 6, 7, 8, 9 or 10 fold of the amounts or levels prior to treatment, such as at least 15, 20, 30, 40, 50 or 100 fold decrease. In some embodiments, the decrease may be a reduction of the amount or level to within about 25% or less of the normal level, wherein the normal level is as defined above. Thus, the decrease may be a reduction to within about 20, 15, 10, 5% or less of the normal level. It will be evident that the range of the decrease or reduction will, to some extent, be dependent on the nature of the one or more cytokines in question. Hence, the above values may be applied to a single cytokine or the decrease or reduction may be measured as an average of the total decrease, i.e. where the level or amount of more than one cytokine is decreased.

In some embodiments, the agent or composition results in a reduction of cytokines and/or chemokines selected from any one or more of TNFα, IL1RA, IL-1β, IL-2, IL-4, IL-5, IL-6, IL-7, IL-8 (CXCL8), IL-9, IL-10, IL-12, IL-13, IL-15, IL-17, CCL11, BasicFGF, G-CSF, GM-CSF, INFγ, CXCL10, CCL2, CCL3, CCL4, PDGF-β, CCL5 and VEGF. In some embodiments, the agent or composition results in a reduction of one or more of TNFα, IL1RA, IL-1β, IL-2, IL-4, IL-6, IL-8 (CXCL8), IL-9, IL-10, IL-17, G-CSF, INFγ, CXCL10, CCL2, CCL3 and CCL4 (e.g. in a disease or condition associated with a bacterial infection). In further embodiments, the agent or composition results in a reduction of one or more of TNFα, IL1RA, IL-1β, IL-2, IL-4, IL-6, IL-8 (CXCL8), IL-9, IL-17, G-CSF and INFγ(e.g. in a disease or condition associated with a bacterial infection). In some more particular embodiments, the agent or composition results in a reduction of one or more of IFNγ, IL-1RA, IL-2, 4, and 9 (e.g. in a disease or condition associated with a bacterial infection). In yet further embodiments, the agent or composition results in a reduction of one or more of TNFα, IL-1β, IL-8 (CXCL8), CXCL10, CCL2, CCL3 and CCL4 (e.g. in a disease or condition associated with a viral infection). In some embodiments, the agent or composition results in a reduction of one or more of TNFα, IL-8 (CXCL8), CXCL10, CCL2, CCL3 and CCL4 (e.g. in a disease or condition associated with a viral infection). In some more particular embodiments the agent or composition results in a reduction of one or more of IL-1RA, CCL2, 3, and 4 (e.g. in a disease or condition associated with a viral infection).

The identification, characterisation, diagnosis and/or progression of the disorder or condition to be treated and/or the efficacy of the treatment may be facilitated by the measurement of one or more cytokines in the blood. Various assays for measuring cytokines are well known in the art and standard kits are commercially available. Typical methods rely on immunoassays, e.g. ELISAs, RIAs, etc., and may be performed using a variety of blood samples, such as serum, plasma or whole blood.

Thus, in a general embodiment the invention the disorder or condition associated with cytokine release from non-proliferating immune cells in blood is an inflammatory disease (e.g. inflammatory arthritis, psoriatic arthritis, rheumatoid arthritis, inflammatory bowel disease) or an autoimmune disease (e.g. systemic lupus erythematosus). Accordingly, the invention may be seen to provide an agent or composition as defined herein for use in the treatment or prevention of an inflammatory or autoimmune disease or a method for treating or preventing an inflammatory or autoimmune disease comprising administering (particularly administering an effective amount of) an agent or composition as defined herein to a subject in need thereof. Alternatively viewed, the invention may be seen to provide an agent or composition as defined herein for use in the treatment or prevention of hypercytokinemia in a subject with an inflammatory or autoimmune disease or a method of treating or preventing hypercytokinemia in a subject with an inflammatory or autoimmune disease comprising administering (particularly administering an effective amount of) an agent or composition as defined herein to a subject in need thereof.

In some more particular embodiments of the invention, the disorder or condition associated with cytokine release from non-proliferating immune cells in blood is an infection or infectious disease, i.e. the agent described herein may be for use in treating an infection or infectious disease or the invention may be seen to provide a method of treating a subject with an infection or infectious disease comprising administering (particularly administering an effective amount of) an agent as described herein to a subject in need thereof. Alternatively viewed, the invention may provide an agent or composition as described herein for use in the treatment or prevention of hypercytokinemia in a subject with an infection or infectious disease or a method of treating or preventing hypercytokinemia in a subject with an infection or infectious disease comprising administering (particularly administering an effective amount of) an agent or composition as described herein to a subject in need thereof. The invention also extends to the use of the agent in the manufacture of a medicament for the above utilities.

An "infection" or "infectious disease" may be defined as a disease, condition or disorder caused by the invasion of a subject, e.g. one or more organs or tissues of said subject, by one or more disease-causing organisms and their subsequent multiplication. In some instances, an infection or infectious disease may be characterised by the reaction of the subject (e.g. organ or tissues of said subject) to said organisms and, in some cases, to the toxins produced by said organisms. An infection or infectious disease may be a microbial, viral or parasitic infection and may be local or systemic. A microbial infection may be any bacterial or fungal infection, i.e. caused by a bacterium or fungus. In particularly preferred embodiments, the disease, condition or disorder caused by a viral infection is not a viral-induced hyperproliferative disease, such as warts and EBV-induced disease (e.g. infectious mononucleosis), scar formation and the like.

In some embodiments, the infectious disease or infection may be a bacterial infection or disease. Examples of bacteria that cause infections or infectious diseases that may be treated or prevented by the agents or compositions described herein may be gram positive or gram negative, or gram test non-responsive. They may be aerobic or anaerobic bacteria. For instance, the bacteria may be from any of the genus *Achromobacter, Acinetobacter, Actinobacillus, Aeromonas, Agrobacterium, Alcaligenes, Alteromonas, Bacillus, Bacteroides, Bartonella, Borrelia, Bordetella, Brucella, Burkholderia, Campylobacter, Cardiobacterium, Chlamydia, Chlamydophila,* Chromobacterium, Chyseobacterium, *Chryseomonas, Citrobacter, Clostridium, Comamonas, Corynebacterium, Coxiella, Cryptobacterium, Edwardsiella, Eikenella, Enterobacter, Enterococcus, Erwinia, Helicobacter, Kingella, Klebsiella, Lactobacillus, Lactococcus, Legionella,* Leptospira, Leptotrichia, *Leuconostoc, Listeria,* Listonella, Mobiluncus, *Moraxella, Morganella, Mycobacterium, Mycoplasma, Neisseria, Nocardia, Nocardiopsis, Pantoea, Parachlamydia, Pasteurella, Peptococcus, Peptostreptococcus, Prevotella, Propionibacterium, Proteus, Providencia, Pseudomonas, Ralstonia, Rickettsia, Salmonella, Shewenella, Shigella, Sphingobacterium, Sphingomonas, Staphylococcus, Stenotrophomonas, Streptobacillus, Streptococcus, Streptomyces,* Treponem and *Yersinia,* such as *Acinetobacter, Bacillus, Burkholderia, Chlamydia, Clostridium, Helicobacter, Staphylococcus,* *Streptococcus, Pseudomonas, Legionella, Listeria, Mycobacterium, Proteus, Klebsiella, Fusobacterium* or other enteric or coliform bacteria.

Thus, for instance, the infection or infectious disease may be caused by a gram-positive bacteria such as, *M. tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies paratuberculosis, *Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides, Actinomyces israelii, Propionibacterium acnes,* and *Enterococcus* species.

In other embodiments, the infection or infectious disease may be caused by a gram-negative bacteria such as *Clostridium tetani, Clostridium perfringens, Clostridium botulinum, Pseudomonas aeruginosa, Vibrio cholerae, Actinobacillus pleuropneumoniae, Pasteurella haemolytica, Pasteurella multocida, Legionella pneumophila, Salmonella typhi, Brucella abortus, Chlamydi trachomatis, Chlamydia psittaci, Coxiella burnetti, Escherichia coli, Neiserria meningitidis, Neiserria gonorrhea, Haemophilus influenzae, Haemophilus ducreyi, Yersinia pestis, Yersinia enterolitica, Escherichia coli, E. hirae, Burkholderia cepacia, Burkholderia pseudomallei, Francisella tularensis, Bacteroides fragilis, Fusobascterium nucleatum,* and *Cowdria ruminantium.*

Thus, a disorder or condition associated with cytokine release from non-proliferating immune cells in blood may be the result of, e.g. caused by, a bacterial infection or infectious disease, such as sepsis.

In some embodiments, a bacterial infection may be associated with a particular disorder or condition, i.e. subjects suffering from a particular disorder or condition may be particularly susceptible to one or more bacterial infections. For instance, it is common for subjects with cystic fibrosis to suffer from chronic *Pseudomonas* infections. Thus, invention may be seen to extend to an agent or composition as defined herein for use in treating a disease or condition (e.g. hypercytokinemia) exacerbated or caused by an infection, e.g. bacterial pneumonia, cystic fibrosis, gastric ulcers, bacterial meningitis, Legionellosis (Legionnaires' disease), Legionellosis (Pontiac fever), Pertussis (Whooping cough), *Salmonellosis, Tuberculosis* etc.

Thus, in some embodiments a condition or disease caused by an infection is sepsis, which is a condition that results from a severe infection. Accordingly, the invention may be seen to provide an agent or composition as defined herein for use in the treatment or prevention of sepsis or a method for treating or preventing sepsis comprising administering (particularly administering an effective amount of) an agent or composition as defined herein to a subject in need thereof. Alternatively viewed, the invention may be seen to provide an agent or composition as defined herein for use in the treatment or prevention of hypercytokinemia in a subject with sepsis or a method of treating or preventing hypercytokinemia in a subject with sepsis comprising administering (particularly administering an effective amount of) an agent or composition as defined herein to a subject in need thereof.

In some embodiments a condition or disease exacerbated by an infection is cystic fibrosis, which is a condition that is commonly associated with a chronic *Pseudomonas* infection. Accordingly, the invention may be seen to provide an agent or composition as defined herein for use in the treatment of cystic fibrosis (or more particularly, treatment of a subject with cystic fibrosis, e.g. suffering from an infection, i.e. alleviating the one or more symptoms of a subject suffering from cystic fibrosis). Thus, the invention provides a method for treating cystic fibrosis (or more particularly, treating a subject with cystic fibrosis, e.g. suffering from an infection, i.e. alleviating the one or more symptoms of a subject suffering from cystic fibrosis) comprising administering (particularly administering an effective amount of) an agent or composition as defined herein to a subject in need thereof.

In some embodiments, the infectious disease or infection may be a fungal infection or disease. In some aspects of the invention the fungus may be a mold or yeast, preferably a yeast. The fungus may be selected from any one or more of a Dermatophyte, *Aspergillus* sp. (such as *Aspergillus fumigatus, Aspergillus nigricans* or *flavescens*), Zygomycota sp., *Fusarium* sp., *Trichophyton* sp,. Basidiobolus ranarum, Piedraia sp. (such as Piedraia hortae), *Blastomyces dermatitidis, Candida* sp. (such as *Candida albicans*), *Chrysosporium, Coccidioides* sp. (such as *Coccidioides immitis* and *Coccidioides posadasii*), Conidiobolus sp. (such as Conidiobolus coronatus and Conidiobolus incongruus), *Cryptococcus* sp. (such as *Cryptococcus gattii* and *Cryptococcus neoformans*), *Histoplasma* sp. (such as *Histoplasma* farciminosum and *Histoplasma capsulatum*), *Exserohilum rostratum, Cladosporium* sp., *Saccharomyces* sp., *Lacazia loboi, Paracoccidioides brasiliensis, Penicillium mameffei, Pneumocystis jirovecii, Sporothrix schenckii, Diheterospora zeaspora, Absidia corymbifera, Apophysomyces elegans, Mucor indicus, Rhizomucor pusillus, Rhizopus oryzae,* Cunninghamella bertholletiae, Cokeromyces *recurvatus,* Saksenaea vasiformis, Syncephalastrum racemosum, and Conidiobolus sp. (such as Conidiobolus coronatus and Conidiobolus incongruus).

By way of a representative example, fungi that cause infections or infectious diseases that may be treated or prevented by the agents and compositions described herein include fungi from the genera *Candida, Aspergillus, Pneumocystis, Penicillium* and *Fusarium*. Representative fungal species include, but are not limited to, *Candida albicans, Candida dubliniensis, Cryptococcus neoformans, Histoplama capsulatum, Aspergillus fumigatus, Coccidiodes immitis, Paracoccidioides brasiliensis, Blastomyces* dermitidis, Pneomocystis *Penicillium* mameffi, and *Alternaria* alternate. etc.

A variety of environmental and physiological conditions can contribute to the development of fungal diseases and infections. Fungal infections (mycoses) commonly start in the lungs or on the skin, e.g. a fungal infection (a mycosis) may result from the inhalation of fungal spores or localized colonization of the skin may initiate persistent infections. Thus, a disease or condition exacerbated or caused by a fungal infection (mycosis) to be treated or prevented by the agent or composition of the invention may be in any tissue or organ of the subject to be treated, such as the lungs (including the respiratory tract), skin (including wounds), mouth, ear, eye etc. Hence, the fungal infection may be a respiratory infection, skin infection, ear infection, eye infection etc.

Thus, a disorder or condition associated with cytokine release from non-proliferating immune cells in blood may be the result of, e.g. caused by, a fungal infection or infectious disease, caused by any one or more of the fungi (or fungi from one or more the genera) described above.

Thus, more generally, a disorder or condition associated with cytokine release from non-proliferating immune cells in blood may be the result of, or exacerbated by, a microbial infection, such as a microbe selected from any one or more of the genera Actinebacter, *Citrobacter, Enterobacter, Escherichia,* Hafnia, *Serratia, Yersinia, Peptostreptococcus, Bacteroides, Pseudomonas, Legionella, Staphylococcus, Enterococcus, Streptococcus, Klebsiella, Candida, Proteus, Burkholderia, Fusobacterium* and *Mycobacterium,* for instance, *Staphylococcus aureus, Staphylococcus epidermidis, Legionella pneumophila, Candida albicans, Pseudomonas aeruginosa, Burkholderia cepacia* and *Streptococcus Pyogenes.*

In some embodiments, the infectious disease or infection may be a viral infection or disease. Examples of viruses that cause infections or infectious diseases that may be treated or prevented by the agents described herein include Australian bat lyssavirus, Banna virus, Barmah forest virus, Bunyamwera virus, Bunyavirus La Crosse, Bunyavirus snowshoe hare, Cercopithecine herpesvirus, Chikungunya virus, Crimean-Congo hemorrhagic fever virus, Dengue virus, Dhori virus, Dugbe virus, Duvenhage virus, Eastern equine encephalitis virus, Ebolavirus, Echovirus, Encephalomyocarditis virus, European bat lyssavirus, Hantaan virus, Hendra virus, Hepatitis A virus, Hepatitis B virus, Hepatitis C virus, Hepatitis E virus, Hepatitis delta virus, Human herpesvirus 1, Human adenovirus, Human astrovirus, Human coronavirus, Human cytomegalovirus, Human enterovirus 68-70, Human herpesvirus 2, Human herpesvirus 6, Human herpesvirus 7, Human herpesvirus 8, Human immunodeficiency virus, Human parainfluenza, Human parvovirus B19, Human respiratory syncytial virus, Human rhinovirus, Human SARS coronavirus, Human T-lymphotropic virus, Human torovirus, Influenza A virus, Influenza B virus, Influenza C virus, Isfahan virus, JC polyomavirus, Japanese encephalitis virus, Junin arenavirus, KI Polyomavirus, Kunjin virus, Lagos bat virus, Lake Victoria marburgvirus, Langat virus, Lassa virus, Lordsdale virus, Louping ill virus, Lymphocytic choriomeningitis virus, Machupo virus, Mayaro virus, Measles virus, Mengo encephalomyocarditis virus, Mokola virus, Molluscum contagiosum virus, Monkeypox virus, Mumps virus, Murray valley encephalitis virus, New York virus, Nipah virus, Norwalk virus, O'nyong-nyong virus, Orf virus, Oropouche virus, Pichinde virus, Poliovirus, Punta toro phlebovirus, Puumala virus, Rabies virus, Rift valley fever virus, Ross river virus, Rotavirus A, Rotavirus B, Rotavirus C, Rubella virus, Sagiyama virus, Sandfly fever sicilian virus, Sapporo virus, Semliki forest virus, Seoul virus, Sindbis virus, Southampton virus, St. louis encephalitis virus, Tick-borne powassan virus, Toscana virus, Uukuniemi virus, Varicella-zoster virus, Variola virus, Venezuelan equine encephalitis virus, Vesicular stomatitis virus, Western equine encephalitis virus, West Nile virus and Yellow fever virus.

By way of a representative example, viruses that cause infections or infectious diseases that may be treated or prevented by the agents and compositions described herein may be particularly selected from any one or more of Dengue virus, Ebolavirus, Echovirus, Encephalomyocarditis virus, Hepatitis A virus, Hepatitis B virus, Hepatitis C virus, Hepatitis E virus, Hepatitis delta virus, Human herpesvirus 1, Human adenovirus, Human astrovirus, Human coronavirus, Human cytomegalovirus, Human enterovirus 68-70, Human herpesvirus 2, Human herpesvirus 6, Human herpesvirus 7, Human herpesvirus 8, Human immunodeficiency virus, Human parainfluenza, Human parvovirus B19, Human respiratory syncytial virus, Human rhinovirus, Human SARS coronavirus, Human T-lymphotropic virus, Human torovirus, Influenza A virus, Influenza B virus, Influenza C virus, Japanese encephalitis virus, Measles virus, Mumps virus, Rotavirus A, Rotavirus B, Rotavirus C, Rubella virus, West Nile virus and Yellow fever virus.

However, as mentioned above, in particularly preferred embodiments, the viral infection is not an infection that causes or results in viral-induced hyperproliferative disease, such as warts and EBV-induced disease (e.g. infectious mononucleosis), scar formation and the like.

Thus, a disorder or condition associated with cytokine release from non-proliferating immune cells in blood may be the result of, e.g. caused by, a viral infection or infectious disease, such as AIDS/HIV, Dengue fever, measles, mumps, rubella, influenza and hepatitis.

Accordingly, the invention may be seen to provide an agent or composition as defined herein for use in the treatment of a viral infection, e.g. AIDS/HIV, Dengue fever, measles, mumps, rubella, influenza or hepatitis (or the treatment of the symptoms of a viral infection, e.g. AIDS/HIV, Dengue fever, measles, mumps, rubella, influenza or hepatitis) or a method for treating a viral infection, e.g. AIDS/HIV, Dengue fever, measles, mumps, rubella, influenza or hepatitis (or treating a subject suffering from a viral infection, e.g. AIDS/HIV, Dengue fever, measles, mumps, rubella, influenza or hepatitis) comprising administering (particularly administering an effective amount of) an agent or composition as defined herein to a subject in need thereof. Alternatively viewed, the invention may be seen to provide an agent or composition as defined herein for use in the treatment or prevention of hypercytokinemia in a subject with a viral infection, e.g. AIDS/HIV, Dengue fever, measles, mumps, rubella, influenza or hepatitis, or a method of treating or preventing hypercytokinemia in a subject with a viral infection, e.g. AIDS/HIV, Dengue fever, measles, mumps, rubella, influenza or hepatitis, comprising administering (particularly administering an effective amount of) an agent as defined herein to a subject in need thereof.

In some embodiments, the infectious disease or infection may be a parasitic infection or disease. Examples of parasites that cause infections or infectious diseases that may be treated or prevented by the agents and compositions described herein include *Plasmodium* sp., such as *Plasmodium falciparum, Plasmodium knowlesi, Plasmodium vivax, Plasmodium berghei* and *Plasmodium yoelii* infections, protozoa such as *Toxoplasma* species e.g. *Toxoplasma Trypanosoma brucei, Trypanosoma cruzi, Leishmania* species such as *Leishmania major, Schistosoma* such as *Schistosoma mansoni* and *Entamoeba histolytica*.

Thus, a disorder or condition associated with cytokine release from non-proliferating immune cells in blood may be the result of, e.g. caused by, a parasitic infection or infectious disease, such as malaria, toxoplasmosis, trypanosomiasis and schistosomiasis.

In further embodiments a condition or disease caused by an infection is a parasitic infection, such as malaria, which is a condition that results from a parasitic infection, e.g. *Plasmodium* infection, such as *Plasmodium falciparum, Plasmodium knowlesi, Plasmodium vivax, Plasmodium berghei* or *Plasmodium yoelii* infection. Accordingly, the invention may be seen to provide an agent or composition as defined herein for use in the treatment of a parasitic infection, e.g. malaria, toxoplasmosis, trypanosomiasis or schistosomiasis, (or the treatment of the symptoms of a parasitic infection, e.g. malaria, toxoplasmosis, trypanosomiasis or schistosomiasis) or a method for treating a parasitic infection, e.g. malaria, toxoplasmosis, trypanosomiasis or schistosomiasis, (or treating a subject suffering from a parasitic infection, e.g. malaria, toxoplasmosis, trypanosomiasis or schistosomiasis) comprising administering (particularly administering an effective amount of) an agent or composition as defined herein to a subject in need thereof. Alternatively viewed, the invention may be seen to provide an agent or composition as defined herein for use in the treatment or prevention of hypercytokinemia in a subject with a parasitic infection, e.g. malaria, toxoplasmosis, trypanosomiasis or schistosomiasis, or a method of treating or preventing hypercytokinemia in a subject with a parasitic infection, e.g. malaria, toxoplasmosis, trypanosomiasis or schistosomiasis, comprising administering (particularly administering an effective amount of) an agent as defined herein to a subject in need thereof.

In yet further embodiments, the disorder or condition associated with cytokine release from non-proliferating immune cells in blood is graft versus host disease (GVHD), i.e. an immune response associated with the transplantation of cells, tissues or organs to a recipient from a genetically non-identical donor of the same species. The transplant is may be viewed as an allograft, allogeneic transplant or homograft. In some embodiments of the invention the transplant may be a stem cell and/or bone marrow transplant. Accordingly, the agent or composition may be for use in treating or preventing graft versus host disease or the invention may be seen to provide a method of treating a subject with graft versus host disease comprising administering (particularly administering an effective amount of) an agent or composition as defined herein to a subject in need thereof. Alternatively viewed, the invention may provide an agent or composition as defined herein for use in the treatment or prevention of hypercytokinemia in a subject with a graft versus host disease or a method of treating or preventing hypercytokinemia in a subject with a graft versus host disease comprising administering (particularly administering an effective amount of) an agent or composition as defined herein to a subject in need thereof. The invention also extends to the use of the agent in the manufacture of a medicament for the above utilities.

In yet further embodiments, the disorder or condition associated with cytokine release from non-proliferating immune cells in blood is trauma, e.g. trauma caused by injury (i.e. a physical wound or injury, such as a fracture or blow, e.g. a polytrauma (affecting multiple sites), a head trauma, chest trauma, abdominal trauma or extremity trauma) or surgery. In some cases, the injury or wound resulting from trauma may be a burn. A burn may be caused by heat, electricity, chemicals, friction or radiation. In some embodiments, the burn is a partial-thickness or second-degree burn (comprising damage to some of the underlying skin layers). In some embodiments, the burn is a full-thickness or third-degree burn (comprising damage that extends to all layers of the skin). In some embodiments, the burn is a fourth-degree burn, which additionally involves injury to deeper tissues, such as muscle or bone.

Accordingly, the agent or composition may be for use in treating trauma (e.g. caused by injury or surgery) or the invention may be seen to provide a method of treating a subject with trauma (e.g. caused by injury or surgery) comprising administering (particularly administering an effective amount of) an agent or composition as defined herein to a subject in need thereof. Alternatively viewed, the invention may provide an agent or composition as defined herein for use in the treatment or prevention of hypercytokinemia in a subject with trauma (e.g. caused by injury or surgery) or a method of treating or preventing hypercytokinemia in a subject with trauma (e.g. caused by injury or surgery) comprising administering (particularly administering an effective amount of) an agent or composition as defined herein to a subject in need thereof. The invention also extends to the use of the agent in the manufacture of a medicament for the above utilities.

In some subjects hypercytokinemia, which may be a result of a disease or condition as described herein, such as sepsis, malaria, graft versus host disease (GVHD) etc. can result in, or increase the risk of, multiple organ dysfunction syndrome (MODS), which is also known as multiple organ failure (MOF) or multisystem organ failure (MSOF). Thus, in some embodiments the invention provides an agent or composition as defined herein for use in the treatment or prevention of MODS or a method for treating or preventing MODS comprising administering (particularly administering an effective amount of) an agent or composition as defined herein to a subject in need thereof. Alternatively viewed, the invention may be seen to provide an agent or composition as defined herein for use in the treatment or prevention of hypercytokinemia in a subject with MODS or a method of treating or preventing hypercytokinemia in a subject with MODS comprising administering (particularly administering an effective amount of) an agent or composition as defined herein to a subject in need thereof.

In some embodiments, the agent or composition as defined herein may be useful for the prevention of hypercytokinemia in a subject suffering from, or at risk from, any of the conditions mentioned above.

As noted above, in some embodiments the agent or composition as defined herein is used in combination with one or more additional active agents, e.g. an immunosuppressive compound, an anti-inflammatory compound, antimicrobial compound, or steroid (e.g. a corticosteroid) or a kinase inhibitor (such as a p38 MAPK inhibitor or a class I PI3K inhibitor), in order to enhance or complement the effect of the agent or composition defined herein, e.g. to treat symptoms of the disease or condition that are not directly affected by the agent or composition of the invention. However, in some embodiments, the agent as defined herein may be used alone, i.e. as the only active agent in a composition and/or medicament.

In some embodiments, the additional active agent is an immunosuppressive compound. Suitable immunosuppressive compounds include but are not limited to any one or more of glucocorticoids, cyclophosphamide, methotrexate, azathioprine, mercaptopurine, dactinomycin, anthracyclines, mitomycin C, bleomycin and mithramycin.

In some embodiments, the additional active agent is an anti-inflammatory compound. Suitable anti-inflammatory compounds include but are not limited to any one or more of diclofenac, ibuprofen, naproxen, celecoxib, mefenamic acid, etoricoxib, indometacin and aspirin.

In some embodiments, the additional active agent is an antibiotic compound. Suitable antibiotic compounds include but are not limited to any one or more of Aminocoumarins (such as Novobiocin, Albamycin, Coumermycin and Clorobiocin), Aminoglycosides (such as Amikacin, Apramycin, Gentamicin, Kanamycin, Neomycin, Netilmicin, Tobramycin, Paromomycin and Spectinomycin), Ansamycins (such as Geldanamycin, Herbimycin, Rifaximin and Streptomycin), Carbapenems (such as Ertapenem, Doripenem, Cilastatin ('Imipenem') and
Meropenem), Cephalosporins (such as Cefadroxil, Cefazolin, Cefalothin (Cefalotin), Cefalexin, Cefaclor, Cefamandole, Cefoxitin, Cefprozil, Cefuroxime, Cefixime, Cefdinir, Cefoperazone, Cefotaxime, Cefpodoxime, Ceftazidime, Ceftibuten, Ceftizoxime, Ceftriaxone, Cefepime, Ceftaroline fosamil and Ceftobiprole) Glycopeptides (such as Teicoplanin, Vancomycin and Telavancin), Lincosamides (such as Clindamycin and Lincomycin), Lipopeptides (such as Daptomycin), Macrolides (such as Azithromycin, Clarithromycin, Dirithromycin, Erythromycin, Roxithromycin, Troleandomycin, Telithromycin and Spiramycin), Monobactams (such as Aztreonam), Nitrofurans (such as Furazolidone and Nitrofurantoin), Oxazolidonones (such as Linezolid, Posizolid, Radezolid and Torezolid), Penicillins (such as Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Temocillin and Ticarcillin), Penicillin combinations (such as Amoxicillin/clavulanate, Ampicillin/sulbactam, Piperacillin/tazobactam and Ticarcillin/clavulanate), Polyethers (such as Monensin), Polypeptides (such as Bacitracin, Colistin and Polymyxin B), Quinolones (such as Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin and Temafloxacin); Sulfonamides (such as Mafenide, Sulfacetamide, Sulfadiazine, Silver sulfadiazine, Sulfadimethoxine, Sulfamethizole, Sulfamethoxazole, Sulfanilimide, Sulfasalazine, Sulfisoxazole, Sulfamethoxazole (Co-trimoxazole, TMP-SMX, 'Trimethoprim') and Sulfonamidochrysoidine), Tetracyclines (such as Demeclocycline, Doxycycline,Minocycline, Oxytetracycline and Tetracycline) and Others (such as Clofazimine, Dapsone, Capreomycin, Cycloserine, Ethambutol, Ethionamide, Isoniazid, Pyrazinamide, Rifampicin ('Rifampin'), Rifabutin, Rifapentine, Streptomycin, Arsphenamine, Chloramphenicol, Fosfomycin, Fusidic acid, Metronidazole, Mupirocin, Platensimycin, Quinupristin (Dalfopristin), Thiamphenicol, Tigecycline, Tinidazole and Trimethoprim).

In some embodiments, the additional active agent is an antifungal compound. Suitable antifungal compounds (antimycotics) include but are not limited to any one or more of Polyene antifungals (such as Amphotericin B, Candicidin, Filipin, Hamycin, Natamycin, Nystatin and Rimocidin), Imidazoles (such as Bifonazole, Butoconazole, Clotrimazole, Econazole, Fenticonazole, Isoconazole, Ketoconazole, Miconazole, Omoconazole, Oxiconazole, Sertaconazole, Sulconazole and Tioconazole), Triazoles (such as Albaconazole, Fluconazole, Isavuconazole, Itraconazole, Posaconazole, Ravuconazole, Terconazole and Voriconazole), Thiazoles (such as Abafungin), Allylamines (such as Amorolfin, Butenafine, Naftifine and Terbinafine), Echinocandins (such as Anidulafungin, Caspofungin and Micafungin) and Others such as Benzoic acid, Ciclopirox, Flucytosine or 5-fluorocytosine, Griseofulvin, Haloprogin, Polygodial, Tolnaftate, Undecylenic acid and Crystal violet.

In some embodiments, the additional active agent is a kinase inhibitor. Suitable kinase inhibitors include but are not limited to any one or more of p38 MAPK inhibitors (such as VX-702, SB203580, VX-745, LY2228820, BIRB 796 (Doramapimod), PH-797804 and TAK-715) and class I PI3K inhibitors (such as AS-605240, BYL719, CAL-101, GDC-0941 (Bismesylate salt), GDC-0941 (free base), GSK2636771, IC-87114, IPI-145, LY294002, NVP-BKM120 (Buparlisib), PIK-75, TG100-115 and TGX-221).

As discussed above, a suitable dose may be defined as a dose that does not induce apoptosis, i.e. an apoptosis non-inducing dose. In some embodiments, a suitable dose may be defined as a "low dose" or "low amount" of the agent (e.g. oligopeptidic compound), which may be seen as a dose or amount that is not sufficient to cause or induce apoptosis either directly or indirectly. Alternatively viewed, a "low dose" or "low amount" of the agent is a dose or amount that is an effective dose or amount for reducing or inhibiting cytokine release from non-proliferating immune cells in blood.

Accordingly, a high dose or amount may be viewed as an effective dose or amount that is sufficient to cause or induce apoptosis either directly or indirectly (i.e. cytotoxic doses or doses that result in an increased sensitivity to other cytotoxic or cytostatic agents).

The effective dose or amount of agent may depend on the characteristics of the peptide, e.g. the strength of the interaction between the PCNA interacting motif and the binding domain of the target protein(s). Furthermore, effective dose or amount of the agent may depend upon the nature of the compound used (i.e. peptide, nucleic acid molecule etc), the mode of administration, the course of treatment, the age and weight of the patient, the medical indication, the body or body area to be treated and may be varied or adjusted according to choice. Generally however, a low dose or amount may result in an active concentration range of about 0.01, 0.05, 0.1, 0.25, 0.5, 0.75, 1.0, 1.25, 1.50, 1.75, 2.0, 3.0, 4.0, 5.0 to 10 µM, e.g. 0.01 to 10 µM, e.g. 0.05 to 7.5 µM, such as 0.1 to 7.5 µM, e.g. 0.5 to 5 µM. A high dose or amount may result in an active concentration range of about 1.0, 2.0, 3.0, 4.0, 5.0, 7.5, 10, 15, 20, 25, 30, 40 to 50 µM, e.g. 1.0 to 50 µM, e.g. 2.0 to 40 µM, such as 3.0 to 30 µM, e.g. 5.0 to 25 µM. Said concentrations are determined by reference to the amount of the compound itself and thus appropriate allowances should be made to take into account the purity of the composition.

The subject is an animal (i.e. any human or non-human animal), preferably a mammal, most preferably a human.

The skilled person will be well aware of suitable methods for introducing the agents as defined herein into cells. By way of example, a few suitable methods are briefly discussed below. As discussed in detail above, peptide-mediated methods of delivery can be used, notably uptake (import) peptides, such as cell penetrating peptides (CPPs), which as discussed above, are short, in some cases polycationic, sequences which can facilitate cellular uptake of peptides, proteins or nucleotide molecules which contain CPPs or to which CPPs are linked, for example by enhancing uptake into endosomes of mammalian cells. As mentioned above, the oligopeptidic compound of defined herein typically comprises an uptake peptide, e.g. a CPP. However, additional mechanisms to facilitate the uptake of the agents of the invention may be useful, particularly for agents comprising or consisting of nucleic acid molecules. Microencapsulation provides a simple and cost-effective way to enclose bioactive materials within a semi-permeable polymeric membrane for the purpose of protecting the bioactive materials and releasing the enclosed substances or their products in a controlled fashion. In photochemical internalisation (PCI) both the molecule of interest and a photosensitising compound are taken up by the cell into a lysosome or an endosome. The cells are then exposed to light of suitable wavelengths to activate the photosensitising compound, causing the photosensitising compound to disrupt the membrane of the lysosome or endosome, thereby releasing the molecule of interest into the cytosol of the cell.

Other methods include microinjection, red blood cell ghost-mediated fusion, liposome fusion, osmotic lysis of pinosomes, scrape loading, electroporation, calcium phosphate and virus-mediated transfection and the use of copolymeric carriers.

Chitosan and water-soluble chitosan derivatives, in particular glycol chitosan, are emerging as the drug carriers of choice because of their biocompatibility and biodegradability in vivo. A preferred example is glycol chitosan hydrophobically modified with 5 β-cholanic acid.

The invention will now be further described with reference to the following non-limiting Examples and Figures in which:

FIG. 1 shows that ATX-101 (SEQ ID NO: 1198, which contains the APIM motif, RWLVK (SEQ ID NO: 28)) affects MAPK and PI3K/Akt pathways in multiple myeloma cell lines, wherein: (A) shows cell growth (MTT assay) of JJN-3 cells untreated (♦) and after addition of 6 µM ATX-101 (▲), 5 µM LY294002 (PI3K class I inhibitor) and 10 µM SB20358 (p38 MAPK inhibitor) (•) (left and right panel, respectively), and combination of ATX-101 and kinase inhibitor (□). Data is from one representative experiment out of three; and (B) shows quantification of p70 S6 kinase Thr389, Akt Ser473, ERK1 Thr202/Tyr204, and ERK2 Thr185/Tyr187 phosphorylation in JJN-3 cells after 4, 8, and 24 h treatment with 6 µM ATX-101 by Western blot analysis. Phosphorylated kinase levels were corrected for loading differences (β-tubulin) and normalized to untreated control cells. Data is from three independent experiments (mean±SD).

FIG. 2 shows that ATX-101 reduces cytokine secretion of monocytes after TLR stimulation, wherein: (A) and (B) show multiplex analysis of cytokine levels produced by peripheral blood monocytes after 4 h treatment with 4 µM ATX-101 in combination with 10 ng/ml LPS (A) and 40 µg/ml polyIC stimulation (B). Measured cytokine levels were normalized to cytokine levels from monocytes stimulated with TLR ligand alone. A two fold or higher increase in cytokine level after TLR stimulation was defined as cytokine induction. Data is from three donors (mean±SD); (C) shows an ELISA of IFN-β levels produced by peripheral blood monocytes from five donors. Isolated monocytes were stimulated with 10 ng/ml LPS and 40 µg/ml polyIC alone and in combination with 4 µM ATX-101 for 4 h. Donor 1 was treated with 6 µM ATX-101. # Under linear range; ¤ over linear range; and (D) shows a confocal fluorescence image of immunofluorescently stained PCNA in freshly isolated peripheral blood monocytes. DRAQS was used for nuclear staining. Bar, 5 µm.

Figure 3:
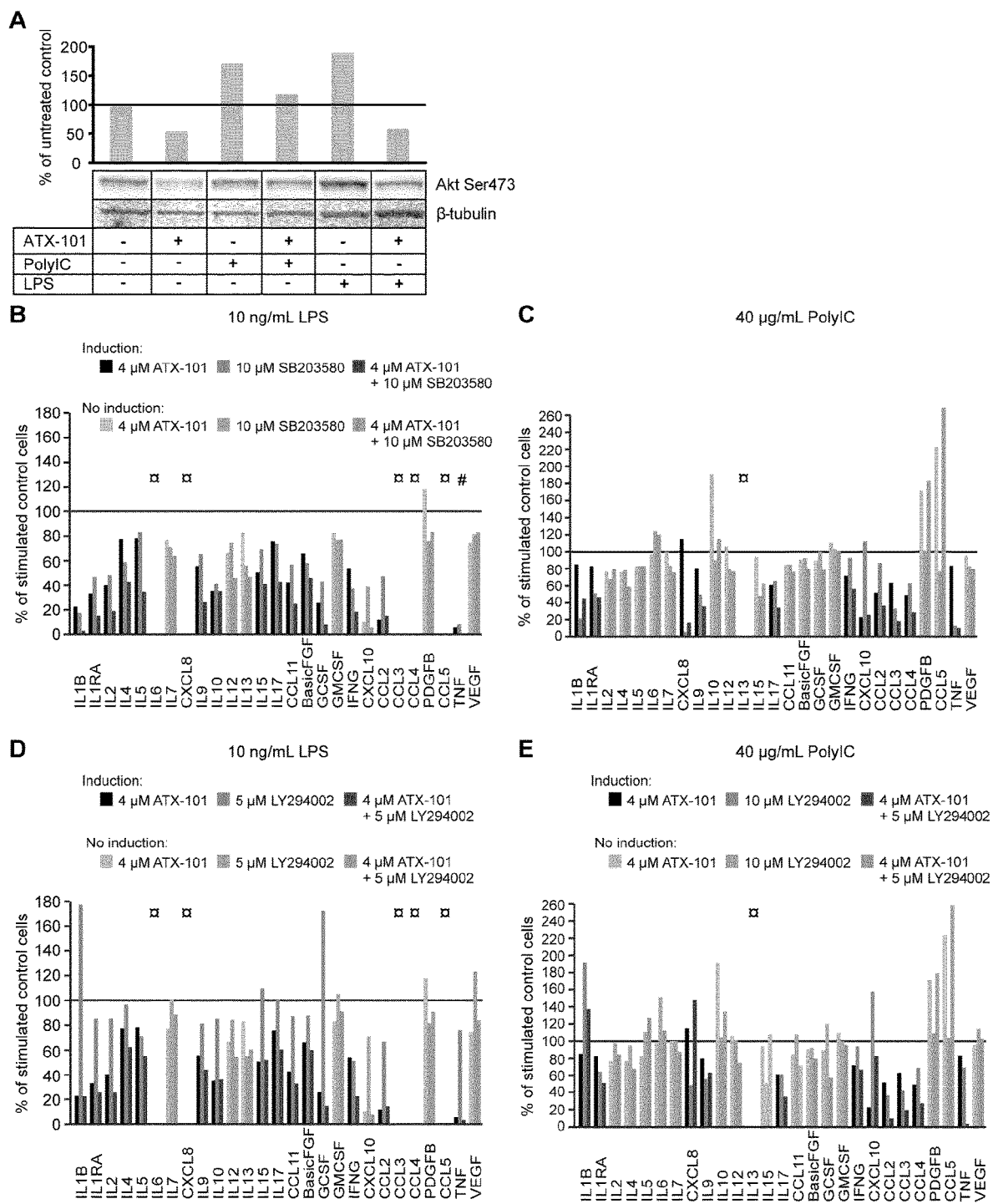

FIG. 3 shows that ATX-101 reduces Akt phosphorylation in monocytes, wherein: (A) shows a Western blot analysis of Akt Ser473 phosphorylation in peripheral blood monocytes stimulated with 10 ng/ml LPS and 40 µg/ml polyIC alone and in combination with 4 µM ATX-101 for 4 h. The upper panel shows the quantification of phosphorylated Akt corrected for loading differences (β-tubulin) and normalized to untreated control cells. Data is from one representative donor out of three; and (B-E) show multiplex analysis of cytokine levels produced by peripheral blood monocytes stimulated with 10 ng/ml LPS (B and D, same donor) and 40 µg/ml polyIC (C and E, same donor) after 4 h. (B and C) Stimulated-monocytes were treated with 4 µM ATX-101, 10 µM SB203580 (p38 MAPK inhibitor), and combination of ATX-101 and SB203580. (D and E) Stimulated-monocytes were treated with 4 µM ATX-101, 5 and 10 µM LY294002 (PI3K class I inhibitor), and combination of ATX-101 and LY294002. Measured cytokine levels were normalized to cytokine levels from monocytes stimulated with TLR ligand alone. A two fold or higher increase in cytokine level after TLR stimulation was defined as cytokine induction. # Value is too low to be visible in the column diagram; ¤ cytokine measurement was out of range. Data is from representative experiments out of two.

FIG. 4 shows that ATX-101 reduces Akt phosphorylation and PACT protein levels in HaCaT cells, wherein: (A) shows quantification of Akt Ser473 phosphorylation and PACT protein levels in HaCaT cells treated with 12 µM ATX-101, 2 µg/ml polyIC, and combination of ATX-101 and polyIC for 4 h by Western blot analysis. Protein levels were corrected for loading differences (β-tubulin) and normalized to untreated control cells. Data is from three independent experiments (mean±SD); and (B) shows a confocal fluorescence image of immunofluorescently stained PCNA in HaCaT cells. Bar, 5 µm.

FIG. 5 shows that ATX-101 reduces cytokine secretion of monocytes after TLR stimulation, wherein: (A) and (B) show multiplex analysis of cytokine levels produced by peripheral blood monocytes after 4 h treatment with 4 µM ATX-101 in combination with 10 ng/ml PAM3Cys (A) and 10 µg/ml R848 stimulation (B). Measured cytokine levels were normalized to cytokine levels from monocytes stimulated with TLR ligand alone. A two fold or higher increase in cytokine level after TLR stimulation was defined as cytokine induction. ¤ Cytokine measurement was out of range. Data is from one experiment out of two.

Figure 6:
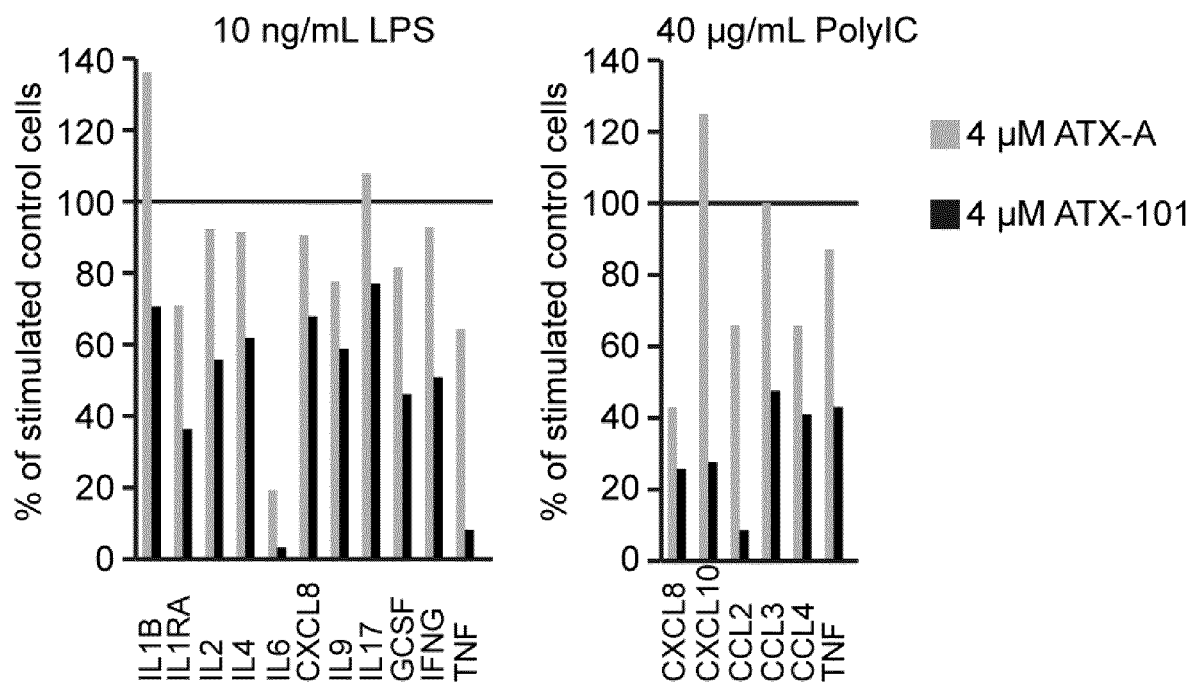

FIG. 6 shows that ATX-A (SEQ ID NO: 1206, which contains the motif RALVK (SEQ ID NO: 1207), which is not capable of interacting with PCNA) reduces less efficiently cytokine secretion of monocytes after TLR stimulation, wherein multiplex analysis of LPS- and polyIC-induced cytokine levels produced by peripheral blood monocytes after 4 h treatment with 4 µM ATX-101 or 4 µM ATX-A in combination with 10 ng/ml LPS and 40 µg/ml polyIC (left and right panel, respectively). Measured cytokine levels were normalized to cytokine levels from monocytes stimulated with TLR ligand alone. Data is from one donor. We obtained similar results for IL-6 secretion in two other donors.

FIG. 7 shows that the Akt inhibitor SC66 reduces cytokine secretion of monocytes to or below the basal levels after TLR stimulation, wherein multiplex analysis of cytokine levels produced by peripheral blood monocytes after 4 h treatment with 4 µM ATX-101 and 1 µg/ml SC66 in combination with 10 ng/ml LPS (left panel) and 40 µg/ml polyIC stimulation (right panel). Measured cytokine levels were normalized to cytokine levels from monocytes stimulated with TLR ligand alone. A two fold or higher increase in cytokine level after TLR stimulation was defined as cytokine induction. # Value is too low to be visible in the column diagram; 0 Cytokine measurement was out of range. Data is from one experiment out of two.

Figure 8:
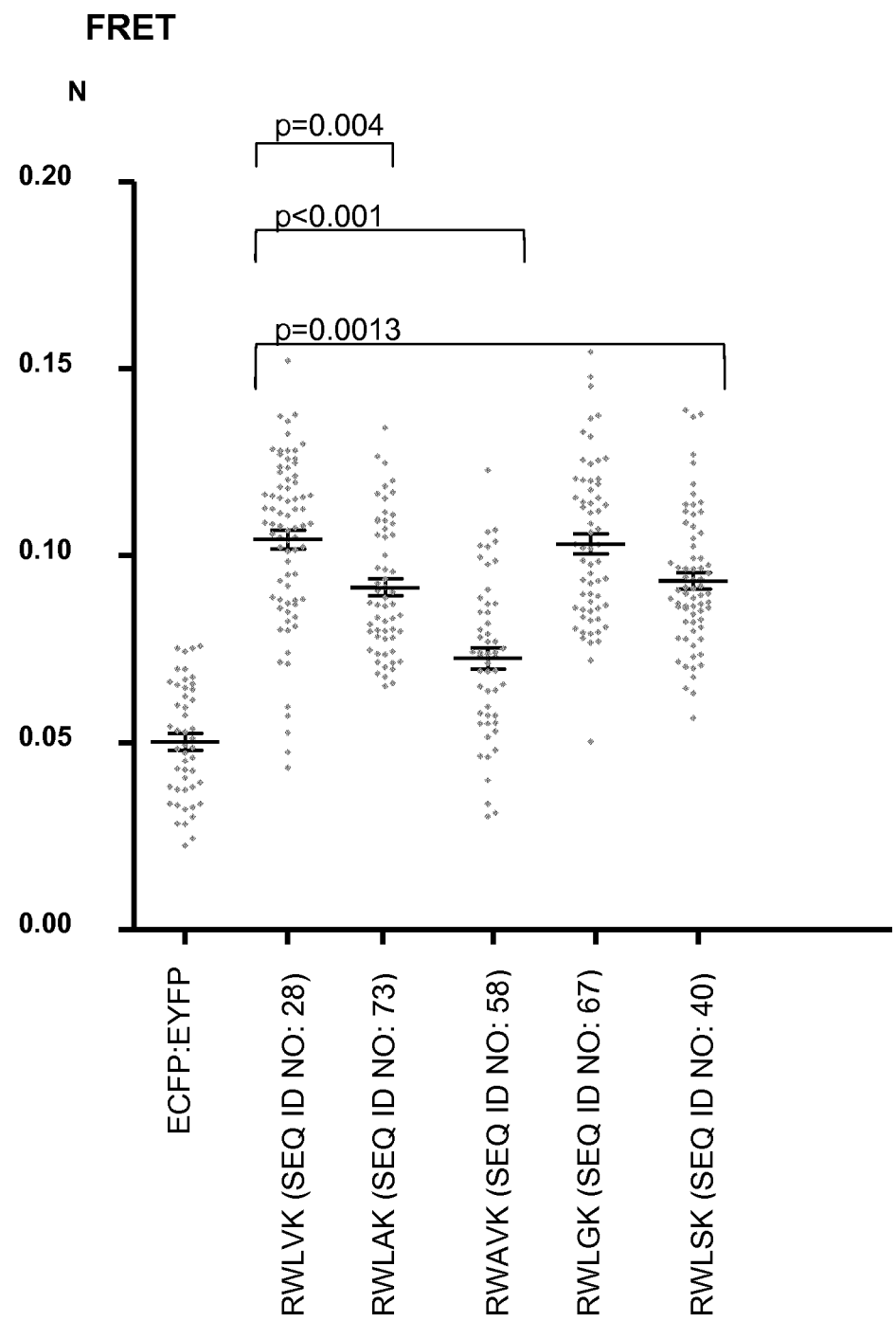

FIG. 8 shows a graph showing the results of FRET analysis. Normalised FRET ($N_{FRET}$) measurements are shown between EYFP (yellow fluorescent protein)/ECFP (cyan fluorescent protein) (Lane 1, background due to dimerisation of the tags). EYFP-APIM motif/ECFP-PCNA for various motifs are shown in the other lanes.

EXAMPLES

Background to the Experiments

The inventors have determined that more than 20 different signalling kinases, mainly cytoplasmic, contain an APIM sequence, suggesting that they interact with PCNA. These include three direct members of the PI3K/Akt pathway (p110-α, p110-γ, and PI3K-C2β) and several kinases directly or indirectly affecting the MAPK pathways (ERK8, MK2, MKS, MST4, and TAO2). PCNA has heretofore not been linked to signal transduction. The inventors have determined that PCNA plays a role in signal transduction pathways downstream of TLRs. The inventors have established that the signal transduction pathways can be disrupted by targeting PCNA oligopeptidic compounds comprising an APIM motif. These compounds are thought to compete with PCNA for PCNA interacting proteins. The effects of oligopeptidic compounds comprising an APIM motif on signal transduction pathways have been established using an exemplary cell-penetrating APIM-containing peptide ATX-101 (SEQ ID NO: 1198, which contains the APIM motif, RWLVK (SEQ ID NO: 28)).

The inventors have surprisingly found that ATX-101 treatment reduced cytokine secretion of peripheral blood monocytes after stimulation with different TLR ligands and reduced Akt phosphorylation. This data indicates that targeting PCNA affects signal transduction pathways, including the PI3K/Akt and MAPK pathways, likely by inhibition of PCNA-binding of signaling proteins containing the APIM-sequence. These data suggest a regulatory role of PCNA in signal transduction and APIM containing peptides will be useful in the treatment or prevention of a disorder or condition associated with cytokine release from non-proliferating immune cells in blood, such as a disorder or condition resulting in or from, or associated with, hypercytokinemia.

Materials and Methods

Cell Lines

The multiple myeloma cell lines JJN-3 (gift from J. Ball, University of Birmingham, United Kingdom) were grown in RPMI 1640 (Sigma-Aldrich, Schnelldorf, Germany) supplemented with 10% FCS, 2 mM glutamine (Sigma-Aldrich), 2.5 µg/ml amphotericin B (Sigma-Aldrich) and 100 µg/ml gentamicin (Invitrogen, Carlsbad, Calif., USA). HaCaT cells (spontaneously transformed keratinocytes) were cultured in DMEM (Sigma-Aldrich) containing FCS, glutamine, amphotericin B, and gentamicin. All cells were cultured at 37° C. in a humidified atmosphere of 5% $CO_2$.

Isolation and stimulation of peripheral blood monocytes

Peripheral blood mononuclear cells were isolated from A+ buffy coats (Blood Bank, St. Olav's University Hospital, Trondheim, Norway) by density gradient centrifugation (Lymphoprep; Axis-Shield PoC, Oslo, Norway). Mononucleated cells were seeded at 4 million cells/ml in serum-free RPMI 1640 supplemented with glutamine and gentamicin. After 60-90 min the adherent cell population was washed before cultured in medium with 10% heat-inactivated human serum (Blood Bank, St. Olav's University Hospital). ATX-101 (4 µM [Innovagen, Lund, Sweden]), ATX-A (4 µM, [Innovagen]) (ATX-A is represented in SEQ ID NO: 1206 and contains the motif RALVK (SEQ ID NO: 1207), which is not capable of interacting with PCNA), p38 inhibitor (SB203580, 10 µM, [Sigma-Aldrich]), PI3K inhibitor (LY294002, 5 and 10 µM, [Sigma-Aldrich]), and Akt inhibitor (Akt inhibitor XVIII SC66, 1 µg/ml, [Sigma-Aldrich]) were added in serum-free medium and incubated for 5 min before LPS (10 ng/ml, [Sigma-Aldrich]), polyIC (40 µg/ml, [GE Healthcare, Little Chalfont, UK]), PAM3Cys (10 ng/ml, [Invivogen, San Diego, Calif., USA]) or R848 (10 µg/ml, [Invivogen]) were added in serum-containing medium. The cells were incubated for 4 h before the supernatants were harvested and frozen prior to further cytokine analysis by the 27-plex assay (Bio-Plex ProTM Human cytokine 27-plex assay).

Preparation of cell extracts and western analysis

Mononucleated cells were seeded and stimulated as described above. JJN-3 cells were treated with ATX-101 (6 µM) for 4 h. HaCaT cells were treated with ATX-101 (12

μM), polyIC (2 μg/ml), and LPS (100 ng/ml) for 4 h. The cells were harvested, the cell pellet was resuspended in 1x packed cell volume of buffer 1 (10 mM Tris-HCl pH 8.0, 200 mM KCl) and diluted in the same volume (packed cell volume+ buffer 1) of buffer 2 (10 mM Tris-HCl pH 8.0, 200 mM KCl, 10 mM EGTA, 10 mM $MgCl_2$, 40% glycerol, 0.5% NP40, 1 mM DTT, 1% phosphatase inhibitor cocktails 1 and 3 [Sigma-Aldrich], 2% Complete EDTA-free protease inhibitor [Roche, Oslo, Norway], and 2 μl/ml Omnicleave [Epicentre Technologies, Madison, WI, USA]). After incubation for 1.5 h at 4° C., the cell extracts were centrifuged at 14,000 rpm for 10 min. Supernatants were collected and separated on 10% Bis-Tris-HCl gels (NuPAGE, Invitrogen). After gel electrophoresis, the polyvinylidene fluoride membranes (Immobilion, Millipore, Oslo, Norway) were blocked in 50% Odyssey blocking buffer (LI-COR Bioscience, Cambridge, UK) in TBS. The primary antibodies against (α) P-Akt (monoclonal, Cell Signaling, Beverly, Mass., USA), PACT (monoclonal, Santa Cruz biotechnology Inc., Dallas, Tex., USA), P-p70 S6 Kinase (monoclonal, Cell Signaling), P-ERK1/2 (monoclonal, Cell Signaling), and β-tubulin (polyclonal, Abcam, Cambridge, UK), as well as the fluorescently labeled secondary antibodies, goat α-rabbit 680RD and goat α-mouse 800CW (LI-COR) were diluted in 20% Odyssey blocking buffer in TBST (TBS with 0.1% Tween 20). The proteins were visualized with the Odyssey infrared imaging system (LI-COR) and quantified using Odyssey Image Studio V2. Protein levels were compared to the protein level in untreated cells, which was set to 100%. β-tubulin was used as reference for data normalization.

Immunofluorescence and Confocal Imaging

HaCaT cells and peripheral blood monocytes were grown on glass bottom dishes and stained as described using an antibody α-PCNA (PC10, Santa Cruz biotechnology Inc.; 1:1000) and Alexa fluor 532 goat α-mouse (Invitrogen). The nuclei were stained with DRAQS prior to imaging according to the manufacturer's manual (eBioscience, San Diego, Calif., USA). The fluorescent images were acquired using a Zeiss LSM 510 Meta laser scanning microscope equipped with a Plan-Apochromate 63x/1.4 oil immersion objective in 2% FCS in PBS at RT using the Zeiss LSM 510 software. The stained cells were excited at λ=543 nm and detected at λ>=560-615 for Alexa fluor 532. DRAQ5 was excited at λ=633 nm and detected at λ>650 nm. The thickness of the slice was 1 μm. All images were acquired with consecutive scans. No image processing was performed, except contrast and intensity adjustments. IFN-β ELISA Monocytes were stimulated as described above. IFN-β was measured in supernatants with the VeriKine-HSTMHuman IFN-β Serum ELISA kit (Pestka Biomedical Laboratories, Piscataway, N.J., USA) according to the manufacturer's instructions with the following adaptions: the amount of supernatant was doubled from 50 to 100 μl; sample buffer was reduced from 50 to 25 μl; and antibody solution was reduced from 50 to 25 μl (reducing assay diluent, keeping same volume of antibody concentrate and diluent additive). The OD was measured at 450 nm.

Cell Survival Assay

Cells were seeded into 96-well plates and ATX-101, kinase inhibitors (SB203580 and BIRB0796), and polyIC were added alone or in combination at the indicated concentrations. Cells were exposed continuously and harvested every day for the next four days using the MTT (3-(4.5-Dimethylthiazol-2-yl)-2.5 diphenyl-tetrazolium bromide) assay (Gilljam et al., 2009, supra). The average from at least 4 wells was used to calculate cell survival.

Example 1

Targeting PCNA with APIM-containing peptides affects signal transduction in multiple myeloma cells Multiple myeloma cells secrete cytokines and respond to various growth-stimulatory factors from their tumor microenvironment in positive feedback loops that support myeloma cell growth. The MAPK and PI3K/Akt pathways have been suggested as potential therapeutic targets in multiple myeloma, alone and in combination because these pathways are frequently dysregulated and extensive crosstalk between these pathways exists. Furthermore, these pathways are important for cytokine production.

We found that ATX-101 increased the growth-inhibitory effect of p38 MAPK and class I PI3K inhibitors in the multiple myeloma cell line JJN-3 (FIG. 1A). In addition, ATX-101 increased the growth-inhibitory effects of ERK5 and MAPK kinase 1 (MEK1) inhibitors, and enhanced the cytotoxic effects of melphalan in combination with these inhibitors as well as the p38 inhibitor in another multiple myeloma cell line (RPMI-8226). To further elucidate whether ATX-101 directly affected the MAPK and PI3K pathways, we analyzed the phosphorylation levels of downstream kinases in JJN-3 cells at different time points after ATX-101 addition. The phosphorylation of Akt and the p70 S6 kinase (downstream of mTOR) were both decreased by ATX-101 treatment. In contrast, a transient increase in ERK1/2 phosphorylation was detected upon ATX-101 treatment (FIG. 1B).

These results indicate that ATX-101 affects important signal transduction pathways in multiple myeloma cells including the PI3K/Akt/mTOR and MAPK pathways.

Example 2

Targeting PCNA with APIM-containing peptides reduces cytokine secretion of monocytes after TLR stimulation Next, we investigated whether ATX-101 could affect cytokine secretion from primary monocytes, which is partly regulated by the PI3K/Akt and MAPK pathways. We stimulated peripheral blood monocytes with different TLR ligands to induce cytokine production and measured the concentration of 27 cytokines in the cell culture supernatants. The secretion of LPS-induced cytokines was efficiently reduced by ATX-101 addition (FIG. 2A). Similarly, ATX-101 treatment reduced the secretion of CXCL10, CCL2, CCL3, and CCL4 after TLR3 stimulation with polyIC (FIG. 2B). We found similar reduction in cytokine secretion induced by the TLR7/8 ligand R848 and the TLR2 ligand PAM3Cys (FIG. 5). These results show that targeting PCNA with APIM-containing peptides affects cytokine production. The mechanism is likely inhibition of multiple kinase-PCNA interactions, affecting signaling pathways downstream of the TLR adaptor proteins because ATX-101 treatment reduced cytokine secretion downstream of TLRs dependent on both MyD88 and TRIF.

ATX-101 treatment decreased the CXCL10 secretion induced by polyIC and also the basal level production of this cytokine from isolated monocytes (FIGS. 2A and B). We measured the IFN-β levels in supernatants from LPS- and polyIC-stimulated monocytes because the induction of CXCL10 expression is a secondary event and requires the initial secretion of IFN-β. Consistent with the reduced CXCL10 secretion, ATX-101 treatment also decreased the IFN-β secretion, supporting that ATX-101 affects signaling downstream of the TLR adaptor TRIF (FIG. 2C). Importantly, ATX-101 treatment at the used concentration did not induce apoptosis in monocytes. Furthermore, a mutant version of ATX-101, ATX-A that does not bind to PCNA, was unable or less efficient in decreasing the secretion of cytokines compared to ATX-101 (FIG. 6). These results therefore indicate that ATX-101 affects cytokine secretion by specifically targeting PCNA. Monocytes contain substantial amounts of PCNA in the cytoplasm as compared to for example HeLa cells (FIG. 2D). Collectively, these data show that PCNA may have a regulatory role in the innate immune response.

Example 3

Reduction of Akt phosphorylation by APIM-containing peptides is likely affecting the cytokine production in TLR-stimulated monocytes Activation of NF-κB, MAPKs, and the PI3K/Akt pathway are important features after TLR activation, and our results indicate that ATX-101 affects two of these pathways in the multiple myeloma cell line JJN-3 (FIG. 1). To examine whether ATX-101 affected the PI3K/Akt pathway in monocytes similar to JJN-3 cells, we analyzed Akt phosphorylation levels in monocytes. LPS- and polyIC-induced Akt phosphorylation as well as the basal Akt phosphorylation level was reduced by ATX-101 treatment (FIG. 3A). To further investigate whether ATX-101 reduced or increased the effect of specific inhibitors of PI3K, Akt, and p38 MAPK with regard to cytokine production similar to the reduced cell growth observed in JJN-3 cells (FIG. 1A), we measured cytokine secretion from LPS- and polyIC-stimulated monocytes in presence of kinase inhibitors alone and in combination with ATX-101.

ATX-101 and a p38 MAPK inhibitor both reduced cytokine secretion from stimulated monocytes, and the combination of ATX-101 and inhibitor resulted in an increased reduction of most cytokines (FIGS. 3B and C). The PI3K inhibitor LY294002 on the other hand had less effect on induced cytokine secretion alone and in combination with ATX-101, but still the combination showed a reduction in the secretion of some cytokines (e.g. IFNγ, IL-1 RA, IL-2, 4, and 9 after LPS, and IL-1RA, CCL2, 3, and 4 after polyIC stimulation) (FIGS. 3D and E). Direct inhibition of Akt, the central kinase further downstream in the PI3K pathway reduced the secretion of all cytokines to or below the basal levels, indicating a vital role in cytokine regulation (FIG. 7); however, this strong single agent response of the inhibitor (in absence of apoptosis) did not allow examination of its combination with ATX-101. In summary, these results verify that both the p38 MAPK and PI3K/Akt pathway are important for cytokine secretion from monocytes, and indicate that targeting PCNA with APIM-peptides enhances the effect of inhibiting these pathways. Thus, the results shown in FIG. 1, i.e. increased inhibition of cell growth by ATX-101 alone and in combination with MAPK and PI3K pathway inhibitors and reduced Akt activation after ATX-101 treatment in JJN-3 cells, correlate with reduced cytokine production and reduced Akt activation in monocytes. These data further support that PCNA has a regulatory role in signal transduction, affecting both cell growth and cytokine production.

Example 4

APIM-containing peptides reduce Akt phosphorylation and PACT protein levels in HaCaT keratinocytes To further support the possible regulatory role of PCNA in the cellular response to TLR agonists, we used the human keratinocyte cell line HaCaT that expresses functional TLR3 and is responsive to polyIC treatment. We examined Akt phosphorylation levels in HaCaT cells and found that ATX-101 treatment reduced Akt phosphorylation in unstimulated and stimulated cells similar to JJN-3 cells and monocytes (FIG. 4A). Human keratinocytes respond to polyIC via the known dsRNA sensing receptors TLR3, PKR, RIG-I, and MDAS. The dsRNA-binding APIM-containing protein PACT is an activator of PKR and RIG-I. Thus, PACT may interact with PCNA and this interaction may have a regulatory role in the response to polyIC in HaCaT cells. We therefore examined PACT protein levels in HaCaT cells treated with polyIC and ATX-101, and a combination of both.

ATX-101 addition to unstimulated cells had no clear effect on the PACT protein level, but the addition of ATX-101 further reduced the protein level of PACT in polyIC-stimulated cells (FIG. 4A). The mutant peptide ATX-A had less effect on Akt phosphorylation and PACT protein levels than ATX-101 similarly to what we observed for cytokine secretion. Thus, these data indicate that APIM-peptides affect the PI3K/Akt pathway as well as PACT protein levels in response to polyIC in HaCaT cells. We hypothesize that APIM-peptides interfere with several signal transduction pathways by targeting PCNA's interactions with cytoplasmic signaling proteins such as PACT. PCNA is mainly detected in the nucleus of HaCaT cells, but some cells also contain PCNA in the cytoplasm (FIG. 4B).

Discussion

We show that targeting PCNA with an APIM-containing peptide, e.g. ATX-101, affects the cellular response to TLR agonists, supporting a role for PCNA in cellular stress responses. ATX-101 treatment reduced the cytokine secretion from monocytes and decreased Akt phosphorylation in monocytes and HaCaT cells stimulated with different TLR ligands. The APIM-sequence is found in over 200 proteins including several signaling kinases that have been described to act in TLR signaling. Therefore, ATX-101 likely affects several signal transduction pathways.

Our data indicate that ATX-101 down regulates the PI3K/Akt pathway, a known regulator of cytokine production as shown by using the Akt inhibitor SC66. Thus, the reduced Akt activation likely contributes to the decreased cytokine secretion from TLR-stimulated monocytes upon ATX-101 treatment.

In our experiments, we observed no strong induction of IL-12 by the TLR ligands tested; however, ATX-101 treatment reduced the basal level of IL-12 (FIG. 2A and FIG. 5). Thus, ATX-101 may also affect cytokine secretion by interfering with PI signaling.

Our data suggest that ATX-101 did not reduce cytokine secretion by its cell-penetrating peptide but rather by targeting PCNA via the APIM-sequence because the mutant ATX-A with a single amino acid change in APIM reduced cytokine secretion far less than ATX-101. The small observed effects of ATX-A are likely because ATX-A still has some weak PCNA-binding ability.

We initially found that ATX-101 interfered with signal transduction pathways including the PI3K/Akt pathway in the multiple myeloma cell line JJN-3 independent of TLR stimulation. The ATX-101-mediated effect on signal transduction pathways is therefore not restricted to TLR signaling. The cellular target of ATX-101 is PCNA and thus our data suggest a new regulatory function of PCNA in signaling pathways likely by acting as cytoplasmic binding platform. Thus, APIM-mediated PCNA interactions play a role in the cellular stress response to pathogens and damage-associated molecular patterns recognized by TLRs. ATX-101 reduces cytokine secretion from monocytes at doses that do not induce apoptosis.

Example 5

In silico characterisation of APIM consensus motif

The inventors have performed sequence analyses to determine how much variation within the APIM motif occurs naturally, i.e. in native sequences across a number of species. As PCNA is highly conserved across eukaryotic organisms, it is expected that sequence variation of the APIM motif in orthologues of polypeptides that are thought to interact with PCNA is representative of the variation that may be used in the oligopeptidic compounds of the invention, i.e. variation of amino acids within the APIM motif at some positions, particularly $X_3$ and $X_4$, may be permitted without losing affinity to PCNA.

The inventors used identified 657 human polypeptide sequences that comprise the motif [K/R]-[F/W/Y]-[A/L/V/I]-[A/L/V/I[-]K/R] (SEQ ID NO:19) from a possible 21,673 polypeptide sequences. Of the 657 sequences identified, 291 were excluded because insignificant information about the function of the polypeptides was available. The remaining 366 were considered to be polypeptides that are likely to interact with PCNA and these sequences were used to identify orthologues in: Bos taurus (288 orthologues); Rattus norvegicus (286 orthologues); Mus musculus (312 orthologues); Gallus gallus (236 orthologues); Xenopus tropicalis (200 orthologues); Danio rerio (189 orthologues); Caenrhabditis elegans (102 orthologues); Drosophila melanogaster (136 orthologues); and Saccharomyces cerevisiae (65 orthologues). Alignment of the domains of the orthologues that comprise the APIM motif suggested that the motif may defined as:

```
                                          (SEQ ID NO: 2)
[R/K/H]-[W/F/Y]-[L/I/V/A/M/S/T/N/Q/C]-[L/I/V/A/M/G/
S/T/N/Q/R/H/K/C]-[K/R/H/P],
``` wherein specific combinations of amino acids at positions 3 and 4 that were identified in the orthologues include: LL, LA, LV, AL, VL, VI, LI, IL, VV, VA, IV, II, AV, IA, AI, AM, LM, LS, LT, IS, MV, TV, AA, IM, LN, LQ, VM, TL, SL, IT, VT, LG, MA, ML, NL, QL, QI, TI, SI, AS, VS, SV, CA, IG, LR, VR, TK and IR. Particularly common combinations are LL, LA, LV, AL, VL, VI, LI, IL, VV, VA, IV, II, AV, IA, AI, AM, LM, LS and LT, the most common being LL, LA, LV, AL, VL, VI, LI, IL, VV, VA, IV, II, AV, IA and AI.

Thus, the broadest definition of the APIM motif was derived from this analysis, and all polypeptides comprising an APIM motif according to this definition could reasonably be expected to interact with, i.e. bind to, PCNA.

Example 6

In vivo characterisation of APIM consensus motif

This work described in this Example investigates interaction between APIM peptides and PCNA.

In living S-phase cells, PCNA tagged with green fluorescent protein (EGFP) forms distinct foci representing sites of replication and thus can be used as a S-phase marker.

PCNA tagged with cyan fluorescent protein (ECFP) was co-expressed with various APIM peptide constructs fused with yellow fluorescent protein (EYFP). To examine the degree of proximity of APIM peptides and PCNA, fluorescence resonance energy transfer (FRET) was measured.

Live HeLa cells were examined 16-24 hours after transient transfection (by Fugene 6 (Roche Inc.) according to the manufacturer's recommendations) of ECFP and EYFP fusion constructs. Fluorescent images were acquired using a Zeiss LSM 510 Meta laser scanning microscope equipped with a Plan-Apochromate 63×/1.4 oil immersion objective. Enhanced cyan fluorescent protein (ECFP) was excited at λ=458 nm and detected at λ=470-500 nm and enhanced yellow fluorescent protein (EYFP) was excited at μ=514 nm and detected at λ=530-600 nm, using consecutive scans. The thickness of the slice was 1 μm.

Fluorescent resonance energy transfer (FRET) occurs if the tags (EYFP and ECFP) are less than 100 Å (10 nm) apart. We detected FRET using the sensitised emission method, measuring acceptor (EYFP) emission upon donor (ECFP) excitation. We had FRET when the intensity of emitted light from EYFP after excitation of the ECFP fluorochrome was stronger than the light emitted by ECFP or EYFP-tagged proteins alone, after excitation with the EYFP and ECFP lasers respectively (bleed through), given by the equation: $FRET=I_2-I_1(I_{D2}/I_{D1})-I_3(I_{A2}/I_{A3})$ is >0. FRET was normalised for expression levels using the equation: $N_{FRET}=FRET/(I_1 \times I_3)^{1/2}$. $N_{FRET}$ was calculated from mean intensities (I) within a region of interest (ROI) containing more than 25 pixels where all pixels had intensities below 250 and the average intensities were between 100 and 200 for both the donor and the acceptor constructs. Channel 1 (ECFP) and 3 (EYFP) were measured as described above for imaging, and channel 2 (FRET) was excited with A=458 nm and detected at λ=530-600 nm. $I_{D1, D2, D3}$ and $I_{A1, A2, A3}$ were determined for cells transfected with ECFP and EYFP constructs only, with same settings and same fluorescence intensities as co-transfected cells ($I_1$ and $I_3$). ECFP-PCNA and EYFP-PCNA were included as positive controls, and due to dimerisation of co-expressed tags, ECFP and EYFP proteins expressed from empty vectors were included as negative controls in all experiments.

FIG. 8 shows that a significant FRET signal could be detected for all of the variants tested, which verifies that a variety of peptides within the APIM motif definition described herein (and that occur in polypeptides that are expected to interact with PCNA) are capable of interacting with PCNA and would therefore be expected to find utility in the method and uses described herein, i.e. as immunosuppressive peptides, e.g. for inhibiting or preventing cytokine release for non-proliferating immune cells in blood and treating or preventing disorders or conditions associated therewith.

Example 7

Identification of cytosolic proteins involved in cellular signalling that interact with PCNA Several cytosolic proteins contain APIM suggesting that they may interact with PCNA. In order to investigate the PCNA-"interactome" further, the inventor performed PCNA co-immunoprecipitation (co-IP) experiments on extracts from HaCaT cells crosslinked using a low concentration of formaldehyde to preserve protein complexes in their in vivo conformation. The eluate was separated on a gel, and the gel pieces were subjected to tryptic digestion and Orbitrap-MS. A mock antibody specific for TOM20 was used in a control co-IP assay. Relevant proteins detected by MS in the PCNA pull down, but not in the mock pull down, are listed in Table 3.

APIM containing proteins detected include MST4 and PLK3, which are involved in regulating ERK and Akt respectively. PACT protein was also detected. These proteins are involved in cytokine and chemokine expression pathways.

PCNA also pulled down the APIM containing protein BRE, a protein part of the BRCA-1-complex in the nuclei and the BRISK-complex in the cytosol, which were recently found to be involved in regulation of TNF-induced apoptosis. One interesting PIP-box protein identified was the TAB2 which is involved in positive feedback in a kinase complex in NFkB signalling. Overall, 20 APIM-containing proteins and 23 PIP-box containing proteins were detected exclusively in the PCNA pull down in absence of cellular stress.

A mock antibody should ideally target an unrelated protein. However, as PCNA has many interaction partners and likely acts as a signalling hub in the cytoplasm, an ideal mock antibody is difficult to obtain. Indeed, the mock protein chosen here (TOM20) was detected in the PCNA pull down by MS (Mascot-score 32.53, not detected by Sequest; data not shown). Table 4 includes several interesting proteins that are not exclusively found, but enriched, in the PCNA pull down compared to mock pull down, based on the number of detected peptides and Mascot/Sequest score. These include several proteins in the MAPK pathways, including TAO3, MAPKK3, ERK1/2 and the APIM-containing proteins MK2 and TA01. Akt1 and p38 alpha were also enriched in PCNA pull down, however, these proteins were detected in gel pieces corresponding to different molecular weights from the α-PCNA and α-mock pull down suggesting that regulation by PTMs is important for their localization to PCNA complexes. The APIM-protein PACT was detected from the gel-piece with the expected molecular weight (MVV) of PACT in the PCNA pull down only (Table 3). PACT was found in both PCNA and mock pull down (less in mock), and in a gel piece with 5-10 kDa higher molecular weight than predicted (Table 4). The increase in molecule weight suggests that PACT may be regulated by PTMs, e.g. polyubiquitination which leads to degradation. Stimulation of HaCat cells with both polyIC and ATX-101, and the combination, led to rapid (4 h) degradation of PACT (FIG. 4A). Overall, the data suggest that PCNA and PACT are in a common complex, directly interacting via APIM. A full list of proteins containing an APIM or PIP-box motif identified in the pull-down assay is set out in Table 5.

TABLE 3

Proteins only in PCNA pull down

| | Unique peptides | Fraction | Predicted Mw |
|---|---|---|---|
| APIM-proteins | | | |
| PACT | AAEAAINILK | 30-40 kDa | 34.4 kDa |
| BRE | VGLDATNCLR SGCTSLTPGPNCDR NNWTGEFSAR ELVQQYHQFQCSR | 40-45 kDa | 43.6 kDa |
| MST4 | SIAVAEAACPGITDK TQQVVAIK NQAIEELEK | 45-55 kDa | 46.5 kDa |
| PLK3 | CIKQVHYTIPASLSL PARQLLAAILR | >150 kDa | 71.6 kDa |
| PIP-proteins | | | |
| TAB2 | TSSTSSSVNSQTLNR | 65-90 kDa | 76.5 kDa |

TABLE 4

Proteins enriched in PCNA pull down

| APIM-proteins | Unique peptides | Fraction | Predicted Mw | Score PCNA (Mascot/Sequest) | Score Tom20 (Mascot/Sequest) |
|---|---|---|---|---|---|
| PACT | AAEAAINILK LPEYTLSCIEGGPAHK** | 40-45 kDa | 34.4 kDa | 23.03/2.06 | 25.12/1.61 |
| MK2 | IEDASNPLLLK* | 40-45 kDa | 45.6 kDa | 27.56/6.33 | —/1.79 |
| TA01 | LDEAQEAECQVLK** EIEAFDSESMR** KFQQHIQAQQK*** | 65-90 kDa | 116.0 kDa | 49.83/11.10 | —/2.09 |

TABLE 5

Proteins containing APIM or PIP in pull down using anti-PCNA* from unstimulated, weakly crosslinked HaCat cells:

| APIM-proteins | | PIP-box proteins | |
|---|---|---|---|
| Uniprot ID | Name | Uniprot ID | Name |
| B2RTY4 | Unconventional myosin-IXa | O15541 | RING finger protein 113A |
| O60573 | Eukaryotic translation initiation factor 4E type 2 | O43502 | DNA repair protein RAD51 homolog 3 |

TABLE 5-continued

Proteins containing APIM or PIP in pull down using anti-PCNA* from unstimulated, weakly crosslinked HaCat cells:

| APIM-proteins | | PIP-box proteins | |
|---|---|---|---|
| Uniprot ID | Name | Uniprot ID | Name |
| O94887 | FERM, RhoGEF and pleckstrin domain-containing protein 2 | O43929 | Origin recognition complex subunit 4 |
| P18858 | DNA ligase 1 | O60256 | Phosphoribosyl pyrophosphate synthase-associated protein 2 |
| P55196 | Afadin | O60303 | Uncharacterized protein KIAA0556 |
| Q09327 | Beta-1,4-mannosyl-glycoprotein 4-beta-N-acetylglucosaminyltransferase | O60890 | Oligophrenin-1 |
| Q15051 | IQ calmodulin-binding motif-containing protein 1 | P18858 | DNA ligase 1 |
| Q4AC94 | C2 domain-containing protein 3 | P19474 | E3 ubiquitin-protein ligase TRIM21 |
| Q5TBA9 | Protein furry homolog | P20585 | DNA mismatch repair protein Msh3 |
| Q8IX01 | SURP and G-patch domain-containing protein 2 | P24386 | Rab proteins geranylgeranyltransferase component A 1 |
| Q8NB46 | Serine/threonine-protein phosphatase 6 regulatory ankyrin repeat subunit C | Q14558 | Phosphoribosyl pyrophosphate synthase-associated protein 1 |
| Q9H4B4 | Serine/threonine-protein kinase PLK3 | Q15172 | Serine/threonine-protein phosphatase 2A 56 kDa regulatory subunit alpha isoform |
| Q9HCE6 | Rho guanine nucleotide exchange factor 10-like protein | Q1ED39 | Lysine-rich nucleolar protein 1 |
| Q9NQW1 | Protein transport protein Sec31B | Q4KMP7 | TBC1 domain family member 10B |
| Q9NXR7 | BRCA1-A complex subunit BRE | Q6VN20 | Ran-binding protein 10 |
| Q9NYT0 | Pleckstrin 2 | Q96DF8 | Protein DGCR14 |
| Q9P289 | Serine/threonine-protein kinase MST4 | Q96S59 | Ran-binding protein 9 |
| Q9UKN7 | Unconventional myosin-XV | Q9H0U9 | Testis-specific Y-encoded-like protein 1 |
| Q9UL63 | Muskelin | Q9HBU6 | Ethanolamine kinase 1 |
| Q9Y6J0 | Calcineurin-binding protein cabin-1 | Q9NYJ8 | TGF-beta-activated kinase 1 and MAP3K7-binding protein 2 |
| | | Q9UIF7 | A/G-specific adenine DNA glycosylase |
| | | Q9UKN7 | Unconventional myosin-XV |
| | | Q9UNZ2 | NSFL1 cofactor p47 |

*These proteins are not detected in MOCK (anti-TOM20) IP

Example 8

Determination of the level of apoptosis in non-proliferating immune cells (monocytes) from blood when treated with APIM-containing peptides Annexin staining was used to determine cell viability and cells were counted using flow cytometry.

Peripheral blood lymphocytes were isolated from A+ buffy coats (Blood Bank, St. Olav's University Hospital) by density gradient centrifugation (Lymphoprep; Axis-Shield PoC, Oslo, Norway). The adherent cell fraction after 90 minute incubation, termed monocytes, were washed twice with HANKS and maintained in RPMI 1640 supplemented with 2 mM glutamine, 100 mg/ml gentamicin and 25% heat-inactivated HS over-night. Cells were cultured at 37° C. in a humidified atmosphere of 5% $CO_2$ over-night. The next day cells were treated with different concentrations of APIM-containing peptides ATX-101 (SEQ ID NO: 1198) and ATX-P (MDRWLVPWKKKRKIRRRRRRRRRRR, SEQ ID NO: 1208). An $R_{11}$ peptide and no peptide treatment were used as controls. After 4 hours, the cells were washed once in PBS, and re-suspended in buffer as recommended by the manufacturer of the Annexin V-Pacific Blue kit (Invitrogen). Cells were identified monocytes according to size (FSC) and granularity (SSC).

Table 6 shows that there was no significant increase in annexin positive cells (apoptotic cells) when treated with APIM peptides.

Furthermore, as discussed herein, a 4 µM dose of ATX-101 reduces the cytokine production from TLS-ligand stimulated monocytes in absence of apoptosis. It is noted that the same dose showed low toxicity on normal cells in BMCS assays (Müller et al,. PloS One, 2013, v. 8: e70430).

TABLE 6

| | Percentage of annexin positive cells | |
|---|---|---|
| Control (no peptide) | 67% | |
| Peptide | 5µM peptide treatment | 10 µM peptide treatment |
| R11 (negative control) | 55% | 56% |
| ATX-101 (SEQ ID NO: 1198) | 72% | 79% |
| ATX-P (SEQ ID NO: 1208) | 65% | 81% |

Example 9

Determination of APIM peptide interaction with PCNA

Microscale thermophoresis (MST) was used to determine the dissociation constant for various APIM containing peptides.

PCNA was labeled with a fluorescent molecule. The concentration of PCNA was kept constant, whereas dilutions of each APIM containing peptide were prepared (1:1). In a mix of protein and peptide, the signal was recorded in all capillaries with varying concentrations of the unlabeled peptide, and any change of thermophoretic properties was observed as a change in fluorescence intensity.

Table 7 shows that ATX-101 and ATX-101-P (natural variant of APIM in ABH2) both show stronger interactions with PCNA than ATX-A, a negative control (a low Kd value indicates a strong interaction, whereas a high Kd value indicates a weak interaction). Furthermore, no data on specific interaction with R11 could be obtained by MST, indicating that this peptide does not interact with PCNA.

TABLE 7

| Peptide | Kd |
|---|---|
| ATX-101 | 177 |
| ATX-101-P | 123 |

TABLE 7-continued

| Peptide | Kd |
|---|---|
| ATX-A | 769 |
| R11 | nd |

The invention claimed is:

1. A method of treating or preventing hypercytokinemia resulting from cytokine release from non-proliferating immune cells in blood, said method comprising administering an agent, or a composition containing an agent, wherein said agent comprises:
   (i) an oligopeptidic compound comprising a PCNA interacting motif and a domain that facilitates the cellular uptake of said compound, wherein the PCNA interacting motif is $X_1X_2X_3X_4X_5$ (SEQ ID NO: 1), wherein:
   $X_1$ is a basic amino acid;
   $X_2$ is an aromatic amino acid;
   $X_3$ is an uncharged amino acid other than an aromatic amino acid, Glycine (G) or Proline (P);
   $X_4$ is any amino acid other than Proline (P), Glutamine (Q), an acidic amino acid or an aromatic amino acid; and
   $X_5$ is a basic amino acid or Proline (P),
   and wherein said PCNA interacting motif is not KYILK (SEQ ID NO: 234); or
   (ii) a nucleic acid molecule comprising a sequence encoding the oligopeptidic compound of (i),
   wherein said agent or composition is provided as a combined preparation with a toll-receptor antagonist for separate, simultaneous or sequential use or administration and wherein said subject has: (i) an inflammatory disease, which is not an infection or infectious disease; or (ii) an autoimmune disease.

2. The method of claim 1, wherein the inflammatory disease is inflammatory arthritis, psoriatic arthritis, rheumatoid arthritis or inflammatory bowel disease.

3. The method of claim 1, wherein the PCNA interacting motif comprises a sequence as set forth in SEQ ID NO: 2, wherein the amino acid at position 4 is not glutamine and the PCNA interacting motif is not KYILK (SEQ ID NO: 234).

4. The method of claim 1, wherein the PCNA interacting motif comprises a sequence selected from any one of SEQ ID NOs: 22 to 233 or 235 to 297.

5. The method of claim 1, wherein the agent comprises a PCNA interacting motif as set forth in SEQ ID NO: 28, a linker as set forth in SEQ ID NO: 1176 and a cell penetrating signal sequence as set forth in SEQ ID NO: 337.

6. The method of claim 1, wherein the agent comprises a sequence as set forth in any one of SEQ ID NOs: 1182 to 1204.

7. A method of treating or preventing hypercytokinemia resulting from cytokine release from non-proliferating immune cells in blood, said method comprising administering an agent, or a composition containing an agent, to a subject in need thereof, wherein said agent comprises:
   (i) an oligopeptidic compound comprising a PCNA interacting motif and a domain that facilitates the cellular uptake of said compound, wherein the PCNA interacting motif is $X_1X_2X_3X_4X_5$ (SEQ ID NO: 1) and wherein:
   $X_1$ is a basic amino acid;
   $X_2$ is an aromatic amino acid;
   $X_3$ is an uncharged amino acid other than an aromatic amino acid, Glycine (G) or Proline (P);
   $X_4$ is any amino acid other than Proline (P), Glutamine (Q), an acidic amino acid or an aromatic amino acid; and
   $X_5$ is a basic amino acid or Proline (P),
   and wherein said PCNA interacting motif is not KYILK (SEQ ID NO: 234); or
   (ii) a nucleic acid molecule comprising a sequence encoding the oligopeptidic compound of (i),
   wherein said agent or composition is provided as a combined preparation with a protein kinase inhibitor for separate, simultaneous or sequential use or administration and wherein said subject has: (i) an inflammatory disease, which is not an infection or an infectious disease; or (ii) an autoimmune disease.

8. The method of claim 7, wherein the protein kinase inhibitor is a p38 MAPK inhibitor or class I PI3K inhibitor.

9. The method of claim 8, wherein the p38 MAPK inhibitor is selected from X-702, SB203580, VX-745, LY2228820, BIRB 796 (Doramapimod), PH-797804 and TAK-715.

10. The method of claim 8, wherein the class I PI3K inhibitor is selected from AS-605240, BYL719, CAL-101, GDC-0941, GSK2636771, IC-87114, IPI-145, LY294002, NVP-BKM120 (Buparlisib), PIK-75, TG100-115 and TGX-221.

11. The method of claim 7, wherein the inflammatory disease is inflammatory arthritis, psoriatic arthritis, rheumatoid arthritis or inflammatory bowel disease.

12. The method of claim 7, wherein the PCNA interacting motif comprises a sequence as set forth in SEQ ID NO: 2, wherein the amino acid at position 4 is not glutamine and the PCNA interacting motif is not KYILK (SEQ ID NO: 234).

13. The method of claim 7, wherein the PCNA interacting motif comprises a sequence selected from any one of SEQ ID NOs: 22 to 233 or 235 to 297.

14. The method of claim 7, wherein the agent comprises a PCNA interacting motif as set forth in SEQ ID NO: 28, a linker as set forth in SEQ ID NO: 1176 and a cell penetrating signal sequence as set forth in SEQ ID NO: 337.

15. The method of claim 7, wherein the agent comprises a sequence as set forth in any one of SEQ ID NOs: 1182 to 1204.

16. A method of treating or preventing hypercytokinemia resulting from cytokine release from non-proliferating immune cells in blood, said method comprising administering an agent, or a composition containing an agent, to a subject in need thereof, wherein said agent comprises:
   (i) an oligopeptidic compound comprising a PCNA interacting motif and a domain that facilitates the cellular uptake of said compound, wherein the PCNA interacting motif is $X_1X_2X_3X_4X_5$ (SEQ ID NO: 1) and wherein:
- X₁ is a basic amino acid;
- X₂ is an aromatic amino acid;
- X₃ is an uncharged amino acid other than an aromatic amino acid, Glycine (G) or Proline (P);
- X₄ is any amino acid other than Proline (P), an acidic amino acid or an aromatic amino acid; and
- X₅ is a basic amino acid or Proline (P);

and wherein X₃ and X₄ are LV, LL, LA, AL, VL, VI, LI, IL, VV, VA, IV, II, AV, IA, AI, AM, LM, LS, LT, IS, MV, TV, AA, IM, LN, LQ, VM, TL, SL, IT, VT, LG, MA, ML, NL, QL, QI, TI, SI, AS, VS, SV, CA, IG, LR, VR, TK or IR, or (ii) a nucleic acid molecule comprising a sequence encoding the oligopeptidic compound of (i), wherein said subject has graft versus host disease (GVHD) or trauma.

17. The method of claim 16, wherein said trauma is caused by injury or surgery.

18. The method of claim 17, wherein said trauma caused by injury is a polytrauma, head trauma, chest trauma, abdominal trauma or extremity trauma.

19. The method of claim 17, wherein said trauma caused by injury is a burn.

20. The method of claim 16, wherein said agent or composition is provided as a combined preparation with one or more additional active agents for separate, simultaneous or sequential use or administration.

21. The method of claim 20, wherein the one or more additional active agents is a kinase inhibitor, an immunosuppressive compound, an anti-inflammatory compound, anti-microbial compound or a steroid.

22. The method of claim 16, wherein the PCNA interacting motif comprises a sequence as set forth in SEQ ID NO: 2 and wherein X₃ and X₄ are LV, LL, LA, AL, VL, VI, LI, IL, VV, VA, IV, II, AV, IA, AI, AM, LM, LS, LT, IS, MV, TV, AA, IM, LN, LQ, VM, TL, SL, IT, VT, LG, MA, ML, NL, QL, QI, TI, SI, AS, VS, SV, CA, IG, LR, VR, TK or IR.

23. The method of claim 16, wherein the PCNA interacting motif comprises a sequence selected from any one of SEQ ID NOs: 22 to 297.

24. The method of claim 16, wherein the agent comprises a PCNA interacting motif as set forth in SEQ ID NO: 28, a linker as set forth in SEQ ID NO: 1176 and a cell penetrating signal sequence as set forth in SEQ ID NO: 337.

25. The method of claim 16, wherein the agent comprises a sequence as set forth in any one of SEQ ID NOs: 1182 to 1204.

* * * * *

SEQUENCE LISTING

```
<160> NUMBER OF SEQ ID NOS: 1235

<210> SEQ ID NO 1
<211> LENGTH: 5
<212> TYPE: PRT
<213> ORGANISM: Artificial sequence
<220> FEATURE:
<223> OTHER INFORMATION: Consensus APIM
<220> FEATURE:
<221> NAME/KEY: VARIANT
<222> LOCATION: (1)..(1)
<223> OTHER INFORMATION: X is a basic amino acid
<220> FEATURE:
<221> NAME/KEY: VARIANT
<222> LOCATION: (2)..(2)
<223> OTHER INFORMATION: X is an aromatic amino acid
<220> FEATURE:
<221> NAME/KEY: VARIANT
<222> LOCATION: (3)..(3)
<223> OTHER INFORMATION: X is an uncharged amino acid other than an
      aromatic amino acid, glycine or proline
<220> FEATURE:
<221> NAME/KEY: VARIANT
<222> LOCATION: (4)..(4)
<223> OTHER INFORMATION: X is any amino acid other than an aromatic
      amino acid, an acidic amino acid, proline or glutamine
<220> FEATURE:
<221> NAME/KEY: VARIANT
<222> LOCATION: (5)..(5)
<223> OTHER INFORMATION: X is a basic amino acid or proline

<400> SEQUENCE: 1

Xaa Xaa Xaa Xaa Xaa
1               5

<210> SEQ ID NO 2
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg" or "His"
<220> FEATURE:
<221> NAME/KEY: variant
<222> LOCATION: (2)..(2)
<223> OTHER INFORMATION: /REPLACE= "Phe" or "Tyr" or "Trp"
<220> FEATURE:
<221> NAME/KEY: variant
<222> LOCATION: (3)..(3)
<223> OTHER INFORMATION: /REPLACE= "Leu" or "Ile" or "Val" or "Ala" or
      "Met" or "Ser" or "Thr" or "Asn" or "Gln" or "Cys"
<220> FEATURE:
<221> NAME/KEY: variant
<222> LOCATION: (4)..(4)
<223> OTHER INFORMATION: /REPLACE= "Leu" or "Ile" or "Val" or "Ala" or
      "Met" or "Ser" or "Thr" or "Asn" or "Cys" or "Gln" or "Gly" or
      "Lys" or "His" or "Arg"
<220> FEATURE:
<221> NAME/KEY: variant
<222> LOCATION: (5)..(5)
<223> OTHER INFORMATION: /REPLACE= "Lys" or "Arg" or "His" or "Pro"

<400> SEQUENCE: 2
```

Xaa Xaa Xaa Xaa Xaa
1               5

<210> SEQ ID NO 3
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg" or "His"
<220> FEATURE:
<221> NAME/KEY: variant
<222> LOCATION: (2)..(2)
<223> OTHER INFORMATION: /REPLACE= "Tyr" or "Trp" or "Phe"
<220> FEATURE:
<221> NAME/KEY: variant
<222> LOCATION: (3)..(3)
<223> OTHER INFORMATION: /REPLACE= "Leu" or "Ile" or "Val" or "Ala" or
      "Met" or "Ser" or "Thr" or "Asn" or "Gln"
<220> FEATURE:
<221> NAME/KEY: variant
<222> LOCATION: (4)..(4)
<223> OTHER INFORMATION: /REPLACE= "Leu" or "Ile" or "Val" or "Ala" or
      "Met" or "Ser" or "Thr" or "Asn" or "Gln" or "Gly" or "Lys" or
      "His" or "Arg"
<220> FEATURE:
<221> NAME/KEY: variant
<222> LOCATION: (5)..(5)
<223> OTHER INFORMATION: /REPLACE= "Lys" or "Arg" or "His" or "Pro"

<400> SEQUENCE: 3

Xaa Xaa Xaa Xaa Xaa
1               5

<210> SEQ ID NO 4
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg" or "His"
<220> FEATURE:
<221> NAME/KEY: variant
<222> LOCATION: (2)..(2)
<223> OTHER INFORMATION: /REPLACE= "Phe" or "Tyr" or "Trp"
<220> FEATURE:
<221> NAME/KEY: variant
<222> LOCATION: (3)..(3)
<223> OTHER INFORMATION: /REPLACE= "Leu" or "Ile" or "Val" or "Ala" or
      "Met" or "Ser" or "Thr"
<220> FEATURE:
<221> NAME/KEY: variant
<222> LOCATION: (4)..(4)
<223> OTHER INFORMATION: /REPLACE= "Leu" or "Ile" or "Val" or "Ala" or
      "Met" or "Ser" or "Thr" or "Asn" or "Gln" or "Gly" or "Lys" or
      "His" or "Arg"
<220> FEATURE:
<221> NAME/KEY: variant
<222> LOCATION: (5)..(5)
<223> OTHER INFORMATION: /REPLACE= "Lys" or "Arg" or "His" or "Pro"

<400> SEQUENCE: 4

Xaa Xaa Xaa Xaa Xaa
1               5

<210> SEQ ID NO 5
<211> LENGTH: 5

```
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg" or "His"
<220> FEATURE:
<221> NAME/KEY: variant
<222> LOCATION: (2)..(2)
<223> OTHER INFORMATION: /REPLACE= "Tyr" or "Trp" or "Phe"
<220> FEATURE:
<221> NAME/KEY: variant
<222> LOCATION: (3)..(3)
<223> OTHER INFORMATION: /REPLACE= "Leu" or "Ile" or "Val" or "Ala" or
      "Met" or "Ser" or "Thr"
<220> FEATURE:
<221> NAME/KEY: variant
<222> LOCATION: (4)..(4)
<223> OTHER INFORMATION: /REPLACE= "Leu" or "Ile" or "Val" or "Ala" or
      "Met" or "Ser" or "Thr" or "Asn" or "Gln" or "Gly" or "Lys" or
      "His" or "Arg"
<220> FEATURE:
<221> NAME/KEY: variant
<222> LOCATION: (5)..(5)
<223> OTHER INFORMATION: /REPLACE= "Lys" or "Arg" or "His"

<400> SEQUENCE: 5

Xaa Xaa Xaa Xaa Xaa
1               5

<210> SEQ ID NO 6
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg" or "His"
<220> FEATURE:
<221> NAME/KEY: variant
<222> LOCATION: (2)..(2)
<223> OTHER INFORMATION: /REPLACE= "Phe" or "Trp" or "Tyr"
<220> FEATURE:
<221> NAME/KEY: variant
<222> LOCATION: (3)..(3)
<223> OTHER INFORMATION: /REPLACE= "Leu" or "Ile" or "Val" or "Ala" or
      "Met" or "Ser" or "Thr"
<220> FEATURE:
<221> NAME/KEY: variant
<222> LOCATION: (4)..(4)
<223> OTHER INFORMATION: /REPLACE= "Leu" or "Ile" or "Val" or "Ala" or
      "Met" or "Ser" or "Thr" or "Gly" or "Lys" or "Arg"
<220> FEATURE:
<221> NAME/KEY: variant
<222> LOCATION: (5)..(5)
<223> OTHER INFORMATION: /REPLACE= "Lys" or "Arg" or "His"

<400> SEQUENCE: 6

Xaa Xaa Xaa Xaa Xaa
1               5

<210> SEQ ID NO 7
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg" or "His"
```

-continued

```
<220> FEATURE:
<221> NAME/KEY: variant
<222> LOCATION: (2)..(2)
<223> OTHER INFORMATION: /REPLACE= "Phe" or "Trp" or "Tyr"
<220> FEATURE:
<221> NAME/KEY: variant
<222> LOCATION: (3)..(3)
<223> OTHER INFORMATION: /REPLACE= "Leu" or "Ile" or "Val" or "Ala" or
      "Met" or "Ser" or "Thr"
<220> FEATURE:
<221> NAME/KEY: variant
<222> LOCATION: (4)..(4)
<223> OTHER INFORMATION: /REPLACE= "Leu" or "Ile" or "Val" or "Ala" or
      "Met" or "Ser" or "Thr"  or "Gly"
<220> FEATURE:
<221> NAME/KEY: variant
<222> LOCATION: (5)..(5)
<223> OTHER INFORMATION: /REPLACE= "Lys" or "Arg" or "His"

<400> SEQUENCE: 7

Xaa Xaa Xaa Xaa Xaa
1               5

<210> SEQ ID NO 8
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg"
<220> FEATURE:
<221> NAME/KEY: variant
<222> LOCATION: (2)..(2)
<223> OTHER INFORMATION: /REPLACE= "Phe" or "Trp" or "Tyr"
<220> FEATURE:
<221> NAME/KEY: variant
<222> LOCATION: (3)..(3)
<223> OTHER INFORMATION: /REPLACE= "Leu" or "Ile" or "Val" or "Ala" or
      "Met" or "Ser" or "Thr"
<220> FEATURE:
<221> NAME/KEY: variant
<222> LOCATION: (4)..(4)
<223> OTHER INFORMATION: /REPLACE= "Leu" or "Ile" or "Val" or "Ala" or
      "Met" or "Ser" or "Thr" or "Gly"
<220> FEATURE:
<221> NAME/KEY: variant
<222> LOCATION: (5)..(5)
<223> OTHER INFORMATION: /REPLACE= "Lys" or "Arg"

<400> SEQUENCE: 8

Xaa Xaa Xaa Xaa Xaa
1               5

<210> SEQ ID NO 9
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg"
<220> FEATURE:
<221> NAME/KEY: variant
<222> LOCATION: (2)..(2)
<223> OTHER INFORMATION: /REPLACE= "Phe" or "Trp"
<220> FEATURE:
<221> NAME/KEY: variant
<222> LOCATION: (3)..(3)
<223> OTHER INFORMATION: /REPLACE= "Leu" or "Ile" or "Val" or "Ala" or
      "Met" or "Ser" or "Thr"
```

```
<220> FEATURE:
<221> NAME/KEY: variant
<222> LOCATION: (4)..(4)
<223> OTHER INFORMATION: /REPLACE= "Leu" or "Ile" or "Val" or "Ala" or
      "Met" or "Ser" or "Thr" or "Gly"
<220> FEATURE:
<221> NAME/KEY: variant
<222> LOCATION: (5)..(5)
<223> OTHER INFORMATION: /REPLACE= "Lys" or "Arg"

<400> SEQUENCE: 9

Xaa Xaa Xaa Xaa Xaa
1               5

<210> SEQ ID NO 10
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg"
<220> FEATURE:
<221> NAME/KEY: variant
<222> LOCATION: (2)..(2)
<223> OTHER INFORMATION: /REPLACE= "Phe" or "Trp"
<220> FEATURE:
<221> NAME/KEY: variant
<222> LOCATION: (3)..(3)
<223> OTHER INFORMATION: /REPLACE= "Leu" or "Ile" or "Val" or "Ala" or
      "Met" or "Thr"
<220> FEATURE:
<221> NAME/KEY: variant
<222> LOCATION: (4)..(4)
<223> OTHER INFORMATION: /REPLACE= "Leu" or "Ile" or "Val" or "Ala" or
      "Met" or "Ser" or "Thr" or "Gly"
<220> FEATURE:
<221> NAME/KEY: variant
<222> LOCATION: (5)..(5)
<223> OTHER INFORMATION: /REPLACE= "Lys" or "Arg"

<400> SEQUENCE: 10

Xaa Xaa Xaa Xaa Xaa
1               5

<210> SEQ ID NO 11
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg"
<220> FEATURE:
<221> NAME/KEY: variant
<222> LOCATION: (2)..(2)
<223> OTHER INFORMATION: /REPLACE= "Trp" or "Phe"
<220> FEATURE:
<221> NAME/KEY: variant
<222> LOCATION: (3)..(3)
<223> OTHER INFORMATION: /REPLACE= "Leu" or "Ile" or "Val" or "Ala" or
      "Met" or "Thr"
<220> FEATURE:
<221> NAME/KEY: variant
<222> LOCATION: (4)..(4)
<223> OTHER INFORMATION: /REPLACE= "Leu" or "Ile" or "Val" or "Ala" or
      "Met" or "Ser" or "Thr"
<220> FEATURE:
<221> NAME/KEY: variant
<222> LOCATION: (5)..(5)
<223> OTHER INFORMATION: /REPLACE= "Lys" or "Arg"
```

```
<400> SEQUENCE: 11

Xaa Xaa Xaa Xaa Xaa
1               5

<210> SEQ ID NO 12
<211> LENGTH: 5
<212> TYPE: PRT
<213> ORGANISM: Artificial Sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg"
<220> FEATURE:
<221> NAME/KEY: variant
<222> LOCATION: (2)..(2)
<223> OTHER INFORMATION: /REPLACE= "Trp" or "Phe"
<220> FEATURE:
<221> NAME/KEY: variant
<222> LOCATION: (3)..(3)
<223> OTHER INFORMATION: /REPLACE= "Leu" or "Ile" or "Val" or "Ala" or
      "Met" or "Ser" or "Thr"
<220> FEATURE:
<221> NAME/KEY: variant
<222> LOCATION: (4)..(4)
<223> OTHER INFORMATION: /REPLACE= "Leu" or "Ile" or "Val" or "Ala" or
      "Met" or "Gly"
<220> FEATURE:
<221> NAME/KEY: variant
<222> LOCATION: (5)..(5)
<223> OTHER INFORMATION: /REPLACE= "Lys" or "Arg"

<400> SEQUENCE: 12

Xaa Xaa Xaa Xaa Xaa
1               5

<210> SEQ ID NO 13
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE=  "Lys" or "Arg"
<220> FEATURE:
<221> NAME/KEY: variant
<222> LOCATION: (2)..(2)
<223> OTHER INFORMATION: /REPLACE=  "Trp" or "Phe"
<220> FEATURE:
<221> NAME/KEY: variant
<222> LOCATION: (3)..(3)
<223> OTHER INFORMATION: /REPLACE= "Leu" or "Ile" or "Val" or "Ala" or
      "Met" or "Thr"
<220> FEATURE:
<221> NAME/KEY: variant
<222> LOCATION: (4)..(4)
<223> OTHER INFORMATION: /REPLACE= "Leu" or "Ile" or "Val" or "Ala" or
      "Met" or "Ser" or "Thr"
<220> FEATURE:
<221> NAME/KEY: variant
<222> LOCATION: (5)..(5)
<223> OTHER INFORMATION: /REPLACE=  "Lys" or "Arg"

<400> SEQUENCE: 13

Xaa Xaa Xaa Xaa Xaa
1               5

<210> SEQ ID NO 14
<211> LENGTH: 5
```

```
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg"
<220> FEATURE:
<221> NAME/KEY: variant
<222> LOCATION: (2)..(2)
<223> OTHER INFORMATION: /REPLACE= "Trp" or "Phe"
<220> FEATURE:
<221> NAME/KEY: variant
<222> LOCATION: (3)..(3)
<223> OTHER INFORMATION: /REPLACE= "Leu" or "Ile" or "Val" or "Ala" or
     "Met" or "Ser" or "Thr"
<220> FEATURE:
<221> NAME/KEY: variant
<222> LOCATION: (4)..(4)
<223> OTHER INFORMATION: /REPLACE= "Leu" or "Ile" or "Val" or "Ala" or
     "Ser" or "Thr"
<220> FEATURE:
<221> NAME/KEY: variant
<222> LOCATION: (5)..(5)
<223> OTHER INFORMATION: /REPLACE= "Lys" or "Arg"

<400> SEQUENCE: 14

Xaa Xaa Xaa Xaa Xaa
1               5

<210> SEQ ID NO 15
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg"
<220> FEATURE:
<221> NAME/KEY: variant
<222> LOCATION: (2)..(2)
<223> OTHER INFORMATION: /REPLACE= "Trp" or "Phe"
<220> FEATURE:
<221> NAME/KEY: variant
<222> LOCATION: (3)..(3)
<223> OTHER INFORMATION: /REPLACE= "Leu" or "Ile" or "Val" or "Ala" or
     "Thr"
<220> FEATURE:
<221> NAME/KEY: variant
<222> LOCATION: (4)..(4)
<223> OTHER INFORMATION: /REPLACE= "Leu" or "Ile" or "Val" or "Ala" or
     "Thr" or "Ser"
<220> FEATURE:
<221> NAME/KEY: variant
<222> LOCATION: (5)..(5)
<223> OTHER INFORMATION: /REPLACE= "Lys" or "Arg"

<400> SEQUENCE: 15

Xaa Xaa Xaa Xaa Xaa
1               5

<210> SEQ ID NO 16
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (2)..(2)
<223> OTHER INFORMATION: /REPLACE= "Trp" or "Try" or "Phe"
<220> FEATURE:
```

```
<221> NAME/KEY: variant
<222> LOCATION: (3)..(3)
<223> OTHER INFORMATION: /REPLACE= "Leu" or "Ile" or "Val" or "Ala"
<220> FEATURE:
<221> NAME/KEY: variant
<222> LOCATION: (4)..(4)
<223> OTHER INFORMATION: /REPLACE= "Leu" or "Val" or "Ala" or "Met" or
      "Ser" or "Thr"
<220> FEATURE:
<221> NAME/KEY: variant
<222> LOCATION: (5)..(5)
<223> OTHER INFORMATION: /REPLACE= "Lys" or "Arg"

<400> SEQUENCE: 16

Arg Xaa Xaa Xaa Xaa
1               5

<210> SEQ ID NO 17
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (2)..(2)
<223> OTHER INFORMATION: /REPLACE= "Trp" or "Tyr" or "Phe"
<220> FEATURE:
<221> NAME/KEY: variant
<222> LOCATION: (3)..(3)
<223> OTHER INFORMATION: /REPLACE= "Leu" or "Ile" or "Val" or "Ala" or
      "Thr"
<220> FEATURE:
<221> NAME/KEY: variant
<222> LOCATION: (4)..(4)
<223> OTHER INFORMATION: /REPLACE= "Leu" or "Val" or "Ala" or "Met" or
      "Ser" or "Thr"

<400> SEQUENCE: 17

Arg Xaa Xaa Xaa Lys
1               5

<210> SEQ ID NO 18
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg"
<220> FEATURE:
<221> NAME/KEY: variant
<222> LOCATION: (2)..(2)
<223> OTHER INFORMATION: /REPLACE= "Phe" or "Tyr"
<220> FEATURE:
<221> NAME/KEY: variant
<222> LOCATION: (3)..(3)
<223> OTHER INFORMATION: /REPLACE= "Leu" or "Ile" or "Val" or "Ala"
<220> FEATURE:
<221> NAME/KEY: variant
<222> LOCATION: (4)..(4)
<223> OTHER INFORMATION: /REPLACE= "Leu" or "Ile" or "Val" or "Ala" or
      "Met"
<220> FEATURE:
<221> NAME/KEY: variant
<222> LOCATION: (5)..(5)
<223> OTHER INFORMATION: /REPLACE= "Lys" or "Arg"

<400> SEQUENCE: 18

Xaa Xaa Xaa Xaa Xaa
1               5
```

```
<210> SEQ ID NO 19
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg"
<220> FEATURE:
<221> NAME/KEY: variant
<222> LOCATION: (2)..(2)
<223> OTHER INFORMATION: /REPLACE= "Trp" or "Phe" or "Tyr"
<220> FEATURE:
<221> NAME/KEY: variant
<222> LOCATION: (3)..(4)
<223> OTHER INFORMATION: /REPLACE= "Leu" or "Ile" or "Val" or "Ala"
<220> FEATURE:
<221> NAME/KEY: variant
<222> LOCATION: (5)..(5)
<223> OTHER INFORMATION: /REPLACE= "Lys" or "Arg"

<400> SEQUENCE: 19

Xaa Xaa Xaa Xaa Xaa
1               5

<210> SEQ ID NO 20
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: /REPLACE= "Lys" or "Arg"
<220> FEATURE:
<221> NAME/KEY: variant
<222> LOCATION: (2)..(2)
<223> OTHER INFORMATION: /REPLACE= "Trp" or "Tyr"
<220> FEATURE:
<221> NAME/KEY: variant
<222> LOCATION: (3)..(3)
<223> OTHER INFORMATION: /REPLACE= "Leu" or "Ile" or "Val" or "Ala" or
      "Ser" or "Thr"
<220> FEATURE:
<221> NAME/KEY: variant
<222> LOCATION: (4)..(4)
<223> OTHER INFORMATION: /REPLACE= "Leu" or "Met" or "Val" or "Ala" or
      "Ser" or "Thr"
<220> FEATURE:
<221> NAME/KEY: variant
<222> LOCATION: (5)..(5)
<223> OTHER INFORMATION: /REPLACE= "Lys" or "Arg"

<400> SEQUENCE: 20

Xaa Xaa Xaa Xaa Xaa
1               5

<210> SEQ ID NO 21
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (2)..(2)
<223> OTHER INFORMATION: /REPLACE= "Phe" or "Tyr" or "Trp"
<220> FEATURE:
<221> NAME/KEY: variant
<222> LOCATION: (3)..(3)
<223> OTHER INFORMATION: /REPLACE= "Leu" or "Ile" or "Val" or "Ala"  or
```

```
        "Thr"
<220> FEATURE:
<221> NAME/KEY: variant
<222> LOCATION: (4)..(4)
<223> OTHER INFORMATION: /REPLACE= "Leu" or "Ile" or "Val" or "Ala" or
      "Met" or "Ser" or "Thr"

<400> SEQUENCE: 21

Lys Xaa Xaa Xaa Lys
1               5

<210> SEQ ID NO 22
<211> LENGTH: 5
<212> TYPE: PRT
<213> ORGANISM: Artificial sequence
<220> FEATURE:
<223> OTHER INFORMATION: APIM variant

<400> SEQUENCE: 22

Arg Trp Leu Leu Lys
1               5

<210> SEQ ID NO 23
<211> LENGTH: 5
<212> TYPE: PRT
<213> ORGANISM: Artificial sequence
<220> FEATURE:
<223> OTHER INFORMATION: APIM variant

<400> SEQUENCE: 23

Arg Phe Leu Leu Lys
1               5

<210> SEQ ID NO 24
<211> LENGTH: 5
<212> TYPE: PRT
<213> ORGANISM: Artificial sequence
<220> FEATURE:
<223> OTHER INFORMATION: APIM variant

<400> SEQUENCE: 24

Arg Tyr Leu Leu Lys
1               5

<210> SEQ ID NO 25
<211> LENGTH: 5
<212> TYPE: PRT
<213> ORGANISM: Artificial sequence
<220> FEATURE:
<223> OTHER INFORMATION: APIM variant

<400> SEQUENCE: 25

Arg Trp Leu Leu Arg
1               5

<210> SEQ ID NO 26
<211> LENGTH: 5
<212> TYPE: PRT
<213> ORGANISM: Artificial sequence
<220> FEATURE:
<223> OTHER INFORMATION: APIM variant

<400> SEQUENCE: 26

Arg Phe Leu Leu Arg
1               5

<210> SEQ ID NO 27
```

```
<211> LENGTH: 5
<212> TYPE: PRT
<213> ORGANISM: Artificial sequence
<220> FEATURE:
<223> OTHER INFORMATION: APIM variant

<400> SEQUENCE: 27

Arg Tyr Leu Leu Arg
1               5

<210> SEQ ID NO 28
<211> LENGTH: 5
<212> TYPE: PRT
<213> ORGANISM: Artificial sequence
<220> FEATURE:
<223> OTHER INFORMATION: APIM variant

<400> SEQUENCE: 28

Arg Trp Leu Val Lys
1               5

<210> SEQ ID NO 29
<211> LENGTH: 5
<212> TYPE: PRT
<213> ORGANISM: Artificial sequence
<220> FEATURE:
<223> OTHER INFORMATION: APIM variant

<400> SEQUENCE: 29

Arg Phe Leu Val Lys
1               5

<210> SEQ ID NO 30
<211> LENGTH: 5
<212> TYPE: PRT
<213> ORGANISM: Artificial sequence
<220> FEATURE:
<223> OTHER INFORMATION: APIM variant

<400> SEQUENCE: 30

Arg Tyr Leu Val Lys
1               5

<210> SEQ ID NO 31
<211> LENGTH: 5
<212> TYPE: PRT
<213> ORGANISM: Artificial sequence
<220> FEATURE:
<223> OTHER INFORMATION: APIM variant

<400> SEQUENCE: 31

Arg Trp Leu Val Arg
1               5

<210> SEQ ID NO 32
<211> LENGTH: 5
<212> TYPE: PRT
<213> ORGANISM: Artificial sequence
<220> FEATURE:
<223> OTHER INFORMATION: APIM variant

<400> SEQUENCE: 32

Arg Phe Leu Val Arg
1               5

<210> SEQ ID NO 33
<211> LENGTH: 5
```

```
<212> TYPE: PRT
<213> ORGANISM: Artificial sequence
<220> FEATURE:
<223> OTHER INFORMATION: APIM variant

<400> SEQUENCE: 33

Arg Tyr Leu Val Arg
1               5

<210> SEQ ID NO 34
<211> LENGTH: 5
<212> TYPE: PRT
<213> ORGANISM: Artificial sequence
<220> FEATURE:
<223> OTHER INFORMATION: APIM variant

<400> SEQUENCE: 34

Arg Trp Ile Val Lys
1               5

<210> SEQ ID NO 35
<211> LENGTH: 5
<212> TYPE: PRT
<213> ORGANISM: Artificial sequence
<220> FEATURE:
<223> OTHER INFORMATION: APIM variant

<400> SEQUENCE: 35

Arg Phe Ile Val Lys
1               5

<210> SEQ ID NO 36
<211> LENGTH: 5
<212> TYPE: PRT
<213> ORGANISM: Artificial sequence
<220> FEATURE:
<223> OTHER INFORMATION: APIM variant

<400> SEQUENCE: 36

Arg Tyr Ile Val Lys
1               5

<210> SEQ ID NO 37
<211> LENGTH: 5
<212> TYPE: PRT
<213> ORGANISM: Artificial sequence
<220> FEATURE:
<223> OTHER INFORMATION: APIM variant

<400> SEQUENCE: 37

Arg Trp Ile Val Arg
1               5

<210> SEQ ID NO 38
<211> LENGTH: 5
<212> TYPE: PRT
<213> ORGANISM: Artificial sequence
<220> FEATURE:
<223> OTHER INFORMATION: APIM variant

<400> SEQUENCE: 38

Arg Phe Ile Val Arg
1               5

<210> SEQ ID NO 39
<211> LENGTH: 5
<212> TYPE: PRT
```

```
<213> ORGANISM: Artificial sequence
<220> FEATURE:
<223> OTHER INFORMATION: APIM variant

<400> SEQUENCE: 39

Arg Tyr Ile Val Arg
1               5

<210> SEQ ID NO 40
<211> LENGTH: 5
<212> TYPE: PRT
<213> ORGANISM: Artificial sequence
<220> FEATURE:
<223> OTHER INFORMATION: APIM variant

<400> SEQUENCE: 40

Arg Trp Leu Ser Lys
1               5

<210> SEQ ID NO 41
<211> LENGTH: 5
<212> TYPE: PRT
<213> ORGANISM: Artificial sequence
<220> FEATURE:
<223> OTHER INFORMATION: APIM variant

<400> SEQUENCE: 41

Arg Phe Leu Ser Lys
1               5

<210> SEQ ID NO 42
<211> LENGTH: 5
<212> TYPE: PRT
<213> ORGANISM: Artificial sequence
<220> FEATURE:
<223> OTHER INFORMATION: APIM variant

<400> SEQUENCE: 42

Arg Tyr Leu Ser Lys
1               5

<210> SEQ ID NO 43
<211> LENGTH: 5
<212> TYPE: PRT
<213> ORGANISM: Artificial sequence
<220> FEATURE:
<223> OTHER INFORMATION: APIM variant

<400> SEQUENCE: 43

Arg Trp Leu Ser Arg
1               5

<210> SEQ ID NO 44
<211> LENGTH: 5
<212> TYPE: PRT
<213> ORGANISM: Artificial sequence
<220> FEATURE:
<223> OTHER INFORMATION: APIM variant

<400> SEQUENCE: 44

Arg Phe Leu Ser Arg
1               5

<210> SEQ ID NO 45
<211> LENGTH: 5
<212> TYPE: PRT
<213> ORGANISM: Artificial sequence
```

```
<220> FEATURE:
<223> OTHER INFORMATION: APIM variant

<400> SEQUENCE: 45

Arg Tyr Leu Ser Arg
1               5

<210> SEQ ID NO 46
<211> LENGTH: 5
<212> TYPE: PRT
<213> ORGANISM: Artificial sequence
<220> FEATURE:
<223> OTHER INFORMATION: APIM variant

<400> SEQUENCE: 46

Arg Trp Ile Ser Lys
1               5

<210> SEQ ID NO 47
<211> LENGTH: 5
<212> TYPE: PRT
<213> ORGANISM: Artificial sequence
<220> FEATURE:
<223> OTHER INFORMATION: APIM variant

<400> SEQUENCE: 47

Arg Phe Ile Ser Lys
1               5

<210> SEQ ID NO 48
<211> LENGTH: 5
<212> TYPE: PRT
<213> ORGANISM: Artificial sequence
<220> FEATURE:
<223> OTHER INFORMATION: APIM variant

<400> SEQUENCE: 48

Arg Tyr Ile Ser Lys
1               5

<210> SEQ ID NO 49
<211> LENGTH: 5
<212> TYPE: PRT
<213> ORGANISM: Artificial sequence
<220> FEATURE:
<223> OTHER INFORMATION: APIM variant

<400> SEQUENCE: 49

Arg Trp Ile Ser Arg
1               5

<210> SEQ ID NO 50
<211> LENGTH: 5
<212> TYPE: PRT
<213> ORGANISM: Artificial sequence
<220> FEATURE:
<223> OTHER INFORMATION: APIM variant

<400> SEQUENCE: 50

Arg Phe Ile Ser Arg
1               5

<210> SEQ ID NO 51
<211> LENGTH: 5
<212> TYPE: PRT
<213> ORGANISM: Artificial sequence
<220> FEATURE:
```

```
<223> OTHER INFORMATION: APIM variant

<400> SEQUENCE: 51

Arg Tyr Ile Ser Arg
1               5

<210> SEQ ID NO 52
<211> LENGTH: 5
<212> TYPE: PRT
<213> ORGANISM: Artificial sequence
<220> FEATURE:
<223> OTHER INFORMATION: APIM variant

<400> SEQUENCE: 52

Arg Trp Ser Val Lys
1               5

<210> SEQ ID NO 53
<211> LENGTH: 5
<212> TYPE: PRT
<213> ORGANISM: Artificial sequence
<220> FEATURE:
<223> OTHER INFORMATION: APIM variant

<400> SEQUENCE: 53

Arg Phe Ser Val Lys
1               5

<210> SEQ ID NO 54
<211> LENGTH: 5
<212> TYPE: PRT
<213> ORGANISM: Artificial sequence
<220> FEATURE:
<223> OTHER INFORMATION: APIM variant

<400> SEQUENCE: 54

Arg Tyr Ser Val Lys
1               5

<210> SEQ ID NO 55
<211> LENGTH: 5
<212> TYPE: PRT
<213> ORGANISM: Artificial sequence
<220> FEATURE:
<223> OTHER INFORMATION: APIM variant

<400> SEQUENCE: 55

Arg Trp Ser Val Arg
1               5

<210> SEQ ID NO 56
<211> LENGTH: 5
<212> TYPE: PRT
<213> ORGANISM: Artificial sequence
<220> FEATURE:
<223> OTHER INFORMATION: APIM variant

<400> SEQUENCE: 56

Arg Phe Ser Val Arg
1               5

<210> SEQ ID NO 57
<211> LENGTH: 5
<212> TYPE: PRT
<213> ORGANISM: Artificial sequence
<220> FEATURE:
<223> OTHER INFORMATION: APIM variant
```

<400> SEQUENCE: 57

Arg Tyr Ser Val Arg
1               5

<210> SEQ ID NO 58
<211> LENGTH: 5
<212> TYPE: PRT
<213> ORGANISM: Artificial sequence
<220> FEATURE:
<223> OTHER INFORMATION: APIM variant

<400> SEQUENCE: 58

Arg Trp Ala Val Lys
1               5

<210> SEQ ID NO 59
<211> LENGTH: 5
<212> TYPE: PRT
<213> ORGANISM: Artificial sequence
<220> FEATURE:
<223> OTHER INFORMATION: APIM variant

<400> SEQUENCE: 59

Arg Phe Ala Val Lys
1               5

<210> SEQ ID NO 60
<211> LENGTH: 5
<212> TYPE: PRT
<213> ORGANISM: Artificial sequence
<220> FEATURE:
<223> OTHER INFORMATION: APIM variant

<400> SEQUENCE: 60

Arg Tyr Ala Val Lys
1               5

<210> SEQ ID NO 61
<211> LENGTH: 5
<212> TYPE: PRT
<213> ORGANISM: Artificial sequence
<220> FEATURE:
<223> OTHER INFORMATION: APIM variant

<400> SEQUENCE: 61

Arg Trp Ala Val Arg
1               5

<210> SEQ ID NO 62
<211> LENGTH: 5
<212> TYPE: PRT
<213> ORGANISM: Artificial sequence
<220> FEATURE:
<223> OTHER INFORMATION: APIM variant

<400> SEQUENCE: 62

Arg Phe Ala Val Arg
1               5

<210> SEQ ID NO 63
<211> LENGTH: 5
<212> TYPE: PRT
<213> ORGANISM: Artificial sequence
<220> FEATURE:
<223> OTHER INFORMATION: APIM variant

```
<400> SEQUENCE: 63

Arg Tyr Ala Val Arg
1               5

<210> SEQ ID NO 64
<211> LENGTH: 5
<212> TYPE: PRT
<213> ORGANISM: Artificial sequence
<220> FEATURE:
<223> OTHER INFORMATION: APIM variant

<400> SEQUENCE: 64

Arg Trp Leu Gly Arg
1               5

<210> SEQ ID NO 65
<211> LENGTH: 5
<212> TYPE: PRT
<213> ORGANISM: Artificial sequence
<220> FEATURE:
<223> OTHER INFORMATION: APIM variant

<400> SEQUENCE: 65

Arg Phe Leu Gly Arg
1               5

<210> SEQ ID NO 66
<211> LENGTH: 5
<212> TYPE: PRT
<213> ORGANISM: Artificial sequence
<220> FEATURE:
<223> OTHER INFORMATION: APIM variant

<400> SEQUENCE: 66

Arg Tyr Leu Gly Arg
1               5

<210> SEQ ID NO 67
<211> LENGTH: 5
<212> TYPE: PRT
<213> ORGANISM: Artificial sequence
<220> FEATURE:
<223> OTHER INFORMATION: APIM variant

<400> SEQUENCE: 67

Arg Trp Leu Gly Lys
1               5

<210> SEQ ID NO 68
<211> LENGTH: 5
<212> TYPE: PRT
<213> ORGANISM: Artificial sequence
<220> FEATURE:
<223> OTHER INFORMATION: APIM variant

<400> SEQUENCE: 68

Arg Phe Leu Gly Lys
1               5

<210> SEQ ID NO 69
<211> LENGTH: 5
<212> TYPE: PRT
<213> ORGANISM: Artificial sequence
<220> FEATURE:
<223> OTHER INFORMATION: APIM variant

<400> SEQUENCE: 69
```

Arg Tyr Leu Gly Lys
1               5

<210> SEQ ID NO 70
<211> LENGTH: 5
<212> TYPE: PRT
<213> ORGANISM: Artificial sequence
<220> FEATURE:
<223> OTHER INFORMATION: APIM variant

<400> SEQUENCE: 70

Arg Trp Leu Ala Arg
1               5

<210> SEQ ID NO 71
<211> LENGTH: 5
<212> TYPE: PRT
<213> ORGANISM: Artificial sequence
<220> FEATURE:
<223> OTHER INFORMATION: APIM variant

<400> SEQUENCE: 71

Arg Phe Leu Ala Arg
1               5

<210> SEQ ID NO 72
<211> LENGTH: 5
<212> TYPE: PRT
<213> ORGANISM: Artificial sequence
<220> FEATURE:
<223> OTHER INFORMATION: APIM variant

<400> SEQUENCE: 72

Arg Tyr Leu Ala Arg
1               5

<210> SEQ ID NO 73
<211> LENGTH: 5
<212> TYPE: PRT
<213> ORGANISM: Artificial sequence
<220> FEATURE:
<223> OTHER INFORMATION: APIM variant

<400> SEQUENCE: 73

Arg Trp Leu Ala Lys
1               5

<210> SEQ ID NO 74
<211> LENGTH: 5
<212> TYPE: PRT
<213> ORGANISM: Artificial sequence
<220> FEATURE:
<223> OTHER INFORMATION: APIM variant

<400> SEQUENCE: 74

Arg Phe Leu Ala Lys
1               5

<210> SEQ ID NO 75
<211> LENGTH: 5
<212> TYPE: PRT
<213> ORGANISM: Artificial sequence
<220> FEATURE:
<223> OTHER INFORMATION: APIM variant

<400> SEQUENCE: 75

Arg Tyr Leu Ala Lys
1               5

<210> SEQ ID NO 76
<211> LENGTH: 5
<212> TYPE: PRT
<213> ORGANISM: Artificial sequence
<220> FEATURE:
<223> OTHER INFORMATION: APIM variant

<400> SEQUENCE: 76

Arg Trp Leu Thr Lys
1               5

<210> SEQ ID NO 77
<211> LENGTH: 5
<212> TYPE: PRT
<213> ORGANISM: Artificial sequence
<220> FEATURE:
<223> OTHER INFORMATION: APIM variant

<400> SEQUENCE: 77

Arg Phe Leu Thr Lys
1               5

<210> SEQ ID NO 78
<211> LENGTH: 5
<212> TYPE: PRT
<213> ORGANISM: Artificial sequence
<220> FEATURE:
<223> OTHER INFORMATION: APIM variant

<400> SEQUENCE: 78

Arg Tyr Leu Thr Lys
1               5

<210> SEQ ID NO 79
<211> LENGTH: 5
<212> TYPE: PRT
<213> ORGANISM: Artificial sequence
<220> FEATURE:
<223> OTHER INFORMATION: APIM variant

<400> SEQUENCE: 79

Arg Trp Leu Thr Arg
1               5

<210> SEQ ID NO 80
<211> LENGTH: 5
<212> TYPE: PRT
<213> ORGANISM: Artificial sequence
<220> FEATURE:
<223> OTHER INFORMATION: APIM variant

<400> SEQUENCE: 80

Arg Phe Leu Thr Arg
1               5

<210> SEQ ID NO 81
<211> LENGTH: 5
<212> TYPE: PRT
<213> ORGANISM: Artificial sequence
<220> FEATURE:
<223> OTHER INFORMATION: APIM variant

<400> SEQUENCE: 81

Arg Tyr Leu Thr Arg

```
<210> SEQ ID NO 82
<211> LENGTH: 5
<212> TYPE: PRT
<213> ORGANISM: Artificial sequence
<220> FEATURE:
<223> OTHER INFORMATION: APIM variant

<400> SEQUENCE: 82

Arg Trp Ile Thr Lys
1               5

<210> SEQ ID NO 83
<211> LENGTH: 5
<212> TYPE: PRT
<213> ORGANISM: Artificial sequence
<220> FEATURE:
<223> OTHER INFORMATION: APIM variant

<400> SEQUENCE: 83

Arg Phe Ile Thr Lys
1               5

<210> SEQ ID NO 84
<211> LENGTH: 5
<212> TYPE: PRT
<213> ORGANISM: Artificial sequence
<220> FEATURE:
<223> OTHER INFORMATION: APIM variant

<400> SEQUENCE: 84

Arg Tyr Ile Thr Lys
1               5

<210> SEQ ID NO 85
<211> LENGTH: 5
<212> TYPE: PRT
<213> ORGANISM: Artificial sequence
<220> FEATURE:
<223> OTHER INFORMATION: APIM variant

<400> SEQUENCE: 85

Arg Trp Ile Thr Arg
1               5

<210> SEQ ID NO 86
<211> LENGTH: 5
<212> TYPE: PRT
<213> ORGANISM: Artificial sequence
<220> FEATURE:
<223> OTHER INFORMATION: APIM variant

<400> SEQUENCE: 86

Arg Phe Ile Thr Arg
1               5

<210> SEQ ID NO 87
<211> LENGTH: 5
<212> TYPE: PRT
<213> ORGANISM: Artificial sequence
<220> FEATURE:
<223> OTHER INFORMATION: APIM variant

<400> SEQUENCE: 87

Arg Tyr Ile Thr Arg
1               5
```

```
<210> SEQ ID NO 88
<211> LENGTH: 5
<212> TYPE: PRT
<213> ORGANISM: Artificial sequence
<220> FEATURE:
<223> OTHER INFORMATION: APIM variant

<400> SEQUENCE: 88

Arg Trp Thr Val Lys
1               5

<210> SEQ ID NO 89
<211> LENGTH: 5
<212> TYPE: PRT
<213> ORGANISM: Artificial sequence
<220> FEATURE:
<223> OTHER INFORMATION: APIM variant

<400> SEQUENCE: 89

Arg Phe Thr Val Lys
1               5

<210> SEQ ID NO 90
<211> LENGTH: 5
<212> TYPE: PRT
<213> ORGANISM: Artificial sequence
<220> FEATURE:
<223> OTHER INFORMATION: APIM variant

<400> SEQUENCE: 90

Arg Tyr Thr Val Lys
1               5

<210> SEQ ID NO 91
<211> LENGTH: 5
<212> TYPE: PRT
<213> ORGANISM: Artificial sequence
<220> FEATURE:
<223> OTHER INFORMATION: APIM variant

<400> SEQUENCE: 91

Arg Trp Thr Val Arg
1               5

<210> SEQ ID NO 92
<211> LENGTH: 5
<212> TYPE: PRT
<213> ORGANISM: Artificial sequence
<220> FEATURE:
<223> OTHER INFORMATION: APIM variant

<400> SEQUENCE: 92

Arg Phe Thr Val Arg
1               5

<210> SEQ ID NO 93
<211> LENGTH: 5
<212> TYPE: PRT
<213> ORGANISM: Artificial sequence
<220> FEATURE:
<223> OTHER INFORMATION: APIM variant

<400> SEQUENCE: 93

Arg Tyr Thr Val Arg
1               5
```

```
<210> SEQ ID NO 94
<211> LENGTH: 5
<212> TYPE: PRT
<213> ORGANISM: Artificial sequence
<220> FEATURE:
<223> OTHER INFORMATION: APIM variant

<400> SEQUENCE: 94

Arg Trp Ile Arg Lys
1               5

<210> SEQ ID NO 95
<211> LENGTH: 5
<212> TYPE: PRT
<213> ORGANISM: Artificial sequence
<220> FEATURE:
<223> OTHER INFORMATION: APIM variant

<400> SEQUENCE: 95

Arg Phe Ile Arg Lys
1               5

<210> SEQ ID NO 96
<211> LENGTH: 5
<212> TYPE: PRT
<213> ORGANISM: Artificial sequence
<220> FEATURE:
<223> OTHER INFORMATION: APIM variant

<400> SEQUENCE: 96

Arg Tyr Ile Arg Lys
1               5

<210> SEQ ID NO 97
<211> LENGTH: 5
<212> TYPE: PRT
<213> ORGANISM: Artificial sequence
<220> FEATURE:
<223> OTHER INFORMATION: APIM variant

<400> SEQUENCE: 97

Arg Trp Ile Arg Arg
1               5

<210> SEQ ID NO 98
<211> LENGTH: 5
<212> TYPE: PRT
<213> ORGANISM: Artificial sequence
<220> FEATURE:
<223> OTHER INFORMATION: APIM variant

<400> SEQUENCE: 98

Arg Phe Ile Arg Arg
1               5

<210> SEQ ID NO 99
<211> LENGTH: 5
<212> TYPE: PRT
<213> ORGANISM: Artificial sequence
<220> FEATURE:
<223> OTHER INFORMATION: APIM variant

<400> SEQUENCE: 99

Arg Tyr Ile Arg Arg
1               5
```

```
<210> SEQ ID NO 100
<211> LENGTH: 5
<212> TYPE: PRT
<213> ORGANISM: Artificial sequence
<220> FEATURE:
<223> OTHER INFORMATION: APIM variant

<400> SEQUENCE: 100

Arg Trp Leu Arg Lys
1               5

<210> SEQ ID NO 101
<211> LENGTH: 5
<212> TYPE: PRT
<213> ORGANISM: Artificial sequence
<220> FEATURE:
<223> OTHER INFORMATION: APIM variant

<400> SEQUENCE: 101

Arg Phe Leu Arg Lys
1               5

<210> SEQ ID NO 102
<211> LENGTH: 5
<212> TYPE: PRT
<213> ORGANISM: Artificial sequence
<220> FEATURE:
<223> OTHER INFORMATION: APIM variant

<400> SEQUENCE: 102

Arg Tyr Leu Arg Lys
1               5

<210> SEQ ID NO 103
<211> LENGTH: 5
<212> TYPE: PRT
<213> ORGANISM: Artificial sequence
<220> FEATURE:
<223> OTHER INFORMATION: APIM variant

<400> SEQUENCE: 103

Arg Trp Leu Arg Arg
1               5

<210> SEQ ID NO 104
<211> LENGTH: 5
<212> TYPE: PRT
<213> ORGANISM: Artificial sequence
<220> FEATURE:
<223> OTHER INFORMATION: APIM variant

<400> SEQUENCE: 104

Arg Phe Leu Arg Arg
1               5

<210> SEQ ID NO 105
<211> LENGTH: 5
<212> TYPE: PRT
<213> ORGANISM: Artificial sequence
<220> FEATURE:
<223> OTHER INFORMATION: APIM variant

<400> SEQUENCE: 105

Arg Tyr Leu Arg Arg
1               5

<210> SEQ ID NO 106
```

```
<211> LENGTH: 5
<212> TYPE: PRT
<213> ORGANISM: Artificial sequence
<220> FEATURE:
<223> OTHER INFORMATION: APIM variant

<400> SEQUENCE: 106

Lys Trp Leu Leu Lys
1               5

<210> SEQ ID NO 107
<211> LENGTH: 5
<212> TYPE: PRT
<213> ORGANISM: Artificial sequence
<220> FEATURE:
<223> OTHER INFORMATION: APIM variant

<400> SEQUENCE: 107

Lys Phe Leu Leu Lys
1               5

<210> SEQ ID NO 108
<211> LENGTH: 5
<212> TYPE: PRT
<213> ORGANISM: Artificial sequence
<220> FEATURE:
<223> OTHER INFORMATION: APIM variant

<400> SEQUENCE: 108

Lys Tyr Leu Leu Lys
1               5

<210> SEQ ID NO 109
<211> LENGTH: 5
<212> TYPE: PRT
<213> ORGANISM: Artificial sequence
<220> FEATURE:
<223> OTHER INFORMATION: APIM variant

<400> SEQUENCE: 109

Lys Trp Leu Leu Arg
1               5

<210> SEQ ID NO 110
<211> LENGTH: 5
<212> TYPE: PRT
<213> ORGANISM: Artificial sequence
<220> FEATURE:
<223> OTHER INFORMATION: APIM variant

<400> SEQUENCE: 110

Lys Phe Leu Leu Arg
1               5

<210> SEQ ID NO 111
<211> LENGTH: 5
<212> TYPE: PRT
<213> ORGANISM: Artificial sequence
<220> FEATURE:
<223> OTHER INFORMATION: APIM variant

<400> SEQUENCE: 111

Lys Tyr Leu Leu Arg
1               5

<210> SEQ ID NO 112
<211> LENGTH: 5
```

```
-continued

<212> TYPE: PRT
<213> ORGANISM: Artificial sequence
<220> FEATURE:
<223> OTHER INFORMATION: APIM variant

<400> SEQUENCE: 112

Lys Trp Leu Val Lys
1               5

<210> SEQ ID NO 113
<211> LENGTH: 5
<212> TYPE: PRT
<213> ORGANISM: Artificial sequence
<220> FEATURE:
<223> OTHER INFORMATION: APIM variant

<400> SEQUENCE: 113

Lys Phe Leu Val Lys
1               5

<210> SEQ ID NO 114
<211> LENGTH: 5
<212> TYPE: PRT
<213> ORGANISM: Artificial sequence
<220> FEATURE:
<223> OTHER INFORMATION: APIM variant

<400> SEQUENCE: 114

Lys Tyr Leu Val Lys
1               5

<210> SEQ ID NO 115
<211> LENGTH: 5
<212> TYPE: PRT
<213> ORGANISM: Artificial sequence
<220> FEATURE:
<223> OTHER INFORMATION: APIM variant

<400> SEQUENCE: 115

Lys Trp Leu Val Arg
1               5

<210> SEQ ID NO 116
<211> LENGTH: 5
<212> TYPE: PRT
<213> ORGANISM: Artificial sequence
<220> FEATURE:
<223> OTHER INFORMATION: APIM variant

<400> SEQUENCE: 116

Lys Phe Leu Val Arg
1               5

<210> SEQ ID NO 117
<211> LENGTH: 5
<212> TYPE: PRT
<213> ORGANISM: Artificial sequence
<220> FEATURE:
<223> OTHER INFORMATION: APIM variant

<400> SEQUENCE: 117

Lys Tyr Leu Val Arg
1               5

<210> SEQ ID NO 118
<211> LENGTH: 5
<212> TYPE: PRT
```

```
<213> ORGANISM: Artificial sequence
<220> FEATURE:
<223> OTHER INFORMATION: APIM variant

<400> SEQUENCE: 118

Lys Trp Ile Val Lys
1               5

<210> SEQ ID NO 119
<211> LENGTH: 5
<212> TYPE: PRT
<213> ORGANISM: Artificial sequence
<220> FEATURE:
<223> OTHER INFORMATION: APIM variant

<400> SEQUENCE: 119

Lys Phe Ile Val Lys
1               5

<210> SEQ ID NO 120
<211> LENGTH: 5
<212> TYPE: PRT
<213> ORGANISM: Artificial sequence
<220> FEATURE:
<223> OTHER INFORMATION: APIM variant

<400> SEQUENCE: 120

Lys Tyr Ile Val Lys
1               5

<210> SEQ ID NO 121
<211> LENGTH: 5
<212> TYPE: PRT
<213> ORGANISM: Artificial sequence
<220> FEATURE:
<223> OTHER INFORMATION: APIM variant

<400> SEQUENCE: 121

Lys Trp Ile Val Arg
1               5

<210> SEQ ID NO 122
<211> LENGTH: 5
<212> TYPE: PRT
<213> ORGANISM: Artificial sequence
<220> FEATURE:
<223> OTHER INFORMATION: APIM variant

<400> SEQUENCE: 122

Lys Phe Ile Val Arg
1               5

<210> SEQ ID NO 123
<211> LENGTH: 5
<212> TYPE: PRT
<213> ORGANISM: Artificial sequence
<220> FEATURE:
<223> OTHER INFORMATION: APIM variant

<400> SEQUENCE: 123

Lys Tyr Ile Val Arg
1               5

<210> SEQ ID NO 124
<211> LENGTH: 5
<212> TYPE: PRT
<213> ORGANISM: Artificial sequence
```

<220> FEATURE:
<223> OTHER INFORMATION: APIM variant

<400> SEQUENCE: 124

Lys Trp Leu Ser Lys
1               5

<210> SEQ ID NO 125
<211> LENGTH: 5
<212> TYPE: PRT
<213> ORGANISM: Artificial sequence
<220> FEATURE:
<223> OTHER INFORMATION: APIM variant

<400> SEQUENCE: 125

Lys Phe Leu Ser Lys
1               5

<210> SEQ ID NO 126
<211> LENGTH: 5
<212> TYPE: PRT
<213> ORGANISM: Artificial sequence
<220> FEATURE:
<223> OTHER INFORMATION: APIM variant

<400> SEQUENCE: 126

Lys Tyr Leu Ser Lys
1               5

<210> SEQ ID NO 127
<211> LENGTH: 5
<212> TYPE: PRT
<213> ORGANISM: Artificial sequence
<220> FEATURE:
<223> OTHER INFORMATION: APIM variant

<400> SEQUENCE: 127

Lys Trp Leu Ser Arg
1               5

<210> SEQ ID NO 128
<211> LENGTH: 5
<212> TYPE: PRT
<213> ORGANISM: Artificial sequence
<220> FEATURE:
<223> OTHER INFORMATION: APIM variant

<400> SEQUENCE: 128

Lys Phe Leu Ser Arg
1               5

<210> SEQ ID NO 129
<211> LENGTH: 5
<212> TYPE: PRT
<213> ORGANISM: Artificial sequence
<220> FEATURE:
<223> OTHER INFORMATION: APIM variant

<400> SEQUENCE: 129

Lys Tyr Leu Ser Arg
1               5

<210> SEQ ID NO 130
<211> LENGTH: 5
<212> TYPE: PRT
<213> ORGANISM: Artificial sequence
<220> FEATURE:

```
<223> OTHER INFORMATION: APIM variant

<400> SEQUENCE: 130

Lys Trp Ile Ser Lys
1               5

<210> SEQ ID NO 131
<211> LENGTH: 5
<212> TYPE: PRT
<213> ORGANISM: Artificial sequence
<220> FEATURE:
<223> OTHER INFORMATION: APIM variant

<400> SEQUENCE: 131

Lys Phe Ile Ser Lys
1               5

<210> SEQ ID NO 132
<211> LENGTH: 5
<212> TYPE: PRT
<213> ORGANISM: Artificial sequence
<220> FEATURE:
<223> OTHER INFORMATION: APIM variant

<400> SEQUENCE: 132

Lys Tyr Ile Ser Lys
1               5

<210> SEQ ID NO 133
<211> LENGTH: 5
<212> TYPE: PRT
<213> ORGANISM: Artificial sequence
<220> FEATURE:
<223> OTHER INFORMATION: APIM variant

<400> SEQUENCE: 133

Lys Trp Ile Ser Arg
1               5

<210> SEQ ID NO 134
<211> LENGTH: 5
<212> TYPE: PRT
<213> ORGANISM: Artificial sequence
<220> FEATURE:
<223> OTHER INFORMATION: APIM variant

<400> SEQUENCE: 134

Lys Phe Ile Ser Arg
1               5

<210> SEQ ID NO 135
<211> LENGTH: 5
<212> TYPE: PRT
<213> ORGANISM: Artificial sequence
<220> FEATURE:
<223> OTHER INFORMATION: APIM variant

<400> SEQUENCE: 135

Lys Tyr Ile Ser Arg
1               5

<210> SEQ ID NO 136
<211> LENGTH: 5
<212> TYPE: PRT
<213> ORGANISM: Artificial sequence
<220> FEATURE:
<223> OTHER INFORMATION: APIM variant
```

```
<400> SEQUENCE: 136

Lys Trp Ser Val Lys
1               5

<210> SEQ ID NO 137
<211> LENGTH: 5
<212> TYPE: PRT
<213> ORGANISM: Artificial sequence
<220> FEATURE:
<223> OTHER INFORMATION: APIM variant

<400> SEQUENCE: 137

Lys Phe Ser Val Lys
1               5

<210> SEQ ID NO 138
<211> LENGTH: 5
<212> TYPE: PRT
<213> ORGANISM: Artificial sequence
<220> FEATURE:
<223> OTHER INFORMATION: APIM variant

<400> SEQUENCE: 138

Lys Tyr Ser Val Lys
1               5

<210> SEQ ID NO 139
<211> LENGTH: 5
<212> TYPE: PRT
<213> ORGANISM: Artificial sequence
<220> FEATURE:
<223> OTHER INFORMATION: APIM variant

<400> SEQUENCE: 139

Lys Trp Ser Val Arg
1               5

<210> SEQ ID NO 140
<211> LENGTH: 5
<212> TYPE: PRT
<213> ORGANISM: Artificial sequence
<220> FEATURE:
<223> OTHER INFORMATION: APIM variant

<400> SEQUENCE: 140

Lys Phe Ser Val Arg
1               5

<210> SEQ ID NO 141
<211> LENGTH: 5
<212> TYPE: PRT
<213> ORGANISM: Artificial sequence
<220> FEATURE:
<223> OTHER INFORMATION: APIM variant

<400> SEQUENCE: 141

Lys Tyr Ser Val Arg
1               5

<210> SEQ ID NO 142
<211> LENGTH: 5
<212> TYPE: PRT
<213> ORGANISM: Artificial sequence
<220> FEATURE:
<223> OTHER INFORMATION: APIM variant
```

```
<400> SEQUENCE: 142

Lys Trp Ala Val Lys
1               5

<210> SEQ ID NO 143
<211> LENGTH: 5
<212> TYPE: PRT
<213> ORGANISM: Artificial sequence
<220> FEATURE:
<223> OTHER INFORMATION: APIM variant

<400> SEQUENCE: 143

Lys Phe Ala Val Lys
1               5

<210> SEQ ID NO 144
<211> LENGTH: 5
<212> TYPE: PRT
<213> ORGANISM: Artificial sequence
<220> FEATURE:
<223> OTHER INFORMATION: APIM variant

<400> SEQUENCE: 144

Lys Tyr Ala Val Lys
1               5

<210> SEQ ID NO 145
<211> LENGTH: 5
<212> TYPE: PRT
<213> ORGANISM: Artificial sequence
<220> FEATURE:
<223> OTHER INFORMATION: APIM variant

<400> SEQUENCE: 145

Lys Trp Ala Val Arg
1               5

<210> SEQ ID NO 146
<211> LENGTH: 5
<212> TYPE: PRT
<213> ORGANISM: Artificial sequence
<220> FEATURE:
<223> OTHER INFORMATION: APIM variant

<400> SEQUENCE: 146

Lys Phe Ala Val Arg
1               5

<210> SEQ ID NO 147
<211> LENGTH: 5
<212> TYPE: PRT
<213> ORGANISM: Artificial sequence
<220> FEATURE:
<223> OTHER INFORMATION: APIM variant

<400> SEQUENCE: 147

Lys Tyr Ala Val Arg
1               5

<210> SEQ ID NO 148
<211> LENGTH: 5
<212> TYPE: PRT
<213> ORGANISM: Artificial sequence
<220> FEATURE:
<223> OTHER INFORMATION: APIM variant

<400> SEQUENCE: 148
```

```
Lys Trp Leu Gly Arg
1               5

<210> SEQ ID NO 149
<211> LENGTH: 5
<212> TYPE: PRT
<213> ORGANISM: Artificial sequence
<220> FEATURE:
<223> OTHER INFORMATION: APIM variant

<400> SEQUENCE: 149

Lys Phe Leu Gly Arg
1               5

<210> SEQ ID NO 150
<211> LENGTH: 5
<212> TYPE: PRT
<213> ORGANISM: Artificial sequence
<220> FEATURE:
<223> OTHER INFORMATION: APIM variant

<400> SEQUENCE: 150

Lys Tyr Leu Gly Arg
1               5

<210> SEQ ID NO 151
<211> LENGTH: 5
<212> TYPE: PRT
<213> ORGANISM: Artificial sequence
<220> FEATURE:
<223> OTHER INFORMATION: APIM variant

<400> SEQUENCE: 151

Lys Trp Leu Gly Lys
1               5

<210> SEQ ID NO 152
<211> LENGTH: 5
<212> TYPE: PRT
<213> ORGANISM: Artificial sequence
<220> FEATURE:
<223> OTHER INFORMATION: APIM variant

<400> SEQUENCE: 152

Lys Phe Leu Gly Lys
1               5

<210> SEQ ID NO 153
<211> LENGTH: 5
<212> TYPE: PRT
<213> ORGANISM: Artificial sequence
<220> FEATURE:
<223> OTHER INFORMATION: APIM variant

<400> SEQUENCE: 153

Lys Tyr Leu Gly Lys
1               5

<210> SEQ ID NO 154
<211> LENGTH: 5
<212> TYPE: PRT
<213> ORGANISM: Artificial sequence
<220> FEATURE:
<223> OTHER INFORMATION: APIM variant

<400> SEQUENCE: 154
```

```
Lys Trp Leu Ala Arg
1               5

<210> SEQ ID NO 155
<211> LENGTH: 5
<212> TYPE: PRT
<213> ORGANISM: Artificial sequence
<220> FEATURE:
<223> OTHER INFORMATION: APIM variant

<400> SEQUENCE: 155

Lys Phe Leu Ala Arg
1               5

<210> SEQ ID NO 156
<211> LENGTH: 5
<212> TYPE: PRT
<213> ORGANISM: Artificial sequence
<220> FEATURE:
<223> OTHER INFORMATION: APIM variant

<400> SEQUENCE: 156

Lys Tyr Leu Ala Arg
1               5

<210> SEQ ID NO 157
<211> LENGTH: 5
<212> TYPE: PRT
<213> ORGANISM: Artificial sequence
<220> FEATURE:
<223> OTHER INFORMATION: APIM variant

<400> SEQUENCE: 157

Lys Trp Leu Ala Lys
1               5

<210> SEQ ID NO 158
<211> LENGTH: 5
<212> TYPE: PRT
<213> ORGANISM: Artificial sequence
<220> FEATURE:
<223> OTHER INFORMATION: APIM variant

<400> SEQUENCE: 158

Lys Phe Leu Ala Lys
1               5

<210> SEQ ID NO 159
<211> LENGTH: 5
<212> TYPE: PRT
<213> ORGANISM: Artificial sequence
<220> FEATURE:
<223> OTHER INFORMATION: APIM variant

<400> SEQUENCE: 159

Lys Tyr Leu Ala Lys
1               5

<210> SEQ ID NO 160
<211> LENGTH: 5
<212> TYPE: PRT
<213> ORGANISM: Artificial sequence
<220> FEATURE:
<223> OTHER INFORMATION: APIM variant

<400> SEQUENCE: 160

Lys Trp Leu Thr Lys
```

```
1               5

<210> SEQ ID NO 161
<211> LENGTH: 5
<212> TYPE: PRT
<213> ORGANISM: Artificial sequence
<220> FEATURE:
<223> OTHER INFORMATION: APIM variant

<400> SEQUENCE: 161

Lys Phe Leu Thr Lys
1               5

<210> SEQ ID NO 162
<211> LENGTH: 5
<212> TYPE: PRT
<213> ORGANISM: Artificial sequence
<220> FEATURE:
<223> OTHER INFORMATION: APIM variant

<400> SEQUENCE: 162

Lys Tyr Leu Thr Lys
1               5

<210> SEQ ID NO 163
<211> LENGTH: 5
<212> TYPE: PRT
<213> ORGANISM: Artificial sequence
<220> FEATURE:
<223> OTHER INFORMATION: APIM variant

<400> SEQUENCE: 163

Lys Trp Leu Thr Arg
1               5

<210> SEQ ID NO 164
<211> LENGTH: 5
<212> TYPE: PRT
<213> ORGANISM: Artificial sequence
<220> FEATURE:
<223> OTHER INFORMATION: APIM variant

<400> SEQUENCE: 164

Lys Phe Leu Thr Arg
1               5

<210> SEQ ID NO 165
<211> LENGTH: 5
<212> TYPE: PRT
<213> ORGANISM: Artificial sequence
<220> FEATURE:
<223> OTHER INFORMATION: APIM variant

<400> SEQUENCE: 165

Lys Tyr Leu Thr Arg
1               5

<210> SEQ ID NO 166
<211> LENGTH: 5
<212> TYPE: PRT
<213> ORGANISM: Artificial sequence
<220> FEATURE:
<223> OTHER INFORMATION: APIM variant

<400> SEQUENCE: 166

Lys Trp Ile Thr Lys
1               5
```

```
<210> SEQ ID NO 167
<211> LENGTH: 5
<212> TYPE: PRT
<213> ORGANISM: Artificial sequence
<220> FEATURE:
<223> OTHER INFORMATION: APIM variant

<400> SEQUENCE: 167

Lys Phe Ile Thr Lys
1               5

<210> SEQ ID NO 168
<211> LENGTH: 5
<212> TYPE: PRT
<213> ORGANISM: Artificial sequence
<220> FEATURE:
<223> OTHER INFORMATION: APIM variant

<400> SEQUENCE: 168

Lys Tyr Ile Thr Lys
1               5

<210> SEQ ID NO 169
<211> LENGTH: 5
<212> TYPE: PRT
<213> ORGANISM: Artificial sequence
<220> FEATURE:
<223> OTHER INFORMATION: APIM variant

<400> SEQUENCE: 169

Lys Trp Ile Thr Arg
1               5

<210> SEQ ID NO 170
<211> LENGTH: 5
<212> TYPE: PRT
<213> ORGANISM: Artificial sequence
<220> FEATURE:
<223> OTHER INFORMATION: APIM variant

<400> SEQUENCE: 170

Lys Phe Ile Thr Arg
1               5

<210> SEQ ID NO 171
<211> LENGTH: 5
<212> TYPE: PRT
<213> ORGANISM: Artificial sequence
<220> FEATURE:
<223> OTHER INFORMATION: APIM variant

<400> SEQUENCE: 171

Lys Tyr Ile Thr Arg
1               5

<210> SEQ ID NO 172
<211> LENGTH: 5
<212> TYPE: PRT
<213> ORGANISM: Artificial sequence
<220> FEATURE:
<223> OTHER INFORMATION: APIM variant

<400> SEQUENCE: 172

Lys Trp Thr Val Lys
1               5
```

```
<210> SEQ ID NO 173
<211> LENGTH: 5
<212> TYPE: PRT
<213> ORGANISM: Artificial sequence
<220> FEATURE:
<223> OTHER INFORMATION: APIM variant

<400> SEQUENCE: 173

Lys Phe Thr Val Lys
1               5

<210> SEQ ID NO 174
<211> LENGTH: 5
<212> TYPE: PRT
<213> ORGANISM: Artificial sequence
<220> FEATURE:
<223> OTHER INFORMATION: APIM variant

<400> SEQUENCE: 174

Lys Tyr Thr Val Lys
1               5

<210> SEQ ID NO 175
<211> LENGTH: 5
<212> TYPE: PRT
<213> ORGANISM: Artificial sequence
<220> FEATURE:
<223> OTHER INFORMATION: APIM variant

<400> SEQUENCE: 175

Lys Trp Thr Val Arg
1               5

<210> SEQ ID NO 176
<211> LENGTH: 5
<212> TYPE: PRT
<213> ORGANISM: Artificial sequence
<220> FEATURE:
<223> OTHER INFORMATION: APIM variant

<400> SEQUENCE: 176

Lys Phe Thr Val Arg
1               5

<210> SEQ ID NO 177
<211> LENGTH: 5
<212> TYPE: PRT
<213> ORGANISM: Artificial sequence
<220> FEATURE:
<223> OTHER INFORMATION: APIM variant

<400> SEQUENCE: 177

Lys Tyr Thr Val Arg
1               5

<210> SEQ ID NO 178
<211> LENGTH: 5
<212> TYPE: PRT
<213> ORGANISM: Artificial sequence
<220> FEATURE:
<223> OTHER INFORMATION: APIM variant

<400> SEQUENCE: 178

Lys Trp Leu Arg Lys
1               5
```

```
<210> SEQ ID NO 179
<211> LENGTH: 5
<212> TYPE: PRT
<213> ORGANISM: Artificial sequence
<220> FEATURE:
<223> OTHER INFORMATION: APIM variant

<400> SEQUENCE: 179

Lys Phe Leu Arg Lys
1               5

<210> SEQ ID NO 180
<211> LENGTH: 5
<212> TYPE: PRT
<213> ORGANISM: Artificial sequence
<220> FEATURE:
<223> OTHER INFORMATION: APIM variant

<400> SEQUENCE: 180

Lys Tyr Leu Arg Lys
1               5

<210> SEQ ID NO 181
<211> LENGTH: 5
<212> TYPE: PRT
<213> ORGANISM: Artificial sequence
<220> FEATURE:
<223> OTHER INFORMATION: APIM variant

<400> SEQUENCE: 181

Lys Trp Leu Arg Arg
1               5

<210> SEQ ID NO 182
<211> LENGTH: 5
<212> TYPE: PRT
<213> ORGANISM: Artificial sequence
<220> FEATURE:
<223> OTHER INFORMATION: APIM variant

<400> SEQUENCE: 182

Lys Phe Leu Arg Arg
1               5

<210> SEQ ID NO 183
<211> LENGTH: 5
<212> TYPE: PRT
<213> ORGANISM: Artificial sequence
<220> FEATURE:
<223> OTHER INFORMATION: APIM variant

<400> SEQUENCE: 183

Lys Tyr Leu Arg Arg
1               5

<210> SEQ ID NO 184
<211> LENGTH: 5
<212> TYPE: PRT
<213> ORGANISM: Artificial sequence
<220> FEATURE:
<223> OTHER INFORMATION: APIM variant

<400> SEQUENCE: 184

Lys Trp Ile Arg Lys
1               5

<210> SEQ ID NO 185
```

```
<211> LENGTH: 5
<212> TYPE: PRT
<213> ORGANISM: Artificial sequence
<220> FEATURE:
<223> OTHER INFORMATION: APIM variant

<400> SEQUENCE: 185

Lys Phe Ile Arg Lys
1               5

<210> SEQ ID NO 186
<211> LENGTH: 5
<212> TYPE: PRT
<213> ORGANISM: Artificial sequence
<220> FEATURE:
<223> OTHER INFORMATION: APIM variant

<400> SEQUENCE: 186

Lys Tyr Ile Arg Lys
1               5

<210> SEQ ID NO 187
<211> LENGTH: 5
<212> TYPE: PRT
<213> ORGANISM: Artificial sequence
<220> FEATURE:
<223> OTHER INFORMATION: APIM variant

<400> SEQUENCE: 187

Lys Trp Ile Arg Arg
1               5

<210> SEQ ID NO 188
<211> LENGTH: 5
<212> TYPE: PRT
<213> ORGANISM: Artificial sequence
<220> FEATURE:
<223> OTHER INFORMATION: APIM variant

<400> SEQUENCE: 188

Lys Phe Ile Arg Arg
1               5

<210> SEQ ID NO 189
<211> LENGTH: 5
<212> TYPE: PRT
<213> ORGANISM: Artificial sequence
<220> FEATURE:
<223> OTHER INFORMATION: APIM variant

<400> SEQUENCE: 189

Lys Tyr Ile Arg Arg
1               5

<210> SEQ ID NO 190
<211> LENGTH: 5
<212> TYPE: PRT
<213> ORGANISM: Artificial sequence
<220> FEATURE:
<223> OTHER INFORMATION: APIM variant

<400> SEQUENCE: 190

Arg Trp Val Val Lys
1               5

<210> SEQ ID NO 191
<211> LENGTH: 5
```

```
<212> TYPE: PRT
<213> ORGANISM: Artificial sequence
<220> FEATURE:
<223> OTHER INFORMATION: APIM variant

<400> SEQUENCE: 191

Arg Phe Val Val Lys
1               5

<210> SEQ ID NO 192
<211> LENGTH: 5
<212> TYPE: PRT
<213> ORGANISM: Artificial sequence
<220> FEATURE:
<223> OTHER INFORMATION: APIM variant

<400> SEQUENCE: 192

Arg Tyr Val Val Lys
1               5

<210> SEQ ID NO 193
<211> LENGTH: 5
<212> TYPE: PRT
<213> ORGANISM: Artificial sequence
<220> FEATURE:
<223> OTHER INFORMATION: APIM variant

<400> SEQUENCE: 193

Arg Trp Val Val Arg
1               5

<210> SEQ ID NO 194
<211> LENGTH: 5
<212> TYPE: PRT
<213> ORGANISM: Artificial sequence
<220> FEATURE:
<223> OTHER INFORMATION: APIM variant

<400> SEQUENCE: 194

Arg Phe Val Val Arg
1               5

<210> SEQ ID NO 195
<211> LENGTH: 5
<212> TYPE: PRT
<213> ORGANISM: Artificial sequence
<220> FEATURE:
<223> OTHER INFORMATION: APIM variant

<400> SEQUENCE: 195

Arg Tyr Val Val Arg
1               5

<210> SEQ ID NO 196
<211> LENGTH: 5
<212> TYPE: PRT
<213> ORGANISM: Artificial sequence
<220> FEATURE:
<223> OTHER INFORMATION: APIM variant

<400> SEQUENCE: 196

Lys Trp Val Val Lys
1               5

<210> SEQ ID NO 197
<211> LENGTH: 5
<212> TYPE: PRT
```

```
<213> ORGANISM: Artificial sequence
<220> FEATURE:
<223> OTHER INFORMATION: APIM variant

<400> SEQUENCE: 197

Lys Phe Val Val Lys
1               5

<210> SEQ ID NO 198
<211> LENGTH: 5
<212> TYPE: PRT
<213> ORGANISM: Artificial sequence
<220> FEATURE:
<223> OTHER INFORMATION: APIM variant

<400> SEQUENCE: 198

Lys Tyr Val Val Lys
1               5

<210> SEQ ID NO 199
<211> LENGTH: 5
<212> TYPE: PRT
<213> ORGANISM: Artificial sequence
<220> FEATURE:
<223> OTHER INFORMATION: APIM variant

<400> SEQUENCE: 199

Lys Trp Val Val Arg
1               5

<210> SEQ ID NO 200
<211> LENGTH: 5
<212> TYPE: PRT
<213> ORGANISM: Artificial sequence
<220> FEATURE:
<223> OTHER INFORMATION: APIM variant

<400> SEQUENCE: 200

Lys Phe Val Val Arg
1               5

<210> SEQ ID NO 201
<211> LENGTH: 5
<212> TYPE: PRT
<213> ORGANISM: Artificial sequence
<220> FEATURE:
<223> OTHER INFORMATION: APIM variant

<400> SEQUENCE: 201

Lys Tyr Val Val Arg
1               5

<210> SEQ ID NO 202
<211> LENGTH: 5
<212> TYPE: PRT
<213> ORGANISM: Artificial sequence
<220> FEATURE:
<223> OTHER INFORMATION: APIM variant

<400> SEQUENCE: 202

Arg Trp Ala Leu Lys
1               5

<210> SEQ ID NO 203
<211> LENGTH: 5
<212> TYPE: PRT
<213> ORGANISM: Artificial sequence
```

```
<220> FEATURE:
<223> OTHER INFORMATION: APIM variant

<400> SEQUENCE: 203

Arg Phe Ala Leu Lys
1               5

<210> SEQ ID NO 204
<211> LENGTH: 5
<212> TYPE: PRT
<213> ORGANISM: Artificial sequence
<220> FEATURE:
<223> OTHER INFORMATION: APIM variant

<400> SEQUENCE: 204

Arg Tyr Ala Leu Lys
1               5

<210> SEQ ID NO 205
<211> LENGTH: 5
<212> TYPE: PRT
<213> ORGANISM: Artificial sequence
<220> FEATURE:
<223> OTHER INFORMATION: APIM variant

<400> SEQUENCE: 205

Arg Trp Ala Leu Arg
1               5

<210> SEQ ID NO 206
<211> LENGTH: 5
<212> TYPE: PRT
<213> ORGANISM: Artificial sequence
<220> FEATURE:
<223> OTHER INFORMATION: APIM variant

<400> SEQUENCE: 206

Arg Phe Ala Leu Arg
1               5

<210> SEQ ID NO 207
<211> LENGTH: 5
<212> TYPE: PRT
<213> ORGANISM: Artificial sequence
<220> FEATURE:
<223> OTHER INFORMATION: APIM variant

<400> SEQUENCE: 207

Arg Tyr Ala Leu Arg
1               5

<210> SEQ ID NO 208
<211> LENGTH: 5
<212> TYPE: PRT
<213> ORGANISM: Artificial sequence
<220> FEATURE:
<223> OTHER INFORMATION: APIM variant

<400> SEQUENCE: 208

Lys Trp Ala Leu Lys
1               5

<210> SEQ ID NO 209
<211> LENGTH: 5
<212> TYPE: PRT
<213> ORGANISM: Artificial sequence
<220> FEATURE:
```

<223> OTHER INFORMATION: APIM variant

<400> SEQUENCE: 209

Lys Phe Ala Leu Lys
1               5

<210> SEQ ID NO 210
<211> LENGTH: 5
<212> TYPE: PRT
<213> ORGANISM: Artificial sequence
<220> FEATURE:
<223> OTHER INFORMATION: APIM variant

<400> SEQUENCE: 210

Lys Tyr Ala Leu Lys
1               5

<210> SEQ ID NO 211
<211> LENGTH: 5
<212> TYPE: PRT
<213> ORGANISM: Artificial sequence
<220> FEATURE:
<223> OTHER INFORMATION: APIM variant

<400> SEQUENCE: 211

Lys Trp Ala Leu Arg
1               5

<210> SEQ ID NO 212
<211> LENGTH: 5
<212> TYPE: PRT
<213> ORGANISM: Artificial sequence
<220> FEATURE:
<223> OTHER INFORMATION: APIM variant

<400> SEQUENCE: 212

Lys Phe Ala Leu Arg
1               5

<210> SEQ ID NO 213
<211> LENGTH: 5
<212> TYPE: PRT
<213> ORGANISM: Artificial sequence
<220> FEATURE:
<223> OTHER INFORMATION: APIM variant

<400> SEQUENCE: 213

Lys Tyr Ala Leu Arg
1               5

<210> SEQ ID NO 214
<211> LENGTH: 5
<212> TYPE: PRT
<213> ORGANISM: Artificial sequence
<220> FEATURE:
<223> OTHER INFORMATION: APIM variant

<400> SEQUENCE: 214

Arg Trp Val Leu Lys
1               5

<210> SEQ ID NO 215
<211> LENGTH: 5
<212> TYPE: PRT
<213> ORGANISM: Artificial sequence
<220> FEATURE:
<223> OTHER INFORMATION: APIM variant

```
<400> SEQUENCE: 215

Arg Phe Val Leu Lys
1               5

<210> SEQ ID NO 216
<211> LENGTH: 5
<212> TYPE: PRT
<213> ORGANISM: Artificial sequence
<220> FEATURE:
<223> OTHER INFORMATION: APIM variant

<400> SEQUENCE: 216

Arg Tyr Val Leu Lys
1               5

<210> SEQ ID NO 217
<211> LENGTH: 5
<212> TYPE: PRT
<213> ORGANISM: Artificial sequence
<220> FEATURE:
<223> OTHER INFORMATION: APIM variant

<400> SEQUENCE: 217

Arg Trp Val Leu Arg
1               5

<210> SEQ ID NO 218
<211> LENGTH: 5
<212> TYPE: PRT
<213> ORGANISM: Artificial sequence
<220> FEATURE:
<223> OTHER INFORMATION: APIM variant

<400> SEQUENCE: 218

Arg Phe Val Leu Arg
1               5

<210> SEQ ID NO 219
<211> LENGTH: 5
<212> TYPE: PRT
<213> ORGANISM: Artificial sequence
<220> FEATURE:
<223> OTHER INFORMATION: APIM variant

<400> SEQUENCE: 219

Arg Tyr Val Leu Arg
1               5

<210> SEQ ID NO 220
<211> LENGTH: 5
<212> TYPE: PRT
<213> ORGANISM: Artificial sequence
<220> FEATURE:
<223> OTHER INFORMATION: APIM variant

<400> SEQUENCE: 220

Lys Trp Val Leu Lys
1               5

<210> SEQ ID NO 221
<211> LENGTH: 5
<212> TYPE: PRT
<213> ORGANISM: Artificial sequence
<220> FEATURE:
<223> OTHER INFORMATION: APIM variant
```

```
<400> SEQUENCE: 221

Lys Phe Val Leu Lys
1               5

<210> SEQ ID NO 222
<211> LENGTH: 5
<212> TYPE: PRT
<213> ORGANISM: Artificial sequence
<220> FEATURE:
<223> OTHER INFORMATION: APIM variant

<400> SEQUENCE: 222

Lys Tyr Val Leu Lys
1               5

<210> SEQ ID NO 223
<211> LENGTH: 5
<212> TYPE: PRT
<213> ORGANISM: Artificial sequence
<220> FEATURE:
<223> OTHER INFORMATION: APIM variant

<400> SEQUENCE: 223

Lys Trp Val Leu Arg
1               5

<210> SEQ ID NO 224
<211> LENGTH: 5
<212> TYPE: PRT
<213> ORGANISM: Artificial sequence
<220> FEATURE:
<223> OTHER INFORMATION: APIM variant

<400> SEQUENCE: 224

Lys Phe Val Leu Arg
1               5

<210> SEQ ID NO 225
<211> LENGTH: 5
<212> TYPE: PRT
<213> ORGANISM: Artificial sequence
<220> FEATURE:
<223> OTHER INFORMATION: APIM variant

<400> SEQUENCE: 225

Lys Tyr Val Leu Arg
1               5

<210> SEQ ID NO 226
<211> LENGTH: 5
<212> TYPE: PRT
<213> ORGANISM: Artificial sequence
<220> FEATURE:
<223> OTHER INFORMATION: APIM variant

<400> SEQUENCE: 226

Arg Trp Ile Leu Lys
1               5

<210> SEQ ID NO 227
<211> LENGTH: 5
<212> TYPE: PRT
<213> ORGANISM: Artificial sequence
<220> FEATURE:
<223> OTHER INFORMATION: APIM variant

<400> SEQUENCE: 227
```

-continued

Arg Phe Ile Leu Lys
1               5

<210> SEQ ID NO 228
<211> LENGTH: 5
<212> TYPE: PRT
<213> ORGANISM: Artificial sequence
<220> FEATURE:
<223> OTHER INFORMATION: APIM variant

<400> SEQUENCE: 228

Arg Tyr Ile Leu Lys
1               5

<210> SEQ ID NO 229
<211> LENGTH: 5
<212> TYPE: PRT
<213> ORGANISM: Artificial sequence
<220> FEATURE:
<223> OTHER INFORMATION: APIM variant

<400> SEQUENCE: 229

Arg Trp Ile Leu Arg
1               5

<210> SEQ ID NO 230
<211> LENGTH: 5
<212> TYPE: PRT
<213> ORGANISM: Artificial sequence
<220> FEATURE:
<223> OTHER INFORMATION: APIM variant

<400> SEQUENCE: 230

Arg Phe Ile Leu Arg
1               5

<210> SEQ ID NO 231
<211> LENGTH: 5
<212> TYPE: PRT
<213> ORGANISM: Artificial sequence
<220> FEATURE:
<223> OTHER INFORMATION: APIM variant

<400> SEQUENCE: 231

Arg Tyr Ile Leu Arg
1               5

<210> SEQ ID NO 232
<211> LENGTH: 5
<212> TYPE: PRT
<213> ORGANISM: Artificial sequence
<220> FEATURE:
<223> OTHER INFORMATION: APIM variant

<400> SEQUENCE: 232

Lys Trp Ile Leu Lys
1               5

<210> SEQ ID NO 233
<211> LENGTH: 5
<212> TYPE: PRT
<213> ORGANISM: Artificial sequence
<220> FEATURE:
<223> OTHER INFORMATION: APIM variant

<400> SEQUENCE: 233

```
Lys Phe Ile Leu Lys
1               5

<210> SEQ ID NO 234
<211> LENGTH: 5
<212> TYPE: PRT
<213> ORGANISM: Artificial sequence
<220> FEATURE:
<223> OTHER INFORMATION: APIM variant

<400> SEQUENCE: 234

Lys Tyr Ile Leu Lys
1               5

<210> SEQ ID NO 235
<211> LENGTH: 5
<212> TYPE: PRT
<213> ORGANISM: Artificial sequence
<220> FEATURE:
<223> OTHER INFORMATION: APIM variant

<400> SEQUENCE: 235

Lys Trp Ile Leu Arg
1               5

<210> SEQ ID NO 236
<211> LENGTH: 5
<212> TYPE: PRT
<213> ORGANISM: Artificial sequence
<220> FEATURE:
<223> OTHER INFORMATION: APIM variant

<400> SEQUENCE: 236

Lys Phe Ile Leu Arg
1               5

<210> SEQ ID NO 237
<211> LENGTH: 5
<212> TYPE: PRT
<213> ORGANISM: Artificial sequence
<220> FEATURE:
<223> OTHER INFORMATION: APIM variant

<400> SEQUENCE: 237

Lys Tyr Ile Leu Arg
1               5

<210> SEQ ID NO 238
<211> LENGTH: 5
<212> TYPE: PRT
<213> ORGANISM: Artificial sequence
<220> FEATURE:
<223> OTHER INFORMATION: APIM variant

<400> SEQUENCE: 238

Arg Trp Val Ile Lys
1               5

<210> SEQ ID NO 239
<211> LENGTH: 5
<212> TYPE: PRT
<213> ORGANISM: Artificial sequence
<220> FEATURE:
<223> OTHER INFORMATION: APIM variant

<400> SEQUENCE: 239

Arg Phe Val Ile Lys
```

```
1               5

<210> SEQ ID NO 240
<211> LENGTH: 5
<212> TYPE: PRT
<213> ORGANISM: Artificial sequence
<220> FEATURE:
<223> OTHER INFORMATION: APIM variant

<400> SEQUENCE: 240

Arg Tyr Val Ile Lys
1               5

<210> SEQ ID NO 241
<211> LENGTH: 5
<212> TYPE: PRT
<213> ORGANISM: Artificial sequence
<220> FEATURE:
<223> OTHER INFORMATION: APIM variant

<400> SEQUENCE: 241

Arg Trp Val Ile Arg
1               5

<210> SEQ ID NO 242
<211> LENGTH: 5
<212> TYPE: PRT
<213> ORGANISM: Artificial sequence
<220> FEATURE:
<223> OTHER INFORMATION: APIM variant

<400> SEQUENCE: 242

Arg Phe Val Ile Arg
1               5

<210> SEQ ID NO 243
<211> LENGTH: 5
<212> TYPE: PRT
<213> ORGANISM: Artificial sequence
<220> FEATURE:
<223> OTHER INFORMATION: APIM variant

<400> SEQUENCE: 243

Arg Tyr Val Ile Arg
1               5

<210> SEQ ID NO 244
<211> LENGTH: 5
<212> TYPE: PRT
<213> ORGANISM: Artificial sequence
<220> FEATURE:
<223> OTHER INFORMATION: APIM variant

<400> SEQUENCE: 244

Lys Trp Val Ile Lys
1               5

<210> SEQ ID NO 245
<211> LENGTH: 5
<212> TYPE: PRT
<213> ORGANISM: Artificial sequence
<220> FEATURE:
<223> OTHER INFORMATION: APIM variant

<400> SEQUENCE: 245

Lys Phe Val Ile Lys
1               5
```

```
<210> SEQ ID NO 246
<211> LENGTH: 5
<212> TYPE: PRT
<213> ORGANISM: Artificial sequence
<220> FEATURE:
<223> OTHER INFORMATION: APIM variant

<400> SEQUENCE: 246

Lys Tyr Val Ile Lys
1               5

<210> SEQ ID NO 247
<211> LENGTH: 5
<212> TYPE: PRT
<213> ORGANISM: Artificial sequence
<220> FEATURE:
<223> OTHER INFORMATION: APIM variant

<400> SEQUENCE: 247

Lys Trp Val Ile Arg
1               5

<210> SEQ ID NO 248
<211> LENGTH: 5
<212> TYPE: PRT
<213> ORGANISM: Artificial sequence
<220> FEATURE:
<223> OTHER INFORMATION: APIM variant

<400> SEQUENCE: 248

Lys Phe Val Ile Arg
1               5

<210> SEQ ID NO 249
<211> LENGTH: 5
<212> TYPE: PRT
<213> ORGANISM: Artificial sequence
<220> FEATURE:
<223> OTHER INFORMATION: APIM variant

<400> SEQUENCE: 249

Lys Tyr Val Ile Arg
1               5

<210> SEQ ID NO 250
<211> LENGTH: 5
<212> TYPE: PRT
<213> ORGANISM: Artificial sequence
<220> FEATURE:
<223> OTHER INFORMATION: APIM variant

<400> SEQUENCE: 250

Arg Trp Ile Ile Lys
1               5

<210> SEQ ID NO 251
<211> LENGTH: 5
<212> TYPE: PRT
<213> ORGANISM: Artificial sequence
<220> FEATURE:
<223> OTHER INFORMATION: APIM variant

<400> SEQUENCE: 251

Arg Phe Ile Ile Lys
1               5
```

```
<210> SEQ ID NO 252
<211> LENGTH: 5
<212> TYPE: PRT
<213> ORGANISM: Artificial sequence
<220> FEATURE:
<223> OTHER INFORMATION: APIM variant

<400> SEQUENCE: 252

Arg Tyr Ile Ile Lys
1               5

<210> SEQ ID NO 253
<211> LENGTH: 5
<212> TYPE: PRT
<213> ORGANISM: Artificial sequence
<220> FEATURE:
<223> OTHER INFORMATION: APIM variant

<400> SEQUENCE: 253

Arg Trp Ile Ile Arg
1               5

<210> SEQ ID NO 254
<211> LENGTH: 5
<212> TYPE: PRT
<213> ORGANISM: Artificial sequence
<220> FEATURE:
<223> OTHER INFORMATION: APIM variant

<400> SEQUENCE: 254

Arg Phe Ile Ile Arg
1               5

<210> SEQ ID NO 255
<211> LENGTH: 5
<212> TYPE: PRT
<213> ORGANISM: Artificial sequence
<220> FEATURE:
<223> OTHER INFORMATION: APIM variant

<400> SEQUENCE: 255

Arg Tyr Ile Ile Arg
1               5

<210> SEQ ID NO 256
<211> LENGTH: 5
<212> TYPE: PRT
<213> ORGANISM: Artificial sequence
<220> FEATURE:
<223> OTHER INFORMATION: APIM variant

<400> SEQUENCE: 256

Lys Trp Ile Ile Lys
1               5

<210> SEQ ID NO 257
<211> LENGTH: 5
<212> TYPE: PRT
<213> ORGANISM: Artificial sequence
<220> FEATURE:
<223> OTHER INFORMATION: APIM variant

<400> SEQUENCE: 257

Lys Phe Ile Ile Lys
1               5
```

```
<210> SEQ ID NO 258
<211> LENGTH: 5
<212> TYPE: PRT
<213> ORGANISM: Artificial sequence
<220> FEATURE:
<223> OTHER INFORMATION: APIM variant

<400> SEQUENCE: 258

Lys Tyr Ile Ile Lys
1               5

<210> SEQ ID NO 259
<211> LENGTH: 5
<212> TYPE: PRT
<213> ORGANISM: Artificial sequence
<220> FEATURE:
<223> OTHER INFORMATION: APIM variant

<400> SEQUENCE: 259

Lys Trp Ile Ile Arg
1               5

<210> SEQ ID NO 260
<211> LENGTH: 5
<212> TYPE: PRT
<213> ORGANISM: Artificial sequence
<220> FEATURE:
<223> OTHER INFORMATION: APIM variant

<400> SEQUENCE: 260

Lys Phe Ile Ile Arg
1               5

<210> SEQ ID NO 261
<211> LENGTH: 5
<212> TYPE: PRT
<213> ORGANISM: Artificial sequence
<220> FEATURE:
<223> OTHER INFORMATION: APIM variant

<400> SEQUENCE: 261

Lys Tyr Ile Ile Arg
1               5

<210> SEQ ID NO 262
<211> LENGTH: 5
<212> TYPE: PRT
<213> ORGANISM: Artificial sequence
<220> FEATURE:
<223> OTHER INFORMATION: APIM variant

<400> SEQUENCE: 262

Arg Trp Leu Ile Lys
1               5

<210> SEQ ID NO 263
<211> LENGTH: 5
<212> TYPE: PRT
<213> ORGANISM: Artificial sequence
<220> FEATURE:
<223> OTHER INFORMATION: APIM variant

<400> SEQUENCE: 263

Arg Phe Leu Ile Lys
1               5

<210> SEQ ID NO 264
```

```
<211> LENGTH: 5
<212> TYPE: PRT
<213> ORGANISM: Artificial sequence
<220> FEATURE:
<223> OTHER INFORMATION: APIM variant

<400> SEQUENCE: 264

Arg Tyr Leu Ile Lys
1               5

<210> SEQ ID NO 265
<211> LENGTH: 5
<212> TYPE: PRT
<213> ORGANISM: Artificial sequence
<220> FEATURE:
<223> OTHER INFORMATION: APIM variant

<400> SEQUENCE: 265

Arg Trp Leu Ile Arg
1               5

<210> SEQ ID NO 266
<211> LENGTH: 5
<212> TYPE: PRT
<213> ORGANISM: Artificial sequence
<220> FEATURE:
<223> OTHER INFORMATION: APIM variant

<400> SEQUENCE: 266

Arg Phe Leu Ile Arg
1               5

<210> SEQ ID NO 267
<211> LENGTH: 5
<212> TYPE: PRT
<213> ORGANISM: Artificial sequence
<220> FEATURE:
<223> OTHER INFORMATION: APIM variant

<400> SEQUENCE: 267

Arg Tyr Leu Ile Arg
1               5

<210> SEQ ID NO 268
<211> LENGTH: 5
<212> TYPE: PRT
<213> ORGANISM: Artificial sequence
<220> FEATURE:
<223> OTHER INFORMATION: APIM variant

<400> SEQUENCE: 268

Lys Trp Leu Ile Lys
1               5

<210> SEQ ID NO 269
<211> LENGTH: 5
<212> TYPE: PRT
<213> ORGANISM: Artificial sequence
<220> FEATURE:
<223> OTHER INFORMATION: APIM variant

<400> SEQUENCE: 269

Lys Phe Leu Ile Lys
1               5

<210> SEQ ID NO 270
<211> LENGTH: 5
```

```
<212> TYPE: PRT
<213> ORGANISM: Artificial sequence
<220> FEATURE:
<223> OTHER INFORMATION: APIM variant

<400> SEQUENCE: 270

Lys Tyr Leu Ile Lys
1               5

<210> SEQ ID NO 271
<211> LENGTH: 5
<212> TYPE: PRT
<213> ORGANISM: Artificial sequence
<220> FEATURE:
<223> OTHER INFORMATION: APIM variant

<400> SEQUENCE: 271

Lys Trp Leu Ile Arg
1               5

<210> SEQ ID NO 272
<211> LENGTH: 5
<212> TYPE: PRT
<213> ORGANISM: Artificial sequence
<220> FEATURE:
<223> OTHER INFORMATION: APIM variant

<400> SEQUENCE: 272

Lys Phe Leu Ile Arg
1               5

<210> SEQ ID NO 273
<211> LENGTH: 5
<212> TYPE: PRT
<213> ORGANISM: Artificial sequence
<220> FEATURE:
<223> OTHER INFORMATION: APIM variant

<400> SEQUENCE: 273

Lys Tyr Leu Ile Arg
1               5

<210> SEQ ID NO 274
<211> LENGTH: 5
<212> TYPE: PRT
<213> ORGANISM: Artificial sequence
<220> FEATURE:
<223> OTHER INFORMATION: APIM variant

<400> SEQUENCE: 274

Arg Trp Ile Ala Lys
1               5

<210> SEQ ID NO 275
<211> LENGTH: 5
<212> TYPE: PRT
<213> ORGANISM: Artificial sequence
<220> FEATURE:
<223> OTHER INFORMATION: APIM variant

<400> SEQUENCE: 275

Arg Phe Ile Ala Lys
1               5

<210> SEQ ID NO 276
<211> LENGTH: 5
<212> TYPE: PRT
```

```
<213> ORGANISM: Artificial sequence
<220> FEATURE:
<223> OTHER INFORMATION: APIM variant

<400> SEQUENCE: 276

Arg Tyr Ile Ala Lys
1               5

<210> SEQ ID NO 277
<211> LENGTH: 5
<212> TYPE: PRT
<213> ORGANISM: Artificial sequence
<220> FEATURE:
<223> OTHER INFORMATION: APIM variant

<400> SEQUENCE: 277

Arg Trp Ile Ala Arg
1               5

<210> SEQ ID NO 278
<211> LENGTH: 5
<212> TYPE: PRT
<213> ORGANISM: Artificial sequence
<220> FEATURE:
<223> OTHER INFORMATION: APIM variant

<400> SEQUENCE: 278

Arg Phe Ile Ala Arg
1               5

<210> SEQ ID NO 279
<211> LENGTH: 5
<212> TYPE: PRT
<213> ORGANISM: Artificial sequence
<220> FEATURE:
<223> OTHER INFORMATION: APIM variant

<400> SEQUENCE: 279

Arg Tyr Ile Ala Arg
1               5

<210> SEQ ID NO 280
<211> LENGTH: 5
<212> TYPE: PRT
<213> ORGANISM: Artificial sequence
<220> FEATURE:
<223> OTHER INFORMATION: APIM variant

<400> SEQUENCE: 280

Lys Trp Ile Ala Lys
1               5

<210> SEQ ID NO 281
<211> LENGTH: 5
<212> TYPE: PRT
<213> ORGANISM: Artificial sequence
<220> FEATURE:
<223> OTHER INFORMATION: APIM variant

<400> SEQUENCE: 281

Lys Phe Ile Ala Lys
1               5

<210> SEQ ID NO 282
<211> LENGTH: 5
<212> TYPE: PRT
<213> ORGANISM: Artificial sequence
```

```
<220> FEATURE:
<223> OTHER INFORMATION: APIM variant

<400> SEQUENCE: 282

Lys Tyr Ile Ala Lys
1               5

<210> SEQ ID NO 283
<211> LENGTH: 5
<212> TYPE: PRT
<213> ORGANISM: Artificial sequence
<220> FEATURE:
<223> OTHER INFORMATION: APIM variant

<400> SEQUENCE: 283

Lys Trp Ile Ala Arg
1               5

<210> SEQ ID NO 284
<211> LENGTH: 5
<212> TYPE: PRT
<213> ORGANISM: Artificial sequence
<220> FEATURE:
<223> OTHER INFORMATION: APIM variant

<400> SEQUENCE: 284

Lys Phe Ile Ala Arg
1               5

<210> SEQ ID NO 285
<211> LENGTH: 5
<212> TYPE: PRT
<213> ORGANISM: Artificial sequence
<220> FEATURE:
<223> OTHER INFORMATION: APIM variant

<400> SEQUENCE: 285

Lys Tyr Ile Ala Arg
1               5

<210> SEQ ID NO 286
<211> LENGTH: 5
<212> TYPE: PRT
<213> ORGANISM: Artificial sequence
<220> FEATURE:
<223> OTHER INFORMATION: APIM variant

<400> SEQUENCE: 286

Arg Trp Val Ala Lys
1               5

<210> SEQ ID NO 287
<211> LENGTH: 5
<212> TYPE: PRT
<213> ORGANISM: Artificial sequence
<220> FEATURE:
<223> OTHER INFORMATION: APIM variant

<400> SEQUENCE: 287

Arg Phe Val Ala Lys
1               5

<210> SEQ ID NO 288
<211> LENGTH: 5
<212> TYPE: PRT
<213> ORGANISM: Artificial sequence
<220> FEATURE:
```

```
<223> OTHER INFORMATION: APIM variant

<400> SEQUENCE: 288

Arg Tyr Val Ala Lys
1               5

<210> SEQ ID NO 289
<211> LENGTH: 5
<212> TYPE: PRT
<213> ORGANISM: Artificial sequence
<220> FEATURE:
<223> OTHER INFORMATION: APIM variant

<400> SEQUENCE: 289

Arg Trp Val Ala Arg
1               5

<210> SEQ ID NO 290
<211> LENGTH: 5
<212> TYPE: PRT
<213> ORGANISM: Artificial sequence
<220> FEATURE:
<223> OTHER INFORMATION: APIM variant

<400> SEQUENCE: 290

Arg Phe Val Ala Arg
1               5

<210> SEQ ID NO 291
<211> LENGTH: 5
<212> TYPE: PRT
<213> ORGANISM: Artificial sequence
<220> FEATURE:
<223> OTHER INFORMATION: APIM variant

<400> SEQUENCE: 291

Arg Tyr Val Ala Arg
1               5

<210> SEQ ID NO 292
<211> LENGTH: 5
<212> TYPE: PRT
<213> ORGANISM: Artificial sequence
<220> FEATURE:
<223> OTHER INFORMATION: APIM variant

<400> SEQUENCE: 292

Lys Trp Val Ala Lys
1               5

<210> SEQ ID NO 293
<211> LENGTH: 5
<212> TYPE: PRT
<213> ORGANISM: Artificial sequence
<220> FEATURE:
<223> OTHER INFORMATION: APIM variant

<400> SEQUENCE: 293

Lys Phe Val Ala Lys
1               5

<210> SEQ ID NO 294
<211> LENGTH: 5
<212> TYPE: PRT
<213> ORGANISM: Artificial sequence
<220> FEATURE:
<223> OTHER INFORMATION: APIM variant
```

```
<400> SEQUENCE: 294

Lys Tyr Val Ala Lys
1               5

<210> SEQ ID NO 295
<211> LENGTH: 5
<212> TYPE: PRT
<213> ORGANISM: Artificial sequence
<220> FEATURE:
<223> OTHER INFORMATION: APIM variant

<400> SEQUENCE: 295

Lys Trp Val Ala Arg
1               5

<210> SEQ ID NO 296
<211> LENGTH: 5
<212> TYPE: PRT
<213> ORGANISM: Artificial sequence
<220> FEATURE:
<223> OTHER INFORMATION: APIM variant

<400> SEQUENCE: 296

Lys Phe Val Ala Arg
1               5

<210> SEQ ID NO 297
<211> LENGTH: 5
<212> TYPE: PRT
<213> ORGANISM: Artificial sequence
<220> FEATURE:
<223> OTHER INFORMATION: APIM variant

<400> SEQUENCE: 297

Lys Tyr Val Ala Arg
1               5

<210> SEQ ID NO 298
<211> LENGTH: 5
<212> TYPE: PRT
<213> ORGANISM: Artificial sequence
<220> FEATURE:
<223> OTHER INFORMATION: APIM variant

<400> SEQUENCE: 298

Lys Tyr Met Val Arg
1               5

<210> SEQ ID NO 299
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: MOD_RES
<222> LOCATION: (5)..(5)
<223> OTHER INFORMATION: Orn

<400> SEQUENCE: 299

Lys Trp Leu Ile Xaa
1               5

<210> SEQ ID NO 300
<211> LENGTH: 5
<212> TYPE: PRT
```

```
<213> ORGANISM: Artificial sequence
<220> FEATURE:
<223> OTHER INFORMATION: APIM variant
<220> FEATURE:
<221> NAME/KEY: MOD_RES
<222> LOCATION: (5)..(5)
<223> OTHER INFORMATION: Dbu

<400> SEQUENCE: 300

Lys Trp Leu Ile Xaa
1               5

<210> SEQ ID NO 301
<211> LENGTH: 5
<212> TYPE: PRT
<213> ORGANISM: Artificial sequence
<220> FEATURE:
<223> OTHER INFORMATION: APIM variant

<400> SEQUENCE: 301

Lys Trp Gln Leu Arg
1               5

<210> SEQ ID NO 302
<211> LENGTH: 16
<212> TYPE: PRT
<213> ORGANISM: Artificial sequence
<220> FEATURE:
<223> OTHER INFORMATION: Penetratin

<400> SEQUENCE: 302

Arg Gln Ile Lys Ile Trp Phe Gln Asn Arg Arg Met Lys Trp Lys Lys
1               5                   10                  15

<210> SEQ ID NO 303
<211> LENGTH: 7
<212> TYPE: PRT
<213> ORGANISM: Artificial sequence
<220> FEATURE:
<223> OTHER INFORMATION: Penetratin derivative

<400> SEQUENCE: 303

Arg Arg Met Lys Trp Lys Lys
1               5

<210> SEQ ID NO 304
<211> LENGTH: 8
<212> TYPE: PRT
<213> ORGANISM: Artificial sequence
<220> FEATURE:
<223> OTHER INFORMATION: Penetratin derivative
<220> FEATURE:
<221> NAME/KEY: MOD_RES
<222> LOCATION: (1)..(1)
<223> OTHER INFORMATION: Nle

<400> SEQUENCE: 304

Xaa Arg Arg Met Lys Trp Lys Lys
1               5

<210> SEQ ID NO 305
<211> LENGTH: 9
<212> TYPE: PRT
<213> ORGANISM: Artificial sequence
<220> FEATURE:
<223> OTHER INFORMATION: Penetratin derivative
<220> FEATURE:
<221> NAME/KEY: MOD_RES
<222> LOCATION: (2)..(2)
```

<223> OTHER INFORMATION: Nle

<400> SEQUENCE: 305

Gln Xaa Arg Arg Met Lys Trp Lys Lys
 1               5

<210> SEQ ID NO 306
<211> LENGTH: 10
<212> TYPE: PRT
<213> ORGANISM: Artificial sequence
<220> FEATURE:
<223> OTHER INFORMATION: Penetratin derivative
<220> FEATURE:
<221> NAME/KEY: MOD_RES
<222> LOCATION: (3)..(3)
<223> OTHER INFORMATION: Nle

<400> SEQUENCE: 306

Phe Gln Xaa Arg Arg Met Lys Trp Lys Lys
 1               5                  10

<210> SEQ ID NO 307
<211> LENGTH: 7
<212> TYPE: PRT
<213> ORGANISM: Artificial sequence
<220> FEATURE:
<223> OTHER INFORMATION: Penetratin derivative

<400> SEQUENCE: 307

Arg Arg Glu Lys Trp Lys Lys
 1               5

<210> SEQ ID NO 308
<211> LENGTH: 7
<212> TYPE: PRT
<213> ORGANISM: Artificial sequence
<220> FEATURE:
<223> OTHER INFORMATION: Penetratin derivative

<400> SEQUENCE: 308

Arg Arg Gln Lys Trp Lys Lys
 1               5

<210> SEQ ID NO 309
<211> LENGTH: 7
<212> TYPE: PRT
<213> ORGANISM: Artificial sequence
<220> FEATURE:
<223> OTHER INFORMATION: Penetratin derivative

<400> SEQUENCE: 309

Lys Arg Met Lys Trp Lys Lys
 1               5

<210> SEQ ID NO 310
<211> LENGTH: 7
<212> TYPE: PRT
<213> ORGANISM: Artificial sequence
<220> FEATURE:
<223> OTHER INFORMATION: Penetratin derivative

<400> SEQUENCE: 310

Arg Lys Met Lys Trp Lys Lys
 1               5

<210> SEQ ID NO 311
<211> LENGTH: 7

```
<212> TYPE: PRT
<213> ORGANISM: Artificial sequence
<220> FEATURE:
<223> OTHER INFORMATION: Penetratin derivative
<220> FEATURE:
<221> NAME/KEY: MOD_RES
<222> LOCATION: (3)..(3)
<223> OTHER INFORMATION: Orn

<400> SEQUENCE: 311

Arg Arg Xaa Lys Trp Lys Lys
1               5

<210> SEQ ID NO 312
<211> LENGTH: 7
<212> TYPE: PRT
<213> ORGANISM: Artificial sequence
<220> FEATURE:
<223> OTHER INFORMATION: Penetratin derivative

<400> SEQUENCE: 312

Arg Arg Met Lys Gln Lys Lys
1               5

<210> SEQ ID NO 313
<211> LENGTH: 7
<212> TYPE: PRT
<213> ORGANISM: Artificial sequence
<220> FEATURE:
<223> OTHER INFORMATION: Penetratin derivative

<400> SEQUENCE: 313

Arg Arg Met Lys Trp Phe Lys
1               5

<210> SEQ ID NO 314
<211> LENGTH: 7
<212> TYPE: PRT
<213> ORGANISM: Artificial sequence
<220> FEATURE:
<223> OTHER INFORMATION: Penetratin derivative
<220> FEATURE:
<221> NAME/KEY: MOD_RES
<222> LOCATION: (2)..(2)
<223> OTHER INFORMATION: Orn

<400> SEQUENCE: 314

Arg Xaa Arg Lys Trp Lys Lys
1               5

<210> SEQ ID NO 315
<211> LENGTH: 7
<212> TYPE: PRT
<213> ORGANISM: Artificial sequence
<220> FEATURE:
<223> OTHER INFORMATION: Penetratin derivative

<400> SEQUENCE: 315

Arg Arg Met Trp Lys Lys Lys
1               5

<210> SEQ ID NO 316
<211> LENGTH: 7
<212> TYPE: PRT
<213> ORGANISM: Artificial sequence
<220> FEATURE:
<223> OTHER INFORMATION: Penetratin derivative

<400> SEQUENCE: 316
```

```
Arg Arg Met Lys Lys Trp Lys
1               5
```

<210> SEQ ID NO 317
<211> LENGTH: 16
<212> TYPE: PRT
<213> ORGANISM: Artificial sequence
<220> FEATURE:
<223> OTHER INFORMATION: D-penetratin

<400> SEQUENCE: 317

```
Arg Gln Ile Lys Ile Trp Phe Gln Asn Arg Arg Met Lys Trp Lys Lys
1               5                   10                  15
```

<210> SEQ ID NO 318
<211> LENGTH: 18
<212> TYPE: PRT
<213> ORGANISM: Artificial sequence
<220> FEATURE:
<223> OTHER INFORMATION: Pegelin (SynB)

<400> SEQUENCE: 318

```
Arg Gly Gly Arg Leu Ser Tyr Ser Arg Arg Arg Phe Ser Thr Ser Thr
1               5                   10                  15

Gly Arg
```

<210> SEQ ID NO 319
<211> LENGTH: 13
<212> TYPE: PRT
<213> ORGANISM: Artificial sequence
<220> FEATURE:
<223> OTHER INFORMATION: HIV-TAT

<400> SEQUENCE: 319

```
Gly Arg Lys Lys Arg Arg Gln Arg Arg Arg Pro Pro Gln
1               5                   10
```

<210> SEQ ID NO 320
<211> LENGTH: 11
<212> TYPE: PRT
<213> ORGANISM: Artificial sequence
<220> FEATURE:
<223> OTHER INFORMATION: Residues 47-57 of HIV-TAT

<400> SEQUENCE: 320

```
Tyr Gly Arg Lys Lys Arg Arg Gln Arg Arg Arg
1               5                   10
```

<210> SEQ ID NO 321
<211> LENGTH: 33
<212> TYPE: PRT
<213> ORGANISM: Artificial sequence
<220> FEATURE:
<223> OTHER INFORMATION: VP22

<400> SEQUENCE: 321

```
Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Val
            20                  25                  30

Asp
```

<210> SEQ ID NO 322
<211> LENGTH: 18

```
<212> TYPE: PRT
<213> ORGANISM: Artificial sequence
<220> FEATURE:
<223> OTHER INFORMATION: MAP

<400> SEQUENCE: 322

Lys Leu Ala Leu Lys Leu Ala Leu Lys Ala Leu Lys Ala Ala Leu Lys
1               5                   10                  15

Leu Ala

<210> SEQ ID NO 323
<211> LENGTH: 27
<212> TYPE: PRT
<213> ORGANISM: Artificial sequence
<220> FEATURE:
<223> OTHER INFORMATION: Transportan

<400> SEQUENCE: 323

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 324
<211> LENGTH: 21
<212> TYPE: PRT
<213> ORGANISM: Artificial sequence
<220> FEATURE:
<223> OTHER INFORMATION: Transportan-10

<400> SEQUENCE: 324

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 325
<211> LENGTH: 30
<212> TYPE: PRT
<213> ORGANISM: Artificial sequence
<220> FEATURE:
<223> OTHER INFORMATION: KALA

<400> SEQUENCE: 325

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 326
<211> LENGTH: 21
<212> TYPE: PRT
<213> ORGANISM: Artificial sequence
<220> FEATURE:
<223> OTHER INFORMATION: Pep-1

<400> SEQUENCE: 326

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 327
<211> LENGTH: 21
```

```
<212> TYPE: PRT
<213> ORGANISM: Artificial sequence
<220> FEATURE:
<223> OTHER INFORMATION: Pep-2

<400> SEQUENCE: 327

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 328
<211> LENGTH: 27
<212> TYPE: PRT
<213> ORGANISM: Artificial sequence
<220> FEATURE:
<223> OTHER INFORMATION: MPG

<400> SEQUENCE: 328

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 329
<211> LENGTH: 19
<212> TYPE: PRT
<213> ORGANISM: Artificial sequence
<220> FEATURE:
<223> OTHER INFORMATION: Vectocell peptide

<400> SEQUENCE: 329

Val Lys Arg Gly Leu Lys Leu Arg His Val Arg Pro Arg Val Thr Arg
1               5                   10                  15

Met Asp Val

<210> SEQ ID NO 330
<211> LENGTH: 14
<212> TYPE: PRT
<213> ORGANISM: Artificial sequence
<220> FEATURE:
<223> OTHER INFORMATION: Vectocell peptide

<400> SEQUENCE: 330

Ser Arg Arg Ala Arg Arg Ser Pro Arg His Leu Gly Ser Gly
1               5                   10

<210> SEQ ID NO 331
<211> LENGTH: 16
<212> TYPE: PRT
<213> ORGANISM: Artificial sequence
<220> FEATURE:
<223> OTHER INFORMATION: Vectocell peptide

<400> SEQUENCE: 331

Leu Arg Arg Glu Arg Gln Ser Arg Leu Arg Arg Glu Arg Gln Ser Arg
1               5                   10                  15

<210> SEQ ID NO 332
<211> LENGTH: 22
<212> TYPE: PRT
<213> ORGANISM: Artificial sequence
<220> FEATURE:
<223> OTHER INFORMATION: Vectocell peptide

<400> SEQUENCE: 332
```

-continued

```
Gly Ala Tyr Asp Leu Arg Arg Arg Glu Arg Gln Ser Arg Leu Arg Arg
1               5                   10                  15

Arg Glu Arg Gln Ser Arg
            20

<210> SEQ ID NO 333
<211> LENGTH: 29
<212> TYPE: PRT
<213> ORGANISM: Artificial sequence
<220> FEATURE:
<223> OTHER INFORMATION: Wr-T transporter
<220> FEATURE:
<221> NAME/KEY: variant
<222> LOCATION: (22)..(29)
<223> OTHER INFORMATION: /REPLACE= D enantiomer arginine

<400> SEQUENCE: 333

Lys Glu Thr Trp Trp Glu Thr Trp Trp Thr Glu Trp Trp Thr Glu Trp
1               5                   10                  15

Ser Gln Gly Pro Gly Xaa Xaa Xaa Xaa Xaa Xaa Xaa Xaa
            20                  25

<210> SEQ ID NO 334
<211> LENGTH: 7
<212> TYPE: PRT
<213> ORGANISM: Artificial sequence
<220> FEATURE:
<223> OTHER INFORMATION: R7

<400> SEQUENCE: 334

Arg Arg Arg Arg Arg Arg Arg
1               5

<210> SEQ ID NO 335
<211> LENGTH: 9
<212> TYPE: PRT
<213> ORGANISM: Artificial sequence
<220> FEATURE:
<223> OTHER INFORMATION: HIV-TAT peptide

<400> SEQUENCE: 335

Arg Lys Lys Arg Arg Gln Arg Arg Arg
1               5

<210> SEQ ID NO 336
<211> LENGTH: 8
<212> TYPE: PRT
<213> ORGANISM: Artificial sequence
<220> FEATURE:
<223> OTHER INFORMATION: R8

<400> SEQUENCE: 336

Arg Arg Arg Arg Arg Arg Arg Arg
1               5

<210> SEQ ID NO 337
<211> LENGTH: 11
<212> TYPE: PRT
<213> ORGANISM: Artificial sequence
<220> FEATURE:
<223> OTHER INFORMATION: R11

<400> SEQUENCE: 337

Arg Arg Arg Arg Arg Arg Arg Arg Arg Arg Arg
1               5                   10
```

<210> SEQ ID NO 338
<211> LENGTH: 10
<212> TYPE: PRT
<213> ORGANISM: Artificial sequence
<220> FEATURE:
<223> OTHER INFORMATION: QSR8

<400> SEQUENCE: 338

Gln Ser Arg Arg Arg Arg Arg Arg Arg
1               5                   10

<210> SEQ ID NO 339
<211> LENGTH: 14
<212> TYPE: PRT
<213> ORGANISM: Artificial sequence
<220> FEATURE:
<223> OTHER INFORMATION: HIV-Tat derivative

<400> SEQUENCE: 339

Gly Arg Lys Lys Arg Arg Gln Arg Arg Arg Pro Pro Gln Gln
1               5                   10

<210> SEQ ID NO 340
<211> LENGTH: 13
<212> TYPE: PRT
<213> ORGANISM: Human immunodeficiency virus type 1

<400> SEQUENCE: 340

Gly Arg Lys Lys Arg Arg Gln Arg Arg Pro Pro Gln
1               5                   10

<210> SEQ ID NO 341
<211> LENGTH: 18
<212> TYPE: PRT
<213> ORGANISM: Human immunodeficiency virus type 1

<400> SEQUENCE: 341

Leu Gly Ile Ser Tyr Gly Arg Lys Lys Arg Arg Gln Arg Arg Arg Pro
1               5                   10                  15

Pro Gln

<210> SEQ ID NO 342
<211> LENGTH: 23
<212> TYPE: PRT
<213> ORGANISM: Human immunodeficiency virus type 1

<400> SEQUENCE: 342

Phe Ile Thr Lys Ala Leu Gly Ile Ser Tyr Gly Arg Lys Lys Arg Arg
1               5                   10                  15

Gln Arg Arg Arg Pro Pro Gln
                20

<210> SEQ ID NO 343
<211> LENGTH: 16
<212> TYPE: PRT
<213> ORGANISM: Human immunodeficiency virus type 1

<400> SEQUENCE: 343

Phe Ile Thr Lys Ala Leu Gly Ile Ser Tyr Gly Arg Lys Lys Arg Arg
1               5                   10                  15

<210> SEQ ID NO 344
<211> LENGTH: 10
<212> TYPE: PRT

<213> ORGANISM: Human immunodeficiency virus type 1

<400> SEQUENCE: 344

Gly Arg Lys Lys Arg Arg Gln Arg Arg Arg
1               5 10

<210> SEQ ID NO 345
<211> LENGTH: 9
<212> TYPE: PRT
<213> ORGANISM: Human immunodeficiency virus type 1

<400> SEQUENCE: 345

Arg Lys Lys Arg Arg Gln Arg Arg Arg
1 5

<210> SEQ ID NO 346
<211> LENGTH: 8
<212> TYPE: PRT
<213> ORGANISM: Human immunodeficiency virus type 1

<400> SEQUENCE: 346

Arg Lys Lys Arg Arg Gln Arg Arg
1 5

<210> SEQ ID NO 347
<211> LENGTH: 7
<212> TYPE: PRT
<213> ORGANISM: Human immunodeficiency virus type 1

<400> SEQUENCE: 347

Arg Lys Lys Arg Arg Gln Arg
1 5

<210> SEQ ID NO 348
<211> LENGTH: 8
<212> TYPE: PRT
<213> ORGANISM: Human immunodeficiency virus type 1

<400> SEQUENCE: 348

Lys Lys Arg Arg Gln Arg Arg Arg
1 5

<210> SEQ ID NO 349
<211> LENGTH: 7
<212> TYPE: PRT
<213> ORGANISM: Human immunodeficiency virus type 1

<400> SEQUENCE: 349

Lys Arg Arg Gln Arg Arg Arg
1 5

<210> SEQ ID NO 350
<211> LENGTH: 9
<212> TYPE: PRT
<213> ORGANISM: Human immunodeficiency virus type 1

<400> SEQUENCE: 350

Arg Lys Lys Arg Arg Gln Arg Arg Arg
1 5

<210> SEQ ID NO 351
<211> LENGTH: 9
<212> TYPE: PRT
<213> ORGANISM: Human immunodeficiency virus type 1

```
<400> SEQUENCE: 351

Arg Arg Arg Gln Arg Arg Lys Lys Arg
1               5

<210> SEQ ID NO 352
<211> LENGTH: 9
<212> TYPE: PRT
<213> ORGANISM: Human immunodeficiency virus type 1

<400> SEQUENCE: 352

Arg Arg Arg Gln Arg Arg Lys Lys Arg
1               5

<210> SEQ ID NO 353
<211> LENGTH: 9
<212> TYPE: PRT
<213> ORGANISM: Human immunodeficiency virus type 1

<400> SEQUENCE: 353

Ala Lys Lys Arg Arg Gln Arg Arg Arg
1               5

<210> SEQ ID NO 354
<211> LENGTH: 9
<212> TYPE: PRT
<213> ORGANISM: Human immunodeficiency virus type 1

<400> SEQUENCE: 354

Arg Ala Lys Arg Arg Gln Arg Arg Arg
1               5

<210> SEQ ID NO 355
<211> LENGTH: 9
<212> TYPE: PRT
<213> ORGANISM: Human immunodeficiency virus type 1

<400> SEQUENCE: 355

Arg Lys Ala Arg Arg Gln Arg Arg Arg
1               5

<210> SEQ ID NO 356
<211> LENGTH: 9
<212> TYPE: PRT
<213> ORGANISM: Human immunodeficiency virus type 1

<400> SEQUENCE: 356

Arg Lys Lys Ala Arg Gln Arg Arg Arg
1               5

<210> SEQ ID NO 357
<211> LENGTH: 9
<212> TYPE: PRT
<213> ORGANISM: Human immunodeficiency virus type 1

<400> SEQUENCE: 357

Arg Lys Lys Arg Ala Gln Arg Arg Arg
1               5

<210> SEQ ID NO 358
<211> LENGTH: 9
<212> TYPE: PRT
<213> ORGANISM: Human immunodeficiency virus type 1

<400> SEQUENCE: 358
```

```
Arg Lys Lys Arg Arg Ala Arg Arg Arg
1               5

<210> SEQ ID NO 359
<211> LENGTH: 9
<212> TYPE: PRT
<213> ORGANISM: Human immunodeficiency virus type 1

<400> SEQUENCE: 359

Arg Lys Lys Arg Arg Gln Ala Arg Arg
1               5

<210> SEQ ID NO 360
<211> LENGTH: 9
<212> TYPE: PRT
<213> ORGANISM: Human immunodeficiency virus type 1

<400> SEQUENCE: 360

Arg Lys Lys Arg Arg Gln Arg Ala Arg
1               5

<210> SEQ ID NO 361
<211> LENGTH: 9
<212> TYPE: PRT
<213> ORGANISM: Human immunodeficiency virus type 1

<400> SEQUENCE: 361

Arg Lys Lys Arg Arg Gln Arg Arg Ala
1               5

<210> SEQ ID NO 362
<211> LENGTH: 13
<212> TYPE: PRT
<213> ORGANISM: Human immunodeficiency virus type 1

<400> SEQUENCE: 362

Gly Arg Lys Lys Arg Arg Gln Arg Arg Pro Pro Gln Cys
1               5                   10

<210> SEQ ID NO 363
<211> LENGTH: 12
<212> TYPE: PRT
<213> ORGANISM: Human immunodeficiency virus type 1

<400> SEQUENCE: 363

Gly Arg Lys Lys Arg Arg Gln Arg Pro Pro Gln Cys
1               5                   10

<210> SEQ ID NO 364
<211> LENGTH: 11
<212> TYPE: PRT
<213> ORGANISM: Human immunodeficiency virus type 1

<400> SEQUENCE: 364

Gly Arg Lys Lys Arg Arg Gln Pro Pro Gln Cys
1               5                   10

<210> SEQ ID NO 365
<211> LENGTH: 11
<212> TYPE: PRT
<213> ORGANISM: Human immunodeficiency virus type 1

<400> SEQUENCE: 365

Gly Arg Lys Lys Arg Arg Gln Arg Arg Arg Cys
1               5                   10
```

```
<210> SEQ ID NO 366
<211> LENGTH: 14
<212> TYPE: PRT
<213> ORGANISM: Human immunodeficiency virus type 1

<400> SEQUENCE: 366

Gly Arg Lys Lys Arg Arg Gln Arg Ala Arg Pro Pro Gln Cys
1               5                   10

<210> SEQ ID NO 367
<211> LENGTH: 14
<212> TYPE: PRT
<213> ORGANISM: Human immunodeficiency virus type 1

<400> SEQUENCE: 367

Gly Arg Lys Lys Arg Arg Gln Ala Arg Ala Pro Pro Gln Cys
1               5                   10

<210> SEQ ID NO 368
<211> LENGTH: 17
<212> TYPE: PRT
<213> ORGANISM: Human immunodeficiency virus type 1

<400> SEQUENCE: 368

Thr Arg Gln Ala Arg Arg Asn Arg Arg Arg Trp Arg Glu Arg Gln
1               5                   10                  15

Arg

<210> SEQ ID NO 369
<211> LENGTH: 30
<212> TYPE: PRT
<213> ORGANISM: Homo sapiens

<400> SEQUENCE: 369

Gly Trp Thr Leu Asn Ser Ala Gly Tyr Leu Leu Gly Pro His Ala Val
1               5                   10                  15

Gly Asn His Arg Ser Phe Ser Asp Lys Asn Gly Leu Thr Ser
                20                  25                  30

<210> SEQ ID NO 370
<211> LENGTH: 14
<212> TYPE: PRT
<213> ORGANISM: Vespula vulgaris

<400> SEQUENCE: 370

Ile Asn Leu Lys Ala Leu Ala Ala Leu Ala Lys Lys Ile Leu
1               5                   10

<210> SEQ ID NO 371
<211> LENGTH: 16
<212> TYPE: PRT
<213> ORGANISM: Drosophila melanogaster

<400> SEQUENCE: 371

Arg Gln Ile Lys Ile Trp Phe Gln Asn Arg Arg Met Lys Trp Lys Lys
1               5                   10                  15

<210> SEQ ID NO 372
<211> LENGTH: 16
<212> TYPE: PRT
<213> ORGANISM: Drosophila melanogaster

<400> SEQUENCE: 372
```

Arg Gln Ile Lys Ile Trp Phe Gln Asn Arg Arg Met Lys Trp Lys Lys
1               5                   10                  15

<210> SEQ ID NO 373
<211> LENGTH: 16
<212> TYPE: PRT
<213> ORGANISM: Drosophila melanogaster

<400> SEQUENCE: 373

Lys Lys Trp Lys Met Arg Arg Asn Gln Phe Trp Ile Lys Ile Gln Arg
1               5                   10                  15

<210> SEQ ID NO 374
<211> LENGTH: 16
<212> TYPE: PRT
<213> ORGANISM: Drosophila melanogaster

<400> SEQUENCE: 374

Arg Gln Ile Lys Ile Trp Phe Gln Asn Arg Arg Met Lys Trp Lys Lys
1               5                   10                  15

<210> SEQ ID NO 375
<211> LENGTH: 16
<212> TYPE: PRT
<213> ORGANISM: Drosophila melanogaster

<400> SEQUENCE: 375

Arg Gln Ile Lys Ile Trp Phe Pro Asn Arg Arg Met Lys Trp Lys Lys
1               5                   10                  15

<210> SEQ ID NO 376
<211> LENGTH: 16
<212> TYPE: PRT
<213> ORGANISM: Drosophila melanogaster

<400> SEQUENCE: 376

Arg Gln Pro Lys Ile Trp Phe Pro Asn Arg Arg Lys Pro Trp Lys Lys
1               5                   10                  15

<210> SEQ ID NO 377
<211> LENGTH: 16
<212> TYPE: PRT
<213> ORGANISM: Drosophila melanogaster

<400> SEQUENCE: 377

Arg Gln Ile Lys Ile Trp Phe Gln Asn Arg Arg Met Lys Trp Lys Lys
1               5                   10                  15

<210> SEQ ID NO 378
<211> LENGTH: 15
<212> TYPE: PRT
<213> ORGANISM: Drosophila melanogaster

<400> SEQUENCE: 378

Arg Gln Ile Lys Ile Trp Phe Gln Asn Arg Arg Met Lys Trp Lys
1               5                   10                  15

<210> SEQ ID NO 379
<211> LENGTH: 14
<212> TYPE: PRT
<213> ORGANISM: Drosophila melanogaster

<400> SEQUENCE: 379

Arg Gln Ile Lys Ile Trp Phe Gln Asn Arg Arg Met Lys Trp

```
1               5                   10
```

<210> SEQ ID NO 380
<211> LENGTH: 13
<212> TYPE: PRT
<213> ORGANISM: Drosophila melanogaster

<400> SEQUENCE: 380

```
Arg Gln Ile Lys Ile Trp Phe Gln Asn Arg Arg Met Lys
1               5                   10
```

<210> SEQ ID NO 381
<211> LENGTH: 12
<212> TYPE: PRT
<213> ORGANISM: Drosophila melanogaster

<400> SEQUENCE: 381

```
Arg Gln Ile Lys Ile Trp Phe Gln Asn Arg Arg Met
1               5                   10
```

<210> SEQ ID NO 382
<211> LENGTH: 11
<212> TYPE: PRT
<213> ORGANISM: Drosophila melanogaster

<400> SEQUENCE: 382

```
Arg Gln Ile Lys Ile Trp Phe Gln Asn Arg Arg
1               5                   10
```

<210> SEQ ID NO 383
<211> LENGTH: 10
<212> TYPE: PRT
<213> ORGANISM: Drosophila melanogaster

<400> SEQUENCE: 383

```
Arg Gln Ile Lys Ile Trp Phe Gln Asn Arg
1               5                   10
```

<210> SEQ ID NO 384
<211> LENGTH: 9
<212> TYPE: PRT
<213> ORGANISM: Drosophila melanogaster

<400> SEQUENCE: 384

```
Arg Gln Ile Lys Ile Trp Phe Gln Asn
1               5
```

<210> SEQ ID NO 385
<211> LENGTH: 8
<212> TYPE: PRT
<213> ORGANISM: Drosophila melanogaster

<400> SEQUENCE: 385

```
Arg Gln Ile Lys Ile Trp Phe Gln
1               5
```

<210> SEQ ID NO 386
<211> LENGTH: 6
<212> TYPE: PRT
<213> ORGANISM: Drosophila melanogaster

<400> SEQUENCE: 386

```
Arg Gln Ile Lys Ile Trp
1               5
```

<210> SEQ ID NO 387
<211> LENGTH: 15
<212> TYPE: PRT
<213> ORGANISM: Drosophila melanogaster

<400> SEQUENCE: 387

Gln Ile Lys Ile Trp Phe Gln Asn Arg Arg Met Lys Trp Lys Lys
1               5                   10                  15

<210> SEQ ID NO 388
<211> LENGTH: 14
<212> TYPE: PRT
<213> ORGANISM: Drosophila melanogaster

<400> SEQUENCE: 388

Ile Lys Ile Trp Phe Gln Asn Arg Arg Met Lys Trp Lys Lys
1               5                   10

<210> SEQ ID NO 389
<211> LENGTH: 13
<212> TYPE: PRT
<213> ORGANISM: Drosophila melanogaster

<400> SEQUENCE: 389

Lys Ile Trp Phe Gln Asn Arg Arg Met Lys Trp Lys Lys
1               5                   10

<210> SEQ ID NO 390
<211> LENGTH: 12
<212> TYPE: PRT
<213> ORGANISM: Drosophila melanogaster

<400> SEQUENCE: 390

Ile Trp Phe Gln Asn Arg Arg Met Lys Trp Lys Lys
1               5                   10

<210> SEQ ID NO 391
<211> LENGTH: 11
<212> TYPE: PRT
<213> ORGANISM: Drosophila melanogaster

<400> SEQUENCE: 391

Trp Phe Gln Asn Arg Arg Met Lys Trp Lys Lys
1               5                   10

<210> SEQ ID NO 392
<211> LENGTH: 10
<212> TYPE: PRT
<213> ORGANISM: Drosophila melanogaster

<400> SEQUENCE: 392

Phe Gln Asn Arg Arg Met Lys Trp Lys Lys
1               5                   10

<210> SEQ ID NO 393
<211> LENGTH: 9
<212> TYPE: PRT
<213> ORGANISM: Drosophila melanogaster

<400> SEQUENCE: 393

Gln Asn Arg Arg Met Lys Trp Lys Lys
1               5

<210> SEQ ID NO 394

```
<211> LENGTH: 8
<212> TYPE: PRT
<213> ORGANISM: Drosophila melanogaster

<400> SEQUENCE: 394

Asn Arg Arg Met Lys Trp Lys Lys
1               5

<210> SEQ ID NO 395
<211> LENGTH: 7
<212> TYPE: PRT
<213> ORGANISM: Drosophila melanogaster

<400> SEQUENCE: 395

Arg Arg Met Lys Trp Lys Lys
1               5

<210> SEQ ID NO 396
<211> LENGTH: 6
<212> TYPE: PRT
<213> ORGANISM: Drosophila melanogaster

<400> SEQUENCE: 396

Arg Met Lys Trp Lys Lys
1               5

<210> SEQ ID NO 397
<211> LENGTH: 16
<212> TYPE: PRT
<213> ORGANISM: Drosophila melanogaster

<400> SEQUENCE: 397

Ala Gln Ile Lys Ile Trp Phe Gln Asn Arg Arg Met Lys Trp Lys Lys
1               5                   10                  15

<210> SEQ ID NO 398
<211> LENGTH: 16
<212> TYPE: PRT
<213> ORGANISM: Drosophila melanogaster

<400> SEQUENCE: 398

Arg Ala Ile Lys Ile Trp Phe Gln Asn Arg Arg Met Lys Trp Lys Lys
1               5                   10                  15

<210> SEQ ID NO 399
<211> LENGTH: 16
<212> TYPE: PRT
<213> ORGANISM: Drosophila melanogaster

<400> SEQUENCE: 399

Arg Gln Ala Lys Ile Trp Phe Gln Asn Arg Arg Met Lys Trp Lys Lys
1               5                   10                  15

<210> SEQ ID NO 400
<211> LENGTH: 16
<212> TYPE: PRT
<213> ORGANISM: Drosophila melanogaster

<400> SEQUENCE: 400

Arg Gln Ile Ala Ile Trp Phe Gln Asn Arg Arg Met Lys Trp Lys Lys
1               5                   10                  15

<210> SEQ ID NO 401
<211> LENGTH: 16
<212> TYPE: PRT
```

<213> ORGANISM: Drosophila melanogaster

<400> SEQUENCE: 401

Arg Gln Ile Lys Ala Trp Phe Gln Asn Arg Arg Met Lys Trp Lys Lys
1               5                   10                  15

<210> SEQ ID NO 402
<211> LENGTH: 16
<212> TYPE: PRT
<213> ORGANISM: Drosophila melanogaster

<400> SEQUENCE: 402

Arg Gln Ile Lys Ile Ala Phe Gln Asn Arg Arg Met Lys Trp Lys Lys
1               5                   10                  15

<210> SEQ ID NO 403
<211> LENGTH: 16
<212> TYPE: PRT
<213> ORGANISM: Drosophila melanogaster

<400> SEQUENCE: 403

Arg Gln Ile Lys Ile Trp Ala Gln Asn Arg Arg Met Lys Trp Lys Lys
1               5                   10                  15

<210> SEQ ID NO 404
<211> LENGTH: 16
<212> TYPE: PRT
<213> ORGANISM: Drosophila melanogaster

<400> SEQUENCE: 404

Arg Gln Ile Lys Ile Trp Phe Ala Asn Arg Arg Met Lys Trp Lys Lys
1               5                   10                  15

<210> SEQ ID NO 405
<211> LENGTH: 16
<212> TYPE: PRT
<213> ORGANISM: Drosophila melanogaster

<400> SEQUENCE: 405

Arg Gln Ile Lys Ile Trp Phe Gln Ala Arg Arg Met Lys Trp Lys Lys
1               5                   10                  15

<210> SEQ ID NO 406
<211> LENGTH: 16
<212> TYPE: PRT
<213> ORGANISM: Drosophila melanogaster

<400> SEQUENCE: 406

Arg Gln Ile Lys Ile Trp Phe Gln Asn Ala Arg Met Lys Trp Lys Lys
1               5                   10                  15

<210> SEQ ID NO 407
<211> LENGTH: 16
<212> TYPE: PRT
<213> ORGANISM: Drosophila melanogaster

<400> SEQUENCE: 407

Arg Gln Ile Lys Ile Trp Phe Gln Asn Arg Ala Met Lys Trp Lys Lys
1               5                   10                  15

<210> SEQ ID NO 408
<211> LENGTH: 16
<212> TYPE: PRT
<213> ORGANISM: Drosophila melanogaster

<400> SEQUENCE: 408

Arg Gln Ile Lys Ile Trp Phe Gln Asn Arg Arg Ala Lys Trp Lys Lys
1               5                   10                  15

<210> SEQ ID NO 409
<211> LENGTH: 16
<212> TYPE: PRT
<213> ORGANISM: Drosophila melanogaster

<400> SEQUENCE: 409

Arg Gln Ile Lys Ile Trp Phe Gln Asn Arg Arg Met Ala Trp Lys Lys
1               5                   10                  15

<210> SEQ ID NO 410
<211> LENGTH: 16
<212> TYPE: PRT
<213> ORGANISM: Drosophila melanogaster

<400> SEQUENCE: 410

Arg Gln Ile Lys Ile Trp Phe Gln Asn Arg Arg Met Lys Ala Lys Lys
1               5                   10                  15

<210> SEQ ID NO 411
<211> LENGTH: 16
<212> TYPE: PRT
<213> ORGANISM: Drosophila melanogaster

<400> SEQUENCE: 411

Arg Gln Ile Lys Ile Trp Phe Gln Asn Arg Arg Met Lys Trp Ala Lys
1               5                   10                  15

<210> SEQ ID NO 412
<211> LENGTH: 16
<212> TYPE: PRT
<213> ORGANISM: Drosophila melanogaster

<400> SEQUENCE: 412

Arg Gln Ile Lys Ile Trp Phe Gln Asn Arg Arg Met Lys Trp Lys Ala
1               5                   10                  15

<210> SEQ ID NO 413
<211> LENGTH: 18
<212> TYPE: PRT
<213> ORGANISM: Drosophila melanogaster

<400> SEQUENCE: 413

Cys Arg Gln Ile Lys Ile Trp Phe Pro Asn Arg Met Lys Trp Lys
1               5                   10                  15

Lys Cys

<210> SEQ ID NO 414
<211> LENGTH: 16
<212> TYPE: PRT
<213> ORGANISM: Drosophila melanogaster

<400> SEQUENCE: 414

Arg Gln Ile Lys Ile Trp Phe Pro Asn Arg Arg Met Lys Trp Lys Lys
1               5                   10                  15

<210> SEQ ID NO 415
<211> LENGTH: 16
<212> TYPE: PRT
<213> ORGANISM: Drosophila melanogaster

<400> SEQUENCE: 415

Arg Gln Ile Lys Ile Trp Phe Gln Asn Arg Arg Met Lys Trp Lys Lys
1               5                   10                  15

<210> SEQ ID NO 416
<211> LENGTH: 16
<212> TYPE: PRT
<213> ORGANISM: Drosophila melanogaster

<400> SEQUENCE: 416

Arg Gln Ile Lys Ile Phe Phe Gln Asn Arg Arg Met Lys Phe Lys Lys
1               5                   10                  15

<210> SEQ ID NO 417
<211> LENGTH: 16
<212> TYPE: PRT
<213> ORGANISM: Drosophila melanogaster

<400> SEQUENCE: 417

Arg Gln Ile Arg Ile Trp Phe Gln Asn Arg Arg Met Arg Trp Arg Arg
1               5                   10                  15

<210> SEQ ID NO 418
<211> LENGTH: 13
<212> TYPE: PRT
<213> ORGANISM: Human immunodeficiency virus type 1

<400> SEQUENCE: 418

Gly Arg Lys Lys Arg Arg Gln Arg Arg Arg Pro Trp Gln
1               5                   10

<210> SEQ ID NO 419
<211> LENGTH: 13
<212> TYPE: PRT
<213> ORGANISM: Human immunodeficiency virus type 1

<400> SEQUENCE: 419

Gly Arg Lys Lys Arg Arg Gln Arg Arg Arg Pro Trp Gln
1               5                   10

<210> SEQ ID NO 420
<211> LENGTH: 16
<212> TYPE: PRT
<213> ORGANISM: Drosophila melanogaster

<400> SEQUENCE: 420

Arg Gln Ile Arg Ile Trp Phe Gln Asn Arg Arg Met Arg Trp Arg Arg
1               5                   10                  15

<210> SEQ ID NO 421
<211> LENGTH: 16
<212> TYPE: PRT
<213> ORGANISM: Drosophila melanogaster

<400> SEQUENCE: 421

Arg Arg Trp Arg Arg Trp Trp Arg Arg Trp Trp Arg Arg Trp Arg Arg
1               5                   10                  15

<210> SEQ ID NO 422
<211> LENGTH: 16
<212> TYPE: PRT
<213> ORGANISM: Drosophila melanogaster

<400> SEQUENCE: 422

Arg Gln Ile Lys Ile Trp Phe Gln Asn Met Arg Arg Lys Trp Lys Lys
1               5                   10                  15

<210> SEQ ID NO 423
<211> LENGTH: 13
<212> TYPE: PRT
<213> ORGANISM: Crotalus durissus

<400> SEQUENCE: 423

Lys Met Asp Cys Arg Trp Arg Trp Lys Cys Cys Lys Lys
1               5                   10

<210> SEQ ID NO 424
<211> LENGTH: 12
<212> TYPE: PRT
<213> ORGANISM: Crotalus durissus

<400> SEQUENCE: 424

Met Asp Cys Arg Trp Arg Trp Lys Cys Cys Lys Lys
1               5                   10

<210> SEQ ID NO 425
<211> LENGTH: 11
<212> TYPE: PRT
<213> ORGANISM: Crotalus durissus

<400> SEQUENCE: 425

Asp Cys Arg Trp Arg Trp Lys Cys Cys Lys Lys
1               5                   10

<210> SEQ ID NO 426
<211> LENGTH: 10
<212> TYPE: PRT
<213> ORGANISM: Crotalus durissus

<400> SEQUENCE: 426

Cys Arg Trp Arg Trp Lys Cys Cys Lys Lys
1               5                   10

<210> SEQ ID NO 427
<211> LENGTH: 9
<212> TYPE: PRT
<213> ORGANISM: Crotalus durissus

<400> SEQUENCE: 427

Arg Trp Arg Trp Lys Cys Cys Lys Lys
1               5

<210> SEQ ID NO 428
<211> LENGTH: 12
<212> TYPE: PRT
<213> ORGANISM: Crotalus durissus

<400> SEQUENCE: 428

Lys Met Asp Cys Arg Trp Arg Trp Lys Cys Lys Lys
1               5                   10

<210> SEQ ID NO 429
<211> LENGTH: 11
<212> TYPE: PRT
<213> ORGANISM: Crotalus durissus

<400> SEQUENCE: 429

Lys Met Asp Cys Arg Trp Arg Trp Lys Lys Lys
1               5                   10

<210> SEQ ID NO 430
<211> LENGTH: 10
<212> TYPE: PRT
<213> ORGANISM: Crotalus durissus

<400> SEQUENCE: 430

Lys Met Asp Arg Trp Arg Trp Lys Lys Lys
1               5                   10

<210> SEQ ID NO 431
<211> LENGTH: 12
<212> TYPE: PRT
<213> ORGANISM: Crotalus durissus

<400> SEQUENCE: 431

Lys Asp Cys Arg Trp Arg Trp Lys Cys Cys Lys Lys
1               5                   10

<210> SEQ ID NO 432
<211> LENGTH: 11
<212> TYPE: PRT
<213> ORGANISM: Crotalus durissus

<400> SEQUENCE: 432

Lys Cys Arg Trp Arg Trp Lys Cys Cys Lys Lys
1               5                   10

<210> SEQ ID NO 433
<211> LENGTH: 10
<212> TYPE: PRT
<213> ORGANISM: Crotalus durissus

<400> SEQUENCE: 433

Lys Arg Trp Arg Trp Lys Cys Cys Lys Lys
1               5                   10

<210> SEQ ID NO 434
<211> LENGTH: 12
<212> TYPE: PRT
<213> ORGANISM: Crotalus durissus
<220> FEATURE:
<221> NAME/KEY: misc_feature
<222> LOCATION: (9)..(9)
<223> OTHER INFORMATION: Xaa can be any naturally occurring amino acid

<400> SEQUENCE: 434

Met Asp Cys Arg Trp Arg Trp Lys Xaa Cys Lys Lys
1               5                   10

<210> SEQ ID NO 435
<211> LENGTH: 11
<212> TYPE: PRT
<213> ORGANISM: Crotalus durissus
<220> FEATURE:
<221> NAME/KEY: misc_feature
<222> LOCATION: (8)..(8)
<223> OTHER INFORMATION: Xaa can be any naturally occurring amino acid

<400> SEQUENCE: 435

Asp Cys Arg Trp Arg Trp Lys Xaa Cys Lys Lys
1               5                   10

<210> SEQ ID NO 436
<211> LENGTH: 11
<212> TYPE: PRT

```
<213> ORGANISM: Crotalus durissus
<220> FEATURE:
<221> NAME/KEY: misc_feature
<222> LOCATION: (9)..(9)
<223> OTHER INFORMATION: Xaa can be any naturally occurring amino acid

<400> SEQUENCE: 436

Asp Cys Arg Trp Arg Trp Lys Cys Xaa Lys Lys
1               5                   10

<210> SEQ ID NO 437
<211> LENGTH: 10
<212> TYPE: PRT
<213> ORGANISM: Crotalus durissus
<220> FEATURE:
<221> NAME/KEY: misc_feature
<222> LOCATION: (7)..(7)
<223> OTHER INFORMATION: Xaa can be any naturally occurring amino acid

<400> SEQUENCE: 437

Cys Arg Trp Arg Trp Lys Xaa Cys Lys Lys
1               5                   10

<210> SEQ ID NO 438
<211> LENGTH: 10
<212> TYPE: PRT
<213> ORGANISM: Crotalus durissus
<220> FEATURE:
<221> NAME/KEY: misc_feature
<222> LOCATION: (8)..(8)
<223> OTHER INFORMATION: Xaa can be any naturally occurring amino acid

<400> SEQUENCE: 438

Cys Arg Trp Arg Trp Lys Cys Xaa Lys Lys
1               5                   10

<210> SEQ ID NO 439
<211> LENGTH: 9
<212> TYPE: PRT
<213> ORGANISM: Crotalus durissus
<220> FEATURE:
<221> NAME/KEY: misc_feature
<222> LOCATION: (6)..(6)
<223> OTHER INFORMATION: Xaa can be any naturally occurring amino acid

<400> SEQUENCE: 439

Arg Trp Arg Trp Lys Xaa Cys Lys Lys
1               5

<210> SEQ ID NO 440
<211> LENGTH: 12
<212> TYPE: PRT
<213> ORGANISM: Crotalus durissus
<220> FEATURE:
<221> NAME/KEY: misc_feature
<222> LOCATION: (9)..(10)
<223> OTHER INFORMATION: Xaa can be any naturally occurring amino acid

<400> SEQUENCE: 440

Met Asp Cys Arg Trp Arg Trp Lys Xaa Xaa Lys Lys
1               5                   10

<210> SEQ ID NO 441
<211> LENGTH: 11
<212> TYPE: PRT
<213> ORGANISM: Crotalus durissus
<220> FEATURE:
<221> NAME/KEY: misc_feature
<222> LOCATION: (8)..(9)
```

```
<223> OTHER INFORMATION: Xaa can be any naturally occurring amino acid

<400> SEQUENCE: 441

Asp Cys Arg Trp Arg Trp Lys Xaa Xaa Lys Lys
1               5                   10

<210> SEQ ID NO 442
<211> LENGTH: 10
<212> TYPE: PRT
<213> ORGANISM: Crotalus durissus
<220> FEATURE:
<221> NAME/KEY: misc_feature
<222> LOCATION: (7)..(8)
<223> OTHER INFORMATION: Xaa can be any naturally occurring amino acid

<400> SEQUENCE: 442

Cys Arg Trp Arg Trp Lys Xaa Xaa Lys Lys
1               5                   10

<210> SEQ ID NO 443
<211> LENGTH: 9
<212> TYPE: PRT
<213> ORGANISM: Crotalus durissus
<220> FEATURE:
<221> NAME/KEY: misc_feature
<222> LOCATION: (6)..(7)
<223> OTHER INFORMATION: Xaa can be any naturally occurring amino acid

<400> SEQUENCE: 443

Arg Trp Arg Trp Lys Xaa Xaa Lys Lys
1               5

<210> SEQ ID NO 444
<211> LENGTH: 10
<212> TYPE: PRT
<213> ORGANISM: Crotalus durissus

<400> SEQUENCE: 444

Cys Arg Trp Arg Trp Lys Cys Ser Lys Lys
1               5                   10

<210> SEQ ID NO 445
<211> LENGTH: 10
<212> TYPE: PRT
<213> ORGANISM: Crotalus durissus

<400> SEQUENCE: 445

Ser Arg Trp Arg Trp Lys Cys Cys Lys Lys
1               5                   10

<210> SEQ ID NO 446
<211> LENGTH: 10
<212> TYPE: PRT
<213> ORGANISM: Crotalus durissus

<400> SEQUENCE: 446

Ser Arg Trp Arg Trp Lys Cys Ser Lys Lys
1               5                   10

<210> SEQ ID NO 447
<211> LENGTH: 10
<212> TYPE: PRT
<213> ORGANISM: Crotalus durissus

<400> SEQUENCE: 447

Ser Arg Trp Arg Trp Lys Ser Cys Lys Lys
```

```
1               5                   10
```

<210> SEQ ID NO 448
<211> LENGTH: 10
<212> TYPE: PRT
<213> ORGANISM: Crotalus durissus

<400> SEQUENCE: 448

Cys Arg Trp Arg Trp Lys Ser Ser Lys Lys
1               5                   10

<210> SEQ ID NO 449
<211> LENGTH: 10
<212> TYPE: PRT
<213> ORGANISM: Crotalus durissus

<400> SEQUENCE: 449

Ser Arg Trp Arg Trp Lys Ser Ser Lys Lys
1               5                   10

<210> SEQ ID NO 450
<211> LENGTH: 10
<212> TYPE: PRT
<213> ORGANISM: Crotalus durissus

<400> SEQUENCE: 450

Cys Arg Phe Arg Trp Lys Cys Cys Lys Lys
1               5                   10

<210> SEQ ID NO 451
<211> LENGTH: 10
<212> TYPE: PRT
<213> ORGANISM: Crotalus durissus

<400> SEQUENCE: 451

Cys Arg Trp Arg Phe Lys Cys Cys Lys Lys
1               5                   10

<210> SEQ ID NO 452
<211> LENGTH: 10
<212> TYPE: PRT
<213> ORGANISM: Crotalus durissus

<400> SEQUENCE: 452

Cys Arg Phe Arg Phe Lys Cys Cys Lys Lys
1               5                   10

<210> SEQ ID NO 453
<211> LENGTH: 10
<212> TYPE: PRT
<213> ORGANISM: Crotalus durissus

<400> SEQUENCE: 453

Cys Arg Trp Arg Trp Lys Cys Cys Lys Lys
1               5                   10

<210> SEQ ID NO 454
<211> LENGTH: 10
<212> TYPE: PRT
<213> ORGANISM: Crotalus durissus

<400> SEQUENCE: 454

Lys Cys Cys Lys Trp Arg Trp Arg Cys Lys
1               5                   10

<210> SEQ ID NO 455
<211> LENGTH: 10
<212> TYPE: PRT
<213> ORGANISM: Crotalus durissus

<400> SEQUENCE: 455

Lys Cys Cys Lys Trp Arg Trp Arg Cys Lys
1               5                   10

<210> SEQ ID NO 456
<211> LENGTH: 10
<212> TYPE: PRT
<213> ORGANISM: Crotalus durissus

<400> SEQUENCE: 456

Cys Arg Trp Arg Trp Lys Cys Cys Lys Lys
1               5                   10

<210> SEQ ID NO 457
<211> LENGTH: 10
<212> TYPE: PRT
<213> ORGANISM: Crotalus durissus

<400> SEQUENCE: 457

Cys Arg Trp Arg Trp Lys Cys Cys Lys Lys
1               5                   10

<210> SEQ ID NO 458
<211> LENGTH: 10
<212> TYPE: PRT
<213> ORGANISM: Crotalus durissus

<400> SEQUENCE: 458

Cys Arg Trp Arg Trp Lys Cys Cys Lys Lys
1               5                   10

<210> SEQ ID NO 459
<211> LENGTH: 10
<212> TYPE: PRT
<213> ORGANISM: Crotalus durissus

<400> SEQUENCE: 459

Cys Arg Trp Arg Trp Lys Cys Cys Lys Lys
1               5                   10

<210> SEQ ID NO 460
<211> LENGTH: 10
<212> TYPE: PRT
<213> ORGANISM: Crotalus durissus

<400> SEQUENCE: 460

Cys Arg Trp Arg Trp Lys Cys Cys Lys Lys
1               5                   10

<210> SEQ ID NO 461
<211> LENGTH: 11
<212> TYPE: PRT
<213> ORGANISM: Crotalus durissus

<400> SEQUENCE: 461

Cys Arg Trp Arg Trp Lys Cys Gly Cys Lys Lys
1               5                   10

<210> SEQ ID NO 462

```
<211> LENGTH: 14
<212> TYPE: PRT
<213> ORGANISM: Crotalus durissus

<400> SEQUENCE: 462

Lys Cys Gly Cys Arg Trp Arg Trp Lys Cys Gly Cys Lys Lys
1               5                   10

<210> SEQ ID NO 463
<211> LENGTH: 8
<212> TYPE: PRT
<213> ORGANISM: Crotalus durissus

<400> SEQUENCE: 463

Cys Arg Trp Arg Trp Lys Cys Gly
1               5

<210> SEQ ID NO 464
<211> LENGTH: 13
<212> TYPE: PRT
<213> ORGANISM: Crotalus durissus
<220> FEATURE:
<221> NAME/KEY: misc_feature
<222> LOCATION: (4)..(4)
<223> OTHER INFORMATION: Xaa can be any naturally occurring amino acid

<400> SEQUENCE: 464

Lys Met Asp Xaa Arg Trp Arg Trp Lys Cys Cys Lys Lys
1               5                   10

<210> SEQ ID NO 465
<211> LENGTH: 13
<212> TYPE: PRT
<213> ORGANISM: Crotalus durissus
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 465

Lys Met Asp Xaa Arg Trp Arg Trp Lys Xaa Cys Lys Lys
1               5                   10

<210> SEQ ID NO 466
<211> LENGTH: 13
<212> TYPE: PRT
<213> ORGANISM: Crotalus durissus
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 466

Lys Met Asp Xaa Arg Trp Arg Trp Lys Xaa Xaa Lys Lys
1               5                   10

<210> SEQ ID NO 467
<211> LENGTH: 13
<212> TYPE: PRT
<213> ORGANISM: Crotalus durissus
<220> FEATURE:
```

```
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 467

Lys Met Asp Xaa Arg Trp Arg Trp Lys Cys Xaa Lys Lys
1               5                   10

<210> SEQ ID NO 468
<211> LENGTH: 12
<212> TYPE: PRT
<213> ORGANISM: Crotalus durissus
<220> FEATURE:
<221> NAME/KEY: misc_feature
<222> LOCATION: (10)..(10)
<223> OTHER INFORMATION: Xaa can be any naturally occurring amino acid

<400> SEQUENCE: 468

Met Asp Cys Arg Trp Arg Trp Lys Cys Xaa Lys Lys
1               5                   10

<210> SEQ ID NO 469
<211> LENGTH: 13
<212> TYPE: PRT
<213> ORGANISM: Crotalus durissus

<400> SEQUENCE: 469

Lys Met Asp Cys Arg Trp Arg Trp Lys Cys Ser Lys Lys
1               5                   10

<210> SEQ ID NO 470
<211> LENGTH: 13
<212> TYPE: PRT
<213> ORGANISM: Crotalus durissus

<400> SEQUENCE: 470

Lys Met Asp Cys Arg Trp Arg Trp Lys Ser Cys Lys Lys
1               5                   10

<210> SEQ ID NO 471
<211> LENGTH: 13
<212> TYPE: PRT
<213> ORGANISM: Crotalus durissus

<400> SEQUENCE: 471

Lys Met Asp Ser Arg Trp Arg Trp Lys Cys Cys Lys Lys
1               5                   10

<210> SEQ ID NO 472
<211> LENGTH: 13
<212> TYPE: PRT
<213> ORGANISM: Crotalus durissus

<400> SEQUENCE: 472

Lys Met Asp Cys Arg Trp Arg Trp Lys Ser Ser Lys Lys
1               5                   10

<210> SEQ ID NO 473
<211> LENGTH: 13
<212> TYPE: PRT
<213> ORGANISM: Crotalus durissus

<400> SEQUENCE: 473
```

```
Lys Met Asp Ser Arg Trp Arg Trp Lys Ser Ser Lys Lys
1               5                   10

<210> SEQ ID NO 474
<211> LENGTH: 13
<212> TYPE: PRT
<213> ORGANISM: Crotalus durissus

<400> SEQUENCE: 474

Lys Met Asp Ser Arg Trp Arg Trp Lys Ser Cys Lys Lys
1               5                   10

<210> SEQ ID NO 475
<211> LENGTH: 13
<212> TYPE: PRT
<213> ORGANISM: Crotalus durissus

<400> SEQUENCE: 475

Lys Met Asp Ser Arg Trp Arg Trp Lys Cys Ser Lys Lys
1               5                   10

<210> SEQ ID NO 476
<211> LENGTH: 13
<212> TYPE: PRT
<213> ORGANISM: Crotalus durissus

<400> SEQUENCE: 476

Lys Met Asp Cys Arg Trp Arg Pro Lys Cys Cys Lys Lys
1               5                   10

<210> SEQ ID NO 477
<211> LENGTH: 13
<212> TYPE: PRT
<213> ORGANISM: Crotalus durissus

<400> SEQUENCE: 477

Lys Met Asp Cys Arg Pro Arg Pro Lys Cys Cys Lys Lys
1               5                   10

<210> SEQ ID NO 478
<211> LENGTH: 13
<212> TYPE: PRT
<213> ORGANISM: Crotalus durissus
<220> FEATURE:
<221> NAME/KEY: misc_feature
<222> LOCATION: (4)..(4)
<223> OTHER INFORMATION: Xaa can be any naturally occurring amino acid

<400> SEQUENCE: 478

Lys Met Asp Xaa Arg Pro Arg Pro Lys Cys Cys Lys Lys
1               5                   10

<210> SEQ ID NO 479
<211> LENGTH: 13
<212> TYPE: PRT
<213> ORGANISM: Crotalus durissus
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 479
```

```
Lys Met Asp Xaa Arg Pro Arg Pro Lys Xaa Cys Lys Lys
1               5                   10
```

<210> SEQ ID NO 480
<211> LENGTH: 13
<212> TYPE: PRT
<213> ORGANISM: Crotalus durissus
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 480

```
Lys Met Asp Xaa Arg Pro Arg Pro Lys Cys Xaa Lys Lys
1               5                   10
```

<210> SEQ ID NO 481
<211> LENGTH: 13
<212> TYPE: PRT
<213> ORGANISM: Crotalus durissus
<220> FEATURE:
<221> NAME/KEY: misc_feature
<222> LOCATION: (10)..(10)
<223> OTHER INFORMATION: Xaa can be any naturally occurring amino acid

<400> SEQUENCE: 481

```
Lys Met Asp Cys Arg Pro Arg Pro Lys Xaa Cys Lys Lys
1               5                   10
```

<210> SEQ ID NO 482
<211> LENGTH: 13
<212> TYPE: PRT
<213> ORGANISM: Crotalus durissus
<220> FEATURE:
<221> NAME/KEY: misc_feature
<222> LOCATION: (11)..(11)
<223> OTHER INFORMATION: Xaa can be any naturally occurring amino acid

<400> SEQUENCE: 482

```
Lys Met Asp Cys Arg Pro Arg Pro Lys Cys Xaa Lys Lys
1               5                   10
```

<210> SEQ ID NO 483
<211> LENGTH: 16
<212> TYPE: PRT
<213> ORGANISM: Drosophila melanogaster

<400> SEQUENCE: 483

```
Arg Gln Ile Lys Ile Trp Phe Gln Asn Arg Arg Met Lys Trp Lys Lys
1               5                   10                  15
```

<210> SEQ ID NO 484
<211> LENGTH: 9
<212> TYPE: PRT
<213> ORGANISM: Human immunodeficiency virus type 1

<400> SEQUENCE: 484

```
Arg Lys Lys Arg Arg Gln Arg Arg Arg
1               5
```

<210> SEQ ID NO 485
<211> LENGTH: 9
<212> TYPE: PRT
<213> ORGANISM: Human immunodeficiency virus type 1

<400> SEQUENCE: 485

Arg Arg Arg Gln Arg Arg Lys Lys Arg
1               5

<210> SEQ ID NO 486
<211> LENGTH: 16
<212> TYPE: PRT
<213> ORGANISM: Homo sapiens

<400> SEQUENCE: 486

Arg Lys Lys Arg Arg Arg Glu Ser Arg Lys Lys Arg Arg Arg Glu Ser
1               5                   10                  15

<210> SEQ ID NO 487
<211> LENGTH: 17
<212> TYPE: PRT
<213> ORGANISM: Homo sapiens

<400> SEQUENCE: 487

Gly Arg Pro Arg Glu Ser Gly Lys Lys Arg Lys Arg Lys Arg Leu Lys
1               5                   10                  15

Pro

<210> SEQ ID NO 488
<211> LENGTH: 15
<212> TYPE: PRT
<213> ORGANISM: Homo sapiens

<400> SEQUENCE: 488

Gly Lys Arg Lys Lys Lys Gly Lys Leu Gly Lys Lys Arg Asp Pro
1               5                   10                  15

<210> SEQ ID NO 489
<211> LENGTH: 17
<212> TYPE: PRT
<213> ORGANISM: Homo sapiens

<400> SEQUENCE: 489

Gly Lys Arg Lys Lys Lys Gly Lys Leu Gly Lys Lys Arg Pro Arg Ser
1               5                   10                  15

Arg

<210> SEQ ID NO 490
<211> LENGTH: 18
<212> TYPE: PRT
<213> ORGANISM: Homo sapiens

<400> SEQUENCE: 490

Arg Lys Lys Arg Arg Arg Glu Ser Arg Lys Ala Arg Lys Ser Pro Arg
1               5                   10                  15

His Leu

<210> SEQ ID NO 491
<211> LENGTH: 19
<212> TYPE: PRT
<213> ORGANISM: Homo sapiens

<400> SEQUENCE: 491

Ser Arg Arg Ala Arg Arg Ser Pro Arg Glu Ser Gly Lys Lys Arg Lys
1               5                   10                  15

Arg Lys Arg

-continued

<210> SEQ ID NO 492
<211> LENGTH: 19
<212> TYPE: PRT
<213> ORGANISM: Homo sapiens

<400> SEQUENCE: 492

Val Lys Arg Gly Leu Lys Leu Arg His Val Arg Pro Arg Val Thr Arg
1               5                   10                  15

Met Asp Val

<210> SEQ ID NO 493
<211> LENGTH: 14
<212> TYPE: PRT
<213> ORGANISM: Homo sapiens

<400> SEQUENCE: 493

Ser Arg Arg Ala Arg Arg Ser Pro Arg His Leu Gly Ser Gly
1               5                   10

<210> SEQ ID NO 494
<211> LENGTH: 16
<212> TYPE: PRT
<213> ORGANISM: Homo sapiens

<400> SEQUENCE: 494

Leu Arg Arg Glu Arg Gln Ser Arg Leu Arg Arg Glu Arg Gln Ser Arg
1               5                   10                  15

<210> SEQ ID NO 495
<211> LENGTH: 22
<212> TYPE: PRT
<213> ORGANISM: Homo sapiens

<400> SEQUENCE: 495

Gly Ala Tyr Asp Leu Arg Arg Arg Glu Arg Gln Ser Arg Leu Arg Arg
1               5                   10                  15

Arg Glu Arg Gln Ser Arg
            20

<210> SEQ ID NO 496
<211> LENGTH: 13
<212> TYPE: PRT
<213> ORGANISM: Human immunodeficiency virus type 1

<400> SEQUENCE: 496

Gly Arg Lys Lys Arg Arg Gln Arg Arg Arg Pro Pro Gln
1               5                   10

<210> SEQ ID NO 497
<211> LENGTH: 5
<212> TYPE: PRT
<213> ORGANISM: Homo sapiens

<400> SEQUENCE: 497

Val Pro Met Leu Lys
1               5

<210> SEQ ID NO 498
<211> LENGTH: 5
<212> TYPE: PRT
<213> ORGANISM: Homo sapiens

<400> SEQUENCE: 498

Val Pro Thr Leu Lys
1               5

<210> SEQ ID NO 499
<211> LENGTH: 5
<212> TYPE: PRT
<213> ORGANISM: Homo sapiens

<400> SEQUENCE: 499

Val Pro Ala Leu Arg
1               5

<210> SEQ ID NO 500
<211> LENGTH: 5
<212> TYPE: PRT
<213> ORGANISM: Homo sapiens

<400> SEQUENCE: 500

Val Ser Ala Leu Lys
1               5

<210> SEQ ID NO 501
<211> LENGTH: 5
<212> TYPE: PRT
<213> ORGANISM: Homo sapiens

<400> SEQUENCE: 501

Pro Met Leu Lys Glu
1               5

<210> SEQ ID NO 502
<211> LENGTH: 5
<212> TYPE: PRT
<213> ORGANISM: Homo sapiens

<400> SEQUENCE: 502

Val Pro Ala Leu Lys
1               5

<210> SEQ ID NO 503
<211> LENGTH: 5
<212> TYPE: PRT
<213> ORGANISM: Homo sapiens

<400> SEQUENCE: 503

Val Ser Leu Lys Lys
1               5

<210> SEQ ID NO 504
<211> LENGTH: 5
<212> TYPE: PRT
<213> ORGANISM: Homo sapiens

<400> SEQUENCE: 504

Val Ser Gly Lys Lys
1               5

<210> SEQ ID NO 505
<211> LENGTH: 5
<212> TYPE: PRT
<213> ORGANISM: Homo sapiens

<400> SEQUENCE: 505

Lys Leu Pro Val Met

```
1               5

<210> SEQ ID NO 506
<211> LENGTH: 5
<212> TYPE: PRT
<213> ORGANISM: Homo sapiens

<400> SEQUENCE: 506

Ile Pro Met Ile Lys
1               5

<210> SEQ ID NO 507
<211> LENGTH: 5
<212> TYPE: PRT
<213> ORGANISM: Homo sapiens

<400> SEQUENCE: 507

Lys Leu Gly Val Met
1               5

<210> SEQ ID NO 508
<211> LENGTH: 5
<212> TYPE: PRT
<213> ORGANISM: Homo sapiens

<400> SEQUENCE: 508

Lys Leu Pro Val Thr
1               5

<210> SEQ ID NO 509
<211> LENGTH: 5
<212> TYPE: PRT
<213> ORGANISM: Homo sapiens

<400> SEQUENCE: 509

Val Pro Met Ile Lys
1               5

<210> SEQ ID NO 510
<211> LENGTH: 5
<212> TYPE: PRT
<213> ORGANISM: Homo sapiens

<400> SEQUENCE: 510

Ile Pro Ala Leu Lys
1               5

<210> SEQ ID NO 511
<211> LENGTH: 5
<212> TYPE: PRT
<213> ORGANISM: Homo sapiens

<400> SEQUENCE: 511

Ile Pro Met Leu Lys
1               5

<210> SEQ ID NO 512
<211> LENGTH: 5
<212> TYPE: PRT
<213> ORGANISM: Homo sapiens

<400> SEQUENCE: 512

Val Pro Thr Leu Gln
1               5
```

```
<210> SEQ ID NO 513
<211> LENGTH: 5
<212> TYPE: PRT
<213> ORGANISM: Homo sapiens

<400> SEQUENCE: 513

Gln Leu Pro Val Met
1               5

<210> SEQ ID NO 514
<211> LENGTH: 5
<212> TYPE: PRT
<213> ORGANISM: Homo sapiens

<400> SEQUENCE: 514

Glu Leu Pro Val Met
1               5

<210> SEQ ID NO 515
<211> LENGTH: 5
<212> TYPE: PRT
<213> ORGANISM: Homo sapiens

<400> SEQUENCE: 515

Val Pro Thr Leu Glu
1               5

<210> SEQ ID NO 516
<211> LENGTH: 5
<212> TYPE: PRT
<213> ORGANISM: Homo sapiens

<400> SEQUENCE: 516

Val Pro Thr Leu Lys
1               5

<210> SEQ ID NO 517
<211> LENGTH: 20
<212> TYPE: PRT
<213> ORGANISM: Limulus polyphemus

<400> SEQUENCE: 517

Ala Tyr Arg Ile Lys Pro Thr Phe Arg Arg Leu Lys Trp Lys Tyr Lys
1               5                   10                  15

Gly Lys Phe Trp
            20

<210> SEQ ID NO 518
<211> LENGTH: 20
<212> TYPE: PRT
<213> ORGANISM: Limulus polyphemus

<400> SEQUENCE: 518

His Ala Arg Ile Lys Pro Thr Phe Arg Arg Leu Lys Trp Lys Tyr Lys
1               5                   10                  15

Gly Lys Phe Trp
            20

<210> SEQ ID NO 519
<211> LENGTH: 20
<212> TYPE: PRT
<213> ORGANISM: Limulus polyphemus

<400> SEQUENCE: 519
```

```
His Tyr Arg Ile Lys Pro Thr Ala Arg Arg Leu Lys Trp Lys Tyr Lys
1               5                   10                  15

Gly Lys Phe Trp
            20

<210> SEQ ID NO 520
<211> LENGTH: 20
<212> TYPE: PRT
<213> ORGANISM: Limulus polyphemus

<400> SEQUENCE: 520

His Tyr Arg Ile Lys Pro Thr Phe Arg Arg Leu Ala Trp Lys Tyr Lys
1               5                   10                  15

Gly Lys Phe Trp
            20

<210> SEQ ID NO 521
<211> LENGTH: 20
<212> TYPE: PRT
<213> ORGANISM: Limulus polyphemus

<400> SEQUENCE: 521

His Tyr Arg Ile Lys Pro Thr Phe Arg Arg Leu Lys Trp Lys Tyr Lys
1               5                   10                  15

Gly Lys Phe Ala
            20

<210> SEQ ID NO 522
<211> LENGTH: 21
<212> TYPE: PRT
<213> ORGANISM: Mycobacterium tuberculosis

<400> SEQUENCE: 522

Val Asn Ala Asp Ile Lys Ala Thr Thr Val Phe Gly Gly Lys Tyr Val
1               5                   10                  15

Ser Leu Thr Thr Pro
            20

<210> SEQ ID NO 523
<211> LENGTH: 22
<212> TYPE: PRT
<213> ORGANISM: Mycobacterium tuberculosis

<400> SEQUENCE: 523

Gly Lys Tyr Val Ser Leu Thr Thr Pro Lys Asn Pro Thr Lys Arg Arg
1               5                   10                  15

Ile Thr Pro Lys Asp Val
            20

<210> SEQ ID NO 524
<211> LENGTH: 22
<212> TYPE: PRT
<213> ORGANISM: Mycobacterium tuberculosis

<400> SEQUENCE: 524

Thr Lys Arg Arg Ile Thr Pro Lys Asp Val Ile Asp Val Arg Ser Val
1               5                   10                  15

Thr Thr Glu Ile Asn Thr
            20

<210> SEQ ID NO 525
```

```
<211> LENGTH: 23
<212> TYPE: PRT
<213> ORGANISM: Mycobacterium tuberculosis

<400> SEQUENCE: 525

Arg Ser Val Thr Thr Glu Ile Asn Thr Leu Phe Gln Thr Leu Thr Ser
1               5                   10                  15

Ile Ala Glu Lys Val Asp Pro
            20

<210> SEQ ID NO 526
<211> LENGTH: 26
<212> TYPE: PRT
<213> ORGANISM: Mycobacterium tuberculosis

<400> SEQUENCE: 526

Ala Glu Lys Val Asp Pro Val Lys Leu Asn Leu Thr Leu Ser Ala Ala
1               5                   10                  15

Ala Glu Ala Leu Thr Gly Leu Gly Asp Lys
            20                  25

<210> SEQ ID NO 527
<211> LENGTH: 34
<212> TYPE: PRT
<213> ORGANISM: Mycobacterium tuberculosis

<400> SEQUENCE: 527

Gly Leu Gly Asp Lys Phe Gly Glu Ser Ile Val Asn Ala Asn Thr Val
1               5                   10                  15

Leu Asp Asp Leu Asn Ser Arg Met Pro Gln Ser Arg His Asp Ile Gln
            20                  25                  30

Gln Leu

<210> SEQ ID NO 528
<211> LENGTH: 27
<212> TYPE: PRT
<213> ORGANISM: Mycobacterium tuberculosis

<400> SEQUENCE: 528

Gly Asp Val Tyr Ala Asp Ala Ala Pro Asp Leu Phe Asp Phe Leu Asp
1               5                   10                  15

Ser Ser Val Thr Thr Ala Arg Thr Ile Asn Ala
            20                  25

<210> SEQ ID NO 529
<211> LENGTH: 32
<212> TYPE: PRT
<213> ORGANISM: Mycobacterium tuberculosis

<400> SEQUENCE: 529

Ala Arg Thr Ile Asn Ala Gln Gln Ala Glu Leu Asp Ser Ala Leu Leu
1               5                   10                  15

Ala Ala Ala Gly Phe Gly Asn Thr Thr Ala Asp Val Phe Asp Arg Gly
            20                  25                  30

<210> SEQ ID NO 530
<211> LENGTH: 30
<212> TYPE: PRT
<213> ORGANISM: Mycobacterium tuberculosis

<400> SEQUENCE: 530

Ala Asp Val Phe Asp Arg Gly Gly Pro Tyr Leu Gln Arg Gly Val Ala
```

```
                1               5                   10                  15
Asp Leu Val Pro Thr Ala Thr Leu Leu Asp Thr Tyr Ser Pro
                20                  25                  30

<210> SEQ ID NO 531
<211> LENGTH: 27
<212> TYPE: PRT
<213> ORGANISM: Mycobacterium tuberculosis

<400> SEQUENCE: 531

Leu Asp Thr Tyr Ser Pro Glu Leu Phe Cys Thr Ile Arg Asn Phe Tyr
1               5                   10                  15

Asp Ala Asp Arg Pro Asp Arg Gly Ala Ala Ala
                20                  25

<210> SEQ ID NO 532
<211> LENGTH: 22
<212> TYPE: PRT
<213> ORGANISM: Mycobacterium tuberculosis

<400> SEQUENCE: 532

Thr Lys Arg Arg Ile Thr Pro Lys Asp Val Ile Asp Val Arg Ser Val
1               5                   10                  15

Thr Thr Glu Ile Asn Thr
                20

<210> SEQ ID NO 533
<211> LENGTH: 22
<212> TYPE: PRT
<213> ORGANISM: Mycobacterium tuberculosis

<400> SEQUENCE: 533

Thr Lys Arg Arg Ile Thr Pro Asp Asp Val Ile Asp Val Arg Ser Val
1               5                   10                  15

Thr Thr Glu Ile Asn Thr
                20

<210> SEQ ID NO 534
<211> LENGTH: 22
<212> TYPE: PRT
<213> ORGANISM: Mycobacterium tuberculosis

<400> SEQUENCE: 534

Thr Lys Arg Arg Ile Thr Pro Lys Lys Val Ile Asp Val Arg Ser Val
1               5                   10                  15

Thr Thr Glu Ile Asn Thr
                20

<210> SEQ ID NO 535
<211> LENGTH: 22
<212> TYPE: PRT
<213> ORGANISM: Mycobacterium tuberculosis

<400> SEQUENCE: 535

Thr Lys Arg Arg Ile Thr Pro Lys Asp Val Ile Asp Val Arg Ser Val
1               5                   10                  15

Thr Thr Lys Ile Asn Thr
                20

<210> SEQ ID NO 536
<211> LENGTH: 13
<212> TYPE: PRT
```

<213> ORGANISM: Mycobacterium tuberculosis

<400> SEQUENCE: 536

Thr Lys Arg Arg Ile Thr Pro Lys Asp Val Ile Asp Val
1               5                   10

<210> SEQ ID NO 537
<211> LENGTH: 22
<212> TYPE: PRT
<213> ORGANISM: Mycobacterium tuberculosis

<400> SEQUENCE: 537

Thr Lys Arg Arg Ile Thr Pro Lys Asp Val Ile Asp Val Glu Ser Val
1               5                   10                  15

Thr Thr Glu Ile Asn Thr
            20

<210> SEQ ID NO 538
<211> LENGTH: 22
<212> TYPE: PRT
<213> ORGANISM: Mycobacterium tuberculosis

<400> SEQUENCE: 538

Thr Ala Arg Arg Ile Thr Pro Lys Asp Val Ile Asp Val Arg Ser Val
1               5                   10                  15

Thr Thr Glu Ile Asn Thr
            20

<210> SEQ ID NO 539
<211> LENGTH: 23
<212> TYPE: PRT
<213> ORGANISM: Mycobacterium tuberculosis

<400> SEQUENCE: 539

Thr Lys Ala Ala Arg Ile Thr Pro Lys Asp Val Ile Asp Val Arg Ser
1               5                   10                  15

Val Thr Thr Glu Ile Asn Thr
            20

<210> SEQ ID NO 540
<211> LENGTH: 28
<212> TYPE: PRT
<213> ORGANISM: Mycobacterium tuberculosis

<400> SEQUENCE: 540

His His His His His His Thr Lys Arg Arg Ile Thr Pro Lys Asp Val
1               5                   10                  15

Ile Asp Val Arg Ser Val Thr Thr Glu Ile Asn Thr
            20                  25

<210> SEQ ID NO 541
<211> LENGTH: 12
<212> TYPE: PRT
<213> ORGANISM: Human immunodeficiency virus type 1

<400> SEQUENCE: 541

Tyr Gly Arg Lys Lys Lys Arg Arg Gln Arg Arg Arg
1               5                   10

<210> SEQ ID NO 542
<211> LENGTH: 18
<212> TYPE: PRT
<213> ORGANISM: Mus musculus

```
<400> SEQUENCE: 542

Leu Leu Ile Ile Leu Arg Arg Arg Ile Arg Lys Gln Ala His Ala His
1               5                   10                  15

Ser Lys

<210> SEQ ID NO 543
<211> LENGTH: 18
<212> TYPE: PRT
<213> ORGANISM: Mus musculus

<400> SEQUENCE: 543

Ala Leu Ile Ile Leu Arg Arg Arg Ile Arg Lys Gln Ala His Ala His
1               5                   10                  15

Ser Lys

<210> SEQ ID NO 544
<211> LENGTH: 18
<212> TYPE: PRT
<213> ORGANISM: Mus musculus

<400> SEQUENCE: 544

Leu Ala Ile Ile Leu Arg Arg Arg Ile Arg Lys Gln Ala His Ala His
1               5                   10                  15

Ser Lys

<210> SEQ ID NO 545
<211> LENGTH: 18
<212> TYPE: PRT
<213> ORGANISM: Mus musculus

<400> SEQUENCE: 545

Leu Leu Ala Ile Leu Arg Arg Arg Ile Arg Lys Gln Ala His Ala His
1               5                   10                  15

Ser Lys

<210> SEQ ID NO 546
<211> LENGTH: 18
<212> TYPE: PRT
<213> ORGANISM: Mus musculus

<400> SEQUENCE: 546

Leu Leu Ile Ala Leu Arg Arg Arg Ile Arg Lys Gln Ala His Ala His
1               5                   10                  15

Ser Lys

<210> SEQ ID NO 547
<211> LENGTH: 18
<212> TYPE: PRT
<213> ORGANISM: Mus musculus

<400> SEQUENCE: 547

Leu Leu Ile Ile Ala Arg Arg Arg Ile Arg Lys Gln Ala His Ala His
1               5                   10                  15

Ser Lys

<210> SEQ ID NO 548
<211> LENGTH: 18
<212> TYPE: PRT
<213> ORGANISM: Mus musculus
```

<400> SEQUENCE: 548

Leu Leu Ile Ile Leu Ala Arg Arg Ile Arg Lys Gln Ala His Ala His
1               5                   10                  15

Ser Lys

<210> SEQ ID NO 549
<211> LENGTH: 18
<212> TYPE: PRT
<213> ORGANISM: Mus musculus

<400> SEQUENCE: 549

Leu Leu Ile Ile Leu Arg Ala Arg Ile Arg Lys Gln Ala His Ala His
1               5                   10                  15

Ser Lys

<210> SEQ ID NO 550
<211> LENGTH: 18
<212> TYPE: PRT
<213> ORGANISM: Mus musculus

<400> SEQUENCE: 550

Leu Leu Ile Ile Leu Arg Arg Ala Ile Arg Lys Gln Ala His Ala His
1               5                   10                  15

Ser Lys

<210> SEQ ID NO 551
<211> LENGTH: 18
<212> TYPE: PRT
<213> ORGANISM: Mus musculus

<400> SEQUENCE: 551

Leu Leu Ile Ile Leu Arg Arg Arg Ala Arg Lys Gln Ala His Ala His
1               5                   10                  15

Ser Lys

<210> SEQ ID NO 552
<211> LENGTH: 19
<212> TYPE: PRT
<213> ORGANISM: Mus musculus

<400> SEQUENCE: 552

Leu Leu Ile Ile Leu Arg Arg Arg Ile Ala Arg Lys Gln Ala His Ala
1               5                   10                  15

His Ser Lys

<210> SEQ ID NO 553
<211> LENGTH: 18
<212> TYPE: PRT
<213> ORGANISM: Mus musculus

<400> SEQUENCE: 553

Leu Leu Ile Ile Leu Arg Arg Arg Ile Ala Gln Ala His Ala His
1               5                   10                  15

Ser Lys

<210> SEQ ID NO 554
<211> LENGTH: 18
<212> TYPE: PRT
<213> ORGANISM: Mus musculus

<400> SEQUENCE: 554

Leu Leu Ile Ile Leu Arg Arg Arg Ile Arg Lys Ala Ala His Ala His
1               5                   10                  15

Ser Lys

<210> SEQ ID NO 555
<211> LENGTH: 18
<212> TYPE: PRT
<213> ORGANISM: Mus musculus

<400> SEQUENCE: 555

Leu Leu Ile Ile Leu Arg Arg Arg Ile Arg Lys Gln Ala His Ala His
1               5                   10                  15

Ser Lys

<210> SEQ ID NO 556
<211> LENGTH: 18
<212> TYPE: PRT
<213> ORGANISM: Mus musculus

<400> SEQUENCE: 556

Leu Leu Ile Ile Leu Arg Arg Arg Ile Arg Lys Gln Ala Ala Ala His
1               5                   10                  15

Ser Lys

<210> SEQ ID NO 557
<211> LENGTH: 18
<212> TYPE: PRT
<213> ORGANISM: Mus musculus

<400> SEQUENCE: 557

Leu Leu Ile Ile Leu Arg Arg Arg Ile Arg Lys Gln Ala His Ala His
1               5                   10                  15

Ser Lys

<210> SEQ ID NO 558
<211> LENGTH: 18
<212> TYPE: PRT
<213> ORGANISM: Mus musculus

<400> SEQUENCE: 558

Leu Leu Ile Ile Leu Arg Arg Arg Ile Arg Lys Gln Ala His Ala Ala
1               5                   10                  15

Ser Lys

<210> SEQ ID NO 559
<211> LENGTH: 18
<212> TYPE: PRT
<213> ORGANISM: Mus musculus

<400> SEQUENCE: 559

Leu Leu Ile Ile Leu Arg Arg Arg Ile Arg Lys Gln Ala His Ala His
1               5                   10                  15

Ala Lys

<210> SEQ ID NO 560
<211> LENGTH: 18
<212> TYPE: PRT
<213> ORGANISM: Mus musculus

<400> SEQUENCE: 560

```
Leu Leu Ile Ile Leu Arg Arg Arg Ile Arg Lys Gln Ala His Ala His
1               5                   10                  15

Ser Ala

<210> SEQ ID NO 561
<211> LENGTH: 18
<212> TYPE: PRT
<213> ORGANISM: Mus musculus

<400> SEQUENCE: 561

Lys Ser His Ala His Ala Gln Lys Arg Ile Arg Arg Arg Leu Ile Ile
1               5                   10                  15

Leu Leu

<210> SEQ ID NO 562
<211> LENGTH: 18
<212> TYPE: PRT
<213> ORGANISM: Mus musculus

<400> SEQUENCE: 562

Leu Leu Ile Ile Leu Arg Arg Arg Ile Arg Lys Gln Ala His Ala His
1               5                   10                  15

Ser Lys

<210> SEQ ID NO 563
<211> LENGTH: 7
<212> TYPE: PRT
<213> ORGANISM: Bos primigenius

<400> SEQUENCE: 563

Arg Arg Ile Arg Pro Arg Pro
1               5

<210> SEQ ID NO 564
<211> LENGTH: 15
<212> TYPE: PRT
<213> ORGANISM: Bos primigenius

<400> SEQUENCE: 564

Arg Arg Ile Arg Pro Arg Pro Pro Arg Leu Pro Arg Pro Arg Pro
1               5                   10                  15

<210> SEQ ID NO 565
<211> LENGTH: 24
<212> TYPE: PRT
<213> ORGANISM: Bos primigenius

<400> SEQUENCE: 565

Arg Arg Ile Arg Pro Arg Pro Pro Arg Leu Pro Arg Pro Arg Pro Arg
1               5                   10                  15

Pro Leu Pro Phe Pro Arg Pro Gly
            20

<210> SEQ ID NO 566
<211> LENGTH: 17
<212> TYPE: PRT
<213> ORGANISM: Bos primigenius

<400> SEQUENCE: 566

Arg Arg Ile Arg Pro Arg Pro Pro Arg Leu Pro Arg Pro Arg Pro Arg
1               5                   10                  15

Pro
```

<210> SEQ ID NO 567
<211> LENGTH: 20
<212> TYPE: PRT
<213> ORGANISM: Bos primigenius

<400> SEQUENCE: 567

Pro Arg Pro Pro Arg Leu Pro Arg Pro Arg Pro Arg Pro Leu Pro Phe
1               5                   10                  15

Pro Arg Pro Gly
            20

<210> SEQ ID NO 568
<211> LENGTH: 18
<212> TYPE: PRT
<213> ORGANISM: Bos primigenius

<400> SEQUENCE: 568

Pro Pro Arg Leu Pro Arg Pro Arg Pro Arg Pro Leu Pro Phe Pro Arg
1               5                   10                  15

Pro Gly

<210> SEQ ID NO 569
<211> LENGTH: 16
<212> TYPE: PRT
<213> ORGANISM: Bos primigenius

<400> SEQUENCE: 569

Arg Leu Pro Arg Pro Arg Pro Arg Pro Leu Pro Phe Pro Arg Pro Gly
1               5                   10                  15

<210> SEQ ID NO 570
<211> LENGTH: 14
<212> TYPE: PRT
<213> ORGANISM: Bos primigenius

<400> SEQUENCE: 570

Pro Arg Pro Arg Pro Arg Pro Leu Pro Phe Pro Arg Pro Gly
1               5                   10

<210> SEQ ID NO 571
<211> LENGTH: 12
<212> TYPE: PRT
<213> ORGANISM: Bos primigenius

<400> SEQUENCE: 571

Pro Arg Pro Arg Pro Leu Pro Phe Pro Arg Pro Gly
1               5                   10

<210> SEQ ID NO 572
<211> LENGTH: 10
<212> TYPE: PRT
<213> ORGANISM: Bos primigenius

<400> SEQUENCE: 572

Pro Arg Pro Leu Pro Phe Pro Arg Pro Gly
1               5                   10

<210> SEQ ID NO 573
<211> LENGTH: 9
<212> TYPE: PRT
<213> ORGANISM: Human immunodeficiency virus type 1

<400> SEQUENCE: 573

```
Arg Lys Lys Arg Arg Gln Arg Arg Arg
1               5

<210> SEQ ID NO 574
<211> LENGTH: 27
<212> TYPE: PRT
<213> ORGANISM: African swine fever virus

<400> SEQUENCE: 574

Arg Gln Gly Ala Ala Arg Val Thr Ser Trp Leu Gly Arg Gln Leu Arg
1               5                   10                  15

Ile Ala Gly Lys Arg Leu Glu Gly Arg Ser Lys
            20                  25

<210> SEQ ID NO 575
<211> LENGTH: 22
<212> TYPE: PRT
<213> ORGANISM: African swine fever virus

<400> SEQUENCE: 575

Arg Val Thr Ser Trp Leu Gly Arg Gln Leu Arg Ile Ala Gly Lys Arg
1               5                   10                  15

Leu Glu Gly Arg Ser Lys
            20

<210> SEQ ID NO 576
<211> LENGTH: 16
<212> TYPE: PRT
<213> ORGANISM: African swine fever virus

<400> SEQUENCE: 576

Gly Arg Gln Leu Arg Ile Ala Gly Lys Arg Leu Glu Gly Arg Ser Lys
1               5                   10                  15

<210> SEQ ID NO 577
<211> LENGTH: 23
<212> TYPE: PRT
<213> ORGANISM: African swine fever virus

<400> SEQUENCE: 577

Arg Arg Val Thr Ser Trp Leu Gly Arg Gln Leu Arg Ile Ala Gly Lys
1               5                   10                  15

Arg Leu Glu Gly Arg Ser Lys
            20

<210> SEQ ID NO 578
<211> LENGTH: 22
<212> TYPE: PRT
<213> ORGANISM: African swine fever virus

<400> SEQUENCE: 578

Arg Val Arg Ser Trp Leu Gly Arg Gln Leu Arg Ile Ala Gly Lys Arg
1               5                   10                  15

Leu Glu Gly Arg Ser Lys
            20

<210> SEQ ID NO 579
<211> LENGTH: 16
<212> TYPE: PRT
<213> ORGANISM: African swine fever virus

<400> SEQUENCE: 579
```

Gly Arg Gln Leu Arg Ile Ala Gly Lys Arg Leu Arg Gly Arg Ser Lys
1               5                   10                  15

<210> SEQ ID NO 580
<211> LENGTH: 16
<212> TYPE: PRT
<213> ORGANISM: African swine fever virus

<400> SEQUENCE: 580

Gly Arg Gln Leu Arg Ile Ala Gly Arg Arg Leu Arg Gly Arg Ser Arg
1               5                   10                  15

<210> SEQ ID NO 581
<211> LENGTH: 16
<212> TYPE: PRT
<213> ORGANISM: African swine fever virus

<400> SEQUENCE: 581

Gly Arg Gln Leu Arg Arg Ala Gly Arg Arg Leu Arg Gly Arg Ser Arg
1               5                   10                  15

<210> SEQ ID NO 582
<211> LENGTH: 16
<212> TYPE: PRT
<213> ORGANISM: African swine fever virus

<400> SEQUENCE: 582

Gly Arg Gln Leu Arg Ile Ala Gly Arg Arg Leu Arg Arg Arg Ser Arg
1               5                   10                  15

<210> SEQ ID NO 583
<211> LENGTH: 16
<212> TYPE: PRT
<213> ORGANISM: African swine fever virus

<400> SEQUENCE: 583

Gly Arg Gln Leu Arg Arg Ala Gly Arg Arg Leu Arg Arg Arg Ser Arg
1               5                   10                  15

<210> SEQ ID NO 584
<211> LENGTH: 15
<212> TYPE: PRT
<213> ORGANISM: African swine fever virus

<400> SEQUENCE: 584

Arg Gln Leu Arg Ile Ala Gly Arg Arg Leu Arg Gly Arg Ser Arg
1               5                   10                  15

<210> SEQ ID NO 585
<211> LENGTH: 16
<212> TYPE: PRT
<213> ORGANISM: African swine fever virus

<400> SEQUENCE: 585

Arg Ser Arg Gly Arg Leu Arg Arg Gly Ala Ile Arg Leu Gln Arg Gly
1               5                   10                  15

<210> SEQ ID NO 586
<211> LENGTH: 29
<212> TYPE: PRT
<213> ORGANISM: Aspergillus restrictus

<400> SEQUENCE: 586

Lys Leu Ile Lys Gly Arg Thr Pro Ile Lys Phe Gly Lys Ala Asp Cys
1               5                   10                  15

Asp Arg Pro Pro Lys His Ser Gln Asn Gly Met Gly Lys
            20                  25

<210> SEQ ID NO 587
<211> LENGTH: 27
<212> TYPE: PRT
<213> ORGANISM: Aspergillus restrictus

<400> SEQUENCE: 587

Lys Leu Ile Lys Gly Arg Thr Pro Ile Lys Phe Gly Lys Ala Asp Cys
1               5                   10                  15

Asp Arg Pro Pro Lys His Ser Gln Asn Gly Met
            20                  25

<210> SEQ ID NO 588
<211> LENGTH: 27
<212> TYPE: PRT
<213> ORGANISM: Aspergillus restrictus

<400> SEQUENCE: 588

Lys Leu Ile Lys Gly Arg Thr Pro Ile Lys Phe Gly Lys Ala Asp Cys
1               5                   10                  15

Asp Arg Pro Pro Lys His Ser Gln Asn Gly Lys
            20                  25

<210> SEQ ID NO 589
<211> LENGTH: 26
<212> TYPE: PRT
<213> ORGANISM: Aspergillus restrictus

<400> SEQUENCE: 589

Lys Gly Arg Thr Pro Ile Lys Phe Gly Lys Ala Asp Cys Asp Arg Pro
1               5                   10                  15

Pro Lys His Ser Gln Asn Gly Met Gly Lys
            20                  25

<210> SEQ ID NO 590
<211> LENGTH: 25
<212> TYPE: PRT
<213> ORGANISM: Aspergillus restrictus

<400> SEQUENCE: 590

Lys Leu Ile Lys Gly Arg Thr Pro Ile Lys Phe Gly Lys Ala Asp Cys
1               5                   10                  15

Asp Arg Pro Pro Lys His Ser Gly Lys
            20                  25

<210> SEQ ID NO 591
<211> LENGTH: 25
<212> TYPE: PRT
<213> ORGANISM: Aspergillus restrictus

<400> SEQUENCE: 591

Lys Leu Ile Lys Gly Arg Thr Pro Ile Lys Phe Gly Lys Ala Arg Cys
1               5                   10                  15

Arg Arg Pro Pro Lys His Ser Gly Lys
            20                  25

<210> SEQ ID NO 592
<211> LENGTH: 13
<212> TYPE: PRT
<213> ORGANISM: Aspergillus restrictus

<400> SEQUENCE: 592

Lys Leu Ile Lys Gly Arg Thr Pro Ile Lys Phe Gly Lys
1               5                   10

<210> SEQ ID NO 593
<211> LENGTH: 37
<212> TYPE: PRT
<213> ORGANISM: Homo sapiens

<400> SEQUENCE: 593

Lys Arg Ile Pro Asn Lys Lys Pro Gly Lys Lys Thr Thr Thr Lys Pro
1               5                   10                  15

Thr Lys Lys Pro Thr Ile Lys Thr Thr Lys Lys Asp Leu Lys Pro Gln
            20                  25                  30

Thr Thr Lys Pro Lys
        35

<210> SEQ ID NO 594
<211> LENGTH: 30
<212> TYPE: PRT
<213> ORGANISM: Homo sapiens

<400> SEQUENCE: 594

Lys Arg Ile Pro Asn Lys Lys Pro Gly Lys Lys Thr Thr Thr Lys Pro
1               5                   10                  15

Thr Lys Lys Pro Thr Ile Lys Thr Thr Lys Lys Asp Leu Lys
            20                  25                  30

<210> SEQ ID NO 595
<211> LENGTH: 27
<212> TYPE: PRT
<213> ORGANISM: Homo sapiens

<400> SEQUENCE: 595

Lys Arg Ile Pro Asn Lys Lys Pro Gly Lys Lys Thr Thr Thr Lys Pro
1               5                   10                  15

Thr Lys Lys Pro Thr Ile Lys Thr Thr Lys Lys
            20                  25

<210> SEQ ID NO 596
<211> LENGTH: 23
<212> TYPE: PRT
<213> ORGANISM: Homo sapiens

<400> SEQUENCE: 596

Lys Arg Ile Pro Asn Lys Lys Pro Gly Lys Lys Thr Thr Thr Lys Pro
1               5                   10                  15

Thr Lys Lys Pro Thr Ile Lys
            20

<210> SEQ ID NO 597
<211> LENGTH: 19
<212> TYPE: PRT
<213> ORGANISM: Homo sapiens

<400> SEQUENCE: 597

Lys Arg Ile Pro Asn Lys Lys Pro Gly Lys Lys Thr Thr Thr Lys Pro
1               5                   10                  15

Thr Lys Lys

```
<210> SEQ ID NO 598
<211> LENGTH: 12
<212> TYPE: PRT
<213> ORGANISM: Homo sapiens

<400> SEQUENCE: 598

Lys Arg Ile Pro Asn Lys Lys Pro Gly Lys Lys Thr
1               5                   10

<210> SEQ ID NO 599
<211> LENGTH: 11
<212> TYPE: PRT
<213> ORGANISM: Homo sapiens

<400> SEQUENCE: 599

Lys Arg Ile Pro Asn Lys Lys Pro Gly Lys Lys
1               5                   10

<210> SEQ ID NO 600
<211> LENGTH: 10
<212> TYPE: PRT
<213> ORGANISM: Homo sapiens

<400> SEQUENCE: 600

Lys Arg Ile Pro Asn Lys Lys Pro Lys Lys
1               5                   10

<210> SEQ ID NO 601
<211> LENGTH: 10
<212> TYPE: PRT
<213> ORGANISM: Homo sapiens

<400> SEQUENCE: 601

Arg Arg Ile Pro Asn Arg Arg Pro Arg Arg
1               5                   10

<210> SEQ ID NO 602
<211> LENGTH: 22
<212> TYPE: PRT
<213> ORGANISM: Homo sapiens

<400> SEQUENCE: 602

Lys Lys Pro Gly Lys Lys Thr Thr Thr Lys Pro Thr Lys Lys Pro Thr
1               5                   10                  15

Ile Lys Thr Thr Lys Lys
            20

<210> SEQ ID NO 603
<211> LENGTH: 14
<212> TYPE: PRT
<213> ORGANISM: Homo sapiens

<400> SEQUENCE: 603

Lys Lys Pro Gly Lys Lys Thr Thr Thr Lys Pro Thr Lys Lys
1               5                   10

<210> SEQ ID NO 604
<211> LENGTH: 10
<212> TYPE: PRT
<213> ORGANISM: Homo sapiens

<400> SEQUENCE: 604

Lys Lys Pro Thr Ile Lys Thr Thr Lys Lys
1               5                   10
```

<210> SEQ ID NO 605
<211> LENGTH: 10
<212> TYPE: PRT
<213> ORGANISM: Homo sapiens

<400> SEQUENCE: 605

Lys Lys Thr Thr Thr Lys Pro Thr Lys Lys
1               5                   10

<210> SEQ ID NO 606
<211> LENGTH: 15
<212> TYPE: PRT
<213> ORGANISM: Homo sapiens

<400> SEQUENCE: 606

Lys Ser Ile Cys Lys Thr Ile Pro Ser Asn Lys Pro Lys Lys Lys
1               5                   10                  15

<210> SEQ ID NO 607
<211> LENGTH: 11
<212> TYPE: PRT
<213> ORGANISM: Homo sapiens

<400> SEQUENCE: 607

Lys Thr Ile Pro Ser Asn Lys Pro Lys Lys Lys
1               5                   10

<210> SEQ ID NO 608
<211> LENGTH: 12
<212> TYPE: PRT
<213> ORGANISM: Homo sapiens

<400> SEQUENCE: 608

Lys Pro Arg Ser Lys Asn Pro Pro Lys Lys Pro Lys
1               5                   10

<210> SEQ ID NO 609
<211> LENGTH: 22
<212> TYPE: PRT
<213> ORGANISM: Human immunodeficiency virus type 1

<400> SEQUENCE: 609

Asp Arg Arg Arg Arg Gly Ser Arg Pro Ser Gly Ala Glu Arg Arg
1               5                   10                  15

Arg Arg Ala Ala Ala Ala
            20

<210> SEQ ID NO 610
<211> LENGTH: 17
<212> TYPE: PRT
<213> ORGANISM: Human immunodeficiency virus type 1

<400> SEQUENCE: 610

Asp Arg Arg Arg Arg Gly Ser Arg Pro Ser Gly Ala Glu Arg Arg
1               5                   10                  15

Arg

<210> SEQ ID NO 611
<211> LENGTH: 15
<212> TYPE: PRT
<213> ORGANISM: Bacteriophage lambda

<400> SEQUENCE: 611

Gln Thr Arg Arg Arg Glu Arg Ala Glu Lys Gln Ala Gln Trp
1               5                   10                  15

<210> SEQ ID NO 612
<211> LENGTH: 9
<212> TYPE: PRT
<213> ORGANISM: Bacteriophage lambda

<400> SEQUENCE: 612

Arg Arg Arg Glu Arg Arg Ala Glu Lys
1               5

<210> SEQ ID NO 613
<211> LENGTH: 11
<212> TYPE: PRT
<213> ORGANISM: Flock house virus

<400> SEQUENCE: 613

Asn Arg Ala Arg Arg Asn Arg Arg Arg Val Arg
1               5                   10

<210> SEQ ID NO 614
<211> LENGTH: 10
<212> TYPE: PRT
<213> ORGANISM: Flock house virus

<400> SEQUENCE: 614

Arg Thr Arg Arg Asn Arg Arg Arg Val Arg
1               5                   10

<210> SEQ ID NO 615
<211> LENGTH: 8
<212> TYPE: PRT
<213> ORGANISM: Alphavirus

<400> SEQUENCE: 615

Arg Asn Arg Ser Arg His Arg Arg
1               5

<210> SEQ ID NO 616
<211> LENGTH: 9
<212> TYPE: PRT
<213> ORGANISM: Alphavirus

<400> SEQUENCE: 616

Lys Cys Pro Ser Arg Arg Pro Lys Arg
1               5

<210> SEQ ID NO 617
<211> LENGTH: 16
<212> TYPE: PRT
<213> ORGANISM: Drosophila melanogaster

<400> SEQUENCE: 617

Lys Arg Pro Ala Ala Ile Lys Lys Ala Gly Gln Ala Lys Lys Lys Lys
1               5                   10                  15

<210> SEQ ID NO 618
<211> LENGTH: 12
<212> TYPE: PRT
<213> ORGANISM: Kaposi's sarcoma-associated herpesvirus

<400> SEQUENCE: 618

Thr Arg Arg Ser Lys Arg Arg Ser His Arg Lys Phe
1               5                   10

<210> SEQ ID NO 619
<211> LENGTH: 17
<212> TYPE: PRT
<213> ORGANISM: Bufo bufo

<400> SEQUENCE: 619

Arg Ala Gly Leu Gln Phe Pro Val Gly Arg Val His Arg Leu Leu Arg
1               5                   10                  15

Lys

<210> SEQ ID NO 620
<211> LENGTH: 22
<212> TYPE: PRT
<213> ORGANISM: Homo sapiens

<400> SEQUENCE: 620

Met Val Arg Arg Phe Leu Val Thr Leu Arg Ile Arg Arg Ala Cys Gly
1               5                   10                  15

Pro Pro Arg Val Arg Val
            20

<210> SEQ ID NO 621
<211> LENGTH: 22
<212> TYPE: PRT
<213> ORGANISM: Homo sapiens

<400> SEQUENCE: 621

Phe Val Thr Arg Gly Cys Pro Arg Arg Leu Val Ala Arg Leu Ile Arg
1               5                   10                  15

Val Met Val Pro Arg Arg
            20

<210> SEQ ID NO 622
<211> LENGTH: 13
<212> TYPE: PRT
<213> ORGANISM: Homo sapiens

<400> SEQUENCE: 622

Val Arg Arg Phe Leu Val Thr Leu Arg Ile Arg Arg Ala
1               5                   10

<210> SEQ ID NO 623
<211> LENGTH: 13
<212> TYPE: PRT
<213> ORGANISM: Homo sapiens

<400> SEQUENCE: 623

Arg Val Arg Ile Leu Ala Arg Phe Leu Arg Thr Arg Val
1               5                   10

<210> SEQ ID NO 624
<211> LENGTH: 13
<212> TYPE: PRT
<213> ORGANISM: Homo sapiens

<400> SEQUENCE: 624

Arg Val Arg Val Phe Val Val His Ile Pro Arg Leu Thr
1               5                   10

<210> SEQ ID NO 625
<211> LENGTH: 13
<212> TYPE: PRT

<213> ORGANISM: Homo sapiens

<400> SEQUENCE: 625

Val Ile Arg Val His Phe Arg Leu Pro Val Arg Thr Val
1               5                   10

<210> SEQ ID NO 626
<211> LENGTH: 37
<212> TYPE: PRT
<213> ORGANISM: Homo sapiens

<400> SEQUENCE: 626

Met Val Arg Arg Phe Leu Val Thr Leu Arg Ile Arg Arg Ala Cys Gly
1               5                   10                  15

Pro Pro Arg Val Arg Val Phe Val His Ile Pro Arg Leu Thr Gly
            20                  25                  30

Glu Trp Ala Ala Pro
        35

<210> SEQ ID NO 627
<211> LENGTH: 37
<212> TYPE: PRT
<213> ORGANISM: Homo sapiens

<400> SEQUENCE: 627

Phe Arg Val Pro Leu Arg Ile Arg Pro Cys Val Val Ala Pro Arg Leu
1               5                   10                  15

Val Met Val Arg His Thr Phe Gly Arg Ile Ala Arg Trp Val Ala Gly
            20                  25                  30

Pro Leu Glu Thr Arg
        35

<210> SEQ ID NO 628
<211> LENGTH: 25
<212> TYPE: PRT
<213> ORGANISM: Homo sapiens

<400> SEQUENCE: 628

Gly Thr Lys Met Ile Phe Val Gly Ile Lys Lys Glu Glu Arg Ala
1               5                   10                  15

Asp Leu Ile Ala Tyr Leu Lys Lys Ala
            20                  25

<210> SEQ ID NO 629
<211> LENGTH: 16
<212> TYPE: PRT
<213> ORGANISM: Homo sapiens

<400> SEQUENCE: 629

Lys Lys Lys Glu Glu Arg Ala Asp Leu Ile Ala Tyr Leu Lys Lys Ala
1               5                   10                  15

<210> SEQ ID NO 630
<211> LENGTH: 14
<212> TYPE: PRT
<213> ORGANISM: Homo sapiens

<400> SEQUENCE: 630

Lys Met Ile Phe Val Gly Ile Lys Lys Lys Glu Glu Arg Ala
1               5                   10

<210> SEQ ID NO 631

```
<210> SEQ ID NO 631
<211> LENGTH: 10
<212> TYPE: PRT
<213> ORGANISM: Homo sapiens

<400> SEQUENCE: 631

Lys Met Ile Phe Val Gly Ile Lys Lys Lys
1               5                   10

<210> SEQ ID NO 632
<211> LENGTH: 10
<212> TYPE: PRT
<213> ORGANISM: Homo sapiens

<400> SEQUENCE: 632

Glu Lys Gly Lys Lys Ile Phe Ile Met Lys
1               5                   10

<210> SEQ ID NO 633
<211> LENGTH: 9
<212> TYPE: PRT
<213> ORGANISM: Homo sapiens

<400> SEQUENCE: 633

Lys Gly Lys Lys Ile Phe Ile Met Lys
1               5

<210> SEQ ID NO 634
<211> LENGTH: 17
<212> TYPE: PRT
<213> ORGANISM: Flock house virus

<400> SEQUENCE: 634

Arg Arg Arg Arg Asn Arg Thr Arg Arg Asn Arg Arg Arg Val Arg Gly
1               5                   10                  15

Cys

<210> SEQ ID NO 635
<211> LENGTH: 15
<212> TYPE: PRT
<213> ORGANISM: Human T-cell lymphotropic virus type 2

<400> SEQUENCE: 635

Thr Arg Arg Gln Arg Thr Arg Arg Ala Arg Arg Asn Arg Gly Cys
1               5                   10                  15

<210> SEQ ID NO 636
<211> LENGTH: 21
<212> TYPE: PRT
<213> ORGANISM: Brome mosaic virus

<400> SEQUENCE: 636

Lys Met Thr Arg Ala Gln Arg Arg Ala Ala Ala Arg Arg Asn Arg Trp
1               5                   10                  15

Thr Ala Arg Gly Cys
                20

<210> SEQ ID NO 637
<211> LENGTH: 21
<212> TYPE: PRT
<213> ORGANISM: Cowpea Chlorotic Mottle Virus

<400> SEQUENCE: 637

Lys Leu Thr Arg Ala Gln Arg Arg Ala Ala Ala Arg Lys Asn Lys Arg
1               5                   10                  15
```

Asn Thr Arg Gly Cys
        20

<210> SEQ ID NO 638
<211> LENGTH: 19
<212> TYPE: PRT
<213> ORGANISM: Bacteriophage P22

<400> SEQUENCE: 638

Asn Ala Lys Thr Arg Arg His Glu Arg Arg Lys Leu Ala Ile Glu
1               5                   10                  15

Arg Gly Cys

<210> SEQ ID NO 639
<211> LENGTH: 24
<212> TYPE: PRT
<213> ORGANISM: Bacteriophage lambda

<400> SEQUENCE: 639

Met Asp Ala Gln Thr Arg Arg Arg Glu Arg Arg Ala Glu Lys Gln Ala
1               5                   10                  15

Gln Trp Lys Ala Ala Asn Gly Cys
        20

<210> SEQ ID NO 640
<211> LENGTH: 20
<212> TYPE: PRT
<213> ORGANISM: Bacteriophage phi-21

<400> SEQUENCE: 640

Thr Ala Lys Thr Arg Tyr Lys Ala Arg Arg Ala Glu Leu Ile Ala Glu
1               5                   10                  15

Arg Arg Gly Cys
        20

<210> SEQ ID NO 641
<211> LENGTH: 14
<212> TYPE: PRT
<213> ORGANISM: Homo sapiens

<400> SEQUENCE: 641

Ser Gln Met Thr Arg Gln Ala Arg Arg Leu Tyr Asx Gly Cys
1               5                   10

<210> SEQ ID NO 642
<211> LENGTH: 28
<212> TYPE: PRT
<213> ORGANISM: Homo sapiens

<400> SEQUENCE: 642

Lys Arg Arg Ile Arg Arg Glu Arg Asn Lys Met Ala Ala Ala Lys Ser
1               5                   10                  15

Arg Asn Arg Arg Arg Glu Leu Thr Asp Thr Gly Cys
        20                  25

<210> SEQ ID NO 643
<211> LENGTH: 30
<212> TYPE: PRT
<213> ORGANISM: Homo sapiens

<400> SEQUENCE: 643

Arg Ile Lys Ala Glu Arg Lys Arg Met Arg Asn Arg Ile Ala Ala Ser

```
                1               5                  10                 15
```

Lys Ser Arg Lys Arg Lys Leu Glu Arg Ile Ala Arg Gly Cys
            20                  25                 30

<210> SEQ ID NO 644
<211> LENGTH: 24
<212> TYPE: PRT
<213> ORGANISM: Saccharomyces cerevisiae

<400> SEQUENCE: 644

Lys Arg Ala Arg Asn Thr Glu Ala Ala Arg Arg Ser Arg Ala Arg Lys
1               5                   10                  15

Leu Gln Arg Met Lys Gln Gly Cys
            20

<210> SEQ ID NO 645
<211> LENGTH: 22
<212> TYPE: PRT
<213> ORGANISM: Homo sapiens

<400> SEQUENCE: 645

Lys Cys Phe Gln Trp Gln Arg Asn Met Arg Lys Val Arg Gly Pro Pro
1               5                   10                  15

Val Ser Cys Ile Lys Arg
            20

<210> SEQ ID NO 646
<211> LENGTH: 19
<212> TYPE: PRT
<213> ORGANISM: Homo sapiens

<400> SEQUENCE: 646

Lys Cys Phe Gln Trp Gln Arg Asn Met Arg Lys Val Arg Gly Pro Pro
1               5                   10                  15

Val Ser Cys

<210> SEQ ID NO 647
<211> LENGTH: 22
<212> TYPE: PRT
<213> ORGANISM: Homo sapiens

<400> SEQUENCE: 647

Lys Cys Phe Gln Trp Gln Arg Asn Met Arg Lys Val Arg Gly Pro Pro
1               5                   10                  15

Val Ser Ser Ile Lys Arg
            20

<210> SEQ ID NO 648
<211> LENGTH: 13
<212> TYPE: PRT
<213> ORGANISM: Homo sapiens

<400> SEQUENCE: 648

Lys Cys Phe Gln Trp Gln Arg Asn Met Arg Lys Val Arg
1               5                   10

<210> SEQ ID NO 649
<211> LENGTH: 16
<212> TYPE: PRT
<213> ORGANISM: Homo sapiens

<400> SEQUENCE: 649

Phe Gln Trp Gln Arg Asn Met Arg Lys Val Arg Gly Pro Pro Val Ser
1               5                   10                  15

<210> SEQ ID NO 650
<211> LENGTH: 19
<212> TYPE: PRT
<213> ORGANISM: Homo sapiens

<400> SEQUENCE: 650

Gln Trp Gln Arg Asn Met Arg Lys Val Arg Gly Pro Pro Val Ser Cys
1               5                   10                  15

Ile Lys Arg

<210> SEQ ID NO 651
<211> LENGTH: 10
<212> TYPE: PRT
<213> ORGANISM: Homo sapiens

<400> SEQUENCE: 651

Gln Trp Gln Arg Asn Met Arg Lys Val Arg
1               5                   10

<210> SEQ ID NO 652
<211> LENGTH: 16
<212> TYPE: PRT
<213> ORGANISM: Drosophila melanogaster

<400> SEQUENCE: 652

Arg Gln Ile Lys Ile Trp Phe Gln Asn Arg Arg Met Lys Trp Lys Lys
1               5                   10                  15

<210> SEQ ID NO 653
<211> LENGTH: 22
<212> TYPE: PRT
<213> ORGANISM: Rattus rattus

<400> SEQUENCE: 653

Lys Cys Phe Met Trp Gln Glu Met Leu Asn Lys Ala Gly Val Pro Lys
1               5                   10                  15

Leu Arg Cys Ala Arg Lys
            20

<210> SEQ ID NO 654
<211> LENGTH: 20
<212> TYPE: PRT
<213> ORGANISM: Homo sapiens

<400> SEQUENCE: 654

Gly Leu Trp Arg Ala Leu Trp Arg Leu Leu Arg Ser Leu Trp Arg Leu
1               5                   10                  15

Leu Trp Arg Ala
            20

<210> SEQ ID NO 655
<211> LENGTH: 20
<212> TYPE: PRT
<213> ORGANISM: Homo sapiens

<400> SEQUENCE: 655

Gly Leu Trp Trp Arg Leu Trp Trp Arg Leu Arg Ser Trp Phe Arg Leu
1               5                   10                  15

Trp Phe Arg Ala
            20

<210> SEQ ID NO 656
<211> LENGTH: 34
<212> TYPE: PRT
<213> ORGANISM: Human herpesvirus 1

<400> SEQUENCE: 656

Asp Ala Ala Thr Ala Thr Arg Gly Arg Ser Ala Ala Ser Arg Pro Thr
1               5                   10                  15

Gln Arg Pro Arg Ala Pro Ala Arg Ser Ala Ser Arg Pro Arg Arg Pro
            20                  25                  30

Val Glu

<210> SEQ ID NO 657
<211> LENGTH: 34
<212> TYPE: PRT
<213> ORGANISM: Homo sapiens

<400> SEQUENCE: 657

Ala Lys Val Lys Asp Glu Pro Gln Arg Arg Ser Ala Arg Leu Ser Ala
1               5                   10                  15

Lys Pro Ala Pro Pro Lys Pro Glu Pro Lys Pro Lys Lys Ala Pro Ala
            20                  25                  30

Lys Lys

<210> SEQ ID NO 658
<211> LENGTH: 34
<212> TYPE: PRT
<213> ORGANISM: Homo sapiens

<400> SEQUENCE: 658

Ala Lys Val Lys Asp Glu Pro Gln Arg Arg Ser Ala Arg Leu Ser Ala
1               5                   10                  15

Lys Pro Ala Pro Pro Lys Pro Glu Pro Lys Pro Lys Lys Ala Pro Ala
            20                  25                  30

Lys Lys

<210> SEQ ID NO 659
<211> LENGTH: 12
<212> TYPE: PRT
<213> ORGANISM: Hepatitis B virus

<400> SEQUENCE: 659

Pro Leu Ser Ser Ile Phe Ser Arg Ile Gly Asp Pro
1               5                   10

<210> SEQ ID NO 660
<211> LENGTH: 12
<212> TYPE: PRT
<213> ORGANISM: Hepatitis B virus

<400> SEQUENCE: 660

Pro Ser Ser Ser Ser Ser Ser Arg Ile Gly Asp Pro
1               5                   10

<210> SEQ ID NO 661
<211> LENGTH: 18
<212> TYPE: PRT
<213> ORGANISM: Zea mays

<400> SEQUENCE: 661

```
Val Arg Leu Pro Pro Val Arg Leu Pro Pro Val Arg Leu Pro
1               5                   10                  15

Pro Pro
```

<210> SEQ ID NO 662
<211> LENGTH: 18
<212> TYPE: PRT
<213> ORGANISM: Zea mays

<400> SEQUENCE: 662

```
Val Glu Leu Pro Pro Val Glu Leu Pro Pro Val Glu Leu Pro
1               5                   10                  15

Pro Pro
```

<210> SEQ ID NO 663
<211> LENGTH: 28
<212> TYPE: PRT
<213> ORGANISM: Homo sapiens

<400> SEQUENCE: 663

```
Ala Leu Trp Met Thr Leu Leu Lys Lys Val Leu Lys Ala Ala Ala Lys
1               5                   10                  15

Ala Ala Leu Asn Ala Val Leu Val Gly Ala Asn Ala
            20                  25
```

<210> SEQ ID NO 664
<211> LENGTH: 13
<212> TYPE: PRT
<213> ORGANISM: Homo sapiens

<400> SEQUENCE: 664

```
Ala Leu Trp Lys Thr Leu Leu Lys Lys Val Leu Lys Ala
1               5                   10
```

<210> SEQ ID NO 665
<211> LENGTH: 10
<212> TYPE: PRT
<213> ORGANISM: Human immunodeficiency virus type 1

<400> SEQUENCE: 665

```
Arg Gln Ala Arg Arg Asn Arg Arg Arg Cys
1               5                   10
```

<210> SEQ ID NO 666
<211> LENGTH: 14
<212> TYPE: PRT
<213> ORGANISM: Human immunodeficiency virus type 1

<400> SEQUENCE: 666

```
Gly Arg Lys Lys Arg Arg Gln Arg Arg Pro Pro Gln Cys
1               5                   10
```

<210> SEQ ID NO 667
<211> LENGTH: 8
<212> TYPE: PRT
<213> ORGANISM: Homo sapiens

<400> SEQUENCE: 667

```
Gly Arg Lys Arg Lys Lys Arg Thr
1               5
```

<210> SEQ ID NO 668
<211> LENGTH: 22

<212> TYPE: PRT
<213> ORGANISM: Homo sapiens

<400> SEQUENCE: 668

Met Val Thr Val Leu Phe Arg Arg Leu Arg Ile Arg Arg Ala Cys Gly
1               5                   10                  15

Pro Pro Arg Val Arg Val
            20

<210> SEQ ID NO 669
<211> LENGTH: 16
<212> TYPE: PRT
<213> ORGANISM: Drosophila melanogaster

<400> SEQUENCE: 669

Arg Gln Ile Lys Ile Trp Phe Gln Asn Arg Arg Met Lys Trp Lys Lys
1               5                   10                  15

<210> SEQ ID NO 670
<211> LENGTH: 10
<212> TYPE: PRT
<213> ORGANISM: Homo sapiens

<400> SEQUENCE: 670

Val Gln Arg Lys Arg Gln Lys Leu Met Pro
1               5                   10

<210> SEQ ID NO 671
<211> LENGTH: 8
<212> TYPE: PRT
<213> ORGANISM: Homo sapiens

<400> SEQUENCE: 671

Ser Lys Lys Lys Lys Thr Lys Val
1               5

<210> SEQ ID NO 672
<211> LENGTH: 8
<212> TYPE: PRT
<213> ORGANISM: Homo sapiens

<400> SEQUENCE: 672

Gly Arg Lys Arg Lys Lys Arg Thr
1               5

<210> SEQ ID NO 673
<211> LENGTH: 11
<212> TYPE: PRT
<213> ORGANISM: Homo sapiens

<400> SEQUENCE: 673

Gly Lys Lys Lys Arg Lys Arg Glu Lys Leu
1               5                   10

<210> SEQ ID NO 674
<211> LENGTH: 7
<212> TYPE: PRT
<213> ORGANISM: Homo sapiens

<400> SEQUENCE: 674

Pro Lys Lys Lys Arg Lys Val
1               5

<210> SEQ ID NO 675

```
<211> LENGTH: 8
<212> TYPE: PRT
<213> ORGANISM: Caenorhabditis elegans

<400> SEQUENCE: 675

Glu Arg Lys Lys Arg Arg Arg Glu
1               5

<210> SEQ ID NO 676
<211> LENGTH: 7
<212> TYPE: PRT
<213> ORGANISM: Homo sapiens

<400> SEQUENCE: 676

Phe Lys Lys Phe Arg Lys Phe
1               5

<210> SEQ ID NO 677
<211> LENGTH: 24
<212> TYPE: PRT
<213> ORGANISM: Homo sapiens

<400> SEQUENCE: 677

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 678
<211> LENGTH: 24
<212> TYPE: PRT
<213> ORGANISM: Homo sapiens

<400> SEQUENCE: 678

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 679
<211> LENGTH: 21
<212> TYPE: PRT
<213> ORGANISM: Homo sapiens

<400> SEQUENCE: 679

Tyr Thr Gln Asp Phe Asn Lys Phe His Thr Phe Pro Gln Thr Ala Ile
1               5                   10                  15

Gly Val Gly Ala Pro
            20

<210> SEQ ID NO 680
<211> LENGTH: 18
<212> TYPE: PRT
<213> ORGANISM: Homo sapiens

<400> SEQUENCE: 680

Asp Phe Asn Lys Phe His Thr Phe Pro Gln Thr Ala Ile Gly Val Gly
1               5                   10                  15

Ala Pro

<210> SEQ ID NO 681
<211> LENGTH: 15
<212> TYPE: PRT
```

```
<213> ORGANISM: Homo sapiens

<400> SEQUENCE: 681

Lys Phe His Thr Phe Pro Gln Thr Ala Ile Gly Val Gly Ala Pro
1               5                   10                  15

<210> SEQ ID NO 682
<211> LENGTH: 12
<212> TYPE: PRT
<213> ORGANISM: Homo sapiens

<400> SEQUENCE: 682

Thr Phe Pro Gln Thr Ala Ile Gly Val Gly Ala Pro
1               5                   10

<210> SEQ ID NO 683
<211> LENGTH: 13
<212> TYPE: PRT
<213> ORGANISM: Human immunodeficiency virus type 1

<400> SEQUENCE: 683

Gly Tyr Gly Arg Lys Lys Arg Arg Gln Arg Arg Arg Gly
1               5                   10

<210> SEQ ID NO 684
<211> LENGTH: 13
<212> TYPE: PRT
<213> ORGANISM: Human immunodeficiency virus type 1

<400> SEQUENCE: 684

Gly Tyr Gly Arg Lys Lys Arg Arg Gln Arg Arg Arg Gly
1               5                   10

<210> SEQ ID NO 685
<211> LENGTH: 13
<212> TYPE: PRT
<213> ORGANISM: Human immunodeficiency virus type 1

<400> SEQUENCE: 685

Gly Tyr Gly Arg Lys Lys Arg Arg Gln Arg Arg Arg Gly
1               5                   10

<210> SEQ ID NO 686
<211> LENGTH: 16
<212> TYPE: PRT
<213> ORGANISM: Drosophila melanogaster

<400> SEQUENCE: 686

Arg Gln Ile Lys Ile Trp Phe Gln Asn Arg Arg Met Lys Trp Lys Lys
1               5                   10                  15

<210> SEQ ID NO 687
<211> LENGTH: 16
<212> TYPE: PRT
<213> ORGANISM: Drosophila melanogaster

<400> SEQUENCE: 687

Arg Gln Ile Lys Ile Trp Phe Gln Asn Arg Arg Met Lys Trp Lys Lys
1               5                   10                  15

<210> SEQ ID NO 688
<211> LENGTH: 16
<212> TYPE: PRT
<213> ORGANISM: Drosophila melanogaster
```

```
<400> SEQUENCE: 688

Arg Gln Ile Lys Ile Trp Phe Gln Asn Arg Arg Met Lys Trp Lys Lys
1               5                   10                  15

<210> SEQ ID NO 689
<211> LENGTH: 15
<212> TYPE: PRT
<213> ORGANISM: Homo sapiens

<400> SEQUENCE: 689

Phe Leu Gly Lys Lys Phe Lys Lys Tyr Phe Leu Gln Leu Leu Lys
1               5                   10                  15

<210> SEQ ID NO 690
<211> LENGTH: 23
<212> TYPE: PRT
<213> ORGANISM: Homo sapiens

<400> SEQUENCE: 690

Phe Leu Ile Phe Ile Arg Val Ile Cys Ile Val Ile Ala Lys Leu Lys
1               5                   10                  15

Ala Asn Leu Met Cys Lys Thr
            20

<210> SEQ ID NO 691
<211> LENGTH: 17
<212> TYPE: PRT
<213> ORGANISM: Homo sapiens

<400> SEQUENCE: 691

Lys Lys Ala Ala Gln Ile Arg Ser Gln Val Met Thr His Leu Arg Val
1               5                   10                  15

Ile

<210> SEQ ID NO 692
<211> LENGTH: 16
<212> TYPE: PRT
<213> ORGANISM: Homo sapiens

<400> SEQUENCE: 692

Tyr Ile Val Leu Arg Arg Arg Lys Arg Val Asn Thr Lys Arg Ser
1               5                   10                  15

<210> SEQ ID NO 693
<211> LENGTH: 11
<212> TYPE: PRT
<213> ORGANISM: Homo sapiens

<400> SEQUENCE: 693

Arg Arg Lys Leu Ser Gln Gln Lys Glu Lys Lys
1               5                   10

<210> SEQ ID NO 694
<211> LENGTH: 15
<212> TYPE: PRT
<213> ORGANISM: Homo sapiens

<400> SEQUENCE: 694

Val Gln Ala Ile Leu Arg Arg Asn Trp Asn Gln Tyr Lys Ile Gln
1               5                   10                  15

<210> SEQ ID NO 695
<211> LENGTH: 19
```

```
<212> TYPE: PRT
<213> ORGANISM: Homo sapiens

<400> SEQUENCE: 695

Lys Leu Pro Cys Arg Ser Asn Thr Phe Leu Asn Ile Phe Arg Arg Lys
1               5                   10                  15

Lys Pro Gly

<210> SEQ ID NO 696
<211> LENGTH: 16
<212> TYPE: PRT
<213> ORGANISM: Homo sapiens

<400> SEQUENCE: 696

Lys Lys Ile Cys Thr Arg Lys Pro Arg Phe Met Ser Ala Trp Ala Gln
1               5                   10                  15

<210> SEQ ID NO 697
<211> LENGTH: 16
<212> TYPE: PRT
<213> ORGANISM: Drosophila melanogaster

<400> SEQUENCE: 697

Arg Gln Ile Lys Ile Trp Phe Gln Asn Arg Arg Met Lys Trp Lys Lys
1               5                   10                  15

<210> SEQ ID NO 698
<211> LENGTH: 18
<212> TYPE: PRT
<213> ORGANISM: Sus scrofa

<400> SEQUENCE: 698

Arg Gly Gly Arg Leu Ser Tyr Ser Arg Arg Phe Ser Thr Ser Thr
1               5                   10                  15

Gly Arg

<210> SEQ ID NO 699
<211> LENGTH: 18
<212> TYPE: PRT
<213> ORGANISM: Sus scrofa

<400> SEQUENCE: 699

Arg Gly Gly Arg Leu Ser Tyr Ser Arg Arg Phe Ser Thr Ser Thr
1               5                   10                  15

Gly Arg

<210> SEQ ID NO 700
<211> LENGTH: 10
<212> TYPE: PRT
<213> ORGANISM: Sus scrofa

<400> SEQUENCE: 700

Arg Arg Leu Ser Tyr Ser Arg Arg Arg Phe
1               5                   10

<210> SEQ ID NO 701
<211> LENGTH: 10
<212> TYPE: PRT
<213> ORGANISM: Sus scrofa

<400> SEQUENCE: 701

Arg Arg Leu Ser Tyr Ser Arg Arg Arg Phe
1               5                   10
```

<210> SEQ ID NO 702
<211> LENGTH: 17
<212> TYPE: PRT
<213> ORGANISM: Sus scrofa

<400> SEQUENCE: 702

Arg Gly Gly Arg Leu Ala Tyr Leu Arg Arg Trp Ala Val Leu Gly
1               5                   10                  15

Arg

<210> SEQ ID NO 703
<211> LENGTH: 16
<212> TYPE: PRT
<213> ORGANISM: Drosophila melanogaster

<400> SEQUENCE: 703

Arg Gln Ile Lys Ile Trp Phe Gln Asn Arg Arg Met Lys Trp Lys Lys
1               5                   10                  15

<210> SEQ ID NO 704
<211> LENGTH: 28
<212> TYPE: PRT
<213> ORGANISM: Mus musculus

<400> SEQUENCE: 704

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 705
<211> LENGTH: 28
<212> TYPE: PRT
<213> ORGANISM: Homo sapiens

<400> SEQUENCE: 705

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro
            20                  25

<210> SEQ ID NO 706
<211> LENGTH: 30
<212> TYPE: PRT
<213> ORGANISM: Bos primigenius

<400> SEQUENCE: 706

Met Val Lys Ser Lys Ile Gly Ser Trp Ile Leu Val Leu Phe Val Ala
1               5                   10                  15

Met Trp Ser Asp Val Gly Leu Cys Lys Lys Arg Pro Lys Pro
            20                  25                  30

<210> SEQ ID NO 707
<211> LENGTH: 38
<212> TYPE: PRT
<213> ORGANISM: Homo sapiens

<400> SEQUENCE: 707

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val

```
                    20                  25                  30

Pro Arg Thr Glu Ser Cys
            35

<210> SEQ ID NO 708
<211> LENGTH: 16
<212> TYPE: PRT
<213> ORGANISM: Drosophila melanogaster

<400> SEQUENCE: 708

Arg Gln Ile Lys Ile Trp Phe Gln Asn Arg Arg Met Lys Trp Lys Lys
1               5                   10                  15

<210> SEQ ID NO 709
<211> LENGTH: 16
<212> TYPE: PRT
<213> ORGANISM: Rattus rattus

<400> SEQUENCE: 709

Arg Val Ile Arg Val Trp Phe Gln Asn Lys Arg Cys Lys Asp Lys Lys
1               5                   10                  15

<210> SEQ ID NO 710
<211> LENGTH: 23
<212> TYPE: PRT
<213> ORGANISM: Xenopus laevis

<400> SEQUENCE: 710

Gly Ile Gly Lys Phe Leu His Ser Ala Lys Lys Trp Gly Lys Ala Phe
1               5                   10                  15

Val Gly Gln Ile Met Asn Cys
            20

<210> SEQ ID NO 711
<211> LENGTH: 24
<212> TYPE: PRT
<213> ORGANISM: Bufo bufo

<400> SEQUENCE: 711

Thr Arg Ser Ser Arg Ala Gly Leu Gln Trp Pro Val Gly Arg Val His
1               5                   10                  15

Arg Leu Leu Arg Lys Gly Gly Cys
            20

<210> SEQ ID NO 712
<211> LENGTH: 11
<212> TYPE: PRT
<213> ORGANISM: Human immunodeficiency virus type 1

<400> SEQUENCE: 712

Tyr Gly Arg Lys Lys Arg Arg Gln Arg Arg Arg
1               5                   10

<210> SEQ ID NO 713
<211> LENGTH: 16
<212> TYPE: PRT
<213> ORGANISM: Homo sapiens

<400> SEQUENCE: 713

Arg His Ile Lys Ile Trp Phe Gln Asn Arg Arg Met Lys Trp Lys Lys
1               5                   10                  15

<210> SEQ ID NO 714
```

```
<211> LENGTH: 9
<212> TYPE: PRT
<213> ORGANISM: Human immunodeficiency virus type 1

<400> SEQUENCE: 714

Arg Lys Lys Arg Arg Gln Arg Arg Arg
1               5

<210> SEQ ID NO 715
<211> LENGTH: 16
<212> TYPE: PRT
<213> ORGANISM: Drosophila melanogaster

<400> SEQUENCE: 715

Arg Gln Ile Lys Ile Trp Phe Gln Asn Arg Arg Met Lys Trp Lys Lys
1               5                   10                  15

<210> SEQ ID NO 716
<211> LENGTH: 60
<212> TYPE: PRT
<213> ORGANISM: Drosophila melanogaster

<400> SEQUENCE: 716

Ser Lys Arg Thr Arg Gln Thr Tyr Thr Arg Tyr Gln Thr Leu Glu Leu
1               5                   10                  15

Glu Lys Glu Phe His Phe Asn Arg Tyr Ile Thr Arg Arg Arg Arg Ile
            20                  25                  30

Asp Ile Ala Asn Ala Leu Ser Leu Ser Glu Arg Gln Ile Lys Ile Trp
        35                  40                  45

Phe Gln Asn Arg Arg Met Lys Ser Lys Lys Asp Arg
    50                  55                  60

<210> SEQ ID NO 717
<211> LENGTH: 61
<212> TYPE: PRT
<213> ORGANISM: Drosophila melanogaster

<400> SEQUENCE: 717

Glu Lys Arg Pro Arg Thr Ala Phe Ser Ser Glu Gln Leu Ala Arg Leu
1               5                   10                  15

Lys Arg Glu Phe Asn Glu Asn Arg Tyr Leu Thr Thr Glu Arg Arg Arg
            20                  25                  30

Gln Gln Leu Ser Ser Glu Leu Gly Leu Asn Glu Ala Gln Ile Lys Ile
        35                  40                  45

Trp Phe Gln Asn Lys Arg Ala Lys Ile Lys Lys Ser Thr
    50                  55                  60

<210> SEQ ID NO 718
<211> LENGTH: 13
<212> TYPE: PRT
<213> ORGANISM: Human immunodeficiency virus type 1

<400> SEQUENCE: 718

Gly Arg Arg Arg Arg Arg Arg Arg Arg Pro Pro Gln
1               5                   10

<210> SEQ ID NO 719
<211> LENGTH: 10
<212> TYPE: PRT
<213> ORGANISM: Homo sapiens

<400> SEQUENCE: 719
```

```
Met Leu Leu Leu Thr Arg Arg Arg Ser Thr
1               5                   10

<210> SEQ ID NO 720
<211> LENGTH: 16
<212> TYPE: PRT
<213> ORGANISM: Homo sapiens

<400> SEQUENCE: 720

Gly Leu Arg Lys Arg Leu Arg Lys Phe Arg Asn Lys Ile Lys Glu Lys
1               5                   10                  15

<210> SEQ ID NO 721
<211> LENGTH: 6
<212> TYPE: PRT
<213> ORGANISM: Zea mays

<400> SEQUENCE: 721

Val Arg Leu Pro Pro Pro
1               5

<210> SEQ ID NO 722
<211> LENGTH: 12
<212> TYPE: PRT
<213> ORGANISM: Zea mays

<400> SEQUENCE: 722

Val Arg Leu Pro Pro Pro Val Arg Leu Pro Pro Pro
1               5                   10

<210> SEQ ID NO 723
<211> LENGTH: 18
<212> TYPE: PRT
<213> ORGANISM: Zea mays

<400> SEQUENCE: 723

Val Arg Leu Pro Pro Pro Val Arg Leu Pro Pro Pro Val Arg Leu Pro
1               5                   10                  15

Pro Pro

<210> SEQ ID NO 724
<211> LENGTH: 6
<212> TYPE: PRT
<213> ORGANISM: Zea mays

<400> SEQUENCE: 724

Val His Leu Pro Pro Pro
1               5

<210> SEQ ID NO 725
<211> LENGTH: 12
<212> TYPE: PRT
<213> ORGANISM: Zea mays

<400> SEQUENCE: 725

Val His Leu Pro Pro Pro Val His Leu Pro Pro Pro
1               5                   10

<210> SEQ ID NO 726
<211> LENGTH: 18
<212> TYPE: PRT
<213> ORGANISM: Zea mays

<400> SEQUENCE: 726
```

```
Val His Leu Pro Pro Val His Leu Pro Pro Val His Leu Pro
1               5                   10                  15

Pro Pro

<210> SEQ ID NO 727
<211> LENGTH: 6
<212> TYPE: PRT
<213> ORGANISM: Zea mays

<400> SEQUENCE: 727

Val Lys Leu Pro Pro Pro
1               5

<210> SEQ ID NO 728
<211> LENGTH: 12
<212> TYPE: PRT
<213> ORGANISM: Zea mays

<400> SEQUENCE: 728

Val Lys Leu Pro Pro Val Lys Leu Pro Pro
1               5                   10

<210> SEQ ID NO 729
<211> LENGTH: 18
<212> TYPE: PRT
<213> ORGANISM: Zea mays

<400> SEQUENCE: 729

Val Lys Leu Pro Pro Pro Val Lys Leu Pro Pro Pro Val Lys Leu Pro
1               5                   10                  15

Pro Pro

<210> SEQ ID NO 730
<211> LENGTH: 16
<212> TYPE: PRT
<213> ORGANISM: Drosophila melanogaster

<400> SEQUENCE: 730

Arg Gln Ile Lys Ile Trp Phe Gln Asn Arg Arg Met Lys Trp Lys Lys
1               5                   10                  15

<210> SEQ ID NO 731
<211> LENGTH: 16
<212> TYPE: PRT
<213> ORGANISM: Drosophila melanogaster

<400> SEQUENCE: 731

Arg Gln Ile Lys Ile Phe Phe Gln Asn Arg Arg Met Lys Trp Lys Lys
1               5                   10                  15

<210> SEQ ID NO 732
<211> LENGTH: 21
<212> TYPE: PRT
<213> ORGANISM: Flock house virus

<400> SEQUENCE: 732

Ala Ser Met Trp Glu Arg Val Lys Ser Ile Ile Lys Ser Ser Leu Ala
1               5                   10                  15

Ala Ala Ser Asn Ile
            20

<210> SEQ ID NO 733
<211> LENGTH: 21
```

```
<212> TYPE: PRT
<213> ORGANISM: Flock house virus

<400> SEQUENCE: 733

Ala Ser Met Trp Glu Arg Val Lys Ser Ile Ile Lys Ser Ser Leu Ala
1               5                   10                  15

Ala Ala Ser Asn Ile
            20

<210> SEQ ID NO 734
<211> LENGTH: 16
<212> TYPE: PRT
<213> ORGANISM: Homo sapiens

<400> SEQUENCE: 734

Cys Ser Ile Pro Pro Glu Val Lys Phe Asn Pro Phe Val Tyr Leu Ile
1               5                   10                  15

<210> SEQ ID NO 735
<211> LENGTH: 16
<212> TYPE: PRT
<213> ORGANISM: Homo sapiens

<400> SEQUENCE: 735

Cys Ser Ile Pro Pro Glu Val Lys Phe Asn Pro Phe Val Tyr Leu Ile
1               5                   10                  15

<210> SEQ ID NO 736
<211> LENGTH: 6
<212> TYPE: PRT
<213> ORGANISM: Homo sapiens

<400> SEQUENCE: 736

Pro Phe Val Tyr Leu Ile
1               5

<210> SEQ ID NO 737
<211> LENGTH: 8
<212> TYPE: PRT
<213> ORGANISM: Homo sapiens

<400> SEQUENCE: 737

Asn Lys Pro Ile Leu Val Phe Tyr
1               5

<210> SEQ ID NO 738
<211> LENGTH: 14
<212> TYPE: PRT
<213> ORGANISM: Crotalus durissus

<400> SEQUENCE: 738

Tyr Lys Gln Cys His Lys Lys Gly Gly Lys Lys Gly Ser Gly
1               5                   10

<210> SEQ ID NO 739
<211> LENGTH: 15
<212> TYPE: PRT
<213> ORGANISM: Crotalus durissus
<220> FEATURE:
<221> NAME/KEY: misc_feature
<222> LOCATION: (10)..(10)
<223> OTHER INFORMATION: Xaa can be any naturally occurring amino acid

<400> SEQUENCE: 739

Tyr Lys Gln Cys His Lys Lys Gly Gly Xaa Lys Lys Gly Ser Gly
```

-continued

```
1               5                   10                  15
```

<210> SEQ ID NO 740
<211> LENGTH: 14
<212> TYPE: PRT
<213> ORGANISM: Crotalus durissus

<400> SEQUENCE: 740

Gly Ser Gly Lys Lys Gly Gly Lys Lys His Cys Gln Lys Tyr
1               5                   10

<210> SEQ ID NO 741
<211> LENGTH: 14
<212> TYPE: PRT
<213> ORGANISM: Crotalus durissus

<400> SEQUENCE: 741

Gly Ser Gly Lys Lys Gly Gly Lys Lys Ile Cys Gln Lys Tyr
1               5                   10

<210> SEQ ID NO 742
<211> LENGTH: 23
<212> TYPE: PRT
<213> ORGANISM: Drosophila melanogaster

<400> SEQUENCE: 742

Leu Ile Arg Leu Trp Ser His Leu Ile His Ile Trp Phe Gln Asn Arg
1               5                   10                  15

Arg Leu Lys Trp Lys Lys Lys
            20

<210> SEQ ID NO 743
<211> LENGTH: 16
<212> TYPE: PRT
<213> ORGANISM: Homo sapiens

<400> SEQUENCE: 743

Ala Ala Val Ala Leu Leu Pro Ala Val Leu Leu Ala Leu Leu Ala Pro
1               5                   10                  15

<210> SEQ ID NO 744
<211> LENGTH: 23
<212> TYPE: PRT
<213> ORGANISM: Homo sapiens

<400> SEQUENCE: 744

Cys Gly Ala Tyr Asp Leu Arg Arg Arg Glu Arg Gln Ser Arg Leu Arg
1               5                   10                  15

Arg Arg Glu Arg Gln Ser Arg
            20

<210> SEQ ID NO 745
<211> LENGTH: 17
<212> TYPE: PRT
<213> ORGANISM: Homo sapiens

<400> SEQUENCE: 745

Arg Lys Lys Arg Arg Arg Glu Ser Arg Lys Lys Arg Arg Arg Glu Ser
1               5                   10                  15

Cys

<210> SEQ ID NO 746
<211> LENGTH: 19

-continued

```
<212> TYPE: PRT
<213> ORGANISM: Homo sapiens

<400> SEQUENCE: 746

Cys Val Lys Arg Gly Leu Lys Leu Arg His Val Arg Pro Arg Val Thr
1               5                   10                  15

Arg Asp Val

<210> SEQ ID NO 747
<211> LENGTH: 17
<212> TYPE: PRT
<213> ORGANISM: Drosophila melanogaster

<400> SEQUENCE: 747

Cys Arg Gln Ile Lys Ile Trp Phe Gln Asn Arg Arg Met Lys Trp Lys
1               5                   10                  15

Lys

<210> SEQ ID NO 748
<211> LENGTH: 15
<212> TYPE: PRT
<213> ORGANISM: Homo sapiens

<400> SEQUENCE: 748

Pro Pro Lys Lys Ser Ala Gln Cys Leu Arg Tyr Lys Lys Pro Glu
1               5                   10                  15

<210> SEQ ID NO 749
<211> LENGTH: 15
<212> TYPE: PRT
<213> ORGANISM: Homo sapiens

<400> SEQUENCE: 749

Asp Pro Val Asp Thr Pro Asn Pro Thr Arg Arg Lys Pro Gly Lys
1               5                   10                  15

<210> SEQ ID NO 750
<211> LENGTH: 13
<212> TYPE: PRT
<213> ORGANISM: Homo sapiens

<400> SEQUENCE: 750

Lys Arg Val Ser Arg Asn Lys Ser Glu Lys Lys Arg Arg
1               5                   10

<210> SEQ ID NO 751
<211> LENGTH: 16
<212> TYPE: PRT
<213> ORGANISM: Homo sapiens

<400> SEQUENCE: 751

Gly Arg Arg His His Cys Arg Ser Lys Ala Lys Arg Ser Arg His His
1               5                   10                  15

<210> SEQ ID NO 752
<211> LENGTH: 16
<212> TYPE: PRT
<213> ORGANISM: Homo sapiens

<400> SEQUENCE: 752

Ser Ala Arg His His Cys Arg Ser Lys Ala Lys Arg Ser Arg His His
1               5                   10                  15
```

-continued

<210> SEQ ID NO 753
<211> LENGTH: 16
<212> TYPE: PRT
<213> ORGANISM: Homo sapiens

<400> SEQUENCE: 753

Ser Arg Ala His His Cys Arg Ser Lys Ala Lys Arg Ser Arg His His
1               5                   10                  15

<210> SEQ ID NO 754
<211> LENGTH: 16
<212> TYPE: PRT
<213> ORGANISM: Homo sapiens

<400> SEQUENCE: 754

Ser Arg Arg Ala His Cys Arg Ser Lys Ala Lys Arg Ser Arg His His
1               5                   10                  15

<210> SEQ ID NO 755
<211> LENGTH: 16
<212> TYPE: PRT
<213> ORGANISM: Homo sapiens

<400> SEQUENCE: 755

Ser Arg Arg His Ala Cys Arg Ser Lys Ala Lys Arg Ser Arg His His
1               5                   10                  15

<210> SEQ ID NO 756
<211> LENGTH: 16
<212> TYPE: PRT
<213> ORGANISM: Homo sapiens

<400> SEQUENCE: 756

Ser Arg Arg His His Ala Arg Ser Lys Ala Lys Arg Ser Arg His His
1               5                   10                  15

<210> SEQ ID NO 757
<211> LENGTH: 16
<212> TYPE: PRT
<213> ORGANISM: Homo sapiens

<400> SEQUENCE: 757

Ser Arg Arg His His Cys Arg Ala Lys Ala Lys Arg Ser Arg His His
1               5                   10                  15

<210> SEQ ID NO 758
<211> LENGTH: 16
<212> TYPE: PRT
<213> ORGANISM: Homo sapiens

<400> SEQUENCE: 758

Ser Arg Arg His His Cys Arg Ser Ala Ala Lys Arg Ser Arg His His
1               5                   10                  15

<210> SEQ ID NO 759
<211> LENGTH: 16
<212> TYPE: PRT
<213> ORGANISM: Homo sapiens

<400> SEQUENCE: 759

Ser Arg Arg His His Cys Arg Ser Lys Ala Ala Arg Ser Arg His His
1               5                   10                  15

<210> SEQ ID NO 760
<211> LENGTH: 16

```
<212> TYPE: PRT
<213> ORGANISM: Homo sapiens

<400> SEQUENCE: 760

Ser Arg Arg His His Cys Arg Ser Lys Ala Lys Ala Ser Arg His His
1               5                   10                  15

<210> SEQ ID NO 761
<211> LENGTH: 16
<212> TYPE: PRT
<213> ORGANISM: Homo sapiens

<400> SEQUENCE: 761

Ser Arg Arg His His Cys Arg Ser Lys Ala Lys Arg Ala Arg His His
1               5                   10                  15

<210> SEQ ID NO 762
<211> LENGTH: 16
<212> TYPE: PRT
<213> ORGANISM: Homo sapiens

<400> SEQUENCE: 762

Ser Arg Arg His His Cys Arg Ser Lys Ala Lys Arg Ser Ala His His
1               5                   10                  15

<210> SEQ ID NO 763
<211> LENGTH: 13
<212> TYPE: PRT
<213> ORGANISM: Homo sapiens

<400> SEQUENCE: 763

Arg Arg His His Cys Arg Ser Lys Ala Lys Arg Ser Arg
1               5                   10

<210> SEQ ID NO 764
<211> LENGTH: 12
<212> TYPE: PRT
<213> ORGANISM: Homo sapiens

<400> SEQUENCE: 764

Gly Arg Lys Gly Lys His Lys Arg Lys Lys Leu Pro
1               5                   10

<210> SEQ ID NO 765
<211> LENGTH: 18
<212> TYPE: PRT
<213> ORGANISM: Homo sapiens

<400> SEQUENCE: 765

Gly Lys Arg Val Ala Lys Arg Lys Leu Ile Glu Gln Asn Arg Glu Arg
1               5                   10                  15

Arg Arg

<210> SEQ ID NO 766
<211> LENGTH: 18
<212> TYPE: PRT
<213> ORGANISM: Homo sapiens

<400> SEQUENCE: 766

Gly Arg Lys Leu Lys Lys Lys Asn Glu Lys Glu Asp Lys Arg Pro
1               5                   10                  15

Arg Thr
```

<210> SEQ ID NO 767
<211> LENGTH: 17
<212> TYPE: PRT
<213> ORGANISM: Homo sapiens

<400> SEQUENCE: 767

Gly Lys Lys Thr Asn Leu Phe Ser Ala Leu Ile Lys Lys Lys Lys Thr
1               5                   10                  15

Ala

<210> SEQ ID NO 768
<211> LENGTH: 18
<212> TYPE: PRT
<213> ORGANISM: Homo sapiens

<400> SEQUENCE: 768

Gly Arg Arg Glu Arg Asn Lys Met Ala Ala Lys Cys Arg Asn
1               5                   10                  15

Arg Arg

<210> SEQ ID NO 769
<211> LENGTH: 18
<212> TYPE: PRT
<213> ORGANISM: Homo sapiens

<400> SEQUENCE: 769

Gly Lys Arg Ala Arg Asn Thr Glu Ala Ala Arg Arg Ser Arg Ala Arg
1               5                   10                  15

Lys Leu

<210> SEQ ID NO 770
<211> LENGTH: 14
<212> TYPE: PRT
<213> ORGANISM: Homo sapiens

<400> SEQUENCE: 770

Gly Arg Arg Arg Arg Ala Thr Ala Lys Tyr Arg Thr Ala His
1               5                   10

<210> SEQ ID NO 771
<211> LENGTH: 15
<212> TYPE: PRT
<213> ORGANISM: Homo sapiens

<400> SEQUENCE: 771

Gly Lys Arg Arg Arg Arg Ala Thr Ala Lys Tyr Arg Ser Ala His
1               5                   10                  15

<210> SEQ ID NO 772
<211> LENGTH: 12
<212> TYPE: PRT
<213> ORGANISM: Homo sapiens

<400> SEQUENCE: 772

Gly Arg Arg Arg Arg Lys Arg Leu Ser His Arg Thr
1               5                   10

<210> SEQ ID NO 773
<211> LENGTH: 10
<212> TYPE: PRT
<213> ORGANISM: Homo sapiens

<400> SEQUENCE: 773

-continued

Gly Arg Arg Arg Arg Glu Arg Asn Lys
1               5                  10

<210> SEQ ID NO 774
<211> LENGTH: 16
<212> TYPE: PRT
<213> ORGANISM: Homo sapiens

<400> SEQUENCE: 774

Gly Lys His Arg His Glu Arg Gly His His Arg Asp Arg Arg Glu Arg
1               5                  10                  15

<210> SEQ ID NO 775
<211> LENGTH: 17
<212> TYPE: PRT
<213> ORGANISM: Homo sapiens

<400> SEQUENCE: 775

Gly Lys Lys Lys Arg Lys Leu Ser Asn Arg Glu Ser Ala Lys Arg Ser
1               5                  10                  15

Arg

<210> SEQ ID NO 776
<211> LENGTH: 10
<212> TYPE: PRT
<213> ORGANISM: Homo sapiens

<400> SEQUENCE: 776

Met Ile Ile Tyr Arg Asp Leu Ile Ser His
1               5                  10

<210> SEQ ID NO 777
<211> LENGTH: 9
<212> TYPE: PRT
<213> ORGANISM: Homo sapiens

<400> SEQUENCE: 777

Met Ile Ile Tyr Arg Asp Leu Ile Ser
1               5

<210> SEQ ID NO 778
<211> LENGTH: 8
<212> TYPE: PRT
<213> ORGANISM: Homo sapiens

<400> SEQUENCE: 778

Met Ile Ile Tyr Arg Asp Leu Ile
1               5

<210> SEQ ID NO 779
<211> LENGTH: 9
<212> TYPE: PRT
<213> ORGANISM: Homo sapiens

<400> SEQUENCE: 779

Ile Ile Tyr Arg Asp Leu Ile Ser His
1               5

<210> SEQ ID NO 780
<211> LENGTH: 7
<212> TYPE: PRT
<213> ORGANISM: Homo sapiens

<400> SEQUENCE: 780

```
Met Ile Ile Tyr Arg Asp Leu
1               5

<210> SEQ ID NO 781
<211> LENGTH: 6
<212> TYPE: PRT
<213> ORGANISM: Homo sapiens

<400> SEQUENCE: 781

Met Ile Ile Tyr Arg Asp
1               5

<210> SEQ ID NO 782
<211> LENGTH: 8
<212> TYPE: PRT
<213> ORGANISM: Homo sapiens

<400> SEQUENCE: 782

Ile Tyr Arg Asp Leu Ile Ser His
1               5

<210> SEQ ID NO 783
<211> LENGTH: 9
<212> TYPE: PRT
<213> ORGANISM: Homo sapiens

<400> SEQUENCE: 783

Ala Ile Ile Tyr Arg Asp Leu Ile Ser
1               5

<210> SEQ ID NO 784
<211> LENGTH: 9
<212> TYPE: PRT
<213> ORGANISM: Homo sapiens

<400> SEQUENCE: 784

Met Ala Ile Tyr Arg Asp Leu Ile Ser
1               5

<210> SEQ ID NO 785
<211> LENGTH: 9
<212> TYPE: PRT
<213> ORGANISM: Homo sapiens

<400> SEQUENCE: 785

Met Ile Ala Tyr Arg Asp Leu Ile Ser
1               5

<210> SEQ ID NO 786
<211> LENGTH: 9
<212> TYPE: PRT
<213> ORGANISM: Homo sapiens

<400> SEQUENCE: 786

Met Ile Ile Ala Arg Asp Leu Ile Ser
1               5

<210> SEQ ID NO 787
<211> LENGTH: 9
<212> TYPE: PRT
<213> ORGANISM: Homo sapiens

<400> SEQUENCE: 787

Met Ile Ile Tyr Ala Asp Leu Ile Ser
1               5
```

```
<210> SEQ ID NO 788
<211> LENGTH: 9
<212> TYPE: PRT
<213> ORGANISM: Homo sapiens

<400> SEQUENCE: 788

Met Ile Ile Tyr Arg Ala Leu Ile Ser
1               5

<210> SEQ ID NO 789
<211> LENGTH: 9
<212> TYPE: PRT
<213> ORGANISM: Homo sapiens

<400> SEQUENCE: 789

Met Ile Ile Tyr Arg Asp Ala Ile Ser
1               5

<210> SEQ ID NO 790
<211> LENGTH: 9
<212> TYPE: PRT
<213> ORGANISM: Homo sapiens

<400> SEQUENCE: 790

Met Ile Ile Tyr Arg Asp Leu Ala Ser
1               5

<210> SEQ ID NO 791
<211> LENGTH: 9
<212> TYPE: PRT
<213> ORGANISM: Homo sapiens

<400> SEQUENCE: 791

Met Ile Ile Tyr Arg Asp Leu Ile Ala
1               5

<210> SEQ ID NO 792
<211> LENGTH: 11
<212> TYPE: PRT
<213> ORGANISM: Homo sapiens

<400> SEQUENCE: 792

Met Ile Ile Tyr Arg Asp Leu Ile Ser Lys Lys
1               5                   10

<210> SEQ ID NO 793
<211> LENGTH: 10
<212> TYPE: PRT
<213> ORGANISM: Homo sapiens

<400> SEQUENCE: 793

Met Ile Ile Tyr Arg Asp Lys Lys Ser His
1               5                   10

<210> SEQ ID NO 794
<211> LENGTH: 10
<212> TYPE: PRT
<213> ORGANISM: Homo sapiens

<400> SEQUENCE: 794

Met Ile Ile Phe Arg Asp Leu Ile Ser His
1               5                   10
```

<210> SEQ ID NO 795
<211> LENGTH: 10
<212> TYPE: PRT
<213> ORGANISM: Homo sapiens

<400> SEQUENCE: 795

Met Ile Ile Ser Arg Asp Leu Ile Ser His
1               5                   10

<210> SEQ ID NO 796
<211> LENGTH: 10
<212> TYPE: PRT
<213> ORGANISM: Homo sapiens

<400> SEQUENCE: 796

Gln Ile Ile Ser Arg Asp Leu Ile Ser His
1               5                   10

<210> SEQ ID NO 797
<211> LENGTH: 10
<212> TYPE: PRT
<213> ORGANISM: Homo sapiens

<400> SEQUENCE: 797

Cys Ile Ile Ser Arg Asp Leu Ile Ser His
1               5                   10

<210> SEQ ID NO 798
<211> LENGTH: 12
<212> TYPE: PRT
<213> ORGANISM: Homo sapiens

<400> SEQUENCE: 798

Met Ile Ile Tyr Arg Ala Leu Ile Ser His Lys Lys
1               5                   10

<210> SEQ ID NO 799
<211> LENGTH: 12
<212> TYPE: PRT
<213> ORGANISM: Homo sapiens

<400> SEQUENCE: 799

Met Ile Ile Tyr Arg Ile Ala Ala Ser His Lys Lys
1               5                   10

<210> SEQ ID NO 800
<211> LENGTH: 10
<212> TYPE: PRT
<213> ORGANISM: Homo sapiens

<400> SEQUENCE: 800

Met Ile Ile Arg Arg Asp Leu Ile Ser Glu
1               5                   10

<210> SEQ ID NO 801
<211> LENGTH: 10
<212> TYPE: PRT
<213> ORGANISM: Homo sapiens

<400> SEQUENCE: 801

Met Ile Ile Tyr Arg Ala Glu Ile Ser His
1               5                   10

<210> SEQ ID NO 802
<211> LENGTH: 10

```
<212> TYPE: PRT
<213> ORGANISM: Homo sapiens

<400> SEQUENCE: 802

Met Ile Ile Tyr Ala Arg Arg Ala Glu Glu
1               5                   10

<210> SEQ ID NO 803
<211> LENGTH: 12
<212> TYPE: PRT
<213> ORGANISM: Homo sapiens

<400> SEQUENCE: 803

Met Ile Ile Phe Arg Ile Ala Ala Ser His Lys Lys
1               5                   10

<210> SEQ ID NO 804
<211> LENGTH: 12
<212> TYPE: PRT
<213> ORGANISM: Homo sapiens

<400> SEQUENCE: 804

Met Ile Ile Phe Arg Ala Leu Ile Ser His Lys Lys
1               5                   10

<210> SEQ ID NO 805
<211> LENGTH: 12
<212> TYPE: PRT
<213> ORGANISM: Homo sapiens

<400> SEQUENCE: 805

Met Ile Ile Phe Arg Ala Ala Ala Ser His Lys Lys
1               5                   10

<210> SEQ ID NO 806
<211> LENGTH: 12
<212> TYPE: PRT
<213> ORGANISM: Homo sapiens

<400> SEQUENCE: 806

Phe Ile Ile Phe Arg Ile Ala Ala Ser His Lys Lys
1               5                   10

<210> SEQ ID NO 807
<211> LENGTH: 12
<212> TYPE: PRT
<213> ORGANISM: Homo sapiens

<400> SEQUENCE: 807

Leu Ile Ile Phe Arg Ile Ala Ala Ser His Lys Lys
1               5                   10

<210> SEQ ID NO 808
<211> LENGTH: 12
<212> TYPE: PRT
<213> ORGANISM: Homo sapiens

<400> SEQUENCE: 808

Trp Ile Ile Phe Arg Ile Ala Ala Ser His Lys Lys
1               5                   10

<210> SEQ ID NO 809
<211> LENGTH: 12
<212> TYPE: PRT
<213> ORGANISM: Homo sapiens
```

<400> SEQUENCE: 809

Trp Ile Ile Phe Arg Ala Ala Ser His Lys Lys
1               5                   10

<210> SEQ ID NO 810
<211> LENGTH: 12
<212> TYPE: PRT
<213> ORGANISM: Homo sapiens

<400> SEQUENCE: 810

Trp Ile Ile Phe Arg Ala Leu Ile Ser His Lys Lys
1               5                   10

<210> SEQ ID NO 811
<211> LENGTH: 12
<212> TYPE: PRT
<213> ORGANISM: Homo sapiens

<400> SEQUENCE: 811

Met Ile Ile Phe Arg Ile Ala Ala Tyr His Lys Lys
1               5                   10

<210> SEQ ID NO 812
<211> LENGTH: 12
<212> TYPE: PRT
<213> ORGANISM: Homo sapiens

<400> SEQUENCE: 812

Trp Ile Ile Phe Arg Ile Ala Ala Tyr His Lys Lys
1               5                   10

<210> SEQ ID NO 813
<211> LENGTH: 12
<212> TYPE: PRT
<213> ORGANISM: Homo sapiens

<400> SEQUENCE: 813

Met Ile Ile Phe Arg Ile Ala Ala Thr His Lys Lys
1               5                   10

<210> SEQ ID NO 814
<211> LENGTH: 12
<212> TYPE: PRT
<213> ORGANISM: Homo sapiens

<400> SEQUENCE: 814

Trp Ile Ile Phe Arg Ile Ala Ala Thr His Lys Lys
1               5                   10

<210> SEQ ID NO 815
<211> LENGTH: 12
<212> TYPE: PRT
<213> ORGANISM: Homo sapiens

<400> SEQUENCE: 815

Met Ile Ile Phe Lys Ile Ala Ala Ser His Lys Lys
1               5                   10

<210> SEQ ID NO 816
<211> LENGTH: 12
<212> TYPE: PRT
<213> ORGANISM: Homo sapiens

<400> SEQUENCE: 816

Trp Ile Ile Phe Lys Ile Ala Ala Ser His Lys Lys
1               5                   10

<210> SEQ ID NO 817
<211> LENGTH: 12
<212> TYPE: PRT
<213> ORGANISM: Homo sapiens

<400> SEQUENCE: 817

Met Ile Ile Phe Ala Ile Ala Ala Ser His Lys Lys
1               5                   10

<210> SEQ ID NO 818
<211> LENGTH: 12
<212> TYPE: PRT
<213> ORGANISM: Homo sapiens

<400> SEQUENCE: 818

Leu Ile Ile Phe Arg Ile Leu Ile Ser His Lys Lys
1               5                   10

<210> SEQ ID NO 819
<211> LENGTH: 12
<212> TYPE: PRT
<213> ORGANISM: Homo sapiens

<400> SEQUENCE: 819

Met Ile Ile Phe Arg Ile Leu Ile Ser His Lys Lys
1               5                   10

<210> SEQ ID NO 820
<211> LENGTH: 12
<212> TYPE: PRT
<213> ORGANISM: Homo sapiens

<400> SEQUENCE: 820

Leu Ile Ile Phe Arg Ile Leu Ile Ser His Arg Arg
1               5                   10

<210> SEQ ID NO 821
<211> LENGTH: 12
<212> TYPE: PRT
<213> ORGANISM: Homo sapiens

<400> SEQUENCE: 821

Leu Ile Ile Phe Arg Ile Leu Ile Ser His His His
1               5                   10

<210> SEQ ID NO 822
<211> LENGTH: 11
<212> TYPE: PRT
<213> ORGANISM: Homo sapiens

<400> SEQUENCE: 822

Leu Ile Ile Phe Arg Ile Leu Ile Ser His Lys
1               5                   10

<210> SEQ ID NO 823
<211> LENGTH: 11
<212> TYPE: PRT
<213> ORGANISM: Homo sapiens

<400> SEQUENCE: 823

Leu Ile Ile Phe Arg Ile Leu Ile Ser His Arg

```
1               5                  10
```

<210> SEQ ID NO 824
<211> LENGTH: 10
<212> TYPE: PRT
<213> ORGANISM: Homo sapiens

<400> SEQUENCE: 824

```
Leu Ile Ile Phe Arg Ile Leu Ile Ser His
1               5                  10
```

<210> SEQ ID NO 825
<211> LENGTH: 12
<212> TYPE: PRT
<213> ORGANISM: Homo sapiens

<400> SEQUENCE: 825

```
Leu Ile Ile Phe Ala Ile Ala Ala Ser His Lys Lys
1               5                  10
```

<210> SEQ ID NO 826
<211> LENGTH: 12
<212> TYPE: PRT
<213> ORGANISM: Homo sapiens

<400> SEQUENCE: 826

```
Leu Ile Ile Phe Ala Ile Leu Ile Ser His Lys Lys
1               5                  10
```

<210> SEQ ID NO 827
<211> LENGTH: 16
<212> TYPE: PRT
<213> ORGANISM: Drosophila melanogaster

<400> SEQUENCE: 827

```
Arg Gln Ile Lys Ile Trp Phe Gln Asn Arg Arg Met Lys Trp Lys Lys
1               5                  10                  15
```

<210> SEQ ID NO 828
<211> LENGTH: 16
<212> TYPE: PRT
<213> ORGANISM: Homo sapiens

<400> SEQUENCE: 828

```
Ala Ala Val Ala Leu Leu Pro Ala Val Leu Leu Ala Leu Leu Ala Lys
1               5                  10                  15
```

<210> SEQ ID NO 829
<211> LENGTH: 26
<212> TYPE: PRT
<213> ORGANISM: Drosophila melanogaster

<400> SEQUENCE: 829

```
Ala His Ala Leu Cys Leu Thr Glu Arg Gln Ile Lys Ile Trp Phe Gln
1               5                  10                  15

Asn Arg Arg Met Lys Trp Lys Lys Glu Asn
                20                  25
```

<210> SEQ ID NO 830
<211> LENGTH: 26
<212> TYPE: PRT
<213> ORGANISM: Drosophila melanogaster

<400> SEQUENCE: 830

Ala His Ala Leu Cys Pro Pro Glu Arg Gln Ile Lys Ile Trp Phe Gln
1               5                   10                  15

Asn Arg Arg Met Lys Trp Lys Lys Glu Asn
            20                  25

<210> SEQ ID NO 831
<211> LENGTH: 26
<212> TYPE: PRT
<213> ORGANISM: Drosophila melanogaster

<400> SEQUENCE: 831

Ala Tyr Ala Leu Cys Leu Thr Glu Arg Gln Ile Lys Ile Trp Phe Ala
1               5                   10                  15

Asn Arg Arg Met Lys Trp Lys Lys Glu Asn
            20                  25

<210> SEQ ID NO 832
<211> LENGTH: 34
<212> TYPE: PRT
<213> ORGANISM: Momordica cochinchinensis

<400> SEQUENCE: 832

Gly Gly Val Cys Pro Lys Ile Leu Lys Lys Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp

<210> SEQ ID NO 833
<211> LENGTH: 34
<212> TYPE: PRT
<213> ORGANISM: Momordica cochinchinensis

<400> SEQUENCE: 833

Gly Gly Val Cys Pro Lys Ile Leu Ala Ala Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp

<210> SEQ ID NO 834
<211> LENGTH: 34
<212> TYPE: PRT
<213> ORGANISM: Momordica cochinchinensis

<400> SEQUENCE: 834

Gly Gly Val Cys Pro Ala Ile Leu Lys Lys Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp

<210> SEQ ID NO 835
<211> LENGTH: 34
<212> TYPE: PRT
<213> ORGANISM: Momordica cochinchinensis

<400> SEQUENCE: 835

Gly Gly Val Cys Pro Lys Ile Leu Ala Lys Cys Arg Arg Asp Ser Asp
1               5                   10                  15

```
Cys Pro Gly Ala Cys Ile Cys Arg Gly Asn Gly Tyr Cys Gly Ser Gly
            20                  25                  30

Ser Asp
```

<210> SEQ ID NO 836
<211> LENGTH: 34
<212> TYPE: PRT
<213> ORGANISM: Momordica cochinchinensis

<400> SEQUENCE: 836

```
Gly Gly Val Cys Pro Lys Ile Leu Lys Ala Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp
```

<210> SEQ ID NO 837
<211> LENGTH: 29
<212> TYPE: PRT
<213> ORGANISM: Otocinclus affinis

<400> SEQUENCE: 837

```
Gly Leu Pro Val Cys Gly Glu Thr Cys Val Gly Gly Thr Cys Asn Thr
1               5                   10                  15

Pro Gly Cys Lys Cys Ser Trp Pro Val Cys Thr Arg Asn
            20                  25
```

<210> SEQ ID NO 838
<211> LENGTH: 29
<212> TYPE: PRT
<213> ORGANISM: Otocinclus affinis

<400> SEQUENCE: 838

```
Gly Leu Pro Val Cys Gly Glu Thr Cys Val Gly Gly Thr Cys Asn Thr
1               5                   10                  15

Pro Gly Cys Thr Cys Ser Trp Pro Lys Cys Thr Arg Asn
            20                  25
```

<210> SEQ ID NO 839
<211> LENGTH: 14
<212> TYPE: PRT
<213> ORGANISM: Helianthus annuus

<400> SEQUENCE: 839

```
Gly Arg Cys Thr Lys Ser Ile Pro Pro Ile Cys Phe Pro Asp
1               5                   10
```

<210> SEQ ID NO 840
<211> LENGTH: 16
<212> TYPE: PRT
<213> ORGANISM: Drosophila melanogaster

<400> SEQUENCE: 840

```
Arg Gln Ile Lys Ile Trp Phe Gln Asn Arg Arg Met Lys Trp Lys Lys
1               5                   10                  15
```

<210> SEQ ID NO 841
<211> LENGTH: 33
<212> TYPE: PRT
<213> ORGANISM: Drosophila melanogaster

<400> SEQUENCE: 841

Arg Gln Ile Lys Ile Trp Phe Gln Asn Arg Arg Met Lys Trp Lys Lys
1               5                   10                  15

Thr Tyr Ala Asp Phe Ile Ala Ser Gly Arg Thr Gly Arg Asn Ala
            20                  25                  30

Ile

<210> SEQ ID NO 842
<211> LENGTH: 13
<212> TYPE: PRT
<213> ORGANISM: Human immunodeficiency virus type 1

<400> SEQUENCE: 842

Gly Arg Lys Lys Arg Arg Gln Arg Arg Pro Pro Gln
1               5                   10

<210> SEQ ID NO 843
<211> LENGTH: 30
<212> TYPE: PRT
<213> ORGANISM: Human immunodeficiency virus type 1

<400> SEQUENCE: 843

Gly Arg Lys Lys Arg Arg Gln Arg Arg Pro Pro Gln Thr Tyr Ala
1               5                   10                  15

Asp Phe Ile Ala Ser Gly Arg Thr Gly Arg Arg Asn Ala Ile
            20                  25                  30

<210> SEQ ID NO 844
<211> LENGTH: 16
<212> TYPE: PRT
<213> ORGANISM: Drosophila melanogaster

<400> SEQUENCE: 844

Arg Gln Ile Lys Ile Trp Phe Gln Asn Arg Arg Met Lys Trp Lys Lys
1               5                   10                  15

<210> SEQ ID NO 845
<211> LENGTH: 16
<212> TYPE: PRT
<213> ORGANISM: Drosophila melanogaster

<400> SEQUENCE: 845

Arg Gln Ile Lys Ile Trp Phe Gln Asn Arg Arg Met Lys Trp Lys Lys
1               5                   10                  15

<210> SEQ ID NO 846
<211> LENGTH: 16
<212> TYPE: PRT
<213> ORGANISM: Drosophila melanogaster

<400> SEQUENCE: 846

Arg Gln Ile Lys Ile Trp Phe Gln Asn Arg Arg Met Lys Trp Lys Lys
1               5                   10                  15

<210> SEQ ID NO 847
<211> LENGTH: 16
<212> TYPE: PRT
<213> ORGANISM: Drosophila melanogaster

<400> SEQUENCE: 847

Arg Gln Ile Lys Ile Trp Phe Gln Asn Arg Arg Met Lys Trp Lys Lys
1               5                   10                  15

<210> SEQ ID NO 848

```
<211> LENGTH: 22
<212> TYPE: PRT
<213> ORGANISM: Homo sapiens

<400> SEQUENCE: 848

Lys Cys Phe Gln Trp Gln Arg Asn Met Arg Lys Val Arg Gly Pro Pro
1               5                   10                  15

Val Ser Cys Ile Lys Arg
            20

<210> SEQ ID NO 849
<211> LENGTH: 22
<212> TYPE: PRT
<213> ORGANISM: Homo sapiens

<400> SEQUENCE: 849

Lys Cys Phe Gln Trp Gln Arg Asn Met Arg Lys Val Arg Gly Pro Pro
1               5                   10                  15

Val Ser Cys Ile Lys Arg
            20

<210> SEQ ID NO 850
<211> LENGTH: 22
<212> TYPE: PRT
<213> ORGANISM: Homo sapiens

<400> SEQUENCE: 850

Lys Cys Phe Gln Trp Gln Arg Asn Met Arg Lys Val Arg Gly Pro Pro
1               5                   10                  15

Val Ser Cys Ile Lys Arg
            20

<210> SEQ ID NO 851
<211> LENGTH: 22
<212> TYPE: PRT
<213> ORGANISM: Homo sapiens

<400> SEQUENCE: 851

Lys Cys Phe Gln Trp Gln Arg Asn Met Arg Lys Val Arg Gly Pro Pro
1               5                   10                  15

Val Ser Cys Ile Lys Arg
            20

<210> SEQ ID NO 852
<211> LENGTH: 14
<212> TYPE: PRT
<213> ORGANISM: Human immunodeficiency virus type 1

<400> SEQUENCE: 852

Gly Arg Lys Lys Arg Arg Gln Arg Arg Arg Pro Pro Gln Cys
1               5                   10

<210> SEQ ID NO 853
<211> LENGTH: 19
<212> TYPE: PRT
<213> ORGANISM: Human immunodeficiency virus type 1

<400> SEQUENCE: 853

Thr Arg Gln Ala Arg Arg Asn Arg Arg Arg Trp Arg Glu Arg Gln
1               5                   10                  15

Arg Gly Cys
```

```
<210> SEQ ID NO 854
<211> LENGTH: 17
<212> TYPE: PRT
<213> ORGANISM: Flock house virus

<400> SEQUENCE: 854

Arg Arg Arg Arg Asn Arg Thr Arg Arg Asn Arg Arg Val Arg Gly
1               5                   10                  15

Cys

<210> SEQ ID NO 855
<211> LENGTH: 21
<212> TYPE: PRT
<213> ORGANISM: Brome mosaic virus

<400> SEQUENCE: 855

Lys Met Thr Arg Ala Gln Arg Arg Ala Ala Ala Arg Arg Asn Arg Trp
1               5                   10                  15

Thr Ala Arg Gly Cys
            20

<210> SEQ ID NO 856
<211> LENGTH: 15
<212> TYPE: PRT
<213> ORGANISM: Human T-cell lymphotropic virus type 2

<400> SEQUENCE: 856

Thr Arg Arg Gln Arg Thr Arg Arg Ala Arg Arg Asn Arg Gly Cys
1               5                   10                  15

<210> SEQ ID NO 857
<211> LENGTH: 30
<212> TYPE: PRT
<213> ORGANISM: Homo sapiens

<400> SEQUENCE: 857

Arg Ile Lys Ala Glu Arg Lys Arg Met Arg Asn Arg Ile Ala Ala Ser
1               5                   10                  15

Lys Ser Arg Lys Arg Lys Leu Glu Arg Ile Ala Arg Gly Cys
            20                  25                  30

<210> SEQ ID NO 858
<211> LENGTH: 28
<212> TYPE: PRT
<213> ORGANISM: Homo sapiens

<400> SEQUENCE: 858

Lys Arg Arg Ile Arg Arg Glu Arg Asn Lys Met Ala Ala Ala Lys Ser
1               5                   10                  15

Arg Asn Arg Arg Arg Glu Leu Thr Asp Thr Gly Cys
            20                  25

<210> SEQ ID NO 859
<211> LENGTH: 23
<212> TYPE: PRT
<213> ORGANISM: Homo sapiens

<400> SEQUENCE: 859

Trp Leu Arg Arg Ile Lys Ala Trp Leu Arg Arg Ile Lys Ala Leu Asn
1               5                   10                  15

Arg Gln Leu Gly Val Ala Ala
            20
```

<210> SEQ ID NO 860
<211> LENGTH: 10
<212> TYPE: PRT
<213> ORGANISM: Human immunodeficiency virus type 1

<400> SEQUENCE: 860

Cys Arg Lys Lys Arg Arg Gln Arg Arg Arg
1               5                   10

<210> SEQ ID NO 861
<211> LENGTH: 12
<212> TYPE: PRT
<213> ORGANISM: Human immunodeficiency virus type 1

<400> SEQUENCE: 861

Gly Arg Lys Lys Arg Arg Gln Arg Arg Arg Pro Pro
1               5                   10

<210> SEQ ID NO 862
<211> LENGTH: 4
<212> TYPE: PRT
<213> ORGANISM: Artificial sequence
<220> FEATURE:
<223> OTHER INFORMATION: CPP

<400> SEQUENCE: 862

Arg Arg Arg Arg
1

<210> SEQ ID NO 863
<211> LENGTH: 5
<212> TYPE: PRT
<213> ORGANISM: Artificial sequence
<220> FEATURE:
<223> OTHER INFORMATION: CPP

<400> SEQUENCE: 863

Arg Arg Arg Arg Arg
1               5

<210> SEQ ID NO 864
<211> LENGTH: 6
<212> TYPE: PRT
<213> ORGANISM: Artificial sequence
<220> FEATURE:
<223> OTHER INFORMATION: CPP

<400> SEQUENCE: 864

Arg Arg Arg Arg Arg Arg
1               5

<210> SEQ ID NO 865
<211> LENGTH: 7
<212> TYPE: PRT
<213> ORGANISM: Artificial sequence
<220> FEATURE:
<223> OTHER INFORMATION: CPP

<400> SEQUENCE: 865

Arg Arg Arg Arg Arg Arg Arg
1               5

<210> SEQ ID NO 866
<211> LENGTH: 8
<212> TYPE: PRT
<213> ORGANISM: Artificial sequence

```
<220> FEATURE:
<223> OTHER INFORMATION: CPP

<400> SEQUENCE: 866

Arg Arg Arg Arg Arg Arg Arg Arg
1               5

<210> SEQ ID NO 867
<211> LENGTH: 9
<212> TYPE: PRT
<213> ORGANISM: Artificial sequence
<220> FEATURE:
<223> OTHER INFORMATION: CPP

<400> SEQUENCE: 867

Arg Arg Arg Arg Arg Arg Arg Arg Arg
1               5

<210> SEQ ID NO 868
<211> LENGTH: 11
<212> TYPE: PRT
<213> ORGANISM: Artificial sequence
<220> FEATURE:
<223> OTHER INFORMATION: CPP

<400> SEQUENCE: 868

Arg Arg Arg Arg Arg Arg Arg Arg Arg Arg Arg
1               5                   10

<210> SEQ ID NO 869
<211> LENGTH: 12
<212> TYPE: PRT
<213> ORGANISM: Artificial sequence
<220> FEATURE:
<223> OTHER INFORMATION: CPP

<400> SEQUENCE: 869

Arg Arg Arg Arg Arg Arg Arg Arg Arg Arg Arg Arg
1               5                   10

<210> SEQ ID NO 870
<211> LENGTH: 16
<212> TYPE: PRT
<213> ORGANISM: Artificial sequence
<220> FEATURE:
<223> OTHER INFORMATION: CPP

<400> SEQUENCE: 870

Arg Arg Arg Arg Arg Arg Arg Arg Arg Arg Arg Arg Arg Arg Arg Arg
1               5                   10                  15

<210> SEQ ID NO 871
<211> LENGTH: 18
<212> TYPE: PRT
<213> ORGANISM: Artificial sequence
<220> FEATURE:
<223> OTHER INFORMATION: CPP

<400> SEQUENCE: 871

Lys Leu Ala Leu Lys Leu Ala Leu Lys Ala Leu Lys Ala Ala Leu Lys
1               5                   10                  15

Leu Ala

<210> SEQ ID NO 872
<211> LENGTH: 18
<212> TYPE: PRT
```

```
<213> ORGANISM: Artificial sequence
<220> FEATURE:
<223> OTHER INFORMATION: CPP

<400> SEQUENCE: 872

Lys Leu Ala Leu Lys Leu Ala Leu Lys Ala Trp Lys Ala Ala Leu Lys
1               5                   10                  15

Leu Ala

<210> SEQ ID NO 873
<211> LENGTH: 18
<212> TYPE: PRT
<213> ORGANISM: Artificial sequence
<220> FEATURE:
<223> OTHER INFORMATION: CPP

<400> SEQUENCE: 873

Lys Leu Ala Leu Lys Ala Ala Leu Lys Ala Trp Lys Ala Ala Ala Lys
1               5                   10                  15

Leu Ala

<210> SEQ ID NO 874
<211> LENGTH: 18
<212> TYPE: PRT
<213> ORGANISM: Artificial sequence
<220> FEATURE:
<223> OTHER INFORMATION: CPP

<400> SEQUENCE: 874

Lys Leu Ala Leu Lys Ala Ala Ala Lys Ala Trp Lys Ala Ala Ala Lys
1               5                   10                  15

Ala Ala

<210> SEQ ID NO 875
<211> LENGTH: 18
<212> TYPE: PRT
<213> ORGANISM: Artificial sequence
<220> FEATURE:
<223> OTHER INFORMATION: CPP

<400> SEQUENCE: 875

Lys Ile Thr Leu Lys Leu Ala Ile Lys Ala Trp Lys Leu Ala Leu Lys
1               5                   10                  15

Ala Ala

<210> SEQ ID NO 876
<211> LENGTH: 18
<212> TYPE: PRT
<213> ORGANISM: Artificial sequence
<220> FEATURE:
<223> OTHER INFORMATION: CPP

<400> SEQUENCE: 876

Lys Ile Ala Ala Lys Ser Ile Ala Lys Ile Trp Lys Ser Ile Leu Lys
1               5                   10                  15

Ile Ala

<210> SEQ ID NO 877
<211> LENGTH: 18
<212> TYPE: PRT
<213> ORGANISM: Artificial sequence
<220> FEATURE:
<223> OTHER INFORMATION: CPP
```

```
<400> SEQUENCE: 877

Lys Ala Leu Ala Lys Ala Leu Ala Lys Leu Trp Lys Ala Leu Ala Lys
1               5                   10                  15

Ala Ala

<210> SEQ ID NO 878
<211> LENGTH: 18
<212> TYPE: PRT
<213> ORGANISM: Artificial sequence
<220> FEATURE:
<223> OTHER INFORMATION: CPP

<400> SEQUENCE: 878

Lys Leu Ala Leu Lys Leu Ala Leu Lys Trp Ala Lys Leu Ala Leu Lys
1               5                   10                  15

Ala Ala

<210> SEQ ID NO 879
<211> LENGTH: 18
<212> TYPE: PRT
<213> ORGANISM: Artificial sequence
<220> FEATURE:
<223> OTHER INFORMATION: CPP

<400> SEQUENCE: 879

Lys Leu Leu Ala Lys Ala Ala Lys Lys Trp Leu Leu Leu Ala Leu Lys
1               5                   10                  15

Ala Ala

<210> SEQ ID NO 880
<211> LENGTH: 18
<212> TYPE: PRT
<213> ORGANISM: Artificial sequence
<220> FEATURE:
<223> OTHER INFORMATION: CPP

<400> SEQUENCE: 880

Lys Leu Leu Ala Lys Ala Ala Leu Lys Trp Leu Leu Lys Ala Leu Lys
1               5                   10                  15

Ala Ala

<210> SEQ ID NO 881
<211> LENGTH: 18
<212> TYPE: PRT
<213> ORGANISM: Artificial sequence
<220> FEATURE:
<223> OTHER INFORMATION: CPP

<400> SEQUENCE: 881

Lys Ala Leu Lys Lys Leu Leu Ala Lys Trp Leu Ala Ala Ala Lys Ala
1               5                   10                  15

Leu Leu

<210> SEQ ID NO 882
<211> LENGTH: 18
<212> TYPE: PRT
<213> ORGANISM: Artificial sequence
<220> FEATURE:
<223> OTHER INFORMATION: CPP

<400> SEQUENCE: 882

Lys Leu Ala Ala Ala Leu Leu Lys Lys Trp Lys Lys Leu Ala Ala Ala
1               5                   10                  15
```

Leu Leu

<210> SEQ ID NO 883
<211> LENGTH: 18
<212> TYPE: PRT
<213> ORGANISM: Artificial sequence
<220> FEATURE:
<223> OTHER INFORMATION: CPP

<400> SEQUENCE: 883

Lys Ala Leu Ala Ala Leu Leu Lys Lys Trp Ala Lys Leu Leu Ala Ala
1               5                   10                  15

Leu Lys

<210> SEQ ID NO 884
<211> LENGTH: 18
<212> TYPE: PRT
<213> ORGANISM: Artificial sequence
<220> FEATURE:
<223> OTHER INFORMATION: CPP

<400> SEQUENCE: 884

Lys Ala Leu Ala Ala Leu Leu Lys Lys Leu Ala Lys Leu Leu Ala Ala
1               5                   10                  15

Leu Lys

<210> SEQ ID NO 885
<211> LENGTH: 16
<212> TYPE: PRT
<213> ORGANISM: Artificial sequence
<220> FEATURE:
<223> OTHER INFORMATION: CPP

<400> SEQUENCE: 885

Lys Leu Ala Leu Lys Leu Ala Leu Lys Ala Leu Lys Ala Ala Leu Lys
1               5                   10                  15

<210> SEQ ID NO 886
<211> LENGTH: 14
<212> TYPE: PRT
<213> ORGANISM: Artificial sequence
<220> FEATURE:
<223> OTHER INFORMATION: CPP

<400> SEQUENCE: 886

Lys Leu Ala Leu Lys Ala Leu Lys Ala Ala Leu Lys Leu Ala
1               5                   10

<210> SEQ ID NO 887
<211> LENGTH: 14
<212> TYPE: PRT
<213> ORGANISM: Artificial sequence
<220> FEATURE:
<223> OTHER INFORMATION: CPP

<400> SEQUENCE: 887

Lys Leu Ala Leu Lys Leu Ala Leu Lys Ala Leu Lys Ala Ala
1               5                   10

<210> SEQ ID NO 888
<211> LENGTH: 18
<212> TYPE: PRT
<213> ORGANISM: Artificial sequence
<220> FEATURE:
<223> OTHER INFORMATION: CPP -continued

<400> SEQUENCE: 888

Lys Leu Gly Leu Lys Leu Gly Leu Lys Gly Leu Lys Gly Gly Leu Lys
1               5                   10                  15

Leu Gly

<210> SEQ ID NO 889
<211> LENGTH: 18
<212> TYPE: PRT
<213> ORGANISM: Artificial sequence
<220> FEATURE:
<223> OTHER INFORMATION: CPP

<400> SEQUENCE: 889

Lys Leu Ala Leu Lys Leu Ala Leu Lys Ala Leu Gln Ala Ala Leu Gln
1               5                   10                  15

Leu Ala

<210> SEQ ID NO 890
<211> LENGTH: 18
<212> TYPE: PRT
<213> ORGANISM: Artificial sequence
<220> FEATURE:
<223> OTHER INFORMATION: CPP

<400> SEQUENCE: 890

Lys Leu Ala Leu Gln Leu Ala Leu Gln Ala Leu Gln Ala Ala Leu Gln
1               5                   10                  15

Leu Ala

<210> SEQ ID NO 891
<211> LENGTH: 18
<212> TYPE: PRT
<213> ORGANISM: Artificial sequence
<220> FEATURE:
<223> OTHER INFORMATION: CPP

<400> SEQUENCE: 891

Gln Leu Ala Leu Gln Leu Ala Leu Gln Ala Leu Gln Ala Ala Leu Gln
1               5                   10                  15

Leu Ala

<210> SEQ ID NO 892
<211> LENGTH: 18
<212> TYPE: PRT
<213> ORGANISM: Artificial sequence
<220> FEATURE:
<223> OTHER INFORMATION: CPP

<400> SEQUENCE: 892

Glu Leu Ala Leu Glu Leu Ala Leu Glu Ala Leu Glu Ala Ala Leu Glu
1               5                   10                  15

Leu Ala

<210> SEQ ID NO 893
<211> LENGTH: 18
<212> TYPE: PRT
<213> ORGANISM: Artificial sequence
<220> FEATURE:
<223> OTHER INFORMATION: CPP

<400> SEQUENCE: 893

Leu Lys Thr Leu Ala Thr Ala Leu Thr Lys Leu Ala Lys Thr Leu Thr

```
1               5                  10                  15

Thr Leu

<210> SEQ ID NO 894
<211> LENGTH: 18
<212> TYPE: PRT
<213> ORGANISM: Artificial sequence
<220> FEATURE:
<223> OTHER INFORMATION: CPP

<400> SEQUENCE: 894

Leu Leu Lys Thr Thr Ala Leu Leu Lys Thr Thr Ala Leu Leu Lys Thr
1               5                  10                  15

Thr Ala

<210> SEQ ID NO 895
<211> LENGTH: 18
<212> TYPE: PRT
<213> ORGANISM: Artificial sequence
<220> FEATURE:
<223> OTHER INFORMATION: CPP

<400> SEQUENCE: 895

Leu Lys Thr Leu Thr Glu Thr Leu Lys Glu Leu Thr Lys Thr Leu Thr
1               5                  10                  15

Glu Leu

<210> SEQ ID NO 896
<211> LENGTH: 18
<212> TYPE: PRT
<213> ORGANISM: Artificial sequence
<220> FEATURE:
<223> OTHER INFORMATION: CPP

<400> SEQUENCE: 896

Leu Leu Lys Thr Thr Glu Leu Leu Lys Thr Thr Glu Leu Leu Lys Thr
1               5                  10                  15

Thr Glu

<210> SEQ ID NO 897
<211> LENGTH: 18
<212> TYPE: PRT
<213> ORGANISM: Artificial sequence
<220> FEATURE:
<223> OTHER INFORMATION: CPP

<400> SEQUENCE: 897

Lys Leu Ala Leu Lys Leu Ala Leu Lys Ala Leu Lys Ala Ala Leu Lys
1               5                  10                  15

Leu Ala

<210> SEQ ID NO 898
<211> LENGTH: 18
<212> TYPE: PRT
<213> ORGANISM: Artificial sequence
<220> FEATURE:
<223> OTHER INFORMATION: CPP

<400> SEQUENCE: 898

Lys Ala Leu Lys Leu Lys Leu Ala Leu Ala Leu Leu Ala Lys Leu Lys
1               5                  10                  15

Leu Ala
```

```
<210> SEQ ID NO 899
<211> LENGTH: 8
<212> TYPE: PRT
<213> ORGANISM: Artificial sequence
<220> FEATURE:
<223> OTHER INFORMATION: CPP

<400> SEQUENCE: 899

Arg Arg Arg Arg Arg Arg Arg Trp
1               5

<210> SEQ ID NO 900
<211> LENGTH: 15
<212> TYPE: PRT
<213> ORGANISM: Artificial sequence
<220> FEATURE:
<223> OTHER INFORMATION: CPP

<400> SEQUENCE: 900

Lys Leu Trp Met Arg Trp Tyr Ser Pro Thr Thr Arg Arg Tyr Gly
1               5                   10                  15

<210> SEQ ID NO 901
<211> LENGTH: 15
<212> TYPE: PRT
<213> ORGANISM: Artificial sequence
<220> FEATURE:
<223> OTHER INFORMATION: CPP

<400> SEQUENCE: 901

Asp Ser Leu Lys Ser Tyr Trp Tyr Leu Gln Lys Phe Ser Trp Arg
1               5                   10                  15

<210> SEQ ID NO 902
<211> LENGTH: 15
<212> TYPE: PRT
<213> ORGANISM: Artificial sequence
<220> FEATURE:
<223> OTHER INFORMATION: CPP

<400> SEQUENCE: 902

Arg Thr Leu Val Asn Glu Tyr Lys Asn Thr Leu Lys Phe Ser Lys
1               5                   10                  15

<210> SEQ ID NO 903
<211> LENGTH: 15
<212> TYPE: PRT
<213> ORGANISM: Artificial sequence
<220> FEATURE:
<223> OTHER INFORMATION: CPP

<400> SEQUENCE: 903

Ile Pro Ser Arg Trp Lys Asp Gln Phe Trp Lys Arg Trp His Tyr
1               5                   10                  15

<210> SEQ ID NO 904
<211> LENGTH: 15
<212> TYPE: PRT
<213> ORGANISM: Artificial sequence
<220> FEATURE:
<223> OTHER INFORMATION: CPP

<400> SEQUENCE: 904

Gly Tyr Gly Asn Cys Arg His Phe Lys Gln Lys Pro Arg Arg Asp
1               5                   10                  15
```

```
<210> SEQ ID NO 905
<211> LENGTH: 15
<212> TYPE: PRT
<213> ORGANISM: Artificial sequence
<220> FEATURE:
<223> OTHER INFORMATION: CPP

<400> SEQUENCE: 905

Lys Asn Ala Trp Lys His Ser Ser Cys His His Arg His Gln Ile
1               5                   10                  15

<210> SEQ ID NO 906
<211> LENGTH: 15
<212> TYPE: PRT
<213> ORGANISM: Artificial sequence
<220> FEATURE:
<223> OTHER INFORMATION: CPP

<400> SEQUENCE: 906

Arg Val Arg Glu Trp Trp Tyr Thr Ile Thr Leu Lys Gln Glu Ser
1               5                   10                  15

<210> SEQ ID NO 907
<211> LENGTH: 15
<212> TYPE: PRT
<213> ORGANISM: Artificial sequence
<220> FEATURE:
<223> OTHER INFORMATION: CPP

<400> SEQUENCE: 907

Gln Gln His Leu Leu Ile Ala Ile Asn Gly Tyr Pro Arg Tyr Asn
1               5                   10                  15

<210> SEQ ID NO 908
<211> LENGTH: 15
<212> TYPE: PRT
<213> ORGANISM: Artificial sequence
<220> FEATURE:
<223> OTHER INFORMATION: CPP

<400> SEQUENCE: 908

Trp Lys Cys Arg Arg Gln Cys Phe Arg Val Leu His His Trp Asn
1               5                   10                  15

<210> SEQ ID NO 909
<211> LENGTH: 15
<212> TYPE: PRT
<213> ORGANISM: Artificial sequence
<220> FEATURE:
<223> OTHER INFORMATION: CPP

<400> SEQUENCE: 909

Arg Leu Trp Met Arg Trp Tyr Ser Pro Thr Thr Arg Arg Tyr Gly
1               5                   10                  15

<210> SEQ ID NO 910
<211> LENGTH: 15
<212> TYPE: PRT
<213> ORGANISM: Artificial sequence
<220> FEATURE:
<223> OTHER INFORMATION: CPP

<400> SEQUENCE: 910

Lys Leu Trp Met Arg Trp Tyr Ser Ala Thr Thr Arg Arg Tyr Gly
1               5                   10                  15

<210> SEQ ID NO 911
```

<211> LENGTH: 15
<212> TYPE: PRT
<213> ORGANISM: Artificial sequence
<220> FEATURE:
<223> OTHER INFORMATION: CPP

<400> SEQUENCE: 911

Lys Leu Trp Met Arg Trp Tyr Ser Pro Trp Thr Arg Arg Tyr Gly
1               5                   10                  15

<210> SEQ ID NO 912
<211> LENGTH: 15
<212> TYPE: PRT
<213> ORGANISM: Artificial sequence
<220> FEATURE:
<223> OTHER INFORMATION: CPP

<400> SEQUENCE: 912

Arg Leu Trp Met Arg Trp Tyr Ser Pro Trp Thr Arg Arg Tyr Gly
1               5                   10                  15

<210> SEQ ID NO 913
<211> LENGTH: 15
<212> TYPE: PRT
<213> ORGANISM: Artificial sequence
<220> FEATURE:
<223> OTHER INFORMATION: CPP

<400> SEQUENCE: 913

Arg Leu Trp Met Arg Trp Tyr Ser Pro Trp Thr Arg Arg Trp Gly
1               5                   10                  15

<210> SEQ ID NO 914
<211> LENGTH: 15
<212> TYPE: PRT
<213> ORGANISM: Artificial sequence
<220> FEATURE:
<223> OTHER INFORMATION: CPP

<400> SEQUENCE: 914

Ala Leu Trp Met Arg Trp Tyr Ser Pro Thr Thr Arg Arg Tyr Gly
1               5                   10                  15

<210> SEQ ID NO 915
<211> LENGTH: 15
<212> TYPE: PRT
<213> ORGANISM: Artificial sequence
<220> FEATURE:
<223> OTHER INFORMATION: CPP

<400> SEQUENCE: 915

Arg Ala Trp Met Arg Trp Tyr Ser Pro Thr Thr Arg Arg Tyr Gly
1               5                   10                  15

<210> SEQ ID NO 916
<211> LENGTH: 15
<212> TYPE: PRT
<213> ORGANISM: Artificial sequence
<220> FEATURE:
<223> OTHER INFORMATION: CPP

<400> SEQUENCE: 916

Arg Leu Ala Met Arg Trp Tyr Ser Pro Thr Thr Arg Arg Tyr Gly
1               5                   10                  15

<210> SEQ ID NO 917
<211> LENGTH: 15

<212> TYPE: PRT
<213> ORGANISM: Artificial sequence
<220> FEATURE:
<223> OTHER INFORMATION: CPP

<400> SEQUENCE: 917

Arg Leu Trp Ala Arg Trp Tyr Ser Pro Thr Thr Arg Arg Tyr Gly
1               5                   10                  15

<210> SEQ ID NO 918
<211> LENGTH: 15
<212> TYPE: PRT
<213> ORGANISM: Artificial sequence
<220> FEATURE:
<223> OTHER INFORMATION: CPP

<400> SEQUENCE: 918

Arg Leu Trp Met Ala Trp Tyr Ser Pro Thr Thr Arg Arg Tyr Gly
1               5                   10                  15

<210> SEQ ID NO 919
<211> LENGTH: 15
<212> TYPE: PRT
<213> ORGANISM: Artificial sequence
<220> FEATURE:
<223> OTHER INFORMATION: CPP

<400> SEQUENCE: 919

Arg Leu Trp Met Arg Ala Tyr Ser Pro Thr Thr Arg Arg Tyr Gly
1               5                   10                  15

<210> SEQ ID NO 920
<211> LENGTH: 15
<212> TYPE: PRT
<213> ORGANISM: Artificial sequence
<220> FEATURE:
<223> OTHER INFORMATION: CPP

<400> SEQUENCE: 920

Arg Leu Trp Met Arg Trp Ala Ser Pro Thr Thr Arg Arg Tyr Gly
1               5                   10                  15

<210> SEQ ID NO 921
<211> LENGTH: 15
<212> TYPE: PRT
<213> ORGANISM: Artificial sequence
<220> FEATURE:
<223> OTHER INFORMATION: CPP

<400> SEQUENCE: 921

Arg Leu Trp Met Arg Trp Tyr Ala Pro Thr Thr Arg Arg Tyr Gly
1               5                   10                  15

<210> SEQ ID NO 922
<211> LENGTH: 15
<212> TYPE: PRT
<213> ORGANISM: Artificial sequence
<220> FEATURE:
<223> OTHER INFORMATION: CPP

<400> SEQUENCE: 922

Arg Leu Trp Met Arg Trp Tyr Ser Pro Ala Thr Arg Arg Tyr Gly
1               5                   10                  15

<210> SEQ ID NO 923
<211> LENGTH: 15
<212> TYPE: PRT

<213> ORGANISM: Artificial sequence
<220> FEATURE:
<223> OTHER INFORMATION: CPP

<400> SEQUENCE: 923

Arg Leu Trp Met Arg Trp Tyr Ser Pro Thr Ala Arg Arg Tyr Gly
1               5                   10                  15

<210> SEQ ID NO 924
<211> LENGTH: 15
<212> TYPE: PRT
<213> ORGANISM: Artificial sequence
<220> FEATURE:
<223> OTHER INFORMATION: CPP

<400> SEQUENCE: 924

Arg Leu Trp Met Arg Trp Tyr Ser Pro Thr Thr Ala Arg Tyr Gly
1               5                   10                  15

<210> SEQ ID NO 925
<211> LENGTH: 15
<212> TYPE: PRT
<213> ORGANISM: Artificial sequence
<220> FEATURE:
<223> OTHER INFORMATION: CPP

<400> SEQUENCE: 925

Arg Leu Trp Met Arg Trp Tyr Ser Pro Thr Thr Arg Ala Tyr Gly
1               5                   10                  15

<210> SEQ ID NO 926
<211> LENGTH: 15
<212> TYPE: PRT
<213> ORGANISM: Artificial sequence
<220> FEATURE:
<223> OTHER INFORMATION: CPP

<400> SEQUENCE: 926

Arg Leu Trp Met Arg Trp Tyr Ser Pro Thr Thr Arg Arg Ala Gly
1               5                   10                  15

<210> SEQ ID NO 927
<211> LENGTH: 15
<212> TYPE: PRT
<213> ORGANISM: Artificial sequence
<220> FEATURE:
<223> OTHER INFORMATION: CPP

<400> SEQUENCE: 927

Arg Leu Trp Met Arg Trp Tyr Ser Pro Thr Thr Arg Arg Tyr Ala
1               5                   10                  15

<210> SEQ ID NO 928
<211> LENGTH: 15
<212> TYPE: PRT
<213> ORGANISM: Artificial sequence
<220> FEATURE:
<223> OTHER INFORMATION: CPP

<400> SEQUENCE: 928

Arg Leu Leu Met Arg Leu Tyr Ser Pro Thr Thr Arg Arg Tyr Gly
1               5                   10                  15

<210> SEQ ID NO 929
<211> LENGTH: 15
<212> TYPE: PRT
<213> ORGANISM: Artificial sequence

```
<220> FEATURE:
<223> OTHER INFORMATION: CPP

<400> SEQUENCE: 929

Arg Leu Phe Met Arg Phe Tyr Ser Pro Thr Thr Arg Arg Tyr Gly
1               5                   10                  15

<210> SEQ ID NO 930
<211> LENGTH: 15
<212> TYPE: PRT
<213> ORGANISM: Artificial sequence
<220> FEATURE:
<223> OTHER INFORMATION: CPP

<400> SEQUENCE: 930

Arg Leu Ile Met Arg Ile Tyr Ser Pro Thr Thr Arg Arg Tyr Gly
1               5                   10                  15

<210> SEQ ID NO 931
<211> LENGTH: 15
<212> TYPE: PRT
<213> ORGANISM: Artificial sequence
<220> FEATURE:
<223> OTHER INFORMATION: CPP

<400> SEQUENCE: 931

Arg Leu Val Met Arg Val Tyr Ser Pro Thr Thr Arg Arg Tyr Gly
1               5                   10                  15

<210> SEQ ID NO 932
<211> LENGTH: 15
<212> TYPE: PRT
<213> ORGANISM: Artificial sequence
<220> FEATURE:
<223> OTHER INFORMATION: CPP

<400> SEQUENCE: 932

Arg Leu Tyr Met Arg Tyr Tyr Ser Pro Thr Thr Arg Arg Tyr Gly
1               5                   10                  15

<210> SEQ ID NO 933
<211> LENGTH: 17
<212> TYPE: PRT
<213> ORGANISM: Artificial sequence
<220> FEATURE:
<223> OTHER INFORMATION: CPP

<400> SEQUENCE: 933

Asp Arg Asp Asp Arg Asp Asp Arg Asp Asp Arg Asp Asp Arg Asp Asp
1               5                   10                  15

Arg

<210> SEQ ID NO 934
<211> LENGTH: 14
<212> TYPE: PRT
<213> ORGANISM: Artificial sequence
<220> FEATURE:
<223> OTHER INFORMATION: CPP

<400> SEQUENCE: 934

Glu Arg Glu Arg Glu Arg Glu Arg Glu Arg Glu Arg Glu Arg
1               5                   10

<210> SEQ ID NO 935
<211> LENGTH: 14
<212> TYPE: PRT
```

```
<213> ORGANISM: Artificial sequence
<220> FEATURE:
<223> OTHER INFORMATION: CPP

<400> SEQUENCE: 935

Trp Arg Trp Arg Trp Arg Trp Arg Trp Arg Trp Arg Trp Arg
1               5                   10

<210> SEQ ID NO 936
<211> LENGTH: 10
<212> TYPE: PRT
<213> ORGANISM: Artificial sequence
<220> FEATURE:
<223> OTHER INFORMATION: CPP

<400> SEQUENCE: 936

Asp Arg Asp Arg Asp Arg Asp Arg Asp Arg
1               5                   10

<210> SEQ ID NO 937
<211> LENGTH: 27
<212> TYPE: PRT
<213> ORGANISM: Artificial sequence
<220> FEATURE:
<223> OTHER INFORMATION: CPP

<400> SEQUENCE: 937

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 938
<211> LENGTH: 4
<212> TYPE: PRT
<213> ORGANISM: Artificial sequence
<220> FEATURE:
<223> OTHER INFORMATION: CPP

<400> SEQUENCE: 938

Glu Glu Glu Ala
1

<210> SEQ ID NO 939
<211> LENGTH: 5
<212> TYPE: PRT
<213> ORGANISM: Artificial sequence
<220> FEATURE:
<223> OTHER INFORMATION: CPP

<400> SEQUENCE: 939

Glu Glu Glu Ala Ala
1               5

<210> SEQ ID NO 940
<211> LENGTH: 8
<212> TYPE: PRT
<213> ORGANISM: Artificial sequence
<220> FEATURE:
<223> OTHER INFORMATION: CPP

<400> SEQUENCE: 940

Glu Glu Glu Ala Ala Lys Lys Lys
1               5

<210> SEQ ID NO 941
```

```
<211> LENGTH: 16
<212> TYPE: PRT
<213> ORGANISM: Artificial sequence
<220> FEATURE:
<223> OTHER INFORMATION: CPP

<400> SEQUENCE: 941

Lys Thr Val Leu Leu Arg Lys Leu Leu Lys Leu Leu Val Arg Lys Ile
1               5                   10                  15

<210> SEQ ID NO 942
<211> LENGTH: 16
<212> TYPE: PRT
<213> ORGANISM: Artificial sequence
<220> FEATURE:
<223> OTHER INFORMATION: CPP

<400> SEQUENCE: 942

Leu Leu Lys Lys Arg Lys Val Val Arg Leu Ile Lys Phe Leu Leu Lys
1               5                   10                  15

<210> SEQ ID NO 943
<211> LENGTH: 9
<212> TYPE: PRT
<213> ORGANISM: Artificial sequence
<220> FEATURE:
<223> OTHER INFORMATION: CPP

<400> SEQUENCE: 943

Cys Gly Asn Lys Arg Thr Arg Gly Cys
1               5

<210> SEQ ID NO 944
<211> LENGTH: 12
<212> TYPE: PRT
<213> ORGANISM: Artificial sequence
<220> FEATURE:
<223> OTHER INFORMATION: CPP

<400> SEQUENCE: 944

Thr Ser Pro Leu Asn Ile His Asn Gly Gln Lys Leu
1               5                   10

<210> SEQ ID NO 945
<211> LENGTH: 13
<212> TYPE: PRT
<213> ORGANISM: Artificial sequence
<220> FEATURE:
<223> OTHER INFORMATION: CPP

<400> SEQUENCE: 945

Cys Val Gln Trp Ser Leu Leu Arg Gly Tyr Gln Pro Cys
1               5                   10

<210> SEQ ID NO 946
<211> LENGTH: 26
<212> TYPE: PRT
<213> ORGANISM: Artificial sequence
<220> FEATURE:
<223> OTHER INFORMATION: CPP

<400> SEQUENCE: 946

Asp Pro Lys Gly Asp Pro Lys Gly Val Thr Val Thr Val Thr Val Thr
1               5                   10                  15

Val Thr Gly Lys Gly Asp Pro Lys Pro Asp
            20                  25
```

```
<210> SEQ ID NO 947
<211> LENGTH: 16
<212> TYPE: PRT
<213> ORGANISM: Artificial sequence
<220> FEATURE:
<223> OTHER INFORMATION: CPP

<400> SEQUENCE: 947

Tyr Thr Ala Ile Ala Trp Val Lys Ala Phe Ile Arg Lys Leu Arg Lys
1               5                   10                  15

<210> SEQ ID NO 948
<211> LENGTH: 17
<212> TYPE: PRT
<213> ORGANISM: Artificial sequence
<220> FEATURE:
<223> OTHER INFORMATION: CPP

<400> SEQUENCE: 948

Ile Ala Trp Val Lys Ala Phe Ile Arg Lys Leu Arg Lys Gly Pro Leu
1               5                   10                  15

Gly

<210> SEQ ID NO 949
<211> LENGTH: 34
<212> TYPE: PRT
<213> ORGANISM: Artificial sequence
<220> FEATURE:
<223> OTHER INFORMATION: CPP

<400> SEQUENCE: 949

Lys Lys Lys Lys Lys Lys Gly Gly Phe Leu Gly Phe Trp Arg Gly Glu
1               5                   10                  15

Asn Gly Arg Lys Thr Arg Ser Ala Tyr Glu Arg Met Cys Ile Leu Lys
            20                  25                  30

Gly Lys

<210> SEQ ID NO 950
<211> LENGTH: 14
<212> TYPE: PRT
<213> ORGANISM: Artificial sequence
<220> FEATURE:
<223> OTHER INFORMATION: CPP

<400> SEQUENCE: 950

Arg Leu Ser Gly Met Asn Glu Val Leu Ser Phe Arg Trp Leu
1               5                   10

<210> SEQ ID NO 951
<211> LENGTH: 13
<212> TYPE: PRT
<213> ORGANISM: Artificial sequence
<220> FEATURE:
<223> OTHER INFORMATION: CPP

<400> SEQUENCE: 951

Gly Pro Phe His Phe Tyr Gln Phe Leu Phe Pro Pro Val
1               5                   10

<210> SEQ ID NO 952
<211> LENGTH: 13
<212> TYPE: PRT
<213> ORGANISM: Artificial sequence
<220> FEATURE:
<223> OTHER INFORMATION: CPP
```

```
<400> SEQUENCE: 952

Gly Ser Pro Trp Gly Leu Gln His His Pro Pro Arg Thr
1               5                   10

<210> SEQ ID NO 953
<211> LENGTH: 30
<212> TYPE: PRT
<213> ORGANISM: Artificial sequence
<220> FEATURE:
<223> OTHER INFORMATION: CPP

<400> SEQUENCE: 953

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 954
<211> LENGTH: 30
<212> TYPE: PRT
<213> ORGANISM: Artificial sequence
<220> FEATURE:
<223> OTHER INFORMATION: CPP

<400> SEQUENCE: 954

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

<210> SEQ ID NO 955
<211> LENGTH: 20
<212> TYPE: PRT
<213> ORGANISM: Artificial sequence
<220> FEATURE:
<223> OTHER INFORMATION: CPP

<400> SEQUENCE: 955

Gly Leu Phe Glu Ala Leu Leu Glu Leu Leu Glu Ser Leu Trp Glu Leu
1               5                   10                  15

Leu Leu Glu Ala
            20

<210> SEQ ID NO 956
<211> LENGTH: 20
<212> TYPE: PRT
<213> ORGANISM: Artificial sequence
<220> FEATURE:
<223> OTHER INFORMATION: CPP

<400> SEQUENCE: 956

Gly Leu Phe Lys Ala Leu Leu Lys Leu Leu Lys Ser Leu Trp Lys Leu
1               5                   10                  15

Leu Leu Lys Ala
            20

<210> SEQ ID NO 957
<211> LENGTH: 20
<212> TYPE: PRT
<213> ORGANISM: Artificial sequence
<220> FEATURE:
<223> OTHER INFORMATION: CPP

<400> SEQUENCE: 957
```

```
Gly Leu Phe Arg Ala Leu Leu Arg Leu Leu Arg Ser Leu Trp Arg Leu
1               5                   10                  15

Leu Leu Arg Ala
            20

<210> SEQ ID NO 958
<211> LENGTH: 11
<212> TYPE: PRT
<213> ORGANISM: Artificial sequence
<220> FEATURE:
<223> OTHER INFORMATION: CPP

<400> SEQUENCE: 958

Tyr Ala Arg Ala Ala Ala Arg Gln Ala Arg Ala
1               5                   10

<210> SEQ ID NO 959
<211> LENGTH: 10
<212> TYPE: PRT
<213> ORGANISM: Artificial sequence
<220> FEATURE:
<223> OTHER INFORMATION: CPP

<400> SEQUENCE: 959

Gly Lys Lys Lys Lys Lys Lys Lys Lys Lys
1               5                   10

<210> SEQ ID NO 960
<211> LENGTH: 20
<212> TYPE: PRT
<213> ORGANISM: Artificial sequence
<220> FEATURE:
<223> OTHER INFORMATION: CPP

<400> SEQUENCE: 960

Arg Ile Leu Gln Gln Leu Leu Phe Ile His Phe Arg Ile Gly Cys Arg
1               5                   10                  15

His Ser Arg Ile
            20

<210> SEQ ID NO 961
<211> LENGTH: 17
<212> TYPE: PRT
<213> ORGANISM: Artificial sequence
<220> FEATURE:
<223> OTHER INFORMATION: CPP

<400> SEQUENCE: 961

Arg Ile Leu Gln Gln Leu Leu Phe Ile His Phe Arg Ile Gly Cys Arg
1               5                   10                  15

His

<210> SEQ ID NO 962
<211> LENGTH: 15
<212> TYPE: PRT
<213> ORGANISM: Artificial sequence
<220> FEATURE:
<223> OTHER INFORMATION: CPP

<400> SEQUENCE: 962

Arg Ile Leu Gln Gln Leu Leu Phe Ile His Phe Arg Ile Gly Cys
1               5                   10                  15

<210> SEQ ID NO 963
```

```
<211> LENGTH: 10
<212> TYPE: PRT
<213> ORGANISM: Artificial sequence
<220> FEATURE:
<223> OTHER INFORMATION: CPP

<400> SEQUENCE: 963

Arg Ile Phe Ile His Phe Arg Ile Gly Cys
1               5                   10

<210> SEQ ID NO 964
<211> LENGTH: 8
<212> TYPE: PRT
<213> ORGANISM: Artificial sequence
<220> FEATURE:
<223> OTHER INFORMATION: CPP

<400> SEQUENCE: 964

Arg Ile Phe Ile Arg Ile Gly Cys
1               5

<210> SEQ ID NO 965
<211> LENGTH: 11
<212> TYPE: PRT
<213> ORGANISM: Artificial sequence
<220> FEATURE:
<223> OTHER INFORMATION: CPP

<400> SEQUENCE: 965

Arg Ile Leu Gln Gln Leu Leu Phe Ile His Phe
1               5                   10

<210> SEQ ID NO 966
<211> LENGTH: 6
<212> TYPE: PRT
<213> ORGANISM: Artificial sequence
<220> FEATURE:
<223> OTHER INFORMATION: CPP

<400> SEQUENCE: 966

Arg Ile Phe Ile Gly Cys
1               5

<210> SEQ ID NO 967
<211> LENGTH: 6
<212> TYPE: PRT
<213> ORGANISM: Artificial sequence
<220> FEATURE:
<223> OTHER INFORMATION: CPP

<400> SEQUENCE: 967

Phe Ile Arg Ile Gly Cys
1               5

<210> SEQ ID NO 968
<211> LENGTH: 22
<212> TYPE: PRT
<213> ORGANISM: Artificial sequence
<220> FEATURE:
<223> OTHER INFORMATION: CPP

<400> SEQUENCE: 968

Asp Thr Trp Ala Gly Val Glu Ala Ile Ile Arg Ile Leu Gln Gln Leu
1               5                   10                  15

Leu Phe Ile His Phe Arg
            20
```

<210> SEQ ID NO 969
<211> LENGTH: 5
<212> TYPE: PRT
<213> ORGANISM: Artificial sequence
<220> FEATURE:
<223> OTHER INFORMATION: CPP

<400> SEQUENCE: 969

Ile Gly Cys Arg His
1               5

<210> SEQ ID NO 970
<211> LENGTH: 23
<212> TYPE: PRT
<213> ORGANISM: Artificial sequence
<220> FEATURE:
<223> OTHER INFORMATION: CPP

<400> SEQUENCE: 970

Gly Tyr Gly Arg Lys Lys Arg Arg Gly Arg Arg Thr His Arg Leu
1               5                  10                  15

Pro Arg Arg Arg Arg Arg Arg
            20

<210> SEQ ID NO 971
<211> LENGTH: 12
<212> TYPE: PRT
<213> ORGANISM: Artificial sequence
<220> FEATURE:
<223> OTHER INFORMATION: CPP

<400> SEQUENCE: 971

Lys Arg Ile Ile Gln Arg Ile Leu Ser Arg Asn Ser
1               5                  10

<210> SEQ ID NO 972
<211> LENGTH: 12
<212> TYPE: PRT
<213> ORGANISM: Artificial sequence
<220> FEATURE:
<223> OTHER INFORMATION: CPP

<400> SEQUENCE: 972

Lys Arg Ile His Pro Arg Leu Thr Arg Ser Ile Arg
1               5                  10

<210> SEQ ID NO 973
<211> LENGTH: 12
<212> TYPE: PRT
<213> ORGANISM: Artificial sequence
<220> FEATURE:
<223> OTHER INFORMATION: CPP

<400> SEQUENCE: 973

Pro Pro Arg Leu Arg Lys Arg Arg Gln Leu Asn Met
1               5                  10

<210> SEQ ID NO 974
<211> LENGTH: 12
<212> TYPE: PRT
<213> ORGANISM: Artificial sequence
<220> FEATURE:
<223> OTHER INFORMATION: CPP

<400> SEQUENCE: 974

Pro Ile Arg Arg Arg Lys Lys Leu Arg Arg Leu Lys

-continued

```
1               5                   10

<210> SEQ ID NO 975
<211> LENGTH: 12
<212> TYPE: PRT
<213> ORGANISM: Artificial sequence
<220> FEATURE:
<223> OTHER INFORMATION: CPP

<400> SEQUENCE: 975

Arg Arg Gln Arg Arg Thr Ser Lys Leu Met Lys Arg
1               5                   10

<210> SEQ ID NO 976
<211> LENGTH: 12
<212> TYPE: PRT
<213> ORGANISM: Artificial sequence
<220> FEATURE:
<223> OTHER INFORMATION: CPP

<400> SEQUENCE: 976

Met His Lys Arg Pro Thr Thr Pro Ser Arg Lys Met
1               5                   10

<210> SEQ ID NO 977
<211> LENGTH: 12
<212> TYPE: PRT
<213> ORGANISM: Artificial sequence
<220> FEATURE:
<223> OTHER INFORMATION: CPP

<400> SEQUENCE: 977

Arg Gln Arg Ser Arg Arg Arg Pro Leu Asn Ile Arg
1               5                   10

<210> SEQ ID NO 978
<211> LENGTH: 12
<212> TYPE: PRT
<213> ORGANISM: Artificial sequence
<220> FEATURE:
<223> OTHER INFORMATION: CPP

<400> SEQUENCE: 978

Arg Ile Arg Met Ile Gln Asn Leu Ile Lys Lys Thr
1               5                   10

<210> SEQ ID NO 979
<211> LENGTH: 12
<212> TYPE: PRT
<213> ORGANISM: Artificial sequence
<220> FEATURE:
<223> OTHER INFORMATION: CPP

<400> SEQUENCE: 979

Ser Arg Arg Lys Arg Gln Arg Ser Asn Met Arg Ile
1               5                   10

<210> SEQ ID NO 980
<211> LENGTH: 12
<212> TYPE: PRT
<213> ORGANISM: Artificial sequence
<220> FEATURE:
<223> OTHER INFORMATION: CPP

<400> SEQUENCE: 980

Gln Arg Ile Arg Lys Ser Lys Ile Ser Arg Thr Leu
1               5                   10
```

```
<210> SEQ ID NO 981
<211> LENGTH: 12
<212> TYPE: PRT
<213> ORGANISM: Artificial sequence
<220> FEATURE:
<223> OTHER INFORMATION: CPP

<400> SEQUENCE: 981

Pro Ser Lys Arg Leu Leu His Asn Asn Leu Arg Arg
1               5                   10

<210> SEQ ID NO 982
<211> LENGTH: 12
<212> TYPE: PRT
<213> ORGANISM: Artificial sequence
<220> FEATURE:
<223> OTHER INFORMATION: CPP

<400> SEQUENCE: 982

His Arg His Ile Arg Arg Gln Ser Leu Ile Met Leu
1               5                   10

<210> SEQ ID NO 983
<211> LENGTH: 12
<212> TYPE: PRT
<213> ORGANISM: Artificial sequence
<220> FEATURE:
<223> OTHER INFORMATION: CPP

<400> SEQUENCE: 983

Pro Gln Asn Arg Leu Gln Ile Arg Arg His Ser Lys
1               5                   10

<210> SEQ ID NO 984
<211> LENGTH: 12
<212> TYPE: PRT
<213> ORGANISM: Artificial sequence
<220> FEATURE:
<223> OTHER INFORMATION: CPP

<400> SEQUENCE: 984

Pro Pro His Asn Arg Ile Gln Arg Arg Leu Asn Met
1               5                   10

<210> SEQ ID NO 985
<211> LENGTH: 12
<212> TYPE: PRT
<213> ORGANISM: Artificial sequence
<220> FEATURE:
<223> OTHER INFORMATION: CPP

<400> SEQUENCE: 985

Ser Met Leu Lys Arg Asn His Ser Thr Ser Asn Arg
1               5                   10

<210> SEQ ID NO 986
<211> LENGTH: 12
<212> TYPE: PRT
<213> ORGANISM: Artificial sequence
<220> FEATURE:
<223> OTHER INFORMATION: CPP

<400> SEQUENCE: 986

Gly Ser Arg His Pro Ser Leu Ile Ile Pro Arg Gln
1               5                   10
```

<210> SEQ ID NO 987
<211> LENGTH: 12
<212> TYPE: PRT
<213> ORGANISM: Artificial sequence
<220> FEATURE:
<223> OTHER INFORMATION: CPP

<400> SEQUENCE: 987

Ser Pro Met Gln Lys Thr Met Asn Leu Pro Pro Met
1               5                   10

<210> SEQ ID NO 988
<211> LENGTH: 12
<212> TYPE: PRT
<213> ORGANISM: Artificial sequence
<220> FEATURE:
<223> OTHER INFORMATION: CPP

<400> SEQUENCE: 988

Asn Lys Arg Ile Leu Ile Arg Ile Met Thr Arg Pro
1               5                   10

<210> SEQ ID NO 989
<211> LENGTH: 12
<212> TYPE: PRT
<213> ORGANISM: Artificial sequence
<220> FEATURE:
<223> OTHER INFORMATION: CPP

<400> SEQUENCE: 989

His Gly Trp Glx Ile His Gly Leu Leu His Arg Ala
1               5                   10

<210> SEQ ID NO 990
<211> LENGTH: 11
<212> TYPE: PRT
<213> ORGANISM: Artificial sequence
<220> FEATURE:
<223> OTHER INFORMATION: CPP

<400> SEQUENCE: 990

Ala Val Pro Ala Lys Lys Arg Glx Lys Ser Val
1               5                   10

<210> SEQ ID NO 991
<211> LENGTH: 11
<212> TYPE: PRT
<213> ORGANISM: Artificial sequence
<220> FEATURE:
<223> OTHER INFORMATION: CPP

<400> SEQUENCE: 991

Pro Asn Thr Arg Val Arg Pro Asp Val Ser Phe
1               5                   10

<210> SEQ ID NO 992
<211> LENGTH: 12
<212> TYPE: PRT
<213> ORGANISM: Artificial sequence
<220> FEATURE:
<223> OTHER INFORMATION: CPP

<400> SEQUENCE: 992

Leu Thr Arg Asn Tyr Glu Ala Trp Val Pro Thr Pro
1               5                   10

```
<210> SEQ ID NO 993
<211> LENGTH: 13
<212> TYPE: PRT
<213> ORGANISM: Artificial sequence
<220> FEATURE:
<223> OTHER INFORMATION: CPP

<400> SEQUENCE: 993

Ser Ala Glu Thr Val Glu Ser Cys Leu Ala Lys Ser His
1               5                   10

<210> SEQ ID NO 994
<211> LENGTH: 12
<212> TYPE: PRT
<213> ORGANISM: Artificial sequence
<220> FEATURE:
<223> OTHER INFORMATION: CPP

<400> SEQUENCE: 994

Tyr Ser His Ile Ala Thr Leu Pro Phe Thr Pro Thr
1               5                   10

<210> SEQ ID NO 995
<211> LENGTH: 12
<212> TYPE: PRT
<213> ORGANISM: Artificial sequence
<220> FEATURE:
<223> OTHER INFORMATION: CPP

<400> SEQUENCE: 995

Ser Tyr Ile Gln Arg Thr Pro Ser Thr Thr Leu Pro
1               5                   10

<210> SEQ ID NO 996
<211> LENGTH: 12
<212> TYPE: PRT
<213> ORGANISM: Artificial sequence
<220> FEATURE:
<223> OTHER INFORMATION: CPP

<400> SEQUENCE: 996

Ala Val Pro Ala Glu Asn Ala Leu Asn Asn Pro Phe
1               5                   10

<210> SEQ ID NO 997
<211> LENGTH: 12
<212> TYPE: PRT
<213> ORGANISM: Artificial sequence
<220> FEATURE:
<223> OTHER INFORMATION: CPP

<400> SEQUENCE: 997

Ser Phe His Gln Phe Ala Arg Ala Thr Leu Ala Ser
1               5                   10

<210> SEQ ID NO 998
<211> LENGTH: 12
<212> TYPE: PRT
<213> ORGANISM: Artificial sequence
<220> FEATURE:
<223> OTHER INFORMATION: CPP

<400> SEQUENCE: 998

Gln Ser Pro Thr Asp Phe Thr Phe Pro Asn Pro Leu
1               5                   10

<210> SEQ ID NO 999
```

```
<211> LENGTH: 12
<212> TYPE: PRT
<213> ORGANISM: Artificial sequence
<220> FEATURE:
<223> OTHER INFORMATION: CPP

<400> SEQUENCE: 999

His Phe Ala Ala Trp Gly Gly Trp Ser Leu Val His
1               5                   10

<210> SEQ ID NO 1000
<211> LENGTH: 12
<212> TYPE: PRT
<213> ORGANISM: Artificial sequence
<220> FEATURE:
<223> OTHER INFORMATION: CPP

<400> SEQUENCE: 1000

His Ile Gln Leu Ser Pro Phe Ser Gln Ser Trp Arg
1               5                   10

<210> SEQ ID NO 1001
<211> LENGTH: 12
<212> TYPE: PRT
<213> ORGANISM: Artificial sequence
<220> FEATURE:
<223> OTHER INFORMATION: CPP

<400> SEQUENCE: 1001

Leu Thr Met Pro Ser Asp Leu Gln Pro Val Leu Trp
1               5                   10

<210> SEQ ID NO 1002
<211> LENGTH: 12
<212> TYPE: PRT
<213> ORGANISM: Artificial sequence
<220> FEATURE:
<223> OTHER INFORMATION: CPP

<400> SEQUENCE: 1002

Phe Gln Pro Tyr Asp His Pro Ala Glu Val Ser Tyr
1               5                   10

<210> SEQ ID NO 1003
<211> LENGTH: 12
<212> TYPE: PRT
<213> ORGANISM: Artificial sequence
<220> FEATURE:
<223> OTHER INFORMATION: CPP

<400> SEQUENCE: 1003

Phe Asp Pro Phe Phe Trp Lys Tyr Ser Pro Arg Asp
1               5                   10

<210> SEQ ID NO 1004
<211> LENGTH: 12
<212> TYPE: PRT
<213> ORGANISM: Artificial sequence
<220> FEATURE:
<223> OTHER INFORMATION: CPP

<400> SEQUENCE: 1004

Phe Ala Pro Trp Asp Thr Ala Ser Phe Met Leu Gly
1               5                   10

<210> SEQ ID NO 1005
<211> LENGTH: 12
```

```
<212> TYPE: PRT
<213> ORGANISM: Artificial sequence
<220> FEATURE:
<223> OTHER INFORMATION: CPP

<400> SEQUENCE: 1005

Phe Thr Tyr Lys Asn Phe Phe Trp Leu Pro Glu Leu
1               5                   10

<210> SEQ ID NO 1006
<211> LENGTH: 12
<212> TYPE: PRT
<213> ORGANISM: Artificial sequence
<220> FEATURE:
<223> OTHER INFORMATION: CPP

<400> SEQUENCE: 1006

Ser Ala Thr Gly Ala Pro Trp Lys Met Trp Val Arg
1               5                   10

<210> SEQ ID NO 1007
<211> LENGTH: 12
<212> TYPE: PRT
<213> ORGANISM: Artificial sequence
<220> FEATURE:
<223> OTHER INFORMATION: CPP

<400> SEQUENCE: 1007

Ser Leu Gly Trp Met Leu Pro Phe Ser Pro Pro Phe
1               5                   10

<210> SEQ ID NO 1008
<211> LENGTH: 12
<212> TYPE: PRT
<213> ORGANISM: Artificial sequence
<220> FEATURE:
<223> OTHER INFORMATION: CPP

<400> SEQUENCE: 1008

Ser His Ala Phe Thr Trp Pro Thr Tyr Leu Gln Leu
1               5                   10

<210> SEQ ID NO 1009
<211> LENGTH: 12
<212> TYPE: PRT
<213> ORGANISM: Artificial sequence
<220> FEATURE:
<223> OTHER INFORMATION: CPP

<400> SEQUENCE: 1009

Ser His Asn Trp Leu Pro Leu Trp Pro Leu Arg Pro
1               5                   10

<210> SEQ ID NO 1010
<211> LENGTH: 12
<212> TYPE: PRT
<213> ORGANISM: Artificial sequence
<220> FEATURE:
<223> OTHER INFORMATION: CPP

<400> SEQUENCE: 1010

Ser Trp Leu Pro Tyr Pro Trp His Val Pro Ser Ser
1               5                   10

<210> SEQ ID NO 1011
<211> LENGTH: 12
<212> TYPE: PRT
```

```
<213> ORGANISM: Artificial sequence
<220> FEATURE:
<223> OTHER INFORMATION: CPP

<400> SEQUENCE: 1011

Ser Trp Trp Thr Pro Trp His Val His Ser Glu Ser
1               5                   10

<210> SEQ ID NO 1012
<211> LENGTH: 12
<212> TYPE: PRT
<213> ORGANISM: Artificial sequence
<220> FEATURE:
<223> OTHER INFORMATION: CPP

<400> SEQUENCE: 1012

Ser Trp Ala Gln His Leu Ser Leu Pro Pro Val Leu
1               5                   10

<210> SEQ ID NO 1013
<211> LENGTH: 12
<212> TYPE: PRT
<213> ORGANISM: Artificial sequence
<220> FEATURE:
<223> OTHER INFORMATION: CPP

<400> SEQUENCE: 1013

Ser Ser Ser Ile Phe Pro Pro Trp Leu Ser Phe Phe
1               5                   10

<210> SEQ ID NO 1014
<211> LENGTH: 12
<212> TYPE: PRT
<213> ORGANISM: Artificial sequence
<220> FEATURE:
<223> OTHER INFORMATION: CPP

<400> SEQUENCE: 1014

Leu Asn Val Pro Pro Ser Trp Phe Leu Ser Gln Arg
1               5                   10

<210> SEQ ID NO 1015
<211> LENGTH: 12
<212> TYPE: PRT
<213> ORGANISM: Artificial sequence
<220> FEATURE:
<223> OTHER INFORMATION: CPP

<400> SEQUENCE: 1015

Leu Asp Ile Thr Pro Phe Leu Ser Leu Thr Leu Pro
1               5                   10

<210> SEQ ID NO 1016
<211> LENGTH: 12
<212> TYPE: PRT
<213> ORGANISM: Artificial sequence
<220> FEATURE:
<223> OTHER INFORMATION: CPP

<400> SEQUENCE: 1016

Leu Pro His Pro Val Leu His Met Gly Pro Leu Arg
1               5                   10

<210> SEQ ID NO 1017
<211> LENGTH: 12
<212> TYPE: PRT
<213> ORGANISM: Artificial sequence
```

```
<220> FEATURE:
<223> OTHER INFORMATION: CPP

<400> SEQUENCE: 1017

Val Ser Lys Gln Pro Tyr Tyr Met Trp Asn Gly Asn
1               5                   10

<210> SEQ ID NO 1018
<211> LENGTH: 12
<212> TYPE: PRT
<213> ORGANISM: Artificial sequence
<220> FEATURE:
<223> OTHER INFORMATION: CPP

<400> SEQUENCE: 1018

Asn Tyr Thr Thr Tyr Lys Ser His Phe Gln Asp Arg
1               5                   10

<210> SEQ ID NO 1019
<211> LENGTH: 12
<212> TYPE: PRT
<213> ORGANISM: Artificial sequence
<220> FEATURE:
<223> OTHER INFORMATION: CPP

<400> SEQUENCE: 1019

Ala Ile Pro Asn Asn Gln Leu Gly Phe Pro Phe Lys
1               5                   10

<210> SEQ ID NO 1020
<211> LENGTH: 12
<212> TYPE: PRT
<213> ORGANISM: Artificial sequence
<220> FEATURE:
<223> OTHER INFORMATION: CPP

<400> SEQUENCE: 1020

Asn Ile Glu Asn Ser Thr Leu Ala Thr Pro Leu Ser
1               5                   10

<210> SEQ ID NO 1021
<211> LENGTH: 12
<212> TYPE: PRT
<213> ORGANISM: Artificial sequence
<220> FEATURE:
<223> OTHER INFORMATION: CPP

<400> SEQUENCE: 1021

Tyr Pro Tyr Asp Ala Asn His Thr Arg Ser Pro Thr
1               5                   10

<210> SEQ ID NO 1022
<211> LENGTH: 12
<212> TYPE: PRT
<213> ORGANISM: Artificial sequence
<220> FEATURE:
<223> OTHER INFORMATION: CPP

<400> SEQUENCE: 1022

Asp Pro Ala Thr Asn Pro Gly Pro His Phe Pro Arg
1               5                   10

<210> SEQ ID NO 1023
<211> LENGTH: 12
<212> TYPE: PRT
<213> ORGANISM: Artificial sequence
<220> FEATURE:
```

```
<223> OTHER INFORMATION: CPP

<400> SEQUENCE: 1023

Thr Leu Pro Ser Pro Leu Ala Leu Leu Thr Val His
1               5                   10

<210> SEQ ID NO 1024
<211> LENGTH: 12
<212> TYPE: PRT
<213> ORGANISM: Artificial sequence
<220> FEATURE:
<223> OTHER INFORMATION: CPP

<400> SEQUENCE: 1024

His Pro Gly Ser Pro Phe Pro Pro Glu His Arg Pro
1               5                   10

<210> SEQ ID NO 1025
<211> LENGTH: 12
<212> TYPE: PRT
<213> ORGANISM: Artificial sequence
<220> FEATURE:
<223> OTHER INFORMATION: CPP

<400> SEQUENCE: 1025

Thr Ser His Thr Asp Ala Pro Pro Ala Arg Ser Pro
1               5                   10

<210> SEQ ID NO 1026
<211> LENGTH: 12
<212> TYPE: PRT
<213> ORGANISM: Artificial sequence
<220> FEATURE:
<223> OTHER INFORMATION: CPP

<400> SEQUENCE: 1026

Met Thr Pro Ser Ser Leu Ser Thr Leu Pro Trp Pro
1               5                   10

<210> SEQ ID NO 1027
<211> LENGTH: 12
<212> TYPE: PRT
<213> ORGANISM: Artificial sequence
<220> FEATURE:
<223> OTHER INFORMATION: CPP

<400> SEQUENCE: 1027

Val Leu Gly Gln Ser Gly Tyr Leu Met Pro Met Arg
1               5                   10

<210> SEQ ID NO 1028
<211> LENGTH: 12
<212> TYPE: PRT
<213> ORGANISM: Artificial sequence
<220> FEATURE:
<223> OTHER INFORMATION: CPP

<400> SEQUENCE: 1028

Gln Pro Ile Ile Ile Thr Ser Pro Tyr Leu Pro Ser
1               5                   10

<210> SEQ ID NO 1029
<211> LENGTH: 12
<212> TYPE: PRT
<213> ORGANISM: Artificial sequence
<220> FEATURE:
<223> OTHER INFORMATION: CPP
```

<400> SEQUENCE: 1029

Thr Pro Lys Thr Met Thr Gln Thr Tyr Asp Phe Ser
1               5                   10

<210> SEQ ID NO 1030
<211> LENGTH: 12
<212> TYPE: PRT
<213> ORGANISM: Artificial sequence
<220> FEATURE:
<223> OTHER INFORMATION: CPP

<400> SEQUENCE: 1030

Asn Ser Gly Thr Met Gln Ser Ala Ser Arg Ala Thr
1               5                   10

<210> SEQ ID NO 1031
<211> LENGTH: 12
<212> TYPE: PRT
<213> ORGANISM: Artificial sequence
<220> FEATURE:
<223> OTHER INFORMATION: CPP

<400> SEQUENCE: 1031

Gln Ala Ala Ser Arg Val Glu Asn Tyr Met His Arg
1               5                   10

<210> SEQ ID NO 1032
<211> LENGTH: 12
<212> TYPE: PRT
<213> ORGANISM: Artificial sequence
<220> FEATURE:
<223> OTHER INFORMATION: CPP

<400> SEQUENCE: 1032

His Gln His Lys Pro Pro Leu Thr Asn Asn Trp
1               5                   10

<210> SEQ ID NO 1033
<211> LENGTH: 12
<212> TYPE: PRT
<213> ORGANISM: Artificial sequence
<220> FEATURE:
<223> OTHER INFORMATION: CPP

<400> SEQUENCE: 1033

Ser Asn Pro Trp Asp Ser Leu Leu Ser Val Ser Thr
1               5                   10

<210> SEQ ID NO 1034
<211> LENGTH: 12
<212> TYPE: PRT
<213> ORGANISM: Artificial sequence
<220> FEATURE:
<223> OTHER INFORMATION: CPP

<400> SEQUENCE: 1034

Lys Thr Ile Glu Ala His Pro Pro Tyr Tyr Ala Ser
1               5                   10

<210> SEQ ID NO 1035
<211> LENGTH: 12
<212> TYPE: PRT
<213> ORGANISM: Artificial sequence
<220> FEATURE:
<223> OTHER INFORMATION: CPP

```
<400> SEQUENCE: 1035

Glu Pro Asp Asn Trp Ser Leu Asp Phe Pro Arg Arg
1               5                   10

<210> SEQ ID NO 1036
<211> LENGTH: 12
<212> TYPE: PRT
<213> ORGANISM: Artificial sequence
<220> FEATURE:
<223> OTHER INFORMATION: CPP

<400> SEQUENCE: 1036

His Gln His Lys Pro Pro Pro Leu Thr Asn Asn Trp
1               5                   10

<210> SEQ ID NO 1037
<211> LENGTH: 20
<212> TYPE: PRT
<213> ORGANISM: Artificial sequence
<220> FEATURE:
<223> OTHER INFORMATION: CPP

<400> SEQUENCE: 1037

Gly Leu Trp Arg Ala Leu Trp Arg Leu Leu Arg Ser Leu Trp Arg Leu
1               5                   10                  15

Leu Trp Lys Ala
            20

<210> SEQ ID NO 1038
<211> LENGTH: 21
<212> TYPE: PRT
<213> ORGANISM: Artificial sequence
<220> FEATURE:
<223> OTHER INFORMATION: CPP

<400> SEQUENCE: 1038

Gly Leu Trp Arg Ala Leu Trp Arg Ala Leu Trp Arg Ser Leu Trp Lys
1               5                   10                  15

Leu Lys Arg Lys Val
            20

<210> SEQ ID NO 1039
<211> LENGTH: 20
<212> TYPE: PRT
<213> ORGANISM: Artificial sequence
<220> FEATURE:
<223> OTHER INFORMATION: CPP

<400> SEQUENCE: 1039

Gly Leu Trp Arg Ala Leu Trp Arg Ala Leu Arg Ser Leu Trp Lys Leu
1               5                   10                  15

Lys Arg Lys Val
            20

<210> SEQ ID NO 1040
<211> LENGTH: 20
<212> TYPE: PRT
<213> ORGANISM: Artificial sequence
<220> FEATURE:
<223> OTHER INFORMATION: CPP

<400> SEQUENCE: 1040

Gly Leu Trp Arg Ala Leu Trp Arg Gly Leu Arg Ser Leu Trp Lys Leu
1               5                   10                  15
```

Lys Arg Lys Val
        20

<210> SEQ ID NO 1041
<211> LENGTH: 20
<212> TYPE: PRT
<213> ORGANISM: Artificial sequence
<220> FEATURE:
<223> OTHER INFORMATION: CPP

<400> SEQUENCE: 1041

Gly Leu Trp Arg Ala Leu Trp Arg Gly Leu Arg Ser Leu Trp Lys Lys
1               5                   10                  15

Lys Arg Lys Val
        20

<210> SEQ ID NO 1042
<211> LENGTH: 21
<212> TYPE: PRT
<213> ORGANISM: Artificial sequence
<220> FEATURE:
<223> OTHER INFORMATION: CPP

<400> SEQUENCE: 1042

Gly Leu Trp Arg Ala Leu Trp Arg Ala Leu Trp Arg Ser Leu Trp Lys
1               5                   10                  15

Leu Lys Trp Lys Val
        20

<210> SEQ ID NO 1043
<211> LENGTH: 21
<212> TYPE: PRT
<213> ORGANISM: Artificial sequence
<220> FEATURE:
<223> OTHER INFORMATION: CPP

<400> SEQUENCE: 1043

Gly Leu Trp Arg Ala Leu Trp Arg Ala Leu Trp Arg Ser Leu Trp Lys
1               5                   10                  15

Ser Lys Arg Lys Val
        20

<210> SEQ ID NO 1044
<211> LENGTH: 21
<212> TYPE: PRT
<213> ORGANISM: Artificial sequence
<220> FEATURE:
<223> OTHER INFORMATION: CPP

<400> SEQUENCE: 1044

Gly Leu Trp Arg Ala Leu Trp Arg Ala Leu Trp Arg Ser Leu Trp Lys
1               5                   10                  15

Lys Lys Arg Lys Val
        20

<210> SEQ ID NO 1045
<211> LENGTH: 21
<212> TYPE: PRT
<213> ORGANISM: Artificial sequence
<220> FEATURE:
<223> OTHER INFORMATION: CPP

<400> SEQUENCE: 1045

Gly Leu Trp Arg Ala Leu Trp Arg Ala Leu Trp Arg Ser Leu Trp Lys
1               5                   10                  15

Leu Lys Arg Lys Val
        20

<210> SEQ ID NO 1046
<211> LENGTH: 27
<212> TYPE: PRT
<213> ORGANISM: Artificial sequence
<220> FEATURE:
<223> OTHER INFORMATION: CPP

<400> SEQUENCE: 1046

Gly Leu Trp Arg Ala Leu Trp Arg Leu Leu Arg Ser Leu Trp Arg Leu
1               5                   10                  15

Leu Trp Ser Gln Pro Lys Lys Arg Lys Val
            20                  25

<210> SEQ ID NO 1047
<211> LENGTH: 11
<212> TYPE: PRT
<213> ORGANISM: Artificial sequence
<220> FEATURE:
<223> OTHER INFORMATION: CPP

<400> SEQUENCE: 1047

Tyr Ala Arg Ala Ala Arg Arg Ala Ala Arg Arg
1               5                   10

<210> SEQ ID NO 1048
<211> LENGTH: 11
<212> TYPE: PRT
<213> ORGANISM: Artificial sequence
<220> FEATURE:
<223> OTHER INFORMATION: CPP

<400> SEQUENCE: 1048

Pro Ala Arg Ala Ala Arg Arg Ala Ala Arg Arg
1               5                   10

<210> SEQ ID NO 1049
<211> LENGTH: 11
<212> TYPE: PRT
<213> ORGANISM: Artificial sequence
<220> FEATURE:
<223> OTHER INFORMATION: CPP

<400> SEQUENCE: 1049

Tyr Pro Arg Ala Ala Arg Arg Ala Ala Arg Arg
1               5                   10

<210> SEQ ID NO 1050
<211> LENGTH: 11
<212> TYPE: PRT
<213> ORGANISM: Artificial sequence
<220> FEATURE:
<223> OTHER INFORMATION: CPP

<400> SEQUENCE: 1050

Tyr Arg Arg Ala Ala Arg Arg Ala Ala Arg Ala
1               5                   10

<210> SEQ ID NO 1051
<211> LENGTH: 11
<212> TYPE: PRT
<213> ORGANISM: Artificial sequence
<220> FEATURE:
<223> OTHER INFORMATION: CPP

<400> SEQUENCE: 1051

Tyr Gly Arg Ala Ala Arg Arg Ala Ala Arg Arg
1               5                   10

<210> SEQ ID NO 1052
<211> LENGTH: 11
<212> TYPE: PRT
<213> ORGANISM: Artificial sequence
<220> FEATURE:
<223> OTHER INFORMATION: CPP

<400> SEQUENCE: 1052

Tyr Ala Arg Glu Ala Arg Arg Ala Ala Arg Arg
1               5                   10

<210> SEQ ID NO 1053
<211> LENGTH: 11
<212> TYPE: PRT
<213> ORGANISM: Artificial sequence
<220> FEATURE:
<223> OTHER INFORMATION: CPP

<400> SEQUENCE: 1053

Tyr Glu Arg Glu Ala Arg Arg Ala Ala Arg Arg
1               5                   10

<210> SEQ ID NO 1054
<211> LENGTH: 11
<212> TYPE: PRT
<213> ORGANISM: Artificial sequence
<220> FEATURE:
<223> OTHER INFORMATION: CPP

<400> SEQUENCE: 1054

Tyr Lys Arg Ala Ala Arg Arg Ala Ala Arg Arg
1               5                   10

<210> SEQ ID NO 1055
<211> LENGTH: 11
<212> TYPE: PRT
<213> ORGANISM: Artificial sequence
<220> FEATURE:
<223> OTHER INFORMATION: CPP

<400> SEQUENCE: 1055

Tyr Ala Arg Lys Ala Arg Arg Ala Ala Arg Arg
1               5                   10

<210> SEQ ID NO 1056
<211> LENGTH: 11
<212> TYPE: PRT
<213> ORGANISM: Artificial sequence
<220> FEATURE:
<223> OTHER INFORMATION: CPP

<400> SEQUENCE: 1056

Tyr Lys Arg Lys Ala Arg Arg Ala Ala Arg Arg
1               5                   10

<210> SEQ ID NO 1057
<211> LENGTH: 11
<212> TYPE: PRT
<213> ORGANISM: Artificial sequence
<220> FEATURE:
<223> OTHER INFORMATION: CPP

<400> SEQUENCE: 1057

Tyr Gly Arg Arg Ala Arg Arg Ala Ala Arg Arg
1               5                   10

<210> SEQ ID NO 1058
<211> LENGTH: 11
<212> TYPE: PRT
<213> ORGANISM: Artificial sequence
<220> FEATURE:
<223> OTHER INFORMATION: CPP

<400> SEQUENCE: 1058

Tyr Gly Arg Arg Ala Arg Arg Arg Ala Arg Arg
1               5                   10

<210> SEQ ID NO 1059
<211> LENGTH: 11
<212> TYPE: PRT
<213> ORGANISM: Artificial sequence
<220> FEATURE:
<223> OTHER INFORMATION: CPP

<400> SEQUENCE: 1059

Tyr Gly Arg Arg Ala Arg Arg Arg Arg Arg Arg
1               5                   10

<210> SEQ ID NO 1060
<211> LENGTH: 11
<212> TYPE: PRT
<213> ORGANISM: Artificial sequence
<220> FEATURE:
<223> OTHER INFORMATION: CPP

<400> SEQUENCE: 1060

Tyr Gly Arg Arg Arg Arg Arg Arg Arg Arg Arg
1               5                   10

<210> SEQ ID NO 1061
<211> LENGTH: 11
<212> TYPE: PRT
<213> ORGANISM: Artificial sequence
<220> FEATURE:
<223> OTHER INFORMATION: CPP

<400> SEQUENCE: 1061

Tyr Arg Arg Arg Arg Arg Arg Arg Arg Arg Arg
1               5                   10

<210> SEQ ID NO 1062
<211> LENGTH: 16
<212> TYPE: PRT
<213> ORGANISM: Artificial sequence
<220> FEATURE:
<223> OTHER INFORMATION: CPP

<400> SEQUENCE: 1062

Gly Lys Ile Asn Leu Lys Ala Leu Ala Ala Leu Ala Lys Lys Ile Leu
1               5                   10                  15

<210> SEQ ID NO 1063
<211> LENGTH: 16
<212> TYPE: PRT
<213> ORGANISM: Artificial sequence
<220> FEATURE:
<223> OTHER INFORMATION: CPP

<400> SEQUENCE: 1063

```
Arg Val Ile Arg Val Trp Phe Gln Asn Lys Arg Cys Lys Asp Lys Lys
1               5                   10                  15
```

<210> SEQ ID NO 1064
<211> LENGTH: 39
<212> TYPE: PRT
<213> ORGANISM: Artificial sequence
<220> FEATURE:
<223> OTHER INFORMATION: CPP

<400> SEQUENCE: 1064

```
Gly Arg Lys Lys Arg Arg Gln Arg Arg Pro Pro Gln Gly Arg Lys
1               5                   10                  15

Lys Arg Arg Gln Arg Arg Pro Pro Gln Gly Arg Lys Lys Arg Arg
                20                  25                  30

Gln Arg Arg Arg Pro Pro Gln
            35
```

<210> SEQ ID NO 1065
<211> LENGTH: 22
<212> TYPE: PRT
<213> ORGANISM: Artificial sequence
<220> FEATURE:
<223> OTHER INFORMATION: CPP

<400> SEQUENCE: 1065

```
Gly Glu Gln Ile Ala Gln Leu Ile Ala Gly Tyr Ile Asp Ile Ile Leu
1               5                   10                  15

Lys Lys Lys Lys Ser Lys
            20
```

<210> SEQ ID NO 1066
<211> LENGTH: 14
<212> TYPE: PRT
<213> ORGANISM: Artificial sequence
<220> FEATURE:
<223> OTHER INFORMATION: CPP

<400> SEQUENCE: 1066

```
Gly Arg Lys Lys Arg Arg Gln Arg Arg Pro Pro Gln Cys
1               5                   10
```

<210> SEQ ID NO 1067
<211> LENGTH: 28
<212> TYPE: PRT
<213> ORGANISM: Artificial sequence
<220> FEATURE:
<223> OTHER INFORMATION: CPP

<400> SEQUENCE: 1067

```
Ala Ala Val Ala Leu Leu Pro Ala Val Leu Leu Ala Leu Leu Ala Pro
1               5                   10                  15

Arg Lys Lys Arg Arg Gln Arg Arg Arg Pro Pro Gln
                20                  25
```

<210> SEQ ID NO 1068
<211> LENGTH: 29
<212> TYPE: PRT
<213> ORGANISM: Artificial sequence
<220> FEATURE:
<223> OTHER INFORMATION: CPP

<400> SEQUENCE: 1068

```
Ala Ala Val Ala Leu Leu Pro Ala Val Leu Leu Ala Leu Leu Ala Pro
```

```
                1               5                   10                  15
Arg Lys Lys Arg Arg Gln Arg Arg Arg Pro Pro Gln Cys
            20                  25
```

<210> SEQ ID NO 1069
<211> LENGTH: 28
<212> TYPE: PRT
<213> ORGANISM: Artificial sequence
<220> FEATURE:
<223> OTHER INFORMATION: CPP

<400> SEQUENCE: 1069

```
Ala Ala Val Ala Leu Leu Pro Ala Val Leu Leu Ala Leu Leu Ala Pro
1               5                   10                  15
Arg Lys Lys Arg Arg Gln Arg Arg Arg Pro Pro Gln
            20                  25
```

<210> SEQ ID NO 1070
<211> LENGTH: 29
<212> TYPE: PRT
<213> ORGANISM: Artificial sequence
<220> FEATURE:
<223> OTHER INFORMATION: CPP

<400> SEQUENCE: 1070

```
Arg Lys Lys Arg Arg Gln Arg Arg Arg Pro Pro Gln Cys Ala Ala Val
1               5                   10                  15
Ala Leu Leu Pro Ala Val Leu Leu Ala Leu Leu Ala Pro
            20                  25
```

<210> SEQ ID NO 1071
<211> LENGTH: 29
<212> TYPE: PRT
<213> ORGANISM: Artificial sequence
<220> FEATURE:
<223> OTHER INFORMATION: CPP

<400> SEQUENCE: 1071

```
Arg Arg Arg Gln Arg Arg Lys Arg Gly Gly Asp Ile Met Gly Glu Trp
1               5                   10                  15
Gly Asn Glu Ile Phe Gly Ala Ile Ala Gly Phe Leu Gly
            20                  25
```

<210> SEQ ID NO 1072
<211> LENGTH: 29
<212> TYPE: PRT
<213> ORGANISM: Artificial sequence
<220> FEATURE:
<223> OTHER INFORMATION: CPP

<400> SEQUENCE: 1072

```
Arg Arg Arg Gln Arg Arg Lys Arg Gly Gly Asp Ile Met Gly Glu Trp
1               5                   10                  15
Gly Asn Glu Ile Phe Gly Ala Ile Ala Gly Phe Leu Gly
            20                  25
```

<210> SEQ ID NO 1073
<211> LENGTH: 25
<212> TYPE: PRT
<213> ORGANISM: Artificial sequence
<220> FEATURE:
<223> OTHER INFORMATION: CPP

<400> SEQUENCE: 1073

```
Tyr Gly Arg Lys Lys Arg Arg Gln Arg Arg Gly Cys Tyr Gly Arg
1               5                   10                  15

Lys Lys Arg Arg Gln Arg Arg Gly
            20                  25
```

<210> SEQ ID NO 1074
<211> LENGTH: 13
<212> TYPE: PRT
<213> ORGANISM: Artificial sequence
<220> FEATURE:
<223> OTHER INFORMATION: CPP

<400> SEQUENCE: 1074

```
Gly Arg Lys Lys Arg Arg Gln Arg Arg Pro Pro Gln
1               5                   10
```

<210> SEQ ID NO 1075
<211> LENGTH: 22
<212> TYPE: PRT
<213> ORGANISM: Artificial sequence
<220> FEATURE:
<223> OTHER INFORMATION: CPP

<400> SEQUENCE: 1075

```
Ala Ala Val Ala Leu Leu Pro Ala Val Leu Leu Ala Leu Leu Ala Pro
1               5                   10                  15

Arg Arg Arg Arg Arg Arg
            20
```

<210> SEQ ID NO 1076
<211> LENGTH: 16
<212> TYPE: PRT
<213> ORGANISM: Artificial sequence
<220> FEATURE:
<223> OTHER INFORMATION: CPP

<400> SEQUENCE: 1076

```
Arg Leu Trp Arg Ala Leu Pro Arg Val Leu Arg Arg Leu Leu Arg Pro
1               5                   10                  15
```

<210> SEQ ID NO 1077
<211> LENGTH: 28
<212> TYPE: PRT
<213> ORGANISM: Artificial sequence
<220> FEATURE:
<223> OTHER INFORMATION: CPP

<400> SEQUENCE: 1077

```
Ala Ala Val Ala Leu Leu Pro Ala Val Leu Leu Ala Leu Leu Ala Pro
1               5                   10                  15

Ser Gly Ala Ser Gly Leu Asp Lys Arg Asp Tyr Val
            20                  25
```

<210> SEQ ID NO 1078
<211> LENGTH: 33
<212> TYPE: PRT
<213> ORGANISM: Artificial sequence
<220> FEATURE:
<223> OTHER INFORMATION: CPP

<400> SEQUENCE: 1078

```
Leu Leu Glu Thr Leu Leu Lys Pro Phe Gln Cys Arg Ile Cys Met Arg
1               5                   10                  15

Asn Phe Ser Thr Arg Gln Ala Arg Arg Asn His Arg Arg Arg His Arg
            20                  25                  30
```

Arg

<210> SEQ ID NO 1079
<211> LENGTH: 27
<212> TYPE: PRT
<213> ORGANISM: Artificial sequence
<220> FEATURE:
<223> OTHER INFORMATION: CPP

<400> SEQUENCE: 1079

Ala Ala Val Ala Cys Arg Ile Cys Met Arg Asn Phe Ser Thr Arg Gln
1               5                   10                  15

Ala Arg Arg Asn His Arg Arg Arg His Arg Arg
            20                  25

<210> SEQ ID NO 1080
<211> LENGTH: 16
<212> TYPE: PRT
<213> ORGANISM: Artificial sequence
<220> FEATURE:
<223> OTHER INFORMATION: CPP

<400> SEQUENCE: 1080

Arg Gln Ile Lys Ile Trp Phe Gln Asn Arg Arg Met Lys Trp Lys Lys
1               5                   10                  15

<210> SEQ ID NO 1081
<211> LENGTH: 16
<212> TYPE: PRT
<213> ORGANISM: Artificial sequence
<220> FEATURE:
<223> OTHER INFORMATION: CPP

<400> SEQUENCE: 1081

Arg Gln Ile Lys Ile Trp Phe Gln Asn Arg Arg Met Lys Trp Lys Lys
1               5                   10                  15

<210> SEQ ID NO 1082
<211> LENGTH: 35
<212> TYPE: PRT
<213> ORGANISM: Artificial sequence
<220> FEATURE:
<223> OTHER INFORMATION: CPP

<400> SEQUENCE: 1082

Arg Gln Ile Lys Ile Trp Phe Gln Asn Arg Arg Met Lys Trp Lys Lys
1               5                   10                  15

Asp Ile Met Gly Glu Trp Gly Asn Glu Ile Phe Gly Ala Ile Ala Gly
            20                  25                  30

Phe Leu Gly
        35

<210> SEQ ID NO 1083
<211> LENGTH: 37
<212> TYPE: PRT
<213> ORGANISM: Artificial sequence
<220> FEATURE:
<223> OTHER INFORMATION: CPP

<400> SEQUENCE: 1083

Ser Gly Arg Gly Lys Gln Gly Gly Lys Ala Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly
        35

<210> SEQ ID NO 1084
<211> LENGTH: 38
<212> TYPE: PRT
<213> ORGANISM: Artificial sequence
<220> FEATURE:
<223> OTHER INFORMATION: CPP

<400> SEQUENCE: 1084

Ser Gly Arg Gly Lys Gln Gly Gly Lys Ala Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly Cys
        35

<210> SEQ ID NO 1085
<211> LENGTH: 25
<212> TYPE: PRT
<213> ORGANISM: Artificial sequence
<220> FEATURE:
<223> OTHER INFORMATION: CPP

<400> SEQUENCE: 1085

Lys Lys Asp Gly Lys Lys Arg Lys Arg Ser Arg Lys Glu Ser Tyr Ser
1               5                   10                  15

Val Tyr Val Tyr Lys Val Leu Lys Gln
            20                  25

<210> SEQ ID NO 1086
<211> LENGTH: 36
<212> TYPE: PRT
<213> ORGANISM: Artificial sequence
<220> FEATURE:
<223> OTHER INFORMATION: CPP

<400> SEQUENCE: 1086

Lys Gly Ser Lys Lys Ala Val Thr Lys Ala Gln Lys Lys Asp Gly Lys
1               5                   10                  15

Lys Arg Lys Arg Ser Arg Lys Glu Ser Tyr Ser Val Tyr Val Tyr Lys
            20                  25                  30

Val Leu Lys Gln
        35

<210> SEQ ID NO 1087
<211> LENGTH: 27
<212> TYPE: PRT
<213> ORGANISM: Artificial sequence
<220> FEATURE:
<223> OTHER INFORMATION: CPP

<400> SEQUENCE: 1087

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 1088
<211> LENGTH: 18
<212> TYPE: PRT
<213> ORGANISM: Artificial sequence

```
<220> FEATURE:
<223> OTHER INFORMATION: CPP

<400> SEQUENCE: 1088

Lys Leu Ala Leu Lys Leu Ala Leu Lys Ala Leu Lys Ala Ala Leu Lys
1               5                   10                  15

Leu Ala

<210> SEQ ID NO 1089
<211> LENGTH: 21
<212> TYPE: PRT
<213> ORGANISM: Artificial sequence
<220> FEATURE:
<223> OTHER INFORMATION: CPP

<400> SEQUENCE: 1089

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 1090
<211> LENGTH: 28
<212> TYPE: PRT
<213> ORGANISM: Artificial sequence
<220> FEATURE:
<223> OTHER INFORMATION: CPP

<400> SEQUENCE: 1090

Lys Glu Thr Trp Trp Glu Thr Trp Trp Thr Glu Trp Ser Gln Pro Gly
1               5                   10                  15

Arg Lys Lys Arg Arg Gln Arg Arg Pro Pro Gln
            20                  25

<210> SEQ ID NO 1091
<211> LENGTH: 15
<212> TYPE: PRT
<213> ORGANISM: Artificial sequence
<220> FEATURE:
<223> OTHER INFORMATION: CPP

<400> SEQUENCE: 1091

Arg Val Ile Arg Trp Phe Gln Asn Lys Arg Cys Lys Asp Lys Lys
1               5                   10                  15

<210> SEQ ID NO 1092
<211> LENGTH: 18
<212> TYPE: PRT
<213> ORGANISM: Artificial sequence
<220> FEATURE:
<223> OTHER INFORMATION: CPP

<400> SEQUENCE: 1092

Leu Gly Leu Leu Leu Arg His Leu Arg His His Ser Asn Leu Leu Ala
1               5                   10                  15

Asn Ile

<210> SEQ ID NO 1093
<211> LENGTH: 16
<212> TYPE: PRT
<213> ORGANISM: Artificial sequence
<220> FEATURE:
<223> OTHER INFORMATION: CPP

<400> SEQUENCE: 1093
```

```
Lys Leu Trp Ser Ala Trp Pro Ser Leu Trp Ser Ser Leu Trp Lys Pro
1               5                   10                  15
```

<210> SEQ ID NO 1094
<211> LENGTH: 22
<212> TYPE: PRT
<213> ORGANISM: Artificial sequence
<220> FEATURE:
<223> OTHER INFORMATION: CPP

<400> SEQUENCE: 1094

```
Gly Leu Gly Ser Leu Leu Lys Lys Ala Gly Lys Lys Leu Lys Gln Pro
1               5                   10                  15

Lys Ser Lys Arg Lys Val
            20
```

<210> SEQ ID NO 1095
<211> LENGTH: 12
<212> TYPE: PRT
<213> ORGANISM: Artificial sequence
<220> FEATURE:
<223> OTHER INFORMATION: CPP

<400> SEQUENCE: 1095

```
Phe Lys Gln Gln Gln Gln Gln Gln Gln Gln Gln Gln
1               5                   10
```

<210> SEQ ID NO 1096
<211> LENGTH: 4
<212> TYPE: PRT
<213> ORGANISM: Artificial sequence
<220> FEATURE:
<223> OTHER INFORMATION: CPP

<400> SEQUENCE: 1096

```
Tyr Arg Phe Lys
1
```

<210> SEQ ID NO 1097
<211> LENGTH: 13
<212> TYPE: PRT
<213> ORGANISM: Artificial sequence
<220> FEATURE:
<223> OTHER INFORMATION: CPP

<400> SEQUENCE: 1097

```
Tyr Arg Phe Lys Tyr Arg Phe Lys Tyr Arg Leu Phe Lys
1               5                   10
```

<210> SEQ ID NO 1098
<211> LENGTH: 10
<212> TYPE: PRT
<213> ORGANISM: Artificial sequence
<220> FEATURE:
<223> OTHER INFORMATION: CPP

<400> SEQUENCE: 1098

```
Trp Arg Phe Lys Lys Ser Lys Arg Lys Val
1               5                   10
```

<210> SEQ ID NO 1099
<211> LENGTH: 20
<212> TYPE: PRT
<213> ORGANISM: Artificial sequence
<220> FEATURE:
<223> OTHER INFORMATION: CPP

<400> SEQUENCE: 1099

Trp Arg Phe Lys Ala Ala Val Ala Leu Leu Pro Ala Val Leu Leu Ala
1               5                   10                  15

Leu Leu Ala Pro
            20

<210> SEQ ID NO 1100
<211> LENGTH: 8
<212> TYPE: PRT
<213> ORGANISM: Artificial sequence
<220> FEATURE:
<223> OTHER INFORMATION: CPP

<400> SEQUENCE: 1100

Trp Arg Phe Lys Trp Arg Phe Lys
1               5

<210> SEQ ID NO 1101
<211> LENGTH: 12
<212> TYPE: PRT
<213> ORGANISM: Artificial sequence
<220> FEATURE:
<223> OTHER INFORMATION: CPP

<400> SEQUENCE: 1101

Trp Arg Phe Lys Trp Arg Phe Lys Trp Arg Phe Lys
1               5                   10

<210> SEQ ID NO 1102
<211> LENGTH: 36
<212> TYPE: PRT
<213> ORGANISM: Artificial sequence
<220> FEATURE:
<223> OTHER INFORMATION: CPP

<400> SEQUENCE: 1102

Lys Gly Ser Lys Lys Ala Val Thr Lys Ala Gln Lys Lys Asp Gly Lys
1               5                   10                  15

Lys Arg Lys Arg Ser Arg Lys Glu Ser Tyr Ser Val Tyr Val Tyr Lys
                20                  25                  30

Val Leu Lys Gln
            35

<210> SEQ ID NO 1103
<211> LENGTH: 36
<212> TYPE: PRT
<213> ORGANISM: Artificial sequence
<220> FEATURE:
<223> OTHER INFORMATION: CPP

<400> SEQUENCE: 1103

Arg Gly Ser Arg Arg Ala Val Thr Arg Ala Gln Arg Arg Asp Gly Arg
1               5                   10                  15

Arg Arg Arg Arg Ser Arg Arg Glu Ser Tyr Ser Val Tyr Val Tyr Arg
                20                  25                  30

Val Leu Arg Gln
            35

<210> SEQ ID NO 1104
<211> LENGTH: 15
<212> TYPE: PRT
<213> ORGANISM: Artificial sequence
<220> FEATURE:

<223> OTHER INFORMATION: CPP

<400> SEQUENCE: 1104

Arg Val Ile Arg Trp Phe Gln Asn Lys Arg Ser Lys Asp Lys Lys
1               5                   10                  15

<210> SEQ ID NO 1105
<211> LENGTH: 27
<212> TYPE: PRT
<213> ORGANISM: Artificial sequence
<220> FEATURE:
<223> OTHER INFORMATION: CPP

<400> SEQUENCE: 1105

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 1106
<211> LENGTH: 28
<212> TYPE: PRT
<213> ORGANISM: Artificial sequence
<220> FEATURE:
<223> OTHER INFORMATION: CPP

<400> SEQUENCE: 1106

Ala Ala Val Ala Leu Leu Pro Ala Val Leu Leu Ala Leu Leu Ala Pro
1               5                   10                  15

Arg Lys Lys Arg Arg Gln Arg Arg Arg Pro Pro Gln
            20                  25

<210> SEQ ID NO 1107
<211> LENGTH: 5
<212> TYPE: PRT
<213> ORGANISM: Artificial sequence
<220> FEATURE:
<223> OTHER INFORMATION: CPP

<400> SEQUENCE: 1107

Cys Trp Lys Lys Lys
1               5

<210> SEQ ID NO 1108
<211> LENGTH: 10
<212> TYPE: PRT
<213> ORGANISM: Artificial sequence
<220> FEATURE:
<223> OTHER INFORMATION: CPP

<400> SEQUENCE: 1108

Cys Trp Lys Lys Lys Lys Lys Lys Lys Lys
1               5                   10

<210> SEQ ID NO 1109
<211> LENGTH: 15
<212> TYPE: PRT
<213> ORGANISM: Artificial sequence
<220> FEATURE:
<223> OTHER INFORMATION: CPP

<400> SEQUENCE: 1109

Cys Trp Lys Lys Lys Lys Lys Lys Lys Lys Lys Lys Lys Lys Lys
1               5                   10                  15

```
<210> SEQ ID NO 1110
<211> LENGTH: 20
<212> TYPE: PRT
<213> ORGANISM: Artificial sequence
<220> FEATURE:
<223> OTHER INFORMATION: CPP

<400> SEQUENCE: 1110

Cys Trp Lys Lys Lys Lys Lys Lys Lys Lys Lys Lys Lys Lys Lys
1               5                   10                  15

Lys Lys Lys Lys
            20

<210> SEQ ID NO 1111
<211> LENGTH: 19
<212> TYPE: PRT
<213> ORGANISM: Artificial sequence
<220> FEATURE:
<223> OTHER INFORMATION: CPP

<400> SEQUENCE: 1111

Lys Lys Lys Lys Lys Lys Lys Lys Lys Lys Lys Lys Lys Lys Lys
1               5                   10                  15

Lys Lys Lys

<210> SEQ ID NO 1112
<211> LENGTH: 19
<212> TYPE: PRT
<213> ORGANISM: Artificial sequence
<220> FEATURE:
<223> OTHER INFORMATION: CPP

<400> SEQUENCE: 1112

Lys Lys Trp Lys Met Arg Arg Gly Ala Gly Arg Arg Arg Arg Arg
1               5                   10                  15

Arg Arg Arg

<210> SEQ ID NO 1113
<211> LENGTH: 12
<212> TYPE: PRT
<213> ORGANISM: Artificial sequence
<220> FEATURE:
<223> OTHER INFORMATION: CPP

<400> SEQUENCE: 1113

Ala Pro Trp His Leu Ser Ser Gln Tyr Ser Arg Thr
1               5                   10

<210> SEQ ID NO 1114
<211> LENGTH: 11
<212> TYPE: PRT
<213> ORGANISM: Artificial sequence
<220> FEATURE:
<223> OTHER INFORMATION: CPP

<400> SEQUENCE: 1114

Arg Arg Arg Arg Arg Arg Arg Arg Arg Arg Arg
1               5                   10

<210> SEQ ID NO 1115
<211> LENGTH: 20
<212> TYPE: PRT
<213> ORGANISM: Artificial sequence
<220> FEATURE:
<223> OTHER INFORMATION: CPP
```

```
<400> SEQUENCE: 1115

Lys Leu Ala Leu Lys Leu Ala Leu Lys Ala Leu Lys Ala Ala Leu Lys
1               5                   10                  15

Leu Ala Gly Cys
            20

<210> SEQ ID NO 1116
<211> LENGTH: 15
<212> TYPE: PRT
<213> ORGANISM: Artificial sequence
<220> FEATURE:
<223> OTHER INFORMATION: CPP

<400> SEQUENCE: 1116

Lys Leu Leu Lys Leu Leu Lys Leu Lys Ala Leu Lys Leu Gly Cys
1               5                   10                  15

<210> SEQ ID NO 1117
<211> LENGTH: 35
<212> TYPE: PRT
<213> ORGANISM: Artificial sequence
<220> FEATURE:
<223> OTHER INFORMATION: CPP

<400> SEQUENCE: 1117

Gly Gly Gly Ala Arg Lys Lys Ala Ala Lys Ala Ala Arg Lys Lys Ala
1               5                   10                  15

Ala Lys Ala Ala Arg Lys Lys Ala Ala Lys Ala Ala Arg Lys Lys Ala
            20                  25                  30

Ala Lys Ala
        35

<210> SEQ ID NO 1118
<211> LENGTH: 10
<212> TYPE: PRT
<213> ORGANISM: Artificial sequence
<220> FEATURE:
<223> OTHER INFORMATION: CPP

<400> SEQUENCE: 1118

Cys Arg Arg Arg Arg Arg Arg Arg Arg Arg
1               5                   10

<210> SEQ ID NO 1119
<211> LENGTH: 10
<212> TYPE: PRT
<213> ORGANISM: Artificial sequence
<220> FEATURE:
<223> OTHER INFORMATION: CPP

<400> SEQUENCE: 1119

Cys Lys Lys Lys Lys Lys Lys Lys Lys Lys
1               5                   10

<210> SEQ ID NO 1120
<211> LENGTH: 27
<212> TYPE: PRT
<213> ORGANISM: Artificial sequence
<220> FEATURE:
<223> OTHER INFORMATION: CPP

<400> SEQUENCE: 1120

Gly Trp Thr Leu Asn Ser Ala Gly Tyr Leu Leu Gly Lys Ile Asn Leu
1               5                   10                  15
```

Lys Ala Leu Ala Ala Leu Ala Lys Lys Ile Leu
            20                  25

<210> SEQ ID NO 1121
<211> LENGTH: 27
<212> TYPE: PRT
<213> ORGANISM: Artificial sequence
<220> FEATURE:
<223> OTHER INFORMATION: CPP

<400> SEQUENCE: 1121

Gly Trp Thr Leu Asn Ser Ala Gly Tyr Leu Leu Gly Lys Ile Asn Leu
1               5                   10                  15

Lys Ala Leu Ala Ala Leu Ala Lys Lys Leu Leu
            20                  25

<210> SEQ ID NO 1122
<211> LENGTH: 26
<212> TYPE: PRT
<213> ORGANISM: Artificial sequence
<220> FEATURE:
<223> OTHER INFORMATION: CPP

<400> SEQUENCE: 1122

Gly Trp Thr Leu Asn Ser Ala Gly Tyr Leu Leu Gly Lys Phe Leu Pro
1               5                   10                  15

Leu Ile Leu Arg Lys Ile Val Thr Ala Leu
            20                  25

<210> SEQ ID NO 1123
<211> LENGTH: 27
<212> TYPE: PRT
<213> ORGANISM: Artificial sequence
<220> FEATURE:
<223> OTHER INFORMATION: CPP

<400> SEQUENCE: 1123

Gly Trp Thr Leu Asn Pro Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 1124
<211> LENGTH: 27
<212> TYPE: PRT
<213> ORGANISM: Artificial sequence
<220> FEATURE:
<223> OTHER INFORMATION: CPP

<400> SEQUENCE: 1124

Gly Trp Thr Leu Asn Pro Pro Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 1125
<211> LENGTH: 24
<212> TYPE: PRT
<213> ORGANISM: Artificial sequence
<220> FEATURE:
<223> OTHER INFORMATION: CPP

<400> SEQUENCE: 1125

Leu Asn Ser Ala Gly Tyr Leu Leu Gly Lys Ile Asn Leu Lys Ala Leu
1               5                   10                  15

Ala Ala Leu Ala Lys Lys Ile Leu
            20

<210> SEQ ID NO 1126
<211> LENGTH: 18
<212> TYPE: PRT
<213> ORGANISM: Artificial sequence
<220> FEATURE:
<223> OTHER INFORMATION: CPP

<400> SEQUENCE: 1126

Leu Leu Gly Lys Ile Asn Leu Lys Ala Leu Ala Ala Leu Ala Lys Lys
1               5                   10                  15

Ile Leu

<210> SEQ ID NO 1127
<211> LENGTH: 25
<212> TYPE: PRT
<213> ORGANISM: Artificial sequence
<220> FEATURE:
<223> OTHER INFORMATION: CPP

<400> SEQUENCE: 1127

Gly Trp Thr Leu Asn Ser Ala Gly Tyr Leu Leu Gly Lys Leu Lys Ala
1               5                   10                  15

Leu Ala Ala Leu Ala Lys Lys Ile Leu
            20                  25

<210> SEQ ID NO 1128
<211> LENGTH: 21
<212> TYPE: PRT
<213> ORGANISM: Artificial sequence
<220> FEATURE:
<223> OTHER INFORMATION: CPP

<400> SEQUENCE: 1128

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 1129
<211> LENGTH: 21
<212> TYPE: PRT
<213> ORGANISM: Artificial sequence
<220> FEATURE:
<223> OTHER INFORMATION: CPP

<400> SEQUENCE: 1129

Gly Trp Thr Leu Asn Ser Lys Ile Asn Leu Lys Ala Leu Ala Ala Leu
1               5                   10                  15

Ala Lys Lys Ile Leu
            20

<210> SEQ ID NO 1130
<211> LENGTH: 21
<212> TYPE: PRT
<213> ORGANISM: Artificial sequence
<220> FEATURE:
<223> OTHER INFORMATION: CPP

<400> SEQUENCE: 1130

Leu Asn Ser Ala Gly Tyr Leu Leu Gly Lys Leu Lys Ala Leu Ala Ala
1               5                   10                  15

Leu Ala Lys Ile Leu
            20

<210> SEQ ID NO 1131
<211> LENGTH: 20
<212> TYPE: PRT
<213> ORGANISM: Artificial sequence
<220> FEATURE:
<223> OTHER INFORMATION: CPP

<400> SEQUENCE: 1131

Leu Asn Ser Ala Gly Tyr Leu Leu Gly Lys Ala Leu Ala Ala Leu Ala
1               5                   10                  15

Lys Lys Ile Leu
            20

<210> SEQ ID NO 1132
<211> LENGTH: 19
<212> TYPE: PRT
<213> ORGANISM: Artificial sequence
<220> FEATURE:
<223> OTHER INFORMATION: CPP

<400> SEQUENCE: 1132

Ala Gly Tyr Leu Leu Gly Lys Leu Lys Ala Leu Ala Ala Leu Ala Lys
1               5                   10                  15

Lys Ile Leu

<210> SEQ ID NO 1133
<211> LENGTH: 19
<212> TYPE: PRT
<213> ORGANISM: Artificial sequence
<220> FEATURE:
<223> OTHER INFORMATION: CPP

<400> SEQUENCE: 1133

Leu Asn Ser Ala Gly Tyr Leu Leu Gly Lys Leu Lys Ala Leu Ala Ala
1               5                   10                  15

Leu Ala Lys

<210> SEQ ID NO 1134
<211> LENGTH: 27
<212> TYPE: PRT
<213> ORGANISM: Artificial sequence
<220> FEATURE:
<223> OTHER INFORMATION: CPP

<400> SEQUENCE: 1134

Gly Trp Thr Leu Asn Ser Ala Gly Tyr Leu Leu Gly Lys Ile Asn Leu
1               5                   10                  15

Lys Ala Pro Ala Ala Leu Ala Lys Lys Ile Leu
            20                  25

<210> SEQ ID NO 1135
<211> LENGTH: 21
<212> TYPE: PRT
<213> ORGANISM: Artificial sequence
<220> FEATURE:
<223> OTHER INFORMATION: CPP

<400> SEQUENCE: 1135

Ala Gly Tyr Leu Leu Gly Lys Ile Asn Leu Lys Ala Leu Ala Ala Leu
1               5                   10                  15

```
Ala Lys Lys Ile Leu
            20

<210> SEQ ID NO 1136
<211> LENGTH: 21
<212> TYPE: PRT
<213> ORGANISM: Artificial sequence
<220> FEATURE:
<223> OTHER INFORMATION: CPP

<400> SEQUENCE: 1136

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 1137
<211> LENGTH: 21
<212> TYPE: PRT
<213> ORGANISM: Artificial sequence
<220> FEATURE:
<223> OTHER INFORMATION: CPP

<400> SEQUENCE: 1137

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 1138
<211> LENGTH: 15
<212> TYPE: PRT
<213> ORGANISM: Artificial sequence
<220> FEATURE:
<223> OTHER INFORMATION: CPP

<400> SEQUENCE: 1138

Lys Trp Phe Glu Thr Trp Phe Thr Glu Trp Pro Lys Lys Arg Lys
1               5                   10                  15

<210> SEQ ID NO 1139
<211> LENGTH: 27
<212> TYPE: PRT
<213> ORGANISM: Artificial sequence
<220> FEATURE:
<223> OTHER INFORMATION: CPP

<400> SEQUENCE: 1139

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 1140
<211> LENGTH: 27
<212> TYPE: PRT
<213> ORGANISM: Artificial sequence
<220> FEATURE:
<223> OTHER INFORMATION: CPP

<400> SEQUENCE: 1140

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25
```

```
<210> SEQ ID NO 1141
<211> LENGTH: 20
<212> TYPE: PRT
<213> ORGANISM: Artificial sequence
<220> FEATURE:
<223> OTHER INFORMATION: CPP

<400> SEQUENCE: 1141

Ala Leu Trp Lys Thr Leu Leu Lys Lys Val Leu Lys Ala Pro Lys Lys
1               5                   10                  15

Lys Arg Lys Val
            20

<210> SEQ ID NO 1142
<211> LENGTH: 20
<212> TYPE: PRT
<213> ORGANISM: Artificial sequence
<220> FEATURE:
<223> OTHER INFORMATION: CPP

<400> SEQUENCE: 1142

Pro Lys Lys Lys Arg Lys Val Ala Leu Trp Lys Thr Leu Leu Lys Lys
1               5                   10                  15

Val Leu Lys Ala
            20

<210> SEQ ID NO 1143
<211> LENGTH: 20
<212> TYPE: PRT
<213> ORGANISM: Artificial sequence
<220> FEATURE:
<223> OTHER INFORMATION: CPP

<400> SEQUENCE: 1143

Val Lys Arg Lys Lys Lys Pro Ala Leu Trp Lys Thr Leu Leu Lys Lys
1               5                   10                  15

Val Leu Lys Ala
            20

<210> SEQ ID NO 1144
<211> LENGTH: 22
<212> TYPE: PRT
<213> ORGANISM: Artificial sequence
<220> FEATURE:
<223> OTHER INFORMATION: CPP

<400> SEQUENCE: 1144

Arg Gln Ala Arg Arg Asn Arg Arg Arg Ala Leu Trp Lys Thr Leu Leu
1               5                   10                  15

Lys Lys Val Leu Lys Ala
            20

<210> SEQ ID NO 1145
<211> LENGTH: 13
<212> TYPE: PRT
<213> ORGANISM: Artificial sequence
<220> FEATURE:
<223> OTHER INFORMATION: CPP

<400> SEQUENCE: 1145

Glu Glu Glu Ala Ala Gly Arg Lys Arg Lys Lys Arg Thr
1               5                   10
```

```
<210> SEQ ID NO 1146
<211> LENGTH: 13
<212> TYPE: PRT
<213> ORGANISM: Artificial sequence
<220> FEATURE:
<223> OTHER INFORMATION: CPP

<400> SEQUENCE: 1146

Phe Phe Phe Ala Ala Gly Arg Lys Arg Lys Lys Arg Thr
1               5                   10

<210> SEQ ID NO 1147
<211> LENGTH: 13
<212> TYPE: PRT
<213> ORGANISM: Artificial sequence
<220> FEATURE:
<223> OTHER INFORMATION: CPP

<400> SEQUENCE: 1147

Asn Asn Asn Ala Ala Gly Arg Lys Arg Lys Lys Arg Thr
1               5                   10

<210> SEQ ID NO 1148
<211> LENGTH: 13
<212> TYPE: PRT
<213> ORGANISM: Artificial sequence
<220> FEATURE:
<223> OTHER INFORMATION: CPP

<400> SEQUENCE: 1148

Tyr Tyr Tyr Ala Ala Gly Arg Lys Arg Lys Lys Arg Thr
1               5                   10

<210> SEQ ID NO 1149
<211> LENGTH: 21
<212> TYPE: PRT
<213> ORGANISM: Artificial sequence
<220> FEATURE:
<223> OTHER INFORMATION: CPP

<400> SEQUENCE: 1149

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 1150
<211> LENGTH: 27
<212> TYPE: PRT
<213> ORGANISM: Artificial sequence
<220> FEATURE:
<223> OTHER INFORMATION: CPP

<400> SEQUENCE: 1150

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 1151
<211> LENGTH: 27
<212> TYPE: PRT
<213> ORGANISM: Artificial sequence
<220> FEATURE:
<223> OTHER INFORMATION: CPP

<400> SEQUENCE: 1151
```

```
Gly Ala Leu Phe Leu Ala Phe Leu Ala Ala Leu Ser Leu Met Gly
1               5                   10                  15

Leu Trp Ser Gln Pro Lys Lys Lys Arg Arg Val
            20                  25
```

<210> SEQ ID NO 1152
<211> LENGTH: 27
<212> TYPE: PRT
<213> ORGANISM: Artificial sequence
<220> FEATURE:
<223> OTHER INFORMATION: CPP

<400> SEQUENCE: 1152

```
Gly Leu Leu Glu Ala Leu Ala Glu Leu Leu Glu Gly Leu Arg Lys Arg
1               5                   10                  15

Leu Arg Lys Phe Arg Asn Lys Ile Lys Glu Lys
            20                  25
```

<210> SEQ ID NO 1153
<211> LENGTH: 41
<212> TYPE: PRT
<213> ORGANISM: Artificial sequence
<220> FEATURE:
<223> OTHER INFORMATION: CPP

<400> SEQUENCE: 1153

```
Ala Ala Val Ala Leu Leu Pro Ala Val Leu Leu Ala Leu Leu Ala Pro
1               5                   10                  15

Glu Ile Leu Leu Pro Asn Asn Tyr Asn Ala Tyr Glu Ser Tyr Lys Tyr
            20                  25                  30

Pro Gly Met Phe Ile Ala Leu Ser Lys
        35                  40
```

<210> SEQ ID NO 1154
<211> LENGTH: 26
<212> TYPE: PRT
<213> ORGANISM: Artificial sequence
<220> FEATURE:
<223> OTHER INFORMATION: CPP

<400> SEQUENCE: 1154

```
Ala Ala Val Ala Leu Leu Pro Ala Val Leu Leu Ala Leu Leu Ala Pro
1               5                   10                  15

Val Gln Arg Lys Arg Gln Lys Leu Met Pro
            20                  25
```

<210> SEQ ID NO 1155
<211> LENGTH: 27
<212> TYPE: PRT
<213> ORGANISM: Artificial sequence
<220> FEATURE:
<223> OTHER INFORMATION: CPP

<400> SEQUENCE: 1155

```
Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25
```

<210> SEQ ID NO 1156
<211> LENGTH: 23
<212> TYPE: PRT
<213> ORGANISM: Artificial sequence

```
<220> FEATURE:
<223> OTHER INFORMATION: CPP

<400> SEQUENCE: 1156

Met Gly Leu Gly Leu His Leu Leu Val Leu Ala Ala Leu Gln Gly
1               5                   10                  15

Ala Lys Lys Lys Arg Lys Val
            20

<210> SEQ ID NO 1157
<211> LENGTH: 26
<212> TYPE: PRT
<213> ORGANISM: Artificial sequence
<220> FEATURE:
<223> OTHER INFORMATION: CPP

<400> SEQUENCE: 1157

Ala Ala Val Ala Leu Leu Pro Ala Val Leu Leu Ala Leu Leu Ala Lys
1               5                   10                  15

Lys Asn Asn Leu Lys Asp Cys Gly Leu Phe
            20                  25

<210> SEQ ID NO 1158
<211> LENGTH: 26
<212> TYPE: PRT
<213> ORGANISM: Artificial sequence
<220> FEATURE:
<223> OTHER INFORMATION: CPP

<400> SEQUENCE: 1158

Ala Ala Val Ala Leu Leu Pro Ala Val Leu Leu Ala Leu Leu Ala Lys
1               5                   10                  15

Lys Asn Asn Leu Lys Glu Cys Gly Leu Tyr
            20                  25

<210> SEQ ID NO 1159
<211> LENGTH: 43
<212> TYPE: PRT
<213> ORGANISM: Artificial sequence
<220> FEATURE:
<223> OTHER INFORMATION: CPP

<400> SEQUENCE: 1159

Ala Ala Val Ala Leu Leu Pro Ala Val Leu Leu Ala Leu Leu Ala Val
1               5                   10                  15

Thr Asp Gln Leu Gly Glu Asp Phe Phe Ala Val Asp Leu Glu Ala Phe
            20                  25                  30

Leu Gln Glu Phe Gly Leu Leu Pro Glu Lys Glu
        35                  40

<210> SEQ ID NO 1160
<211> LENGTH: 21
<212> TYPE: PRT
<213> ORGANISM: Artificial sequence
<220> FEATURE:
<223> OTHER INFORMATION: CPP

<400> SEQUENCE: 1160

Ala Gly Tyr Leu Leu Gly Lys Ile Asn Leu Lys Ala Leu Ala Ala Leu
1               5                   10                  15

Ala Lys Lys Ile Leu
            20
```

```
<210> SEQ ID NO 1161
<211> LENGTH: 38
<212> TYPE: PRT
<213> ORGANISM: Artificial sequence
<220> FEATURE:
<223> OTHER INFORMATION: CPP

<400> SEQUENCE: 1161

Ala Gly Tyr Leu Leu Gly Lys Ile Asn Leu Lys Ala Leu Ala Ala Leu
1               5                   10                  15

Ala Lys Lys Ile Leu Thr Tyr Ala Asp Phe Ile Ala Ser Gly Arg Thr
            20                  25                  30

Gly Arg Arg Asn Ala Ile
        35

<210> SEQ ID NO 1162
<211> LENGTH: 28
<212> TYPE: PRT
<213> ORGANISM: Artificial sequence
<220> FEATURE:
<223> OTHER INFORMATION: CPP

<400> SEQUENCE: 1162

Arg Arg Arg Arg Arg Arg Arg Arg Arg Arg Thr Tyr Ala Asp Phe
1               5                   10                  15

Ile Ala Ser Gly Arg Thr Gly Arg Arg Asn Ala Ile
            20                  25

<210> SEQ ID NO 1163
<211> LENGTH: 4
<212> TYPE: PRT
<213> ORGANISM: Artificial sequence
<220> FEATURE:
<223> OTHER INFORMATION: NLS

<400> SEQUENCE: 1163

Arg Lys Arg His
1

<210> SEQ ID NO 1164
<211> LENGTH: 7
<212> TYPE: PRT
<213> ORGANISM: Artificial sequence
<220> FEATURE:
<223> OTHER INFORMATION: SV40 large T antigen NLS

<400> SEQUENCE: 1164

Pro Lys Lys Lys Arg Lys Val
1               5

<210> SEQ ID NO 1165
<211> LENGTH: 16
<212> TYPE: PRT
<213> ORGANISM: Artificial sequence
<220> FEATURE:
<223> OTHER INFORMATION: Nucleoplasmin NLS

<400> SEQUENCE: 1165

Lys Arg Pro Ala Ala Thr Lys Lys Ala Gly Gln Ala Lys Lys Lys Lys
1               5                   10                  15

<210> SEQ ID NO 1166
<211> LENGTH: 4
<212> TYPE: PRT
<213> ORGANISM: Artificial sequence
<220> FEATURE:
```

```
<223> OTHER INFORMATION: NLS consensus sequence
<220> FEATURE:
<221> NAME/KEY: variant
<222> LOCATION: (2)..(2)
<223> OTHER INFORMATION: /REPLACE= "Arg" or "Lys"
<220> FEATURE:
<221> NAME/KEY: variant
<222> LOCATION: (3)..(3)
<223> OTHER INFORMATION: /REPLACE= any amino acid
<220> FEATURE:
<221> NAME/KEY: variant
<222> LOCATION: (4)..(4)
<223> OTHER INFORMATION: /REPLACE= "Arg" or "Lys"

<400> SEQUENCE: 1166

Lys Xaa Xaa Xaa
1

<210> SEQ ID NO 1167
<211> LENGTH: 7
<212> TYPE: PRT
<213> ORGANISM: Artificial sequence
<220> FEATURE:
<223> OTHER INFORMATION: NLS variant
<220> FEATURE:
<221> NAME/KEY: variant
<222> LOCATION: (3)..(3)
<223> OTHER INFORMATION: /REPLACE= any amino acid
<220> FEATURE:
<221> NAME/KEY: repeat
<222> LOCATION: (3)..(3)
<223> OTHER INFORMATION: X can be 5 to 20 residues

<400> SEQUENCE: 1167

Lys Arg Xaa Lys Lys Lys Lys
1               5

<210> SEQ ID NO 1168
<211> LENGTH: 16
<212> TYPE: PRT
<213> ORGANISM: Artificial sequence
<220> FEATURE:
<223> OTHER INFORMATION: NLS variant
<220> FEATURE:
<221> NAME/KEY: variant
<222> LOCATION: (3)..(12)
<223> OTHER INFORMATION: /REPLACE= any amino acid

<400> SEQUENCE: 1168

Lys Arg Xaa Xaa Xaa Xaa Xaa Xaa Xaa Xaa Xaa Xaa Lys Lys Lys Lys
1               5                   10                  15

<210> SEQ ID NO 1169
<211> LENGTH: 7
<212> TYPE: PRT
<213> ORGANISM: Artificial sequence
<220> FEATURE:
<223> OTHER INFORMATION: NLS variant
<220> FEATURE:
<221> NAME/KEY: variant
<222> LOCATION: (5)..(5)
<223> OTHER INFORMATION: /REPLACE= any amino acid
<220> FEATURE:
<221> NAME/KEY: repeat
<222> LOCATION: (5)..(5)
<223> OTHER INFORMATION: 2 to 10
<220> FEATURE:
<221> NAME/KEY: repeat
<222> LOCATION: (5)..(5)
<223> OTHER INFORMATION: X can be 2 to 10 residues

<400> SEQUENCE: 1169
```

Arg Lys Arg His Xaa Lys Lys
1               5

<210> SEQ ID NO 1170
<211> LENGTH: 8
<212> TYPE: PRT
<213> ORGANISM: Artificial sequence
<220> FEATURE:
<223> OTHER INFORMATION: NLS variant
<220> FEATURE:
<221> NAME/KEY: variant
<222> LOCATION: (5)..(6)
<223> OTHER INFORMATION: /REPLACE= any amino acid

<400> SEQUENCE: 1170

Arg Lys Arg His Xaa Xaa Lys Lys
1               5

<210> SEQ ID NO 1171
<211> LENGTH: 8
<212> TYPE: PRT
<213> ORGANISM: Artificial sequence
<220> FEATURE:
<223> OTHER INFORMATION: NLS variant

<400> SEQUENCE: 1171

Arg Lys Arg His Ile Ile Lys Lys
1               5

<210> SEQ ID NO 1172
<211> LENGTH: 9
<212> TYPE: PRT
<213> ORGANISM: Artificial sequence
<220> FEATURE:
<223> OTHER INFORMATION: Oncoprotein c-myc NLS

<400> SEQUENCE: 1172

Pro Ala Ala Lys Arg Val Lys Leu Asp
1               5

<210> SEQ ID NO 1173
<211> LENGTH: 4
<212> TYPE: PRT
<213> ORGANISM: Artificial sequence
<220> FEATURE:
<223> OTHER INFORMATION: NLS cluster of basic amino acids

<400> SEQUENCE: 1173

Lys Lys Lys Lys
1

<210> SEQ ID NO 1174
<211> LENGTH: 8
<212> TYPE: PRT
<213> ORGANISM: Artificial sequence
<220> FEATURE:
<223> OTHER INFORMATION: NLS variant

<400> SEQUENCE: 1174

Pro Ala Ala Lys Lys Lys Leu Asp
1               5

<210> SEQ ID NO 1175
<211> LENGTH: 8
<212> TYPE: PRT
<213> ORGANISM: Artificial sequence
<220> FEATURE:
<223> OTHER INFORMATION: NLS variant

```
<400> SEQUENCE: 1175

Pro Lys Lys Lys Arg Lys Val Leu
1               5

<210> SEQ ID NO 1176
<211> LENGTH: 5
<212> TYPE: PRT
<213> ORGANISM: Artificial sequence
<220> FEATURE:
<223> OTHER INFORMATION: NLS variant

<400> SEQUENCE: 1176

Lys Lys Lys Arg Lys
1               5

<210> SEQ ID NO 1177
<211> LENGTH: 6
<212> TYPE: PRT
<213> ORGANISM: Artificial sequence
<220> FEATURE:
<223> OTHER INFORMATION: NLS variant

<400> SEQUENCE: 1177

Lys Lys Lys Arg Val Lys
1               5

<210> SEQ ID NO 1178
<211> LENGTH: 7
<212> TYPE: PRT
<213> ORGANISM: Artificial sequence
<220> FEATURE:
<223> OTHER INFORMATION: NLS variant

<400> SEQUENCE: 1178

Lys Lys Lys Arg Lys Val Leu
1               5

<210> SEQ ID NO 1179
<211> LENGTH: 7
<212> TYPE: PRT
<213> ORGANISM: Artificial sequence
<220> FEATURE:
<223> OTHER INFORMATION: NLS variant

<400> SEQUENCE: 1179

Arg Lys Lys Arg Lys Val Leu
1               5

<210> SEQ ID NO 1180
<211> LENGTH: 5
<212> TYPE: PRT
<213> ORGANISM: Artificial Sequence
<220> FEATURE:
<223> OTHER INFORMATION: Linker

<400> SEQUENCE: 1180

Ile Ile Leu Val Ile
1               5

<210> SEQ ID NO 1181
<211> LENGTH: 7
<212> TYPE: PRT
<213> ORGANISM: Artificial sequence
<220> FEATURE:
<223> OTHER INFORMATION: Linker
```

```
<400> SEQUENCE: 1181

Ile Ile Leu Val Ile Ile Ile
1               5

<210> SEQ ID NO 1182
<211> LENGTH: 14
<212> TYPE: PRT
<213> ORGANISM: Artificial Sequence
<220> FEATURE:
<223> OTHER INFORMATION: APIM Oligopeptidic compound

<400> SEQUENCE: 1182

Met Asp Arg Trp Leu Val Lys Arg Ile Leu Val Ala Thr Lys
1               5                   10

<210> SEQ ID NO 1183
<211> LENGTH: 20
<212> TYPE: PRT
<213> ORGANISM: Artificial sequence
<220> FEATURE:
<223> OTHER INFORMATION: APIM Oligopeptidic compound

<400> SEQUENCE: 1183

Met Asp Arg Trp Leu Val Lys Arg Ile Leu Lys Lys Arg Lys Val
1               5                   10                  15

Ala Thr Lys Gly
            20

<210> SEQ ID NO 1184
<211> LENGTH: 34
<212> TYPE: PRT
<213> ORGANISM: Artificial sequence
<220> FEATURE:
<223> OTHER INFORMATION: MDR2

<400> SEQUENCE: 1184

Met Asp Arg Trp Leu Val Lys Gly Ala Gln Pro Lys Lys Lys Arg Lys
1               5                   10                  15

Val Leu Arg Gln Ile Lys Ile Trp Phe Gln Asn Arg Arg Met Lys Trp
            20                  25                  30

Lys Lys

<210> SEQ ID NO 1185
<211> LENGTH: 28
<212> TYPE: PRT
<213> ORGANISM: Artificial sequence
<220> FEATURE:
<223> OTHER INFORMATION: MDR27

<400> SEQUENCE: 1185

Met Asp Arg Trp Leu Val Lys Gly Ala Trp Lys Lys Arg Val Lys
1               5                   10                  15

Ile Ile Arg Lys Lys Arg Arg Gln Arg Arg Lys
            20                  25

<210> SEQ ID NO 1186
<211> LENGTH: 27
<212> TYPE: PRT
<213> ORGANISM: Artificial sequence
<220> FEATURE:
<223> OTHER INFORMATION: MDR26-0

<400> SEQUENCE: 1186

Met Asp Arg Trp Leu Val Lys Gly Ala Trp Lys Lys Arg Lys Ile
```

```
                1               5                  10                 15
Ile Arg Lys Lys Arg Arg Gln Arg Arg Gly
            20                  25

<210> SEQ ID NO 1187
<211> LENGTH: 27
<212> TYPE: PRT
<213> ORGANISM: Artificial sequence
<220> FEATURE:
<223> OTHER INFORMATION: MDR26-1

<400> SEQUENCE: 1187

Met Asp Arg Trp Leu Val Lys Gly Ala Trp Lys Lys Lys Arg Lys Ile
1               5                  10                 15

Ile Arg Lys Lys Arg Arg Gln Arg Arg Lys
            20                  25

<210> SEQ ID NO 1188
<211> LENGTH: 27
<212> TYPE: PRT
<213> ORGANISM: Artificial sequence
<220> FEATURE:
<223> OTHER INFORMATION: MDR26-2

<400> SEQUENCE: 1188

Met Asp Arg Trp Leu Val Lys Arg Ile Trp Lys Lys Lys Arg Lys Ile
1               5                  10                 15

Ile Arg Lys Lys Arg Arg Gln Arg Arg Lys
            20                  25

<210> SEQ ID NO 1189
<211> LENGTH: 27
<212> TYPE: PRT
<213> ORGANISM: Artificial sequence
<220> FEATURE:
<223> OTHER INFORMATION: MDR26-3

<400> SEQUENCE: 1189

Met Asp Arg Trp Leu Val Lys Trp Trp Lys Lys Lys Arg Lys Ile
1               5                  10                 15

Ile Arg Lys Lys Arg Arg Gln Arg Arg Lys
            20                  25

<210> SEQ ID NO 1190
<211> LENGTH: 27
<212> TYPE: PRT
<213> ORGANISM: Artificial sequence
<220> FEATURE:
<223> OTHER INFORMATION: MDR26-4

<400> SEQUENCE: 1190

Met Asp Arg Trp Leu Val Lys Trp Trp Arg Lys Arg His Ile Ile Lys
1               5                  10                 15

Lys Arg Lys Lys Arg Arg Gln Arg Arg Lys
            20                  25

<210> SEQ ID NO 1191
<211> LENGTH: 29
<212> TYPE: PRT
<213> ORGANISM: Artificial sequence
<220> FEATURE:
<223> OTHER INFORMATION: MDR26-7

<400> SEQUENCE: 1191
```

Met Asp Arg Trp Leu Val Lys Arg Ile Trp Lys Lys Arg Lys Ile
1               5                   10                  15

Ile Arg Arg Arg Arg Arg Arg Arg Arg Arg Lys
            20                  25

<210> SEQ ID NO 1192
<211> LENGTH: 33
<212> TYPE: PRT
<213> ORGANISM: Artificial sequence
<220> FEATURE:
<223> OTHER INFORMATION: MDR26-8

<400> SEQUENCE: 1192

Met Asp Arg Trp Leu Val Lys Arg Ile Trp Lys Lys Arg Lys Ile
1               5                   10                  15

Ile Arg Gln Ile Lys Ile Trp Phe Gln Asn Arg Arg Met Lys Trp Lys
            20                  25                  30

Lys

<210> SEQ ID NO 1193
<211> LENGTH: 28
<212> TYPE: PRT
<213> ORGANISM: Artificial sequence
<220> FEATURE:
<223> OTHER INFORMATION: MDr26-10

<400> SEQUENCE: 1193

Met Asp Arg Phe Leu Val Lys Gly Ala Trp Arg Lys Arg His Ile Ile
1               5                   10                  15

Lys Lys Arg Lys Lys Arg Arg Gln Arg Arg Lys
            20                  25

<210> SEQ ID NO 1194
<211> LENGTH: 26
<212> TYPE: PRT
<213> ORGANISM: Artificial sequence
<220> FEATURE:
<223> OTHER INFORMATION: MDR26-72

<400> SEQUENCE: 1194

Met Asp Arg Trp Leu Val Lys Trp Lys Lys Arg Lys Ile Arg Arg
1               5                   10                  15

Arg Arg Arg Arg Arg Arg Arg Arg Lys
            20                  25

<210> SEQ ID NO 1195
<211> LENGTH: 24
<212> TYPE: PRT
<213> ORGANISM: Artificial sequence
<220> FEATURE:
<223> OTHER INFORMATION: MDR26-32

<400> SEQUENCE: 1195

Met Asp Arg Trp Leu Val Lys Trp Lys Lys Arg Lys Ile Arg Lys
1               5                   10                  15

Lys Arg Arg Gln Arg Arg Arg Lys
            20

<210> SEQ ID NO 1196
<211> LENGTH: 23
<212> TYPE: PRT
<213> ORGANISM: Artificial sequence
<220> FEATURE:
<223> OTHER INFORMATION: MDR26-42

```
<400> SEQUENCE: 1196

Met Asp Arg Trp Leu Val Lys Trp Arg Lys Arg His Ile Arg Lys Lys
1               5                   10                  15

Arg Arg Gln Arg Arg Arg Lys
            20

<210> SEQ ID NO 1197
<211> LENGTH: 25
<212> TYPE: PRT
<213> ORGANISM: Artificial sequence
<220> FEATURE:
<223> OTHER INFORMATION: MDR24-43
<220> FEATURE:
<221> NAME/KEY: MOD_RES
<222> LOCATION: (1)..(1)
<223> OTHER INFORMATION: ACETYLATION

<400> SEQUENCE: 1197

Met Asp Arg Trp Leu Val Lys Gly Ala Trp Arg Lys Arg His Ile Arg
1               5                   10                  15

Lys Lys Arg Arg Gln Arg Arg Arg Lys
            20                  25

<210> SEQ ID NO 1198
<211> LENGTH: 25
<212> TYPE: PRT
<213> ORGANISM: Artificial sequence
<220> FEATURE:
<223> OTHER INFORMATION: MDR26-72-0
<220> FEATURE:
<221> NAME/KEY: MOD_RES
<222> LOCATION: (1)..(1)
<223> OTHER INFORMATION: ACETYLATION

<400> SEQUENCE: 1198

Met Asp Arg Trp Leu Val Lys Trp Lys Lys Lys Arg Lys Ile Arg Arg
1               5                   10                  15

Arg Arg Arg Arg Arg Arg Arg Arg Arg
            20                  25

<210> SEQ ID NO 1199
<211> LENGTH: 25
<212> TYPE: PRT
<213> ORGANISM: Artificial sequence
<220> FEATURE:
<223> OTHER INFORMATION: MDR26-72-A
<220> FEATURE:
<221> NAME/KEY: MOD_RES
<222> LOCATION: (1)..(1)
<223> OTHER INFORMATION: ACETYLATION

<400> SEQUENCE: 1199

Met Asp Arg Phe Leu Val Lys Trp Lys Lys Arg Lys Ile Arg Arg
1               5                   10                  15

Arg Arg Arg Arg Arg Arg Arg Arg Arg
            20                  25

<210> SEQ ID NO 1200
<211> LENGTH: 24
<212> TYPE: PRT
<213> ORGANISM: Artificial sequence
<220> FEATURE:
<223> OTHER INFORMATION: MDR26-72-011
<220> FEATURE:
<221> NAME/KEY: MOD_RES
<222> LOCATION: (1)..(1)
```

<223> OTHER INFORMATION: ACETYLATION

<400> SEQUENCE: 1200

Met Asp Arg Trp Leu Val Lys Lys Lys Arg Lys Arg Arg Arg
1               5                   10                  15

Arg Arg Arg Arg Arg Arg Arg Lys
            20

<210> SEQ ID NO 1201
<211> LENGTH: 23
<212> TYPE: PRT
<213> ORGANISM: Artificial sequence
<220> FEATURE:
<223> OTHER INFORMATION: MDR26-01
<220> FEATURE:
<221> NAME/KEY: MOD_RES
<222> LOCATION: (1)..(1)
<223> OTHER INFORMATION: ACETYLATION

<400> SEQUENCE: 1201

Met Asp Arg Trp Leu Val Lys Lys Lys Arg Lys Arg Arg Arg
1               5                   10                  15

Arg Arg Arg Arg Arg Arg Arg
            20

<210> SEQ ID NO 1202
<211> LENGTH: 35
<212> TYPE: PRT
<213> ORGANISM: Artificial sequence
<220> FEATURE:
<223> OTHER INFORMATION: MDR34

<400> SEQUENCE: 1202

Met Asp Arg Trp Leu Val Lys Arg Ile Trp Lys Lys Lys Arg Lys Ile
1               5                   10                  15

Ile Arg Trp Leu Val Lys Trp Trp Trp Arg Lys Lys Arg Arg Gln Arg
            20                  25                  30

Arg Arg Lys
        35

<210> SEQ ID NO 1203
<211> LENGTH: 25
<212> TYPE: PRT
<213> ORGANISM: Artificial sequence
<220> FEATURE:
<223> OTHER INFORMATION: APIM peptide

<400> SEQUENCE: 1203

Met Asp Arg Trp Ser Val Lys Trp Lys Lys Lys Arg Lys Ile Arg Arg
1               5                   10                  15

Arg Arg Arg Arg Arg Arg Arg Arg Arg
            20                  25

<210> SEQ ID NO 1204
<211> LENGTH: 25
<212> TYPE: PRT
<213> ORGANISM: Artificial sequence
<220> FEATURE:
<223> OTHER INFORMATION: APIM peptide

<400> SEQUENCE: 1204

Met Asp Arg Trp Ala Val Lys Trp Lys Lys Lys Arg Lys Ile Arg Arg
1               5                   10                  15

Arg Arg Arg Arg Arg Arg Arg Arg Arg

```
                        20                  25

<210> SEQ ID NO 1205
<211> LENGTH: 8
<212> TYPE: PRT
<213> ORGANISM: Artificial sequence
<220> FEATURE:
<223> OTHER INFORMATION: PIP-box
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: variant
<222> LOCATION: (4)..(4)
<223> OTHER INFORMATION: /REPLACE: "Leu" or "Ile" or "Met"
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: variant
<222> LOCATION: (7)..(7)
<223> OTHER INFORMATION: /REPLACE: "Phe" or "Asp"
<220> FEATURE:
<221> NAME/KEY: variant
<222> LOCATION: (8)..(8)
<223> OTHER INFORMATION: /REPLACE: "Phe" or "Tyr"

<400> SEQUENCE: 1205

Gln Xaa Xaa Xaa Xaa Xaa Xaa Xaa
1               5

<210> SEQ ID NO 1206
<211> LENGTH: 25
<212> TYPE: PRT
<213> ORGANISM: Artificial sequence
<220> FEATURE:
<223> OTHER INFORMATION: APIM negative control peptide

<400> SEQUENCE: 1206

Met Asp Arg Ala Leu Val Lys Trp Lys Lys Arg Lys Ile Arg Arg
1               5                   10                  15

Arg Arg Arg Arg Arg Arg Arg Arg Arg
                20                  25

<210> SEQ ID NO 1207
<211> LENGTH: 5
<212> TYPE: PRT
<213> ORGANISM: Artificial sequence
<220> FEATURE:
<223> OTHER INFORMATION: APIM negative control motif

<400> SEQUENCE: 1207

Arg Ala Leu Val Lys
1               5

<210> SEQ ID NO 1208
<211> LENGTH: 25
<212> TYPE: PRT
<213> ORGANISM: Artificial sequence
<220> FEATURE:
<223> OTHER INFORMATION: APIM peptide

<400> SEQUENCE: 1208

Met Asp Arg Trp Leu Val Pro Trp Lys Lys Arg Lys Ile Arg Arg
1               5                   10                  15

Arg Arg Arg Arg Arg Arg Arg Arg Arg
                20                  25
```

```
<210> SEQ ID NO 1209
<211> LENGTH: 5
<212> TYPE: PRT
<213> ORGANISM: Artificial sequence
<220> FEATURE:
<223> OTHER INFORMATION: APIM variant

<400> SEQUENCE: 1209

Arg Trp Leu Val Pro
1               5

<210> SEQ ID NO 1210
<211> LENGTH: 22
<212> TYPE: PRT
<213> ORGANISM: Artificial sequence
<220> FEATURE:
<223> OTHER INFORMATION: R41
<220> FEATURE:
<221> NAME/KEY: MISC_FEATURE
<222> LOCATION: (22)..(22)
<223> OTHER INFORMATION: Amide

<400> SEQUENCE: 1210

Phe Ile Leu Phe Ile Leu Phe Ile Leu Gly Gly Lys His Lys His Lys
1               5                   10                  15

His Lys His Lys His Lys
            20

<210> SEQ ID NO 1211
<211> LENGTH: 22
<212> TYPE: PRT
<213> ORGANISM: Artificial sequence
<220> FEATURE:
<223> OTHER INFORMATION: R8
<220> FEATURE:
<221> NAME/KEY: MISC_FEATURE
<222> LOCATION: (22)..(22)
<223> OTHER INFORMATION: Amide

<400> SEQUENCE: 1211

Gly Pro Pro Arg Phe Pro Pro Arg Phe Pro Pro Arg Phe Pro Pro Arg
1               5                   10                  15

Phe Pro Pro Arg Phe Pro
            20

<210> SEQ ID NO 1212
<211> LENGTH: 22
<212> TYPE: PRT
<213> ORGANISM: Artificial sequence
<220> FEATURE:
<223> OTHER INFORMATION: M918
<220> FEATURE:
<221> NAME/KEY: MISC_FEATURE
<222> LOCATION: (22)..(22)
<223> OTHER INFORMATION: amide

<400> SEQUENCE: 1212

Met Val Thr Val Leu Phe Arg Arg Leu Arg Ile Arg Arg Ala Ser Gly
1               5                   10                  15

Pro Pro Arg Val Arg Val
            20

<210> SEQ ID NO 1213
<211> LENGTH: 17
<212> TYPE: PRT
<213> ORGANISM: Artificial sequence
```

```
<220> FEATURE:
<223> OTHER INFORMATION: YTA-4
<220> FEATURE:
<221> NAME/KEY: MISC_FEATURE
<222> LOCATION: (1)..(1)
<223> OTHER INFORMATION: Acetyl
<220> FEATURE:
<221> NAME/KEY: MISC_FEATURE
<222> LOCATION: (17)..(17)
<223> OTHER INFORMATION: amide

<400> SEQUENCE: 1213

Ile Ala Trp Val Lys Ala Phe Ile Arg Lys Leu Arg Lys Gly Pro Leu
1               5                   10                  15
Gly

<210> SEQ ID NO 1214
<211> LENGTH: 8
<212> TYPE: PRT
<213> ORGANISM: Artificial sequence
<220> FEATURE:
<223> OTHER INFORMATION: cyclic CPP
<220> FEATURE:
<221> NAME/KEY: MISC_FEATURE
<222> LOCATION: (1)..(8)
<223> OTHER INFORMATION: cyclic
<220> FEATURE:
<221> NAME/KEY: MISC_FEATURE
<222> LOCATION: (1)..(8)
<223> OTHER INFORMATION: may be cyclic

<400> SEQUENCE: 1214

Arg Arg Arg Arg Trp Trp Trp Trp
1               5

<210> SEQ ID NO 1215
<211> LENGTH: 7
<212> TYPE: PRT
<213> ORGANISM: Artificial sequence
<220> FEATURE:
<223> OTHER INFORMATION: Cyclic CPP
<220> FEATURE:
<221> NAME/KEY: MISC_FEATURE
<222> LOCATION: (1)..(7)
<223> OTHER INFORMATION: may be cyclic

<400> SEQUENCE: 1215

Arg Arg Arg Arg Trp Trp Trp
1               5

<210> SEQ ID NO 1216
<211> LENGTH: 8
<212> TYPE: PRT
<213> ORGANISM: Artificial sequence
<220> FEATURE:
<223> OTHER INFORMATION: cyclic CPP
<220> FEATURE:
<221> NAME/KEY: MISC_FEATURE
<222> LOCATION: (1)..(8)
<223> OTHER INFORMATION: cyclic

<400> SEQUENCE: 1216

Glu Glu Glu Glu Trp Trp Trp Trp
1               5

<210> SEQ ID NO 1217
<211> LENGTH: 7
<212> TYPE: PRT
<213> ORGANISM: Artificial sequence
<220> FEATURE:
```

```
<223> OTHER INFORMATION: cyclic CPP
<220> FEATURE:
<221> NAME/KEY: MISC_FEATURE
<222> LOCATION: (1)..(7)
<223> OTHER INFORMATION: cyclic

<400> SEQUENCE: 1217

Glu Glu Glu Glu Trp Trp Trp
1               5

<210> SEQ ID NO 1218
<211> LENGTH: 6
<212> TYPE: PRT
<213> ORGANISM: Artificial sequence
<220> FEATURE:
<223> OTHER INFORMATION: cyclic CPP
<220> FEATURE:
<221> NAME/KEY: MISC_FEATURE
<222> LOCATION: (1)..(1)
<223> OTHER INFORMATION: may comprise a fatty acyl group containing at
      least 8 carbons
<220> FEATURE:
<221> NAME/KEY: MISC_FEATURE
<222> LOCATION: (1)..(6)
<223> OTHER INFORMATION: may be cyclic

<400> SEQUENCE: 1218

Lys Arg Arg Arg Arg Arg
1               5

<210> SEQ ID NO 1219
<211> LENGTH: 7
<212> TYPE: PRT
<213> ORGANISM: Artificial sequence
<220> FEATURE:
<223> OTHER INFORMATION: cyclic CPP
<220> FEATURE:
<221> NAME/KEY: MISC_FEATURE
<222> LOCATION: (1)..(1)
<223> OTHER INFORMATION: may comprise a fatty acyl group containing at
      least 8 carbons
<220> FEATURE:
<221> NAME/KEY: MISC_FEATURE
<222> LOCATION: (1)..(7)
<223> OTHER INFORMATION: cyclic

<400> SEQUENCE: 1219

Lys Arg Arg Arg Arg Arg Arg
1               5

<210> SEQ ID NO 1220
<211> LENGTH: 10
<212> TYPE: PRT
<213> ORGANISM: Artificial sequence
<220> FEATURE:
<223> OTHER INFORMATION: cyclic CPP
<220> FEATURE:
<221> NAME/KEY: MISC_FEATURE
<222> LOCATION: (1)..(10)
<223> OTHER INFORMATION: cyclic
<220> FEATURE:
<221> NAME/KEY: MISC_FEATURE
<222> LOCATION: (1)..(1)
<223> OTHER INFORMATION: N-acetyl

<400> SEQUENCE: 1220

Trp Trp Trp Trp Lys Arg Arg Arg Arg Arg
1               5                   10

<210> SEQ ID NO 1221
<211> LENGTH: 10
```

```
<212> TYPE: PRT
<213> ORGANISM: Homo sapiens

<400> SEQUENCE: 1221

Ala Ala Glu Ala Ala Ile Asn Ile Leu Lys
1               5                   10

<210> SEQ ID NO 1222
<211> LENGTH: 10
<212> TYPE: PRT
<213> ORGANISM: Homo sapiens

<400> SEQUENCE: 1222

Val Gly Leu Asp Ala Thr Asn Cys Leu Arg
1               5                   10

<210> SEQ ID NO 1223
<211> LENGTH: 14
<212> TYPE: PRT
<213> ORGANISM: Homo sapiens

<400> SEQUENCE: 1223

Ser Gly Cys Thr Ser Leu Thr Pro Gly Pro Asn Cys Asp Arg
1               5                   10

<210> SEQ ID NO 1224
<211> LENGTH: 10
<212> TYPE: PRT
<213> ORGANISM: Homo sapiens

<400> SEQUENCE: 1224

Asn Asn Trp Thr Gly Glu Phe Ser Ala Arg
1               5                   10

<210> SEQ ID NO 1225
<211> LENGTH: 13
<212> TYPE: PRT
<213> ORGANISM: Homo sapiens

<400> SEQUENCE: 1225

Glu Leu Val Gln Gln Tyr His Gln Phe Gln Cys Ser Arg
1               5                   10

<210> SEQ ID NO 1226
<211> LENGTH: 15
<212> TYPE: PRT
<213> ORGANISM: Homo sapiens

<400> SEQUENCE: 1226

Ser Ile Ala Val Ala Glu Ala Ala Cys Pro Gly Ile Thr Asp Lys
1               5                   10                  15

<210> SEQ ID NO 1227
<211> LENGTH: 8
<212> TYPE: PRT
<213> ORGANISM: Homo sapiens

<400> SEQUENCE: 1227

Thr Gln Gln Val Val Ala Ile Lys
1               5

<210> SEQ ID NO 1228
<211> LENGTH: 9
<212> TYPE: PRT
<213> ORGANISM: Homo sapiens
```

<400> SEQUENCE: 1228

Asn Gln Ala Ile Glu Glu Leu Glu Lys
1               5

<210> SEQ ID NO 1229
<211> LENGTH: 26
<212> TYPE: PRT
<213> ORGANISM: Homo sapiens

<400> SEQUENCE: 1229

Cys Ile Lys Gln Val His Tyr Thr Leu Pro Ala Ser Leu Ser Leu Pro
1               5                   10                  15

Ala Arg Gln Leu Leu Ala Ala Ile Leu Arg
            20                  25

<210> SEQ ID NO 1230
<211> LENGTH: 15
<212> TYPE: PRT
<213> ORGANISM: Homo sapiens

<400> SEQUENCE: 1230

Thr Ser Ser Thr Ser Ser Ser Val Asn Ser Gln Thr Leu Asn Arg
1               5                   10                  15

<210> SEQ ID NO 1231
<211> LENGTH: 15
<212> TYPE: PRT
<213> ORGANISM: Homo sapiens

<400> SEQUENCE: 1231

Leu Pro Glu Tyr Thr Leu Ser Gln Glu Gly Gly Pro Ala His Lys
1               5                   10                  15

<210> SEQ ID NO 1232
<211> LENGTH: 11
<212> TYPE: PRT
<213> ORGANISM: Homo sapiens

<400> SEQUENCE: 1232

Ile Glu Asp Ala Ser Asn Pro Leu Leu Leu Lys
1               5                   10

<210> SEQ ID NO 1233
<211> LENGTH: 13
<212> TYPE: PRT
<213> ORGANISM: Homo sapiens

<400> SEQUENCE: 1233

Leu Asp Glu Ala Gln Glu Ala Glu Cys Gln Val Leu Lys
1               5                   10

<210> SEQ ID NO 1234
<211> LENGTH: 11
<212> TYPE: PRT
<213> ORGANISM: Homo sapiens

<400> SEQUENCE: 1234

Glu Ile Glu Ala Phe Asp Ser Glu Ser Met Arg
1               5                   10

<210> SEQ ID NO 1235
<211> LENGTH: 11
<212> TYPE: PRT

```
<213> ORGANISM: Homo sapiens

<400> SEQUENCE: 1235

Lys Phe Gln Gln His Ile Gln Ala Gln Gln Lys
1               5                   10
```